US008263412B2

(12) United States Patent
Wachter et al.

(10) Patent No.: US 8,263,412 B2
(45) Date of Patent: Sep. 11, 2012

(54) LONG WAVELENGTH ENGINEERED FLUORESCENT PROTEINS

(75) Inventors: Rebekka M. Wachter, Creswell, OR (US); James S. Remington, Eugene, OR (US)

(73) Assignee: The State of Oregon, Acting by and through the State Board of Higher Education on Behalf of the University of Oregon, Eugene, OR (US)

( * ) Notice: Subject to any disclaimer, the term of this patent is extended or adjusted under 35 U.S.C. 154(b) by 0 days.

(21) Appl. No.: 13/011,432

(22) Filed: Jan. 21, 2011

(65) Prior Publication Data

US 2011/0275107 A1     Nov. 10, 2011

Related U.S. Application Data

(60) Continuation of application No. 12/432,576, filed on Apr. 29, 2009, now abandoned, which is a continuation of application No. 10/620,099, filed on Jul. 14, 2003, now Pat. No. 7,544,776, which is a division of application No. 09/575,847, filed on May 19, 2000, now Pat. No. 6,593,135, which is a continuation-in-part of application No. 08/974,737, filed on Nov. 19, 1997, now Pat. No. 6,077,707, which is a continuation of application No. 08/911,825, filed on Aug. 15, 1997, now Pat. No. 6,054,321, which is a continuation-in-part of application No. 08/706,408, filed on Aug. 30, 1996, now Pat. No. 6,124,128.

(60) Provisional application No. 60/024,050, filed on Aug. 16, 1996.

(51) Int. Cl.
*G01N 21/76* (2006.01)
*C07K 14/435* (2006.01)
*C12N 15/12* (2006.01)

(52) U.S. Cl. .......................... 436/172; 530/350; 536/23.5

(58) Field of Classification Search .................... None
See application file for complete search history.

(56) References Cited

U.S. PATENT DOCUMENTS

| 5,491,084 A | 2/1996 | Chalfie et al. |
| 5,625,048 A | 4/1997 | Tsien et al. |
| 5,777,079 A | 7/1998 | Tsien et al. |
| 5,795,737 A | 8/1998 | Seed et al. |
| 5,804,387 A | 9/1998 | Cormack et al. |
| 5,981,200 A | 11/1999 | Tsien et al. |
| 5,998,204 A | 12/1999 | Tsien et al. |

(Continued)

FOREIGN PATENT DOCUMENTS

WO     WO 91/01305 A1     2/1991

(Continued)

OTHER PUBLICATIONS

Knight, M.R., et al., 1991, "Recombinant aequorin as a probe for cytolosic free Ca2+ in *Escherichia coli*", FEBS Letters, vol. 282, No. 2, pp. 405-408.*

(Continued)

*Primary Examiner* — Manjunath Rao
*Assistant Examiner* — William W Moore
(74) *Attorney, Agent, or Firm* — Kilpatrick Townsend & Stockton LLP

(57) ABSTRACT

Engineered fluorescent proteins, nucleic acids encoding them and methods of use.

6 Claims, 62 Drawing Sheets

U.S. PATENT DOCUMENTS

| | | | |
|---|---|---|---|
| 6,046,925 | A | 4/2000 | Tsien et al. |
| 6,054,321 | A | 4/2000 | Tsien et al. |
| 6,077,707 | A | 6/2000 | Tsien et al. |
| 6,124,128 | A | 9/2000 | Tsien et al. |
| 6,140,132 | A | 10/2000 | Tsien et al. |
| 6,150,176 | A | 11/2000 | Tsien et al. |
| 6,197,928 | B1 | 3/2001 | Tsien et al. |
| 6,403,374 | B1 | 6/2002 | Tsien et al. |
| 6,469,154 | B1 | 10/2002 | Tsien et al. |
| 6,593,135 | B2 | 7/2003 | Wachter et al. |
| 6,608,189 | B1 | 8/2003 | Tsien et al. |
| 6,627,449 | B1 | 9/2003 | Tsien et al. |
| 6,699,687 | B1 | 3/2004 | Tsien et al. |
| 6,780,975 | B2 | 8/2004 | Tsien et al. |
| 6,803,188 | B1 | 10/2004 | Tsien et al. |
| 7,015,310 | B2 | 3/2006 | Remington et al. |
| 7,060,793 | B2 | 6/2006 | Tsien et al. |
| 7,060,869 | B2 | 6/2006 | Tsien et al. |
| 7,544,776 | B2 * | 6/2009 | Wachter et al. ............... 530/350 |
| 2002/0164577 | A1 | 11/2002 | Tsien et al. |
| 2002/0164674 | A1 | 11/2002 | Tsien et al. |
| 2003/0119085 | A1 | 6/2003 | Tsien et al. |
| 2003/0212265 | A1 | 11/2003 | Tsien et al. |
| 2005/0079525 | A1 | 4/2005 | Tsien et al. |
| 2005/0131217 | A1 | 6/2005 | Tsien et al. |
| 2006/0112440 | A1 | 5/2006 | Tsien et al. |

FOREIGN PATENT DOCUMENTS

| | | |
|---|---|---|
| WO | WO 95/07463 A1 | 3/1995 |
| WO | WO 95/21191 A1 | 8/1995 |
| WO | WO 96/23810 A1 | 11/1995 |
| WO | WO 96/23898 A1 | 8/1996 |
| WO | WO 96/27027 A1 | 9/1996 |
| WO | WO 96/27675 A1 | 9/1996 |
| WO | WO 97/11094 A1 | 3/1997 |
| WO | WO 97/26333 A1 | 7/1997 |
| WO | WO 97/28261 A1 | 8/1997 |
| WO | WO 97/42320 A1 | 11/1997 |

OTHER PUBLICATIONS

Sheu, Y-A., et al., 1993, "Measurement of intracellular calcium using bioluminescent aequorin expressed in human cells", Analytical Biochemistry, vol. 209, pp. 343-347.*

Marshall, J., et al., 1995, "The jellyfish green fluorescent protein: a new tool for studying ion channel expression and function", Neuron, vol. 14, pp. 211-115.*

Ormo, M., et al., Sep. 1996, "Crystal structure of the Aequoria victoria green fluorescent protein", Science, vol. 273, pp. 1392-1395.*

U.S. Appl. No. 11/550,275, filed Oct. 17, 2006, Tsien et al.

Baldwin et al., Biochemistry, 29:5509-5915 (1990).

Chalfie et al., Science, 263:802-804 (1994).

Cheng et al., Nature Biotechnology, 14:606-609 (1996).

Cody et al., Biochemistry, 32:1212-1218 (1993).

Cormack et al., Gene, 173:33-38 (1995).

Crameri et al., Nature Biotech., 14:315-319 (1996).

Cubin et al., Trends in Biochem. Sci., 20:488-455 (1995).

Delagrave, S. et al., "Searching sequence space to engineer proteins, exponential ensemble mutagenesis," Bio Technology, 11:1548-1552 (Dec. 1993).

Delagrave, S. et al., Bio/Technology, 13:151-154 (1995).

Dickson et al., Science, 274:966-969 (1996).

Ehrig et al., FEBS Letters, 367:163-166 (1995).

Elsliger, Marc-Andre et al., "Structural and Spectral Response of Green Fluorescent Protein Variants to Changes in pH," Biochemistry, vol. 38, pp. 5296-5301 (1999).

Giuliano et al., Ann. Rev. Biophys. Biomol. Struc., 24:405-435 (1995).

Heim et al., Current Biology, 6:178-182 (Feb. 1996).

Heim et al., Nature, 373:663-664 (1995).

Heim et al., Proc. Natl. Acad. Sci., 91:12501-12505 (1994).

Inouye and Tsuji, FEBS Letters, 341:277-280 (1994).

Jayaraman, Sujatha et al., "Mechanism and Cellular Applications of a Green Fluorescent Protein-based Halide Sensor," J. Biol. Chem., 275(9) 6047-6050 (2000).

Kain et al., BioTechniques, 19:650-655 (1995).

Levine et al., Comp. Biochem. Physiol., 728:77-85 (1982).

Mitra et al., Gene, 173:13-17 (1996).

Muhirad et al., Yeast, 8:79-82 (1992).

Niws et al.. Proc. Natl. Acad. Sci., 93:13617-13622 (1996).

Norris, et al., Plant Molecular Biology, 24:673-677 (1994).

Ormo et al., Science, 273:1392-1395 (1996).

Palm et al., Nature Struct. Biol., 4:361-365 (1997).

Perozzo et al., J. Biol. Chem., 263:7713-7716 (1988).

Prasher et al., Gene, 111:229-233 (1992).

Roth Thesis from the graduate program in Biochemistry from Rutgers, the state University of New Jersey (Oct. 1985).

Wachter, Rebekka M. et al., "Crystal Structure and Photodynamic Behavior of the Blue Emission Variant Y66H/Y145F of Green Fluorescent Protein," Biochemistry, vol. 36, pp. 9759-9765 (1997).

Wachter, Rebekka M. et al., "Sensitivity of the Yellow Varian of Green Fluorescent Protein to Halides and Nitrate," Current Biology, vol. 9, No. 17, pp. R628-R629 (1999).

Wachter, Rebekka M. et al., "Structural Basis of Spectral Shifts in the Yellow-emission Variants of Green Fluorescent Protein," Structure, vol . 6, No. 10, pp. 1267-1277 (1998).

Ward et al., Biochemistry, 21:4535-4540 (1982).

Ward et al., Photochem Photobiol., 35:803-808 (1982).

Ward in Bioluminescence and Chemiluminescence (eds DeLuca et al., 235-242 (Academic Press, Ny, 1981)).

Yang et al., Nature Biotechnology, 14:1246-1251.

Yokoe and Meyer, Nature Biotech, 14:1252-1256 (1996).

Campbell, Robert, et al. "A monomeric red fluorescent protein," PNAS, Jun. 11, 2002, vol. 99, No. 12, pp. 7877-7882.

Dopf, Jill, et al., "Deletion mapping of the Aequorea victoria green fluorescent protein," Gene, 1996, vol. 173, pp. 39-44.

Guo, Haiwei H., et al. "Protein tolerance to random amino acid change," PNAS, Jun. 22, 2004, vol. 101, No. 25, pp. 9205-9210.

Heim, Roger, et al. "Improved green fluorescence," Nature, Scientific Correspondence, Nature, Feb. 23, 1995, vol. 373, pp. 663-664.

Kimata, Yukio, et al. "A Novel Mutation which Enhances the Fluorescence of Green Fluorescent Protein at High Temperatures," Biochemical and Biophysical Research Communications, 1997, vol. 232, pp. 69-73.

Lawrence, Michael., et al. "Supercharging Proteins Can Impart Unusual Resilience," J. Am. Chem. Soc., 2007, vol. 129, No. 33, pp. 10110-10112.

Matz, Mikhail, et al., "Fluorescent proteins from nonbioluminescent Anthozoa species," Nature Biotechnology, Oct. 1999, vol. 17, pp. 969-973.

Nagai, Takeharu, et al. "A variant of yellow fluorescent protein with fast and efficient maturation for cell-biological applications," Nature Publishing Group, Jan. 2002, vol. 20, pp. 87-90.

Nature Publishing Group, "The structural basis for spectral variations in green fluorescent protein," Nature Structural Biology, 1997, vol. 4, No. 5, pp. 361-365.

Prasher, Douglas, et al. "Primary structure of the Aequorea victoria green-fluorecent protein," Gene, 1992, vol. 111, pp. 229-233.

Siemering, Kirby, et al. "Mutations that suppress the thermosensitivity of green fluorescent protein," Current Biology, vol. 6, No. 12, pp. 1653-1663, 1996.

Tsien, Roger Y., "The Green Fluorescent Protein," Annu. Rev. Biochem., 1998, vol. 67, pp. 509-544.

* cited by examiner (xi) SEQUENCE DESCRIPTION:

SEQ ID NO:1:

SEQ ID NO:2:

| ATG | AGT | AAA | GGA | GAA | GAA | CTT | TTC | ACT | GGA | GTT | GTC | CCA | ATT | CTT | GTT | 48 |
|---|---|---|---|---|---|---|---|---|---|---|---|---|---|---|---|---|
| Met | Ser | Lys | Gly | Glu | Glu | Leu | Phe | Thr | Gly | Val | Val | Pro | Ile | Leu | Val | |
| 1 | | | | 5 | | | | | 10 | | | | | 15 | | |
| GAA | TTA | GAT | GGT | GAT | GTT | AAT | GGG | CAC | AAA | TTT | TCT | GTC | AGT | GGA | GAG | 96 |
| Glu | Leu | Asp | Gly | Asp | Val | Asn | Gly | His | Lys | Phe | Ser | Val | Ser | Gly | Glu | |
| | | | 20 | | | | | 25 | | | | | 30 | | | |
| GGT | GAA | GGT | GAT | GCA | ACA | TAC | GGA | AAA | CTT | ACC | CTT | AAA | TTT | ATT | TGC | 144 |
| Gly | Glu | Gly | Asp | Ala | Thr | Tyr | Gly | Lys | Leu | Thr | Leu | Lys | Phe | Ile | Cys | |
| | | 35 | | | | | 40 | | | | | 45 | | | | |
| ACT | ACT | GGA | AAA | CTA | CCT | GTT | CCA | TGG | CCA | ACA | CTT | GTC | ACT | ACT | TTC | 192 |
| Thr | Thr | Gly | Lys | Leu | Pro | Val | Pro | Trp | Pro | Thr | Leu | Val | Thr | Thr | Phe | |
| | 50 | | | | | 55 | | | | | 60 | | | | | |
| TCT | TAT | GGT | GTT | CAA | TGC | TTT | TCA | AGA | TAC | CCA | GAT | CAT | ATG | AAA | CGG | 240 |
| Ser | Tyr | Gly | Val | Gln | Cys | Phe | Ser | Arg | Tyr | Pro | Asp | His | Met | Lys | Arg | |
| 65 | | | | | 70 | | | | | 75 | | | | | 80 | |
| CAT | GAC | TTT | TTC | AAG | AGT | GCC | ATG | CCC | GAA | GGT | TAT | GTA | CAG | GAA | AGA | 288 |
| His | Asp | Phe | Phe | Lys | Ser | Ala | Met | Pro | Glu | Gly | Tyr | Val | Gln | Glu | Arg | |
| | | | | 85 | | | | | 90 | | | | | 95 | | |
| ACT | ATA | TTT | TTC | AAA | GAT | GAC | GGG | AAC | TAC | AAG | ACA | CGT | GCT | GAA | GTC | 336 |
| Thr | Ile | Phe | Phe | Lys | Asp | Asp | Gly | Asn | Tyr | Lys | Thr | Arg | Ala | Glu | Val | |
| | | | | 100 | | | | | 105 | | | | | 110 | | |
| AAG | TTT | GAA | GGT | GAT | ACC | CTT | GTT | AAT | AGA | ATC | GAG | TTA | AAA | GGT | ATT | 384 |
| Lys | Phe | Glu | Gly | Asp | Thr | Leu | Val | Asn | Arg | Ile | Glu | Leu | Lys | Gly | Ile | |
| | | | 115 | | | | | 120 | | | | | 125 | | | |
| GAT | TTT | AAA | GAA | GAT | GGA | AAC | ATT | CTT | GGA | CAC | AAA | TTG | GAA | TAC | AAC | 432 |
| Asp | Phe | Lys | Glu | Asp | Gly | Asn | Ile | Leu | Gly | His | Lys | Leu | Glu | Tyr | Asn | |
| | | | 130 | | | | | 135 | | | | | 140 | | | |
| TAT | AAC | TCA | CAC | AAT | GTA | TAC | ATC | ATG | GCA | GAC | AAA | CAA | AAG | AAT | GGA | 480 |
| Tyr | Asn | Ser | His | Asn | Val | Tyr | Ile | Met | Ala | Asp | Lys | Gln | Lys | Asn | Gly | |
| 145 | | | | | 150 | | | | | 155 | | | | | 160 | |
| ATC | AAA | GTT | AAC | TTC | AAA | ATT | AGA | CAC | AAC | ATT | GAA | GAT | GGA | AGC | GTT | 528 |
| Ile | Lys | Val | Asn | Phe | Lys | Ile | Arg | His | Asn | Ile | Glu | Asp | Gly | Ser | Val | |
| | | | | 165 | | | | | 170 | | | | | 175 | | |
| CAA | CTA | GCA | GAC | CAT | TAT | CAA | CAA | AAT | ACT | CCA | ATT | GGC | GAT | GGC | CCT | 576 |
| Gln | Leu | Ala | Asp | His | Tyr | Gln | Gln | Asn | Thr | Pro | Ile | Gly | Asp | Gly | Pro | |
| | | | 180 | | | | | 185 | | | | | 190 | | | |
| GTC | CTT | TTA | CCA | GAC | AAC | CAT | TAC | CTG | TCC | ACA | CAA | TCT | GCC | CTT | TCG | 624 |
| Val | Leu | Leu | Pro | Asp | Asn | His | Tyr | Leu | Ser | Thr | Gln | Ser | Ala | Leu | Ser | |
| | | | 195 | | | | | 200 | | | | | 205 | | | |
| AAA | GAT | CCC | AAC | GAA | AAG | AGA | GAC | CAC | ATG | GTC | CTT | CTT | GAG | TTT | GTA | 672 |
| Lys | Asp | Pro | Asn | Glu | Lys | Arg | Asp | His | Met | Val | Leu | Leu | Glu | Phe | Val | |
| | | 210 | | | | | 215 | | | | | 220 | | | | |
| ACA | GCT | GCT | GGG | ATT | ACA | CAT | GGC | ATG | GAT | GAA | CTA | TAC | AAA | TA | | 717 |
| Thr | Ala | Ala | Gly | Ile | Thr | His | Gly | Met | Asp | Glu | Leu | Tyr | Lys | | | |
| 225 | | | | | 230 | | | | | 235 | | | | | | |

FIG. 3

T203Y, S65G, S72A humanized codon usage, with an additional amino acid ater the start met to provide optimal kozak sequence

```
            9              18              27              36              45              54
ATG GTG AGC AAG GGC GAG GAG CTG TTC ACC GGG GTG GTG CCC ATC CTG GTC GAG
--- --- --- --- --- --- --- --- --- --- --- --- --- --- --- --- --- ---
Met Val Ser Lys Gly Glu Glu Leu Phe Thr Gly Val Val Pro Ile Leu Val Glu 63              72              81              90              99             108
CTG GAC GGC GAC GTA AAC GGC CAC AAG TTC AGC GTG TCC GGC GAG GGC GAG GGC
--- --- --- --- --- --- --- --- --- --- --- --- --- --- --- --- --- ---
Leu Asp Gly Asp Val Asn Gly His Lys Phe Ser Val Ser Gly Glu Gly Glu Gly 117             126             135             144             153             162
GAT GCC ACC TAC GGC AAG CTG ACC CTG AAG TTC ATC TGC ACC ACC GGC AAG CTG
--- --- --- --- --- --- --- --- --- --- --- --- --- --- --- --- --- ---
Asp Ala Thr Tyn Gly Lys Leu Thr Leu Lys Phe Ile Cys Thr Thr Gly Lys Leu 171             180             189             198             207             216
CCC GTG CCC TGG CCC ACC CTC GTG ACC ACC TTC GGC TAC GGC GTG CAG TGC TTC
--- --- --- --- --- --- --- --- --- --- --- --- --- --- --- --- --- ---
Pro Val Pro Trp Pro Thr Leu Val Thr Thr Phe Gly Tyr Gly Val Gln Cys Phe 225             234             243             252             261             270
GCC CGC TAC CCC GAC CAC ATG AAG CAG CAC GAC TTC TTC AAG TCC GCC ATG CCC
--- --- --- --- --- --- --- --- --- --- --- --- --- --- --- --- --- ---
Ala Arg Tyr Pro Asp His Met Lys Gln His Asp Phe Phe Lys Ser Ala Met Pro 279             288             297             306             315             324
GAA GGC TAC GTC CAG GAG CGC ACC ATC TTC TTC AAG GAC GAC GGC AAC TAC AAG
--- --- --- --- --- --- --- --- --- --- --- --- --- --- --- --- --- ---
Glu Gly Tyr Val Gln Glu Arg Thr Ile Phe Phe Lys Asp Asp Gly Asn Tyr Lys 333             342             351             360             369             378
ACC CGC GCC GAG GTG AAG TTC GAG GGC GAC ACC CTG GTG AAC CGC ATC GAG CTG
--- --- --- --- --- --- --- --- --- --- --- --- --- --- --- --- --- ---
Thr Arg Ala Glu Val Lys Phe Glu Gly Asp Thr Leu Val Asn Arg Ile Glu Leu 387             396             405             414             423             432
AAG GGC ATC GAC TTC AAG GAG GAC GGC AAC ATC CTG GGG CAC AAG CTG GAG TAC
--- --- --- --- --- --- --- --- --- --- --- --- --- --- --- --- --- ---
Lys Gly Ile Asp Phe Lys Glu Asp Gly Asn Ile Leu Gly His Lys Leu Glu Tyr 441             450             459             468             477             486
AAC TAC AAC AGC CAC AAC GTC TAT ATC ATG GCC GAC AAG CAG AAG AAC GGC ATC
--- --- --- --- --- --- --- --- --- --- --- --- --- --- --- --- --- ---
Asn Tyr Asn Ser His Asn Val Tyr Ile Met Ala Asp Lys Gln Lys Asn Gly Ile
```

FIG. 4A

```
      495         504         513         522         531         540
AAG GTG AAC TTC AAG ATC CGC CAC AAC ATC GAG GAC GGC AGC GTG CAG CTC GCC
--- --- --- --- --- --- --- --- --- --- --- --- --- --- --- --- --- ---
Lys Val Asn Phe Lys Ile Arg His Asn Ile Glu Asp Gly Ser Val Gln Leu Ala 549         558         567         576         585         594
GAC CAC TAC CAG CAG AAC ACC CCC ATC GGC GAC GGC CCC GTG CTG CTG CCC GAC
--- --- --- --- --- --- --- --- --- --- --- --- --- --- --- --- --- ---
Asp His Tyr Gln Gln Asn Thr Pro Ile Gly Asp Gly Pro Val Leu Leu Pro Asp 603         612         621         630         639         648
AAC CAC TAC CTG AGC TAC CAG TCC GCC CTG AGC AAA GAC CCC AAC GAG AAG CGC
--- --- --- --- --- --- --- --- --- --- --- --- --- --- --- --- --- ---
Asn His Tyr Leu Ser Tyr Gln Ser Ala Leu Ser Lys Asp Pro Asn Glu Lys Arg 657         666         675         684         693         702
GAT CAC ATG GTC CTG CTG GAG TTC GTG ACC GCC GCC GGG ATC ACT CAC GGC ATG
--- --- --- --- --- --- --- --- --- --- --- --- --- --- --- --- --- ---
Asp His Met Val Leu Leu Glu Phe Val Thr Ala Ala Gly Ile Thr His Gly Met

711
GAC GAG CTG TAC AAG TAA 3'
--- --- --- --- --- ---
Asp Glu Leu Tyr Lys ***
```

FIG. 4B

| | | | | | | | | |
|---|---|---|---|---|---|---|---|---|
| CRYST1 | | 51.767 | 62.845 | 70.666 | 90.00 | 90.00 | 90.00 | |
| ORIGX1 | | | 1.000000 | 0.000000 | 0.000000 | | 0.000000 | |
| ORIGX2 | | | 0.000000 | 1.000000 | 0.000000 | | 0.000000 | |
| ORIGX3 | | | 0.000000 | 0.000000 | 1.000000 | | 0.000000 | |
| SCALE1 | | | 0.019317 | 0.000000 | 0.000000 | | 0.000000 | |
| SCALE2 | | | 0.000000 | 0.015912 | 0.000000 | | 0.000000 | |
| SCALE3 | | | 0.000000 | 0.000000 | 0.014151 | | 0.000000 | |
| ATOM | 1 | N | SER | 2 | 28.888 | 9.409 | 52.301 | 1.00 85.05 |
| ATOM | 2 | CA | SER | 2 | 27.638 | 10.125 | 52.516 | 1.00 80.05 |
| ATOM | 3 | C | SER | 2 | 26.499 | 9.639 | 51.644 | 1.00 85.36 |
| ATOM | 4 | O | SER | 2 | 26.606 | 8.656 | 50.915 | 1.00 84.56 |
| ATOM | 5 | CB | SER | 2 | 27.783 | 11.635 | 52.378 | 1.00 70.97 |
| ATOM | 6 | OG | SER | 2 | 27.690 | 12.033 | 51.012 | 1.00 44.08 |
| ATOM | 7 | N | LYS | 3 | 25.418 | 10.403 | 51.731 | 1.00 87.71 |
| ATOM | 8 | CA | LYS | 3 | 24.141 | 10.191 | 51.036 | 1.00 87.15 |
| ATOM | 9 | C | LYS | 3 | 24.214 | 10.266 | 49.497 | 1.00 76.86 |
| ATOM | 10 | O | LYS | 3 | 24.107 | 9.258 | 48.774 | 1.00 78.27 |
| ATOM | 11 | CB | LYS | 3 | 23.127 | 11.240 | 51.521 | 1.00 89.44 |
| ATOM | 12 | CG | LYS | 3 | 21.768 | 10.697 | 51.949 | 1.00 75.06 |
| ATOM | 13 | CD | LYS | 3 | 20.681 | 11.781 | 51.987 | 1.00 76.58 |
| ATOM | 14 | CE | LYS | 3 | 20.711 | 12.655 | 53.243 | 1.00 68.55 |
| ATOM | 15 | NZ | LYS | 3 | 20.816 | 14.103 | 52.953 | 1.00 46.24 |
| ATOM | 16 | N | GLY | 4 | 24.318 | 11.495 | 49.015 | 1.00 53.62 |
| ATOM | 17 | CA | GLY | 4 | 24.297 | 11.798 | 47.605 | 1.00 45.97 |
| ATOM | 18 | C | GLY | 4 | 25.425 | 11.206 | 46.796 | 1.00 31.90 |
| ATOM | 19 | O | GLY | 4 | 25.234 | 10.923 | 45.619 | 1.00 33.63 |
| ATOM | 20 | N | GLU | 5 | 26.606 | 11.082 | 47.420 | 1.00 32.54 |
| ATOM | 21 | CA | GLU | 5 | 27.821 | 10.598 | 46.726 | 1.00 32.57 |
| ATOM | 22 | C | GLU | 5 | 27.523 | 9.590 | 45.616 | 1.00 28.40 |
| ATOM | 23 | O | GLU | 5 | 27.850 | 9.803 | 44.444 | 1.00 26.12 |
| ATOM | 24 | CB | GLU | 5 | 28.873 | 10.053 | 47.718 | 1.00 38.53 |
| ATOM | 25 | CG | GLU | 5 | 30.337 | 10.461 | 47.425 | 1.00 41.36 |
| ATOM | 26 | CD | GLU | 5 | 31.311 | 9.584 | 48.170 | 1.00 90.82 |
| ATOM | 27 | OE1 | GLU | 5 | 31.508 | 9.677 | 49.381 | 1.00 74.80 |
| ATOM | 28 | OE2 | GLU | 5 | 31.839 | 8.653 | 47.403 | 1.00 100.00 |
| ATOM | 29 | N | GLU | 6 | 26.883 | 8.499 | 46.017 | 1.00 28.57 |
| ATOM | 30 | CA | GLU | 6 | 26.479 | 7.410 | 45.150 | 1.00 31.50 |
| ATOM | 31 | C | GLU | 6 | 25.561 | 7.837 | 43.979 | 1.00 31.10 |
| ATOM | 32 | O | GLU | 6 | 25.479 | 7.142 | 42.955 | 1.00 30.96 |
| ATOM | 33 | CB | GLU | 6 | 25.780 | 6.330 | 45.992 | 1.00 35.64 |
| ATOM | 34 | CG | GLU | 6 | 25.260 | 6.893 | 47.338 | 1.00 55.53 |
| ATOM | 35 | N | LEU | 7 | 24.864 | 8.966 | 44.138 | 1.00 22.26 |

FIG. 5A

| ATOM | 36 | CA  | LEU | 7  | 23.954 | 9.456  | 43.089 | 1.00 | 21.61 |
| ATOM | 37 | C   | LEU | 7  | 24.693 | 10.061 | 41.917 | 1.00 | 16.90 |
| ATOM | 38 | O   | LEU | 7  | 24.152 | 10.250 | 40.836 | 1.00 | 18.38 |
| ATOM | 39 | CB  | LEU | 7  | 23.050 | 10.548 | 43.665 | 1.00 | 22.41 |
| ATOM | 40 | CG  | LEU | 7  | 21.672 | 10.058 | 44.098 | 1.00 | 32.84 |
| ATOM | 41 | CD1 | LEU | 7  | 21.597 | 8.536  | 44.074 | 1.00 | 31.64 |
| ATOM | 42 | CD2 | LEU | 7  | 21.332 | 10.591 | 45.485 | 1.00 | 33.14 |
| ATOM | 43 | N   | PHE | 8  | 25.944 | 10.407 | 42.157 | 1.00 | 20.75 |
| ATOM | 44 | CA  | PHE | 8  | 26.740 | 11.132 | 41.159 | 1.00 | 21.64 |
| ATOM | 45 | C   | PHE | 8  | 27.818 | 10.333 | 40.427 | 1.00 | 30.59 |
| ATOM | 46 | O   | PHE | 8  | 28.590 | 10.856 | 39.600 | 1.00 | 30.05 |
| ATOM | 47 | CB  | PHE | 8  | 27.309 | 12.376 | 41.820 | 1.00 | 16.95 |
| ATOM | 48 | CG  | PHE | 8  | 26.222 | 13.355 | 42.163 | 1.00 | 13.29 |
| ATOM | 49 | CD1 | PHE | 8  | 25.672 | 13.378 | 43.447 | 1.00 | 17.27 |
| ATOM | 50 | CD2 | PHE | 8  | 25.726 | 14.227 | 41.189 | 1.00 | 13.12 |
| ATOM | 51 | CE1 | PHE | 8  | 24.661 | 14.290 | 43.772 | 1.00 | 15.14 |
| ATOM | 52 | CE2 | PHE | 8  | 24.712 | 15.137 | 41.499 | 1.00 | 13.19 |
| ATOM | 53 | CZ  | PHE | 8  | 24.192 | 15.170 | 42.794 | 1.00 | 5.69  |
| ATOM | 54 | N   | THR | 9  | 27.798 | 9.074  | 40.699 | 1.00 | 27.35 |
| ATOM | 55 | CA  | THR | 9  | 28.704 | 8.122  | 40.175 | 1.00 | 34.93 |
| ATOM | 56 | C   | THR | 9  | 28.709 | 7.998  | 38.636 | 1.00 | 45.22 |
| ATOM | 57 | O   | THR | 9  | 29.642 | 7.452  | 38.062 | 1.00 | 50.55 |
| ATOM | 58 | CB  | THR | 9  | 28.447 | 6.795  | 40.892 | 1.00 | 44.60 |
| ATOM | 59 | OG1 | THR | 9  | 29.629 | 6.330  | 41.527 | 1.00 | 40.40 |
| ATOM | 60 | CG2 | THR | 9  | 27.801 | 5.779  | 39.959 | 1.00 | 29.76 |
| ATOM | 61 | N   | GLY | 10 | 27.690 | 8.510  | 37.956 | 1.00 | 30.53 |
| ATOM | 62 | CA  | GLY | 10 | 27.689 | 8.458  | 36.507 | 1.00 | 23.21 |
| ATOM | 63 | C   | GLY | 10 | 27.144 | 9.746  | 35.914 | 1.00 | 16.55 |
| ATOM | 64 | O   | GLY | 10 |        | 729    | 36.617 | 1.00 | 25.70 |
| ATOM | 65 | N   | VAL | 11 | 26.835 | 9.719  | 34.629 | 1.00 | 16.39 |
| ATOM | 66 | CA  | VAL | 11 | 26.209 | 10.863 | 33.971 | 1.00 | 22.28 |
| ATOM | 67 | C   | VAL | 11 | 24.758 | 11.020 | 34.479 | 1.00 | 29.60 |
| ATOM | 68 | O   | VAL | 11 | 23.972 | 10.062 | 34.456 | 1.00 | 20.43 |
| ATOM | 69 | CB  | VAL | 11 | 26.173 | 10.664 | 32.467 | 1.00 | 30.87 |
| ATOM | 70 | CG1 | VAL | 11 | 25.912 | 11.980 | 31.734 | 1.00 | 31.75 |
| ATOM | 71 | CG2 | VAL | 11 | 27.480 | 10.048 | 32.015 | 1.00 | 33.85 |
| ATOM | 72 | N   | VAL | 12 | 24.417 | 12.227 | 34.931 | 1.00 | 20.12 |
| ATOM | 73 | CA  | VAL | 12 | 23.080 | 12.561 | 35.433 | 1.00 | 12.88 |
| ATOM | 74 | C   | VAL | 12 | 22.407 | 13.624 | 34.516 | 1.00 | 14.37 |
| ATOM | 75 | O   | VAL | 12 | 23.007 | 14.639 | 34.179 | 1.00 | 13.42 |
| ATOM | 76 | CB  | VAL | 12 | 23.270 | 13.077 | 36.839 | 1.00 | 15.01 |

FIG. 5B

| | | | | | | | |
|---|---|---|---|---|---|---|---|
| ATOM | 77 | CG1 VAL | 12 | 22.000 | 13.662 | 37.422 | 1.00 17.57 |
| ATOM | 78 | CG2 VAL | 12 | 23.781 | 11.936 | 37.728 | 1.00 16.55 |
| ATOM | 79 | N PRO | 13 | 21.180 | 13.382 | 34.066 | 1.00 14.72 |
| ATOM | 80 | CA PRO | 13 | 20.493 | 14.382 | 33.265 | 1.00 10.76 |
| ATOM | 81 | C PRO | 13 | 20.116 | 15.589 | 34.141 | 1.00 7.65 |
| ATOM | 82 | O PRO | 13 | 19.797 | 15.468 | 35.337 | 1.00 15.14 |
| ATOM | 83 | CB PRO | 13 | 19.225 | 13.707 | 32.745 | 1.00 17.36 |
| ATOM | 84 | CG PRO | 13 | 19.043 | 12.422 | 33.550 | 1.00 19.69 |
| ATOM | 85 | CD PRO | 13 | 20.315 | 12.195 | 34.340 | 1.00 15.41 |
| ATOM | 86 | N ILE | 14 | 20.196 | 16.766 | 33.557 | 1.00 14.91 |
| ATOM | 87 | CA ILE | 14 | 19.893 | 17.991 | 34.266 | 1.00 12.93 |
| ATOM | 88 | C ILE | 14 | 18.768 | 18.760 | 33.596 | 1.00 12.08 |
| ATOM | 89 | O ILE | 14 | 18.724 | 18.878 | 32.399 | 1.00 11.04 |
| ATOM | 90 | CB ILE | 14 | 21.109 | 18.905 | 34.325 | 1.00 16.54 |
| ATOM | 91 | CG1 ILE | 14 | 22.271 | 18.169 | 35.015 | 1.00 18.08 |
| ATOM | 92 | CG2 ILE | 14 | 20.783 | 20.207 | 35.084 | 1.00 11.56 |
| ATOM | 93 | CD1 ILE | 14 | 23.642 | 18.836 | 34.738 | 1.00 16.15 |
| ATOM | 94 | N LEU | 15 | 17.899 | 19.307 | 34.421 | 1.00 13.85 |
| ATOM | 95 | CA LEU | 15 | 16.811 | 20.136 | 33.955 | 1.00 14.82 |
| ATOM | 96 | C LEU | 15 | 16.915 | 21.474 | 34.685 | 1.00 3.62 |
| ATOM | 97 | O LEU | 15 | 17.080 | 21.509 | 35.901 | 1.00 10.00 |
| ATOM | 98 | CB LEU | 15 | 15.462 | 19.450 | 34.285 | 1.00 21.25 |
| ATOM | 99 | CG LEU | 15 | 14.412 | 19.541 | 33.199 | 1.00 40.50 |
| ATOM | 100 | CD1 LEU | 15 | 13.279 | 20.440 | 33.679 | 1.00 46.97 |
| ATOM | 101 | CD2 LEU | 15 | 15.008 | 20.098 | 31.913 | 1.00 49.22 |
| ATOM | 102 | N VAL | 16 | 16.885 | 22.556 | 33.919 | 1.00 10.56 |
| ATOM | 103 | CA VAL | 16 | 16.964 | 23.905 | 34.479 | 1.00 10.23 |
| ATOM | 104 | C VAL | 16 | 15.716 | 24.727 | 34.063 | 1.00 9.47 |
| ATOM | 105 | O VAL | 16 | 15.347 | 24.748 | 32.904 | 1.00 16.72 |
| ATOM | 106 | CB VAL | 16 | 18.273 | 24.668 | 34.098 | 1.00 12.85 |
| ATOM | 107 | CG1 VAL | 16 | 18.226 | 26.075 | 34.691 | 1.00 12.58 |
| ATOM | 108 | CG2 VAL | 16 | 19.520 | 23.945 | 34.628 | 1.00 14.24 |
| ATOM | 109 | N GLU | 17 | 15.059 | 25.317 | 35.060 | 1.00 14.43 |
| ATOM | 110 | CA GLU | 17 | 13.904 | 26.144 | 34.870 | 1.00 13.61 |
| ATOM | 111 | C GLU | 17 | 14.086 | 27.474 | 35.571 | 1.00 9.38 |
| ATOM | 112 | O GLU | 17 | 14.331 | 27.524 | 36.765 | 1.00 15.74 |
| ATOM | 113 | CB GLU | 17 | 12.650 | 25.402 | 35.344 | 1.00 14.15 |
| ATOM | 114 | CG GLU | 17 | 12.436 | 24.178 | 34.447 | 1.00 15.37 |
| ATOM | 115 | CD GLU | 17 | 11.865 | 24.573 | 33.105 | 1.00 49.50 |
| ATOM | 116 | OE1 GLU | 17 | 11.160 | 25.557 | 32.950 | 1.00 83.46 |
| ATOM | 117 | OE2 GLU | 17 | 12.220 | 23.766 | 32.127 | 1.00 38.75 |

FIG. 5C

| | | | | | | | | |
|---|---|---|---|---|---|---|---|---|
| ATOM | 118 | N | LEU | 18 | 13.990 | 28.571 | 34.805 | 1.00 17.82 |
| ATOM | 119 | CA | LEU | 18 | 14.116 | 29.914 | 35.401 | 1.00 16.61 |
| ATOM | 120 | C | LEU | 18 | 12.962 | 30.855 | 35.057 | 1.00 14.91 |
| ATOM | 121 | O | LEU | 18 | 12.585 | 30.978 | 33.917 | 1.00 14.31 |
| ATOM | 122 | CB | LEU | 18 | 15.426 | 30.630 | 35.005 | 1.00 13.56 |
| ATOM | 123 | CG | LEU | 18 | 15.533 | 32.049 | 35.579 | 1.00 19.27 |
| ATOM | 124 | CD1 | LEU | 18 | 16.740 | 32.182 | 36.489 | 1.00 21.40 |
| ATOM | 125 | CD2 | LEU | 18 | 15.682 | 33.033 | 34.438 | 1.00 18.38 |
| ATOM | 126 | N | ASP | 19 | 12.480 | 31.551 | 36.082 | 1.00 17.88 |
| ATOM | 127 | CA | ASP | 19 | 11.476 | 32.577 | 35.940 | 1.00 19.57 |
| ATOM | 128 | C | ASP | 19 | 12.098 | 33.896 | 36.360 | 1.00 11.65 |
| ATOM | 129 | O | ASP | 19 | 12.486 | 34.044 | 37.493 | 1.00 16.82 |
| ATOM | 130 | CB | ASP | 19 | 10.234 | 32.305 | 36.847 | 1.00 24.92 |
| ATOM | 131 | CG | ASP | 19 | 9.305 | 31.262 | 36.282 | 1.00 38.46 |
| ATOM | 132 | OD1 | ASP | 19 | 8.572 | 30.587 | 36.989 | 1.00 61.49 |
| ATOM | 133 | OD2 | ASP | 19 | 9.337 | 31.189 | 34.949 | 1.00 22.44 |
| ATOM | 134 | N | GLY | 20 | 12.178 | 34.863 | 35.471 | 1.00 16.82 |
| ATOM | 135 | CA | GLY | 20 | 12.784 | 36.101 | 35.908 | 1.00 19.52 |
| ATOM | 136 | C | GLY | 20 | 12.048 | 37.385 | 35.538 | 1.00 19.35 |
| ATOM | 137 | O | GLY | 20 | 11.240 | 37.443 | 34.628 | 1.00 18.22 |
| ATOM | 138 | N | ASP | 21 | 12.401 | 38.407 | 36.286 | 1.00 13.19 |
| ATOM | 139 | CA | ASP | 21 | 11.908 | 39.737 | 36.112 | 1.00 16.36 |
| ATOM | 140 | C | ASP | 21 | 13.039 | 40.683 | 36.424 | 1.00 12.77 |
| ATOM | 141 | O | ASP | 21 | 13.517 | 40.742 | 37.569 | 1.00 15.18 |
| ATOM | 142 | CB | ASP | 21 | 10.701 | 40.036 | 37.040 | 1.00 22.26 |
| ATOM | 143 | CG | ASP | 21 | 10.230 | 41.491 | 37.022 | 1.00 30.80 |
| ATOM | 144 | OD1 | ASP | 21 | 10.878 | 42.407 | 36.557 | 1.00 27.40 |
| ATOM | 145 | OD2 | ASP | 21 | 9.062 | 41.658 | 37.604 | 1.00 45.92 |
| ATOM | 146 | N | VAL | 22 | 13.464 | 41.393 | 35.397 | 1.00 19.66 |
| ATOM | 147 | CA | VAL | 22 | 14.524 | 42.388 | 35.542 | 1.00 25.10 |
| ATOM | 148 | C | VAL | 22 | 14.010 | 43.780 | 35.154 | 1.00 18.26 |
| ATOM | 149 | O | VAL | 22 | 13.769 | 44.062 | 33.955 | 1.00 15.10 |
| ATOM | 150 | CB | VAL | 22 | 15.803 | 42.012 | 34.750 | 1.00 26.57 |
| ATOM | 151 | CG1 | VAL | 22 | 16.861 | 43.127 | 34.896 | 1.00 24.27 |
| ATOM | 152 | CG2 | VAL | 22 | 16.365 | 40.710 | 35.297 | 1.00 22.98 |
| ATOM | 153 | N | ASN | 23 | 13.823 | 44.641 | 36.166 | 1.00 25.32 |
| ATOM | 154 | CA | ASN | 23 | 13.319 | 45.993 | 35.908 | 1.00 32.81 |
| ATOM | 155 | C | ASN | 23 | 11.987 | 45.958 | 35.142 | 1.00 32.77 |
| ATOM | 156 | O | ASN | 23 | 11.774 | 46.730 | 34.187 | 1.00 30.47 |
| ATOM | 157 | CB | ASN | 23 | 14.344 | 46.831 | 35.096 | 1.00 31.26 |
| ATOM | 158 | CG | ASN | 23 | 15.374 | 47.607 | 35.938 | 1.00 24.72 |

FIG. 5D

| ATOM | 159 | OD1 | ASN | 23 | 15.795 | 47.183 | 37.024 | 1.00 | 27.22 |
|------|-----|-----|-----|----|--------|--------|--------|------|-------|
| ATOM | 160 | ND2 | ASN | 23 | 15.829 | 48.723 | 35.389 | 1.00 | 41.15 |
| ATOM | 161 | N   | GLY | 24 | 11.118 | 45.024 | 35.519 | 1.00 | 24.95 |
| ATOM | 162 | CA  | GLY | 24 | 9.831  | 44.919 | 34.848 | 1.00 | 23.22 |
| ATOM | 163 | C   | GLY | 24 | 9.832  | 44.111 | 33.573 | 1.00 | 23.31 |
| ATOM | 164 | O   | GLY | 24 | 8.780  | 43.868 | 33.024 | 1.00 | 28.37 |
| ATOM | 165 | N   | HIS | 25 | 11.000 | 43.691 | 33.071 | 1.00 | 20.89 |
| ATOM | 166 | CA  | HIS | 25 | 11.042 | 42.840 | 31.877 | 1.00 | 19.30 |
| ATOM | 167 | C   | HIS | 25 | 10.981 | 41.373 | 32.316 | 1.00 | 27.26 |
| ATOM | 168 | O   | HIS | 25 | 11.898 | 40.850 | 32.951 | 1.00 | 26.47 |
| ATOM | 169 | CB  | HIS | 25 | 12.268 | 43.060 | 30.958 | 1.00 | 24.20 |
| ATOM | 170 | CG  | HIS | 25 | 12.313 | 44.382 | 30.218 | 1.00 | 33.04 |
| ATOM | 171 | ND1 | HIS | 25 | 12.917 | 45.514 | 30.758 | 1.00 | 37.58 |
| ATOM | 172 | CD2 | HIS | 25 | 11.876 | 44.716 | 28.971 | 1.00 | 42.76 |
| ATOM | 173 | CE1 | HIS | 25 | 12.801 | 46.497 | 29.867 | 1.00 | 39.14 |
| ATOM | 174 | NE2 | HIS | 25 | 12.185 | 46.050 | 28.778 | 1.00 | 42.80 |
| ATOM | 175 | N   | LYS | 26 | 9.872  | 40.728 | 32.028 | 1.00 | 25.90 |
| ATOM | 176 | CA  | LYS | 26 | 9.675  | 39.355 | 32.446 | 1.00 | 26.27 |
| ATOM | 177 | C   | LYS | 26 | 10.154 | 38.361 | 31.429 | 1.00 | 27.09 |
| ATOM | 178 | O   | LYS | 26 | 10.027 | 38.576 | 30.232 | 1.00 | 25.75 |
| ATOM | 179 | CB  | LYS | 26 | 8.230  | 39.069 | 32.863 | 1.00 | 27.58 |
| ATOM | 180 | CG  | LYS | 26 | 7.873  | 39.770 | 34.166 | 1.00 | 44.94 |
| ATOM | 181 | CD  | LYS | 26 | 6.369  | 39.914 | 34.400 | 1.00 | 71.44 |
| ATOM | 182 | CE  | LYS | 26 | 6.008  | 41.000 | 35.421 | 1.00 | 45.29 |
| ATOM | 183 | N   | PHE | 27 | 10.703 | 37.250 | 31.910 | 1.00 | 22.04 |
| ATOM | 184 | CA  | PHE | 27 | 11.164 | 36.236 | 30.978 | 1.00 | 18.78 |
| ATOM | 185 | C   | PHE | 27 | 11.273 | 34.863 | 31.619 | 1.00 | 14.75 |
| ATOM | 186 | O   | PHE | 27 | 11.293 | 34.722 | 32.842 | 1.00 | 15.94 |
| ATOM | 187 | CB  | PHE | 27 | 12.495 | 36.638 | 30.287 | 1.00 | 21.58 |
| ATOM | 188 | CG  | PHE | 27 | 13.599 | 36.826 | 31.311 | 1.00 | 22.06 |
| ATOM | 189 | CD1 | PHE | 27 | 14.490 | 35.791 | 31.612 | 1.00 | 23.61 |
| ATOM | 190 | CD2 | PHE | 27 | 13.722 | 38.029 | 32.005 | 1.00 | 17.55 |
| ATOM | 191 | CE1 | PHE | 27 | 15.487 | 35.963 | 32.579 | 1.00 | 16.61 |
| ATOM | 192 | CE2 | PHE | 27 | 14.747 | 38.234 | 32.931 | 1.00 | 19.75 |
| ATOM | 193 | CZ  | PHE | 27 | 15.621 | 37.187 | 33.234 | 1.00 | 13.83 |
| ATOM | 194 | N   | SER | 28 | 11.370 | 33.857 | 30.752 | 1.00 | 12.40 |
| ATOM | 195 | CA  | SER | 28 | 11.492 | 32.479 | 31.186 | 1.00 | 15.59 |
| ATOM | 196 | C   | SER | 28 | 12.579 | 31.749 | 30.379 | 1.00 | 15.96 |
| ATOM | 197 | O   | SER | 28 | 12.699 | 31.933 | 29.167 | 1.00 | 18.99 |
| ATOM | 198 | CB  | SER | 28 | 10.143 | 31.702 | 31.086 | 1.00 | 14.48 |
| ATOM | 199 | OG  | SER | 28 | 9.510  | 31.678 | 32.353 | 1.00 | 31.95 |

FIG. 5E

| ATOM | 200 | N    | VAL | 29 | 13.335 | 30.902 | 31.073 | 1.00 | 16.73 |
|------|-----|------|-----|----|--------|--------|--------|------|-------|
| ATOM | 201 | CA   | VAL | 29 | 14.361 | 30.093 | 30.435 | 1.00 | 14.06 |
| ATOM | 202 | C    | VAL | 29 | 14.258 | 28.614 | 30.187 | 1.00 | 6.80  |
| ATOM | 203 | O    | VAL | 29 | 14.058 | 28.266 | 31.987 | 1.00 | 10.85 |
| ATOM | 204 | CB   | VAL | 29 | 15.768 | 30.570 | 30.839 | 1.00 | 17.96 |
| ATOM | 205 | CG1  | VAL | 29 | 16.826 | 29.599 | 30.234 | 1.00 | 15.30 |
| ATOM | 206 | CG2  | VAL | 29 | 15.989 | 32.001 | 30.357 | 1.00 | 16.37 |
| ATOM | 207 | N    | SER | 30 | 14.462 | 27.781 | 29.824 | 1.00 | 11.31 |
| ATOM | 208 | CA   | SER | 30 | 14.535 | 26.351 | 30.011 | 1.00 | 17.96 |
| ATOM | 209 | C    | SER | 30 | 15.917 | 25.818 | 29.571 | 1.00 | 11.26 |
| ATOM | 210 | O    | SER | 30 | 16.398 | 26.157 | 28.513 | 1.00 | 13.17 |
| ATOM | 211 | CB   | SER | 30 | 13.471 | 25.603 | 29.202 | 1.00 | 19.91 |
| ATOM | 212 | OG   | SER | 30 | 12.249 | 25.667 | 29.882 | 1.00 | 48.74 |
| ATOM | 213 | N    | GLY | 31 | 16.480 | 24.926 | 30.364 | 1.00 | 9.88  |
| ATOM | 214 | CA   | GLY | 31 | 17.718 | 24.321 | 29.977 | 1.00 | 12.44 |
| ATOM | 215 | C    | GLY | 31 | 17.737 | 22.816 | 30.249 | 1.00 | 13.16 |
| ATOM | 216 | O    | GLY | 31 | 17.149 | 22.324 | 31.176 | 1.00 | 12.41 |
| ATOM | 217 | N    | GLU | 32 | 18.459 | 22.112 | 29.433 | 1.00 | 13.44 |
| ATOM | 218 | CA   | GLU | 32 | 18.622 | 20.670 | 29.570 | 1.00 | 13.73 |
| ATOM | 219 | C    | GLU | 32 | 20.079 | 20.297 | 29.262 | 1.00 | 17.33 |
| ATOM | 220 | O    | GLU | 32 | 20.734 | 20.946 | 28.456 | 1.00 | 15.56 |
| ATOM | 221 | CB   | GLU | 32 | 17.761 | 19.893 | 28.543 | 1.00 | 12.67 |
| ATOM | 222 | CG   | GLU | 32 | 16.264 | 20.187 | 28.618 | 1.00 | 26.43 |
| ATOM | 223 | CD   | GLU | 32 | 15.501 | 19.547 | 27.468 | 1.00 | 21.13 |
| ATOM | 224 | OE1  | GLU | 32 | 15.996 | 18.767 | 26.698 | 1.00 | 23.45 |
| ATOM | 225 | OE2  | GLU | 32 | 14.292 | 20.022 | 27.337 | 1.00 | 30.63 |
| ATOM | 226 | N    | GLY | 33 | 20.534 | 19.207 | 29.822 | 1.00 | 15.36 |
| ATOM | 227 | CA   | GLY | 33 | 21.860 | 18.687 | 29.518 | 1.00 | 12.84 |
| ATOM | 228 | C    | GLY | 33 | 22.236 | 17.602 | 30.467 | 1.00 | 14.69 |
| ATOM | 229 | O    | GLY | 33 | 21.390 | 16.919 | 31.011 | 1.00 | 13.56 |
| ATOM | 230 | N    | GLU | 34 | 23.525 | 17.453 | 30.702 | 1.00 | 15.15 |
| ATOM | 231 | CA   | GLU | 34 | 23.971 | 16.450 | 31.621 | 1.00 | 18.14 |
| ATOM | 232 | C    | GLU | 34 | 25.220 | 16.874 | 32.367 | 1.00 | 16.26 |
| ATOM | 233 | O    | GLU | 34 | 25.926 | 17.760 | 31.944 | 1.00 | 18.67 |
| ATOM | 234 | CB   | GLU | 34 | 24.180 | 15.114 | 30.927 | 1.00 | 22.53 |
| ATOM | 235 | CG   | GLU | 34 | 24.948 | 15.261 | 29.624 | 1.00 | 33.78 |
| ATOM | 236 | CD   | GLU | 34 | 24.879 | 14.020 | 28.796 | 1.00 | 55.15 |
| ATOM | 237 | OE1  | GLU | 34 | 25.861 | 13.352 | 28.534 | 1.00 | 45.39 |
| ATOM | 238 | OE2  | GLU | 34 | 23.653 | 13.719 | 28.430 | 1.00 | 56.26 |
| ATOM | 239 | N    | GLY | 35 | 25.461 | 16.222 | 33.485 | 1.00 | 11.20 |
| ATOM | 240 | CA   | GLY | 35 | 26.611 | 16.502 | 34.315 | 1.00 | 10.62 |

FIG. 5F

| ATOM | 241 | C | GLY | 35 | 27.293 | 15.192 | 34.662 | 1.00 | 19.92 |
| --- | --- | --- | --- | --- | --- | --- | --- | --- | --- |
| ATOM | 242 | O | GLY | 35 | 26.650 | 14.161 | 34.750 | 1.00 | 16.69 |
| ATOM | 243 | N | ASP | 36 | 28.594 | 15.238 | 34.860 | 1.00 | 16.92 |
| ATOM | 244 | CA | ASP | 36 | 29.367 | 14.061 | 35.221 | 1.00 | 16.19 |
| ATOM | 245 | C | ASP | 36 | 30.396 | 14.505 | 36.233 | 1.00 | 13.94 |
| ATOM | 246 | O | ASP | 36 | 31.469 | 15.004 | 35.879 | 1.00 | 15.77 |
| ATOM | 247 | CB | ASP | 36 | 30.032 | 13.457 | 33.948 | 1.00 | 19.98 |
| ATOM | 248 | CG | ASP | 36 | 30.681 | 12.066 | 34.075 | 1.00 | 31.92 |
| ATOM | 249 | OD1 | ASP | 36 | 31.236 | 11.519 | 33.141 | 1.00 | 30.97 |
| ATOM | 250 | OD2 | ASP | 36 | 30.587 | 11.515 | 35.248 | 1.00 | 25.32 |
| ATOM | 251 | N | ALA | 37 | 30.015 | 14.402 | 37.490 | 1.00 | 13.40 |
| ATOM | 252 | CA | ALA | 37 | 30.818 | 14.846 | 38.582 | 1.00 | 12.98 |
| ATOM | 253 | C | ALA | 37 | 32.181 | 14.145 | 38.637 | 1.00 | 21.94 |
| ATOM | 254 | O | ALA | 37 | 33.084 | 14.604 | 39.331 | 1.00 | 13.61 |
| ATOM | 255 | CB | ALA | 37 | 30.070 | 14.741 | 39.916 | 1.00 | 11.49 |
| ATOM | 256 | N | THR | 38 | 32.307 | 13.016 | 37.945 | 1.00 | 15.63 |
| ATOM | 257 | CA | THR | 38 | 33.581 | 12.280 | 37.943 | 1.00 | 19.94 |
| ATOM | 258 | C | THR | 38 | 34.705 | 13.114 | 37.335 | 1.00 | 25.61 |
| ATOM | 259 | O | THR | 38 | 35.850 | 13.069 | 37.775 | 1.00 | 17.89 |
| ATOM | 260 | CB | THR | 38 | 33.462 | 10.898 | 37.299 | 1.00 | 22.57 |
| ATOM | 261 | OG1 | THR | 38 | 32.543 | 10.146 | 38.067 | 1.00 | 29.86 |
| ATOM | 262 | CG2 | THR | 38 | 34.821 | 10.213 | 37.355 | 1.00 | 22.90 |
| ATOM | 263 | N | TYR | 39 | 34.323 | 13.920 | 36.347 | 1.00 | 18.45 |
| ATOM | 264 | CA | TYR | 39 | 35.210 | 14.837 | 35.675 | 1.00 | 9.39 |
| ATOM | 265 | C | TYR | 39 | 34.874 | 16.291 | 35.991 | 1.00 | 14.41 |
| ATOM | 266 | O | TYR | 39 | 35.454 | 17.177 | 35.410 | 1.00 | 16.24 |
| ATOM | 267 | CB | TYR | 39 | 35.156 | 14.582 | 34.180 | 1.00 | 11.82 |
| ATOM | 268 | CG | TYR | 39 | 35.426 | 13.137 | 33.929 | 1.00 | 28.73 |
| ATOM | 269 | CD1 | TYR | 39 | 36.715 | 12.633 | 34.065 | 1.00 | 33.75 |
| ATOM | 270 | CD2 | TYR | 39 | 34.392 | 12.249 | 33.642 | 1.00 | 39.19 |
| ATOM | 271 | CE1 | TYR | 39 | 36.982 | 11.276 | 33.828 | 1.00 | 29.75 |
| ATOM | 272 | CE2 | TYR | 39 | 34.635 | 10.885 | 33.435 | 1.00 | 45.41 |
| ATOM | 273 | CZ | TYR | 39 | 35.943 | 10.410 | 33.570 | 1.00 | 57.62 |
| ATOM | 274 | OH | TYR | 39 | 36.199 | 9.070 | 33.364 | 1.00 | 70.77 |
| ATOM | 275 | N | GLY | 40 | 33.935 | 16.525 | 36.929 | 1.00 | 9.94 |
| ATOM | 276 | CA | GLY | 40 | 33.474 | 17.879 | 37.266 | 1.00 | 7.02 |
| ATOM | 277 | C | GLY | 40 | 32.952 | 18.600 | 36.004 | 1.00 | 9.45 |
| ATOM | 278 | O | GLY | 40 | 33.068 | 19.830 | 35.829 | 1.00 | 12.63 |
| ATOM | 279 | N | LYS | 41 | 32.380 | 17.823 | 35.092 | 1.00 | 5.44 |
| ATOM | 280 | CA | LYS | 41 | 31.954 | 18.335 | 33.842 | 1.00 | 6.63 |
| ATOM | 281 | C | LYS | 41 | 30.414 | 18.554 | 33.703 | 1.00 | 20.92 |

FIG. 5G

| | | | | | | | | |
|---|---|---|---|---|---|---|---|---|
| ATOM | 282 | O | LYS | 41 | 29.617 | 17.693 | 34.085 | 1.00 12.94 |
| ATOM | 283 | CB | LYS | 41 | 32.360 | 17.357 | 32.827 | 1.00 8.27 |
| ATOM | 284 | CG | LYS | 41 | 32.099 | 17.771 | 31.419 | 1.00 13.19 |
| ATOM | 285 | CD | LYS | 41 | 32.521 | 16.644 | 30.481 | 1.00 20.20 |
| ATOM | 286 | CE | LYS | 41 | 32.690 | 17.068 | 29.032 | 1.00 35.79 |
| ATOM | 287 | NZ | LYS | 41 | 33.113 | 15.954 | 28.147 | 1.00 47.56 |
| ATOM | 288 | N | LEU | 42 | 30.049 | 19.684 | 33.069 | 1.00 18.31 |
| ATOM | 289 | CA | LEU | 42 | 28.643 | 20.064 | 32.794 | 1.00 16.08 |
| ATOM | 290 | C | LEU | 42 | 28.456 | 20.422 | 31.330 | 1.00 14.23 |
| ATOM | 291 | O | LEU | 42 | 29.240 | 21.168 | 30.787 | 1.00 14.79 |
| ATOM | 292 | CB | LEU | 42 | 28.223 | 21.300 | 33.621 | 1.00 13.22 |
| ATOM | 293 | CG | LEU | 42 | 28.007 | 21.061 | 35.082 | 1.00 16.70 |
| ATOM | 294 | CD1 | LEU | 42 | 27.894 | 22.406 | 35.782 | 1.00 13.79 |
| ATOM | 295 | CD2 | LEU | 42 | 26.732 | 20.243 | 35.295 | 1.00 18.70 |
| ATOM | 296 | N | THR | 43 | 27.395 | 19.914 | 30.672 | 1.00 8.04 |
| ATOM | 297 | CA | THR | 43 | 27.103 | 20.275 | 29.282 | 1.00 4.87 |
| ATOM | 298 | C | THR | 43 | 25.636 | 20.666 | 29.186 | 1.00 17.23 |
| ATOM | 299 | O | THR | 43 | 24.811 | 19.818 | 29.442 | 1.00 14.38 |
| ATOM | 300 | CB | THR | 43 | 27.351 | 19.140 | 28.317 | 1.00 21.59 |
| ATOM | 301 | OG1 | THR | 43 | 28.692 | 18.743 | 28.415 | 1.00 42.74 |
| ATOM | 302 | CG2 | THR | 43 | 27.073 | 19.675 | 26.917 | 1.00 31.23 |
| ATOM | 303 | N | LEU | 44 | 25.327 | 21.934 | 28.830 | 1.00 11.83 |
| ATOM | 304 | CA | LEU | 44 | 23.944 | 22.409 | 28.847 | 1.00 13.81 |
| ATOM | 305 | C | LEU | 44 | 23.589 | 23.307 | 27.668 | 1.00 18.19 |
| ATOM | 306 | O | LEU | 44 | 24.416 | 23.989 | 27.107 | 1.00 13.86 |
| ATOM | 307 | CB | LEU | 44 | 23.725 | 23.275 | 30.125 | 1.00 15.37 |
| ATOM | 308 | CG | LEU | 44 | 23.369 | 22.584 | 31.456 | 1.00 24.69 |
| ATOM | 309 | CD1 | LEU | 44 | 21.869 | 22.381 | 31.601 | 1.00 23.20 |
| ATOM | 310 | CD2 | LEU | 44 | 24.083 | 21.286 | 31.650 | 1.00 46.18 |
| ATOM | 311 | N | LYS | 45 | 22.294 | 23.331 | 27.339 | 1.00 10.29 |
| ATOM | 312 | CA | LYS | 45 | 21.752 | 24.224 | 26.358 | 1.00 11.94 |
| ATOM | 313 | C | LYS | 45 | 20.534 | 24.913 | 26.957 | 1.00 19.35 |
| ATOM | 314 | O | LYS | 45 | 19.665 | 24.248 | 27.530 | 1.00 18.43 |
| ATOM | 315 | CB | LYS | 45 | 21.409 | 23.560 | 25.060 | 1.00 13.75 |
| ATOM | 316 | CG | LYS | 45 | 20.878 | 24.556 | 24.045 | 1.00 8.83 |
| ATOM | 317 | CD | LYS | 45 | 20.486 | 23.863 | 22.746 | 1.00 26.87 |
| ATOM | 318 | CE | LYS | 45 | 19.574 | 24.688 | 21.842 | 1.00 16.58 |
| ATOM | 319 | NZ | LYS | 45 | 19.318 | 24.024 | 20.555 | 1.00 18.33 |
| ATOM | 320 | N | PHE | 46 | 20.535 | 26.236 | 26.910 | 1.00 12.34 |
| ATOM | 321 | CA | PHE | 46 | 19.463 | 27.048 | 27.451 | 1.00 13.32 |
| ATOM | 322 | C | PHE | 46 | 18.759 | 27.718 | 26.343 | 1.00 18.26 |

FIG. 5H

| ATOM | 323 | O   | PHE | 46 | 19.386 | 28.093 | 25.360 | 1.00 | 16.83 |
|------|-----|-----|-----|----|--------|--------|--------|------|-------|
| ATOM | 324 | CB  | PHE | 46 | 19.934 | 28.101 | 28.473 | 1.00 | 15.29 |
| ATOM | 325 | CG  | PHE | 46 | 20.773 | 27.495 | 29.552 | 1.00 | 13.81 |
| ATOM | 326 | CD1 | PHE | 46 | 22.132 | 27.268 | 29.337 | 1.00 | 17.06 |
| ATOM | 327 | CD2 | PHE | 46 | 20.209 | 27.121 | 30.774 | 1.00 | 8.24  |
| ATOM | 328 | CE1 | PHE | 46 | 22.924 | 26.693 | 30.331 | 1.00 | 15.95 |
| ATOM | 329 | CE2 | PHE | 46 | 20.979 | 26.524 | 31.767 | 1.00 | 11.90 |
| ATOM | 330 | CZ  | PHE | 46 | 22.340 | 26.309 | 31.540 | 1.00 | 8.84  |
| ATOM | 331 | N   | ILE | 47 | 17.440 | 27.845 | 26.498 | 1.00 | 13.24 |
| ATOM | 332 | CA  | ILE | 47 | 16.588 | 28.453 | 25.479 | 1.00 | 18.02 |
| ATOM | 333 | C   | ILE | 47 | 15.645 | 29.460 | 26.118 | 1.00 | 20.14 |
| ATOM | 334 | O   | ILE | 47 | 15.039 | 29.162 | 27.148 | 1.00 | 17.67 |
| ATOM | 335 | CB  | ILE | 47 | 15.737 | 27.386 | 24.801 | 1.00 | 22.67 |
| ATOM | 336 | CG1 | ILE | 47 | 16.585 | 26.271 | 24.291 | 1.00 | 20.66 |
| ATOM | 337 | CG2 | ILE | 47 | 15.024 | 28.002 | 23.641 | 1.00 | 33.79 |
| ATOM | 338 | CD1 | ILE | 47 | 16.639 | 26.293 | 22.805 | 1.00 | 23.69 |
| ATOM | 339 | N   | CYS | 48 | 15.564 | 30.653 | 25.561 | 1.00 | 14.68 |
| ATOM | 340 | CA  | CYS | 48 | 14.681 | 31.635 | 26.170 | 1.00 | 16.93 |
| ATOM | 341 | C   | CYS | 48 | 13.323 | 31.352 | 25.628 | 1.00 | 24.18 |
| ATOM | 342 | O   | CYS | 48 | 13.122 | 31.513 | 24.453 | 1.00 | 20.63 |
| ATOM | 343 | CB  | CYS | 48 | 15.063 | 33.116 | 25.885 | 1.00 | 16.85 |
| ATOM | 344 | SG  | CYS | 48 | 13.913 | 34.268 | 26.712 | 1.00 | 22.06 |
| ATOM | 345 | N   | THR | 49 | 12.424 | 30.871 | 26.484 | 1.00 | 27.31 |
| ATOM | 346 | CA  | THR | 49 | 11.101 | 30.458 | 26.042 | 1.00 | 32.18 |
| ATOM | 347 | C   | THR | 49 | 10.106 | 31.572 | 25.803 | 1.00 | 37.51 |
| ATOM | 348 | O   | THR | 49 | 9.150  | 31.407 | 25.061 | 1.00 | 35.71 |
| ATOM | 349 | CB  | THR | 49 | 10.537 | 29.417 | 26.972 | 1.00 | 23.66 |
| ATOM | 350 | OG1 | THR | 49 | 10.387 | 29.989 | 28.258 | 1.00 | 30.10 |
| ATOM | 351 | CG2 | THR | 49 | 11.512 | 28.226 | 27.022 | 1.00 | 29.98 |
| ATOM | 352 | N   | THR | 50 | 10.314 | 32.693 | 26.447 | 1.00 | 32.34 |
| ATOM | 353 | CA  | THR | 50 | 9.416  | 33.810 | 26.283 | 1.00 | 28.67 |
| ATOM | 354 | C   | THR | 50 | 9.836  | 34.711 | 25.126 | 1.00 | 37.98 |
| ATOM | 355 | O   | THR | 50 | 9.228  | 35.763 | 24.904 | 1.00 | 39.17 |
| ATOM | 356 | CB  | THR | 50 | 9.251  | 34.611 | 27.589 | 1.00 | 36.23 |
| ATOM | 357 | OG1 | THR | 50 | 10.512 | 34.980 | 28.118 | 1.00 | 35.37 |
| ATOM | 358 | CG2 | THR | 50 | 8.507  | 33.773 | 28.602 | 1.00 | 27.78 |
| ATOM | 359 | N   | GLY | 51 | 10.881 | 34.282 | 24.372 | 1.00 | 31.04 |
| ATOM | 360 | CA  | GLY | 51 | 11.394 | 35.059 | 23.239 | 1.00 | 32.42 |
| ATOM | 361 | C   | GLY | 51 | 12.865 | 35.542 | 23.427 | 1.00 | 48.45 |
| ATOM | 362 | O   | GLY | 51 | 13.779 | 34.737 | 23.701 | 1.00 | 57.11 |
| ATOM | 363 | N   | LYS | 52 | 13.087 | 36.862 | 23.282 | 1.00 | 36.08 |

FIG. 5I

| | | | | | | | |
|---|---|---|---|---|---|---|---|
| ATOM | 364 | CA | LYS | 52 | 14.416 | 37.460 | 23.416 | 1.00 35.75 |
| ATOM | 365 | C | LYS | 52 | 14.827 | 37.726 | 24.861 | 1.00 29.65 |
| ATOM | 366 | O | LYS | 52 | 14.140 | 38.420 | 25.620 | 1.00 25.70 |
| ATOM | 367 | CB | LYS | 52 | 14.577 | 38.714 | 22.582 | 1.00 43.37 |
| ATOM | 368 | CG | LYS | 52 | 15.772 | 38.649 | 21.644 | 1.00 78.17 |
| ATOM | 369 | N | LEU | 53 | 15.983 | 37.190 | 25.250 | 1.00 19.22 |
| ATOM | 370 | CA | LEU | 53 | 16.439 | 37.430 | 26.596 | 1.00 13.52 |
| ATOM | 371 | C | LEU | 53 | 16.717 | 38.932 | 26.775 | 1.00 17.76 |
| ATOM | 372 | O | LEU | 53 | 17.392 | 39.539 | 25.973 | 1.00 21.59 |
| ATOM | 373 | CB | LEU | 53 | 17.705 | 36.567 | 26.845 | 1.00 17.39 |
| ATOM | 374 | CG | LEU | 53 | 18.100 | 36.435 | 28.302 | 1.00 17.43 |
| ATOM | 375 | CD1 | LEU | 53 | 17.048 | 35.621 | 29.053 | 1.00 20.12 |
| ATOM | 376 | CD2 | LEU | 53 | 19.440 | 35.718 | 28.368 | 1.00 16.11 |
| ATOM | 377 | N | PRO | 54 | 16.197 | 39.525 | 27.817 | 1.00 16.69 |
| ATOM | 378 | CA | PRO | 54 | 16.324 | 40.962 | 28.092 | 1.00 18.60 |
| ATOM | 379 | C | PRO | 54 | 17.638 | 41.414 | 28.707 | 1.00 25.39 |
| ATOM | 380 | O | PRO | 54 | 17.865 | 42.609 | 28.861 | 1.00 18.88 |
| ATOM | 381 | CB | PRO | 54 | 15.268 | 41.265 | 29.139 | 1.00 22.52 |
| ATOM | 382 | CG | PRO | 54 | 14.832 | 39.933 | 29.720 | 1.00 26.02 |
| ATOM | 383 | CD | PRO | 54 | 15.318 | 38.855 | 28.779 | 1.00 21.26 |
| ATOM | 384 | N | VAL | 55 | 18.435 | 40.455 | 29.161 | 1.00 23.32 |
| ATOM | 385 | CA | VAL | 55 | 19.746 | 40.716 | 29.711 | 1.00 15.83 |
| ATOM | 386 | C | VAL | 55 | 20.688 | 39.868 | 28.973 | 1.00 19.38 |
| ATOM | 387 | O | VAL | 55 | 20.268 | 39.035 | 28.219 | 1.00 20.34 |
| ATOM | 388 | CB | VAL | 55 | 19.814 | 40.409 | 31.147 | 1.00 17.67 |
| ATOM | 389 | CG1 | VAL | 55 | 18.864 | 41.340 | 31.851 | 1.00 22.52 |
| ATOM | 390 | CG2 | VAL | 55 | 19.402 | 38.959 | 31.397 | 1.00 19.11 |
| ATOM | 391 | N | PRO | 56 | 21.963 | 40.070 | 29.167 | 1.00 19.37 |
| ATOM | 392 | CA | PRO | 56 | 22.911 | 39.258 | 28.447 | 1.00 13.09 |
| ATOM | 393 | C | PRO | 56 | 23.059 | 37.834 | 29.038 | 1.00 5.83 |
| ATOM | 394 | O | PRO | 56 | 23.067 | 37.631 | 30.254 | 1.00 12.35 |
| ATOM | 395 | CB | PRO | 56 | 24.231 | 40.062 | 28.420 | 1.00 18.34 |
| ATOM | 396 | CG | PRO | 56 | 23.851 | 41.478 | 28.849 | 1.00 20.73 |
| ATOM | 397 | CD | PRO | 56 | 22.525 | 41.379 | 29.578 | 1.00 18.66 |
| ATOM | 398 | N | TRP | 57 | 23.202 | 36.848 | 28.158 | 1.00 11.12 |
| ATOM | 399 | CA | TRP | 57 | 23.354 | 35.458 | 28.595 | 1.00 12.55 |
| ATOM | 400 | C | TRP | 57 | 24.411 | 35.239 | 29.700 | 1.00 14.13 |
| ATOM | 401 | O | TRP | 57 | 24.178 | 34.586 | 30.709 | 1.00 11.49 |
| ATOM | 402 | CB | TRP | 57 | 23.604 | 34.535 | 27.406 | 1.00 10.56 |
| ATOM | 403 | CG | TRP | 57 | 22.335 | 34.237 | 26.641 | 1.00 12.65 |
| ATOM | 404 | CD1 | TRP | 57 | 21.999 | 34.714 | 25.426 | 1.00 16.24 |

FIG. 5J

| | | | | | | | |
|---|---|---|---|---|---|---|---|
| ATOM | 405 | CD2 TRP | 57 | 21.281 | 33.327 | 27.013 | 1.00 12.50 |
| ATOM | 406 | NE1 TRP | 57 | 20.784 | 34.200 | 25.018 | 1.00 14.25 |
| ATOM | 407 | CE2 TRP | 57 | 20.315 | 22.354 | 25.963 | 1.00 14.65 |
| ATOM | 408 | CE3 TRP | 57 | 21.052 | 32.521 | 28.129 | 1.00 12.01 |
| ATOM | 409 | CZ2 TRP | 57 | 19.148 | 32.583 | 26.007 | 1.00 14.36 |
| ATOM | 410 | CZ3 TRP | 57 | 19.887 | 31.767 | 28.170 | 1.00 14.23 |
| ATOM | 411 | CH2 TRP | 57 | 18.945 | 31.818 | 27.128 | 1.00 10.01 |
| ATOM | 412 | N   PRO | 58 | 25.594 | 35.800 | 29.518 | 1.00 15.78 |
| ATOM | 413 | CA  PRO | 58 | 26.629 | 35.616 | 30.503 | 1.00  9.53 |
| ATOM | 414 | C   PRO | 58 | 26.241 | 36.010 | 31.878 | 1.00  9.71 |
| ATOM | 415 | O   PRO | 58 | 26.760 | 35.467 | 32.825 | 1.00 11.70 |
| ATOM | 416 | CB  PRO | 58 | 27.833 | 36.441 | 30.040 | 1.00 10.83 |
| ATOM | 417 | CG  PRO | 58 | 27.597 | 36.748 | 28.582 | 1.00 18.50 |
| ATOM | 418 | CD  PRO | 58 | 26.137 | 36.432 | 28.278 | 1.00 15.82 |
| ATOM | 419 | N   THR | 59 | 25.336 | 36.977 | 32.021 | 1.00  7.54 |
| ATOM | 420 | CA  THR | 59 | 24.976 | 37.366 | 33.357 | 1.00  4.53 |
| ATOM | 421 | C   THR | 59 | 24.228 | 36.258 | 34.137 | 1.00  8.41 |
| ATOM | 422 | O   THR | 59 | 24.174 | 36.261 | 35.367 | 1.00 10.57 |
| ATOM | 423 | CB  THR | 59 | 24.187 | 38.691 | 33.384 | 1.00 16.64 |
| ATOM | 424 | OG1 THR | 59 | 22.895 | 38.480 | 32.844 | 1.00 15.51 |
| ATOM | 425 | CG2 THR | 59 | 24.917 | 39.731 | 32.542 | 1.00 15.76 |
| ATOM | 426 | N   LEU | 60 | 23.686 | 35.304 | 33.427 | 1.00 11.99 |
| ATOM | 427 | CA  LEU | 60 | 22.899 | 34.248 | 34.073 | 1.00  9.15 |
| ATOM | 428 | C   LEU | 60 | 23.657 | 32.944 | 34.385 | 1.00 15.62 |
| ATOM | 429 | O   LEU | 60 | 23.118 | 32.027 | 35.042 | 1.00 11.99 |
| ATOM | 430 | CB  LEU | 60 | 21.645 | 33.914 | 33.203 | 1.00  7.67 |
| ATOM | 431 | CG  LEU | 60 | 20.728 | 35.111 | 33.042 | 1.00 14.06 |
| ATOM | 432 | CD1 LEU | 60 | 19.620 | 34.775 | 32.062 | 1.00 14.54 |
| ATOM | 433 | CD2 LEU | 60 | 20.142 | 35.456 | 34.394 | 1.00 10.67 |
| ATOM | 434 | N   VAL | 61 | 24.893 | 32.837 | 33.917 | 1.00 11.27 |
| ATOM | 435 | CA  VAL | 61 | 25.656 | 31.587 | 34.094 | 1.00  4.37 |
| ATOM | 436 | C   VAL | 61 | 25.678 | 31.013 | 35.496 | 1.00  6.02 |
| ATOM | 437 | O   VAL | 61 | 25.385 | 29.805 | 35.743 | 1.00 10.75 |
| ATOM | 438 | CB  VAL | 61 | 27.050 | 31.643 | 33.406 | 1.00  7.14 |
| ATOM | 439 | CG1 VAL | 61 | 27.888 | 30.396 | 33.805 | 1.00  6.47 |
| ATOM | 440 | CG2 VAL | 61 | 26.890 | 31.745 | 31.876 | 1.00  6.63 |
| ATOM | 441 | N   THR | 62 | 26.053 | 31.843 | 36.442 | 1.00  7.02 |
| ATOM | 442 | CA  THR | 62 | 26.178 | 31.421 | 37.808 | 1.00  6.51 |
| ATOM | 443 | C   THR | 62 | 24.862 | 30.954 | 38.410 | 1.00  9.22 |
| ATOM | 444 | O   THR | 62 | 24.801 | 30.163 | 39.352 | 1.00  6.99 |
| ATOM | 445 | CB  THR | 62 | 26.816 | 32.520 | 38.660 | 1.00 16.97 |

FIG. 5K

| | | | | | | | |
|---|---|---|---|---|---|---|---|
| ATOM | 446 | OG1 THR | 62 | 26.103 | 33.744 | 38.453 | 1.00 12.00 |
| ATOM | 447 | CG2 THR | 62 | 28.297 | 32.708 | 39.225 | 1.00 8.86 |
| ATOM | 448 | N THR | 63 | 23.814 | 31.547 | 37.910 | 1.00 9.98 |
| ATOM | 449 | CA THR | 63 | 22.457 | 31.212 | 38.388 | 1.00 6.69 |
| ATOM | 450 | C THR | 63 | 22.033 | 29.830 | 37.865 | 1.00 8.14 |
| ATOM | 451 | O THR | 63 | 21.499 | 28.984 | 38.604 | 1.00 13.48 |
| ATOM | 452 | CB THR | 63 | 21.458 | 32.312 | 37.295 | 1.00 11.14 |
| ATOM | 453 | OG1 THR | 63 | 21.785 | 33.498 | 38.602 | 1.00 11.75 |
| ATOM | 454 | OG2 THR | 63 | 20.024 | 31.897 | 38.296 | 1.00 9.31 |
| ATOM | 455 | N PHE | 64 | 22.250 | 29.620 | 36.583 | 1.00 10.19 |
| ATOM | 456 | CA PHE | 64 | 21.895 | 28.371 | 35.995 | 1.00 8.00 |
| ATOM | 457 | C PHE | 64 | 22.774 | 27.253 | 36.518 | 1.00 25.26 |
| ATOM | 458 | O PHE | 64 | 23.313 | 26.147 | 36.761 | 1.00 9.64 |
| ATOM | 459 | CB PHE | 64 | 22.114 | 28.438 | 34.513 | 1.00 6.88 |
| ATOM | 460 | CG PHE | 64 | 21.233 | 29.357 | 33.750 | 1.00 10.96 |
| ATOM | 461 | CD1 PHE | 64 | 21.724 | 29.954 | 32.593 | 1.00 9.15 |
| ATOM | 462 | CD2 PHE | 64 | 19.899 | 29.563 | 34.106 | 1.00 14.43 |
| ATOM | 463 | CE1 PHE | 64 | 20.936 | 30.792 | 31.805 | 1.00 14.20 |
| ATOM | 464 | CE2 PHE | 64 | 19.077 | 30.375 | 33.317 | 1.00 13.95 |
| ATOM | 465 | CZ PHE | 64 | 19.597 | 30.983 | 32.171 | 1.00 16.35 |
| HETATM | 466 | N1 CRO | 66 | 24.077 | 27.513 | 36.610 | 1.00 11.86 |
| HETATM | 467 | CG1 CRO | 66 | 25.155 | 25.422 | 34.796 | 1.00 16.67 |
| HETATM | 468 | OG1 CRO | 66 | 26.679 | 27.129 | 35.461 | 1.00 14.22 |
| HETATM | 469 | CB1 CRO | 66 | 25.931 | 26.035 | 35.930 | 1.00 10.77 |
| HETATM | 470 | CA1 CRO | 66 | 25.011 | 26.478 | 37.078 | 1.00 7.34 |
| HETATM | 471 | C1 CRO | 66 | 25.718 | 26.991 | 38.253 | 1.00 17.70 |
| HETATM | 472 | N2 CRO | 66 | 26.975 | 27.732 | 38.216 | 1.00 9.21 |
| HETATM | 473 | OH CRO | 66 | 32.894 | 30.804 | 36.971 | 1.00 13.84 |
| HETATM | 474 | CD2 CRO | 66 | 30.487 | 30.110 | 39.805 | 1.00 10.79 |
| HETATM | 475 | CE2 CRO | 66 | 31.614 | 30.563 | 39.085 | 1.00 10.01 |
| HETATM | 476 | CZ CRO | 66 | 31.718 | 30.300 | 37.721 | 1.00 9.48 |
| HETATM | 477 | CE1 CRO | 66 | 30.707 | 29.546 | 37.033 | 1.00 17.44 |
| HETATM | 478 | CD1 CRO | 66 | 29.541 | 29.103 | 37.742 | 1.00 11.31 |
| HETATM | 479 | CG2 CRO | 66 | 29.437 | 29.370 | 39.124 | 1.00 7.67 |
| HETATM | 480 | CB2 CRO | 66 | 28.329 | 28.822 | 39.960 | 1.00 10.75 |
| HETATM | 481 | CA2 CRO | 66 | 27.197 | 28.245 | 39.512 | 1.00 16.08 |
| HETATM | 482 | C2 CRO | 66 | 26.043 | 27.875 | 40.370 | 1.00 5.46 |
| HETATM | 483 | O2 CRO | 66 | 26.022 | 27.962 | 41.566 | 1.00 13.20 |
| HETATM | 484 | N3 CRO | 66 | 25.240 | 26.978 | 39.517 | 1.00 18.43 |
| HETATM | 485 | CA3 CRO | 66 | 23.840 | 26.511 | 39.734 | 1.00 10.40 |
| HETATM | 486 | C3 CRO | 66 | 23.413 | 25.550 | 40.817 | 1.00 11.96 |

FIG. 5L

| | | | | | | | |
|---|---|---|---|---|---|---|---|
| HETATM | 487 | O3 | CRO | 66 | 22.747 | 26.014 | 41.764 | 1.00 100.00 |
| ATOM | 488 | N | VAL | 68 | 23.737 | 24.208 | 41.005 | 1.00 29.95 |
| ATOM | 489 | CA | VAL | 68 | 24.209 | 22.972 | 40.304 | 1.00 17.16 |
| ATOM | 490 | C | VAL | 68 | 25.692 | 22.550 | 40.734 | 1.00 14.88 |
| ATOM | 491 | O | VAL | 68 | 26.378 | 21.821 | 40.026 | 1.00 9.03 |
| ATOM | 492 | CB | VAL | 68 | 23.870 | 22.899 | 38.831 | 1.00 18.94 |
| ATOM | 493 | CG1 | VAL | 68 | 24.685 | 22.088 | 37.942 | 1.00 17.17 |
| ATOM | 494 | CG2 | VAL | 68 | 22.396 | 22.538 | 38.680 | 1.00 18.80 |
| ATOM | 495 | N | GLN | 69 | 26.129 | 22.965 | 41.914 | 1.00 11.04 |
| ATOM | 496 | CA | GLN | 69 | 27.465 | 22.764 | 42.394 | 1.00 15.00 |
| ATOM | 497 | C | GLN | 69 | 27.749 | 21.366 | 42.893 | 1.00 22.46 |
| ATOM | 498 | O | GLN | 69 | 28.876 | 21.026 | 43.154 | 1.00 15.84 |
| ATOM | 499 | CB | GLN | 69 | 27.929 | 23.852 | 43.414 | 1.00 10.93 |
| ATOM | 500 | CG | GLN | 69 | 28.202 | 25.174 | 42.615 | 1.00 14.13 |
| ATOM | 501 | CD | GLN | 69 | 28.216 | 26.385 | 43.520 | 1.00 17.01 |
| ATOM | 502 | OE1 | GLN | 69 | 27.433 | 26.476 | 44.448 | 1.00 18.94 |
| ATOM | 503 | NE2 | GLN | 69 | 29.151 | 27.300 | 43.241 | 1.00 8.52 |
| ATOM | 504 | N | CYS | 70 | 26.703 | 20.540 | 42.906 | 1.00 12.10 |
| ATOM | 505 | CA | CYS | 70 | 26.862 | 19.171 | 43.287 | 1.00 11.84 |
| ATOM | 506 | C | CYS | 70 | 27.611 | 18.391 | 42.175 | 1.00 10.54 |
| ATOM | 507 | O | CYS | 70 | 28.036 | 17.242 | 42.367 | 1.00 14.70 |
| ATOM | 508 | CB | CYS | 70 | 25.476 | 18.584 | 43.596 | 1.00 14.52 |
| ATOM | 509 | SG | CYS | 70 | 24.325 | 19.012 | 42.251 | 1.00 15.61 |
| ATOM | 510 | N | PHE | 71 | 27.801 | 19.029 | 41.005 | 1.00 8.64 |
| ATOM | 511 | CA | PHE | 71 | 28.525 | 18.419 | 39.883 | 1.00 6.59 |
| ATOM | 512 | C | PHE | 71 | 30.041 | 18.754 | 39.876 | 1.00 16.43 |
| ATOM | 513 | O | PHE | 71 | 30.753 | 18.481 | 38.916 | 1.00 13.05 |
| ATOM | 514 | CB | PHE | 71 | 27.951 | 18.771 | 38.523 | 1.00 7.61 |
| ATOM | 515 | CG | PHE | 71 | 26.669 | 18.016 | 38.303 | 1.00 14.73 |
| ATOM | 516 | CD1 | PHE | 71 | 26.693 | 16.642 | 38.050 | 1.00 10.34 |
| ATOM | 517 | CD2 | PHE | 71 | 25.434 | 18.660 | 38.453 | 1.00 17.14 |
| ATOM | 518 | CE1 | PHE | 71 | 25.506 | 15.931 | 37.866 | 1.00 15.09 |
| ATOM | 519 | CE2 | PHE | 71 | 24.238 | 17.961 | 38.300 | 1.00 20.92 |
| ATOM | 520 | CZ | PHE | 71 | 24.282 | 16.598 | 37.990 | 1.00 18.49 |
| ATOM | 521 | N | SER | 72 | 30.500 | 19.370 | 40.938 | 1.00 13.13 |
| ATOM | 522 | CA | SER | 72 | 31.889 | 19.715 | 41.075 | 1.00 11.65 |
| ATOM | 523 | C | SER | 72 | 32.689 | 18.446 | 41.357 | 1.00 14.56 |
| ATOM | 524 | O | SER | 72 | 32.256 | 17.566 | 42.122 | 1.00 10.90 |
| ATOM | 525 | CB | SER | 72 | 32.075 | 20.672 | 42.257 | 1.00 8.65 |
| ATOM | 526 | OG | SER | 72 | 31.361 | 21.874 | 42.038 | 1.00 19.29 |
| ATOM | 527 | N | ARG | 73 | 33.905 | 18.358 | 40.794 | 1.00 16.27 |

FIG. 5M

| | | | | | | | |
|---|---|---|---|---|---|---|---|
| ATOM | 528 | CA | ARG | 73 | 34.695 | 17.212 | 41.117 | 1.00 13.56 |
| ATOM | 529 | C | ARG | 73 | 35.414 | 17.426 | 42.443 | 1.00 19.96 |
| ATOM | 530 | O | ARG | 73 | 36.182 | 18.376 | 42.599 | 1.00 16.14 |
| ATOM | 531 | CB | ARG | 73 | 35.694 | 16.817 | 40.013 | 1.00 16.80 |
| ATOM | 532 | CG | ARG | 73 | 36.549 | 15.616 | 40.460 | 1.00 20.13 |
| ATOM | 533 | CD | ARG | 73 | 37.489 | 15.093 | 39.381 | 1.00 28.47 |
| ATOM | 534 | NE | ARG | 73 | 38.743 | 15.859 | 39.260 | 1.00 25.48 |
| ATOM | 535 | CZ | ARG | 73 | 39.756 | 15.777 | 40.127 | 1.00 28.04 |
| ATOM | 536 | NH1 | ARG | 73 | 39.688 | 15.004 | 41.195 | 1.00 28.76 |
| ATOM | 537 | NH2 | ARG | 73 | 40.865 | 16.504 | 39.918 | 1.00 39.65 |
| ATOM | 538 | N | TYR | 74 | 35.151 | 16.561 | 43.424 | 1.00 12.05 |
| ATOM | 539 | CA | TYR | 74 | 35.861 | 16.659 | 44.690 | 1.00 11.57 |
| ATOM | 540 | C | TYR | 74 | 36.946 | 15.566 | 44.721 | 1.00 25.02 |
| ATOM | 541 | O | TYR | 74 | 36.658 | 14.387 | 44.558 | 1.00 19.71 |
| ATOM | 542 | CB | TYR | 74 | 34.978 | 16.528 | 45.934 | 1.00 15.51 |
| ATOM | 543 | CG | TYR | 74 | 34.395 | 17.850 | 46.402 | 1.00 16.59 |
| ATOM | 544 | CD1 | TYR | 74 | 33.455 | 18.546 | 45.631 | 1.00 14.44 |
| ATOM | 545 | CD2 | TYR | 74 | 34.799 | 18.399 | 47.618 | 1.00 15.94 |
| ATOM | 546 | CE1 | TYR | 74 | 32.901 | 19.756 | 46.059 | 1.00 7.99 |
| ATOM | 547 | CE2 | TYR | 74 | 34.261 | 19.612 | 48.058 | 1.00 18.29 |
| ATOM | 548 | CZ | TYR | 74 | 33.294 | 20.276 | 47.298 | 1.00 13.87 |
| ATOM | 549 | OH | TYR | 74 | 32.829 | 21.507 | 47.738 | 1.00 18.39 |
| ATOM | 550 | N | PRO | 75 | 38.181 | 15.947 | 44.902 | 1.00 19.20 |
| ATOM | 551 | CA | PRO | 75 | 39.213 | 14.940 | 44.995 | 1.00 18.42 |
| ATOM | 552 | C | PRO | 75 | 38.958 | 13.993 | 46.175 | 1.00 15.60 |
| ATOM | 553 | O | PRO | 75 | 39.373 | 14.361 | 47.174 | 1.00 11.99 |
| ATOM | 554 | CB | PRO | 75 | 40.514 | 15.681 | 45.196 | 1.00 18.31 |
| ATOM | 555 | CG | PRO | 75 | 40.242 | 17.158 | 44.868 | 1.00 24.81 |
| ATOM | 556 | CD | PRO | 75 | 38.742 | 17.306 | 44.694 | 1.00 15.41 |
| ATOM | 557 | N | ASP | 76 | 39.433 | 12.756 | 46.038 | 1.00 18.63 |
| ATOM | 558 | CA | ASP | 76 | 39.269 | 11.770 | 47.062 | 1.00 16.19 |
| ATOM | 559 | C | ASP | 76 | 39.581 | 12.280 | 48.431 | 1.00 15.92 |
| ATOM | 560 | O | ASP | 76 | 38.862 | 12.042 | 49.389 | 1.00 17.35 |
| ATOM | 561 | CB | ASP | 76 | 40.083 | 10.507 | 46.790 | 1.00 18.69 |
| ATOM | 562 | CG | ASP | 76 | 39.826 | 9.432 | 47.825 | 1.00 24.04 |
| ATOM | 563 | OD1 | ASP | 76 | 40.523 | 9.268 | 48.817 | 1.00 29.72 |
| ATOM | 564 | OD2 | ASP | 76 | 38.732 | 8.743 | 47.584 | 1.00 40.96 |
| ATOM | 565 | N | HIS | 77 | 40.647 | 12.984 | 48.561 | 1.00 18.79 |
| ATOM | 566 | CA | HIS | 77 | 40.978 | 13.418 | 49.877 | 1.00 19.36 |
| ATOM | 567 | C | HIS | 77 | 40.117 | 14.507 | 50.397 | 1.00 24.57 |
| ATOM | 568 | O | HIS | 77 | 40.205 | 14.826 | 51.551 | 1.00 27.15 |

FIG. 5N

| ATOM | 569 | CB | HIS | 77 | 42.435 | 13.806 | 50.042 | 1.00 | 19.84 |
| --- | --- | --- | --- | --- | --- | --- | --- | --- | --- |
| ATOM | 570 | CG | HIS | 77 | 42.743 | 15.035 | 49.322 | 1.00 | 17.31 |
| ATOM | 571 | ND1 | HIS | 77 | 42.925 | 15.028 | 47.953 | 1.00 | 21.86 |
| ATOM | 572 | CD2 | HIS | 77 | 42.925 | 16.295 | 49.774 | 1.00 | 18.70 |
| ATOM | 573 | CE1 | HIS | 77 | 43.203 | 16.289 | 47.593 | 1.00 | 17.49 |
| ATOM | 574 | NE2 | HIS | 77 | 43.213 | 17.069 | 48.668 | 1.00 | 18.11 |
| ATOM | 575 | N | MSE | 78 | 39.277 | 15.069 | 49.565 | 1.00 | 25.36 |
| ATOM | 576 | CA | MSE | 78 | 38.412 | 16.140 | 50.026 | 1.00 | 24.65 |
| ATOM | 577 | C | MSE | 78 | 36.920 | 15.774 | 50.066 | 1.00 | 26.47 |
| ATOM | 578 | O | MSE | 78 | 36.070 | 16.636 | 50.260 | 1.00 | 28.16 |
| ATOM | 579 | CB | MSE | 78 | 38.596 | 17.331 | 49.121 | 1.00 | 26.38 |
| ATOM | 580 | CG | MSE | 78 | 39.803 | 18.177 | 49.406 | 1.00 | 27.01 |
| ATOM | 581 | SE | MSE | 78 | 39.987 | 19.608 | 48.177 | 1.00 | 43.09 |
| ATOM | 582 | CE | MSE | 78 | 38.874 | 20.873 | 49.044 | 1.00 | 27.11 |
| ATOM | 583 | N | LYS | 79 | 36.606 | 14.509 | 49.856 | 1.00 | 18.68 |
| ATOM | 584 | CA | LYS | 79 | 35.216 | 14.061 | 49.853 | 1.00 | 21.54 |
| ATOM | 585 | C | LYS | 79 | 34.406 | 14.449 | 51.082 | 1.00 | 20.21 |
| ATOM | 586 | O | LYS | 79 | 33.186 | 14.652 | 51.025 | 1.00 | 21.08 |
| ATOM | 587 | CB | LYS | 79 | 35.152 | 12.581 | 49.612 | 1.00 | 23.48 |
| ATOM | 588 | CG | LYS | 79 | 35.859 | 12.225 | 48.317 | 1.00 | 41.09 |
| ATOM | 589 | CD | LYS | 79 | 35.159 | 11.134 | 47.535 | 1.00 | 34.66 |
| ATOM | 590 | CE | LYS | 79 | 35.796 | 10.881 | 46.181 | 1.00 | 53.46 |
| ATOM | 591 | NZ | LYS | 79 | 35.084 | 11.549 | 45.080 | 1.00 | 49.53 |
| ATOM | 592 | N | ARG | 80 | 35.069 | 14.542 | 52.213 | 1.00 | 19.77 |
| ATOM | 593 | CA | ARG | 80 | 34.365 | 14.874 | 53.434 | 1.00 | 20.13 |
| ATOM | 594 | C | ARG | 80 | 33.898 | 16.311 | 53.481 | 1.00 | 26.42 |
| ATOM | 595 | O | ARG | 80 | 33.251 | 16.717 | 54.467 | 1.00 | 23.51 |
| ATOM | 596 | CB | ARG | 80 | 35.155 | 14.549 | 54.700 | 1.00 | 24.58 |
| ATOM | 597 | CG | ARG | 80 | 36.204 | 15.620 | 55.034 | 1.00 | 29.71 |
| ATOM | 598 | CD | ARG | 80 | 36.964 | 15.344 | 56.335 | 1.00 | 61.30 |
| ATOM | 599 | NE | ARG | 80 | 36.551 | 16.230 | 57.415 | 1.00 | 71.14 |
| ATOM | 600 | CZ | ARG | 80 | 37.398 | 16.882 | 58.192 | 1.00 | 100.00 |
| ATOM | 601 | NH1 | ARG | 80 | 38.714 | 16.758 | 48.040 | 1.00 | 100.00 |
| ATOM | 602 | NH2 | ARG | 80 | 36.917 | 17.679 | 59.155 | 1.00 | 99.06 |
| ATOM | 603 | N | HIS | 81 | 34.275 | 17.121 | 52.473 | 1.00 | 18.77 |
| ATOM | 604 | CA | HIS | 81 | 33.903 | 18.547 | 52.499 | 1.00 | 19.60 |
| ATOM | 605 | C | HIS | 81 | 32.841 | 18.883 | 51.486 | 1.00 | 18.62 |
| ATOM | 606 | O | HIS | 81 | 32.557 | 20.043 | 51.295 | 1.00 | 17.76 |
| ATOM | 607 | CB | HIS | 81 | 35.129 | 19.472 | 52.283 | 1.00 | 20.39 |
| ATOM | 608 | CG | HIS | 81 | 36.221 | 19.224 | 53.305 | 1.00 | 28.02 |
| ATOM | 609 | ND1 | HIS | 81 | 36.127 | 19.701 | 54.618 | 1.00 | 30.59 |

FIG. 5O

| ATOM | 610 | CD2 HIS | 81 | 37.392 | 18.535 | 53.202 | 1.00 29.02 |
|---|---|---|---|---|---|---|---|
| ATOM | 611 | CE1 HIS | 81 | 37.218 | 19.308 | 55.265 | 1.00 26.24 |
| ATOM | 612 | NE2 HIS | 81 | 37.991 | 18.603 | 54.452 | 1.00 28.18 |
| ATOM | 613 | N ASP | 82 | 32.298 | 17.843 | 50.841 | 1.00 12.20 |
| ATOM | 614 | CA ASP | 82 | 31.358 | 18.011 | 49.769 | 1.00 13.24 |
| ATOM | 615 | C ASP | 82 | 29.922 | 18.148 | 50.259 | 1.00 24.30 |
| ATOM | 616 | O ASP | 82 | 29.175 | 17.195 | 50.243 | 1.00 16.55 |
| ATOM | 617 | CB ASP | 82 | 31.480 | 16.917 | 48.730 | 1.00 12.23 |
| ATOM | 618 | CG ASP | 82 | 30.642 | 17.209 | 47.518 | 1.00 9.92 |
| ATOM | 619 | OD1 ASP | 82 | 29.870 | 18.134 | 47.459 | 1.00 20.31 |
| ATOM | 620 | OD2 ASP | 82 | 30.938 | 16.466 | 46.507 | 1.00 11.12 |
| ATOM | 621 | N PHE | 83 | 29.566 | 19.353 | 50.705 | 1.00 23.66 |
| ATOM | 622 | CA PHE | 83 | 28.220 | 19.634 | 51.201 | 1.00 20.23 |
| ATOM | 623 | C PHE | 83 | 27.154 | 19.333 | 50.168 | 1.00 20.93 |
| ATOM | 624 | O PHE | 83 | 26.116 | 18.733 | 50.503 | 1.00 15.97 |
| ATOM | 625 | CB PHE | 83 | 28.077 | 21.106 | 51.666 | 1.00 19.59 |
| ATOM | 626 | CG PHE | 83 | 26.624 | 21.613 | 51.805 | 1.00 16.91 |
| ATOM | 627 | CD1 PHE | 83 | 25.946 | 21.498 | 53.021 | 1.00 17.76 |
| ATOM | 628 | CD2 PHE | 83 | 25.968 | 22.236 | 50.734 | 1.00 18.88 |
| ATOM | 629 | CE1 PHE | 83 | 24.635 | 21.960 | 53.156 | 1.00 24.13 |
| ATOM | 630 | CE2 PHE | 83 | 24.650 | 22.690 | 50.840 | 1.00 19.24 |
| ATOM | 631 | CZ PHE | 83 | 24.001 | 22.575 | 52.068 | 1.00 20.67 |
| ATOM | 632 | N PHE | 84 | 27.432 | 19.784 | 48.921 | 1.00 14.06 |
| ATOM | 633 | CA PHE | 84 | 26.515 | 19.693 | 47.809 | 1.00 12.96 |
| ATOM | 634 | C PHE | 84 | 25.893 | 18.332 | 47.602 | 1.00 24.96 |
| ATOM | 635 | O PHE | 84 | 24.674 | 18.200 | 47.534 | 1.00 21.55 |
| ATOM | 636 | CB PHE | 84 | 27.085 | 20.265 | 46.513 | 1.00 13.44 |
| ATOM | 637 | CG PHE | 84 | 27.630 | 21.645 | 46.721 | 1.00 14.27 |
| ATOM | 638 | CD1 PHE | 84 | 29.001 | 21.845 | 46.890 | 1.00 15.17 |
| ATOM | 639 | CD2 PHE | 84 | 26.781 | 22.753 | 46.752 | 1.00 13.48 |
| ATOM | 640 | CE1 PHE | 84 | 29.520 | 23.129 | 47.073 | 1.00 14.63 |
| ATOM | 641 | CE2 PHE | 84 | 27.276 | 24.041 | 46.969 | 1.00 16.34 |
| ATOM | 642 | CZ PHE | 84 | 28.650 | 24.221 | 47.137 | 1.00 15.77 |
| ATOM | 643 | N LYS | 85 | 26.738 | 17.330 | 47.482 | 1.00 14.07 |
| ATOM | 644 | CA LYS | 85 | 26.294 | 15.985 | 47.283 | 1.00 13.30 |
| ATOM | 645 | C LYS | 85 | 25.657 | 15.371 | 48.547 | 1.00 13.43 |
| ATOM | 646 | O LYS | 85 | 24.773 | 14.509 | 48.429 | 1.00 18.46 |
| ATOM | 647 | CB LYS | 85 | 27.434 | 15.089 | 46.757 | 1.00 17.38 |
| ATOM | 648 | CG LYS | 85 | 27.873 | 15.372 | 45.323 | 1.00 13.93 |
| ATOM | 649 | CD LYS | 85 | 28.969 | 14.381 | 44.888 | 1.00 13.23 |
| ATOM | 650 | CE LYS | 85 | 29.766 | 14.819 | 43.662 | 1.00 10.36 |

FIG. 5P

| | | | | | | | | |
|---|---|---|---|---|---|---|---|---|
| ATOM | 651 | NZ | LYS | 85 | 30.319 | 16.185 | 43.773 | 1.00 12.92 |
| ATOM | 652 | N | SER | 86 | 26.119 | 15.795 | 49.752 | 1.00 11.03 |
| ATOM | 653 | CA | SER | 86 | 25.610 | 15.267 | 50.998 | 1.00 12.09 |
| ATOM | 654 | C | SER | 86 | 24.156 | 15.639 | 51.240 | 1.00 21.58 |
| ATOM | 655 | O | SER | 86 | 23.452 | 14.979 | 52.013 | 1.00 19.89 |
| ATOM | 656 | CB | SER | 86 | 26.448 | 15.661 | 52.208 | 1.00 16.45 |
| ATOM | 657 | OG | SER | 86 | 26.308 | 17.042 | 52.495 | 1.00 22.05 |
| ATOM | 658 | N | ALA | 87 | 23.705 | 16.698 | 50.582 | 1.00 15.09 |
| ATOM | 659 | CA | ALA | 87 | 22.333 | 17.138 | 50.762 | 1.00 19.52 |
| ATOM | 660 | C | ALA | 87 | 21.337 | 16.399 | 49.870 | 1.00 18.60 |
| ATOM | 661 | O | ALA | 87 | 20.162 | 16.557 | 50.040 | 1.00 19.55 |
| ATOM | 662 | CB | ALA | 87 | 22.204 | 18.647 | 50.632 | 1.00 19.23 |
| ATOM | 663 | N | MSE | 88 | 21.835 | 15.536 | 48.976 | 1.00 14.05 |
| ATOM | 664 | CA | MSE | 88 | 21.007 | 14.796 | 48.035 | 1.00 15.32 |
| ATOM | 665 | C | MSE | 88 | 20.496 | 13.448 | 48.579 | 1.00 21.48 |
| ATOM | 666 | O | MSE | 88 | 21.109 | 12.876 | 49.457 | 1.00 23.03 |
| ATOM | 667 | CB | MSE | 88 | 21.848 | 14.593 | 46.791 | 1.00 16.98 |
| ATOM | 668 | CG | MSE | 88 | 22.263 | 15.891 | 46.131 | 1.00 10.66 |
| ATOM | 669 | SE | MSE | 88 | 20.737 | 16.894 | 45.394 | 1.00 31.99 |
| ATOM | 670 | CE | MSE | 88 | 21.318 | 18.684 | 45.748 | 1.00 28.86 |
| ATOM | 671 | N | PRO | 89 | 19.363 | 12.930 | 48.084 | 1.00 14.78 |
| ATOM | 672 | CA | PRO | 89 | 18.552 | 13.475 | 47.008 | 1.00 14.80 |
| ATOM | 673 | C | PRO | 89 | 17.572 | 14.611 | 47.385 | 1.00 12.10 |
| ATOM | 674 | O | PRO | 89 | 17.085 | 15.301 | 46.493 | 1.00 18.06 |
| ATOM | 675 | CB | PRO | 89 | 17.733 | 12.294 | 46.494 | 1.00 17.00 |
| ATOM | 676 | CG | PRO | 89 | 17.726 | 11.261 | 47.607 | 1.00 15.83 |
| ATOM | 677 | CD | PRO | 89 | 18.844 | 11.642 | 48.560 | 1.00 17.16 |
| ATOM | 678 | N | GLU | 90 | 17.278 | 14.795 | 48.695 | 1.00 14.63 |
| ATOM | 679 | CA | GLU | 90 | 16.348 | 15.838 | 49.157 | 1.00 20.68 |
| ATOM | 680 | C | GLU | 90 | 16.701 | 17.229 | 48.645 | 1.00 25.59 |
| ATOM | 681 | O | GLU | 90 | 15.833 | 18.042 | 48.368 | 1.00 21.57 |
| ATOM | 682 | CB | GLU | 90 | 16.031 | 15.816 | 50.682 | 1.00 22.21 |
| ATOM | 683 | CG | GLU | 90 | 15.782 | 14.403 | 51.223 | 1.00 37.69 |
| ATOM | 684 | CD | GLU | 90 | 17.071 | 13.641 | 51.447 | 1.00 83.49 |
| ATOM | 685 | OE1 | GLU | 90 | 18.179 | 14.151 | 51.342 | 1.00 54.80 |
| ATOM | 686 | OE2 | GLU | 90 | 16.875 | 12.373 | 51.749 | 1.00 64.65 |
| ATOM | 687 | N | GLY | 91 | 17.977 | 17.509 | 48.510 | 1.00 21.39 |
| ATOM | 688 | CA | GLY | 91 | 18.394 | 18.769 | 47.906 | 1.00 17.77 |
| ATOM | 689 | C | GLY | 91 | 18.673 | 19.911 | 48.839 | 1.00 12.17 |
| ATOM | 690 | O | GLY | 91 | 18.769 | 19.764 | 50.055 | 1.00 16.81 |
| ATOM | 691 | N | TYR | 92 | 18.861 | 21.086 | 48.225 | 1.00 13.02 |

FIG. 5Q

| ATOM | 692 | CA | TYR | 92 | 19.143 | 22.266 | 48.994 | 1.00 | 10.33 |
|------|-----|----|-----|----|--------|--------|--------|------|-------|
| ATOM | 693 | C | TYR | 92 | 18.575 | 23.478 | 48.347 | 1.00 | 9.87 |
| ATOM | 694 | O | TYR | 92 | 18.270 | 23.483 | 47.144 | 1.00 | 15.89 |
| ATOM | 695 | CB | TYR | 92 | 20.678 | 22.488 | 49.278 | 1.00 | 15.40 |
| ATOM | 696 | CG | TYR | 92 | 21.546 | 22.468 | 48.012 | 1.00 | 15.13 |
| ATOM | 697 | CD1 | TYR | 92 | 21.620 | 23.576 | 47.166 | 1.00 | 14.75 |
| ATOM | 698 | CD2 | TYR | 92 | 22.317 | 21.350 | 47.683 | 1.00 | 16.09 |
| ATOM | 699 | CE1 | TYR | 92 | 22.404 | 23.561 | 46.006 | 1.00 | 6.50 |
| ATOM | 700 | CE2 | TYR | 92 | 23.067 | 21.300 | 46.504 | 1.00 | 15.12 |
| ATOM | 701 | CZ | TYR | 92 | 23.156 | 22.424 | 45.683 | 1.00 | 18.13 |
| ATOM | 702 | OH | TYR | 92 | 23.944 | 22.393 | 44.517 | 1.00 | 13.37 |
| ATOM | 703 | N | VAL | 93 | 18.447 | 24.504 | 49.189 | 1.00 | 11.93 |
| ATOM | 704 | CA | VAL | 93 | 18.025 | 25.822 | 48.778 | 1.00 | 14.74 |
| ATOM | 705 | C | VAL | 93 | 19.281 | 26.666 | 48.625 | 1.00 | 16.00 |
| ATOM | 706 | O | VAL | 93 | 20.172 | 26.625 | 49.451 | 1.00 | 16.16 |
| ATOM | 707 | CB | VAL | 93 | 17.073 | 26.480 | 49.791 | 1.00 | 23.45 |
| ATOM | 708 | CG1 | VAL | 93 | 16.855 | 27.937 | 49.413 | 1.00 | 26.05 |
| ATOM | 709 | CG2 | VAL | 93 | 15.716 | 25.764 | 49.771 | 1.00 | 22.90 |
| ATOM | 710 | N | GLN | 94 | 19.361 | 27.345 | 47.521 | 1.00 | 13.78 |
| ATOM | 711 | CA | GLN | 94 | 20.480 | 28.195 | 47.227 | 1.00 | 10.53 |
| ATOM | 712 | C | GLN | 94 | 19.948 | 29.583 | 46.998 | 1.00 | 12.23 |
| ATOM | 713 | O | GLN | 94 | 19.153 | 29.788 | 46.061 | 1.00 | 15.52 |
| ATOM | 714 | CB | GLN | 94 | 21.232 | 27.727 | 45.934 | 1.00 | 7.95 |
| ATOM | 715 | CG | GLN | 94 | 22.361 | 28.708 | 45.469 | 1.00 | 11.87 |
| ATOM | 716 | CD | GLN | 94 | 23.431 | 27.999 | 44.632 | 1.00 | 12.04 |
| ATOM | 717 | OE1 | GLN | 94 | 23.805 | 26.879 | 44.946 | 1.00 | 13.60 |
| ATOM | 718 | NE2 | GLN | 94 | 23.719 | 28.527 | 43.449 | 1.00 | 7.98 |
| ATOM | 719 | N | GLU | 95 | 20.396 | 30.531 | 47.820 | 1.00 | 11.78 |
| ATOM | 720 | CA | GLU | 95 | 19.974 | 31.899 | 47.643 | 1.00 | 13.47 |
| ATOM | 721 | C | GLU | 95 | 21.149 | 32.804 | 47.398 | 1.00 | 18.42 |
| ATOM | 722 | O | GLU | 95 | 22.206 | 32.623 | 47.985 | 1.00 | 19.23 |
| ATOM | 723 | CB | GLU | 95 | 19.277 | 32.427 | 48.878 | 1.00 | 13.52 |
| ATOM | 724 | CG | GLU | 95 | 18.009 | 31.684 | 49.215 | 1.00 | 28.46 |
| ATOM | 725 | CD | GLU | 95 | 17.657 | 32.016 | 50.622 | 1.00 | 45.93 |
| ATOM | 726 | OE1 | GLU | 95 | 17.574 | 33.166 | 51.011 | 1.00 | 100.00 |
| ATOM | 727 | OE2 | GLU | 95 | 17.764 | 30.987 | 51.423 | 1.00 | 61.33 |
| ATOM | 728 | N | ARG | 96 | 20.929 | 33.838 | 46.601 | 1.00 | 16.51 |
| ATOM | 729 | CA | ARG | 96 | 21.978 | 34.783 | 46.342 | 1.00 | 16.87 |
| ATOM | 730 | C | ARG | 96 | 21.510 | 36.195 | 46.206 | 1.00 | 15.84 |
| ATOM | 731 | O | ARG | 96 | 20.389 | 36.488 | 45.806 | 1.00 | 15.01 |
| ATOM | 732 | CB | ARG | 96 | 22.582 | 34.463 | 44.967 | 1.00 | 16.19 |

FIG. 5R

| ATOM | 733 | CG ARG | 96 | 23.495 | 33.247 | 44.929 | 1.00 17.61 |
|------|-----|--------|-----|--------|--------|--------|------------|
| ATOM | 734 | CD ARG | 96 | 24.615 | 33.453 | 43.908 | 1.00 9.06 |
| ATOM | 735 | NE ARG | 96 | 25.411 | 32.277 | 43.766 | 1.00 9.88 |
| ATOM | 736 | CZ ARG | 96 | 25.434 | 31.493 | 42.693 | 1.00 20.03 |
| ATOM | 737 | NH1ARG | 96 | 24.684 | 31.709 | 41.615 | 1.00 15.29 |
| ATOM | 738 | NH2ARG | 96 | 26.236 | 30.430 | 42.714 | 1.00 11.03 |
| ATOM | 739 | N THR | 97 | 22.470 | 37.068 | 46.344 | 1.00 13.39 |
| ATOM | 740 | CA THR | 97 | 22.368 | 38.424 | 45.935 | 1.00 13.12 |
| ATOM | 741 | C THR | 97 | 23.593 | 38.688 | 45.084 | 1.00 16.81 |
| ATOM | 742 | O THR | 97 | 24.686 | 38.347 | 45.485 | 1.00 19.25 |
| ATOM | 743 | CB THR | 97 | 22.282 | 39.442 | 47.066 | 1.00 26.27 |
| ATOM | 744 | OG1THR | 97 | 21.225 | 39.101 | 47.945 | 1.00 31.43 |
| ATOM | 745 | CG2THR | 97 | 22.038 | 40.804 | 46.445 | 1.00 15.90 |
| ATOM | 746 | N ILE | 98 | 23.396 | 39.219 | 43.899 | 1.00 16.23 |
| ATOM | 747 | CA ILE | 98 | 24.486 | 39.526 | 42.977 | 1.00 16.70 |
| ATOM | 748 | C ILE | 98 | 24.533 | 41.017 | 42.686 | 1.00 21.10 |
| ATOM | 749 | O ILE | 98 | 23.628 | 41.566 | 42.075 | 1.00 14.58 |
| ATOM | 750 | CB ILE | 98 | 24.385 | 38.752 | 41.660 | 1.00 13.47 |
| ATOM | 751 | CG1ILE | 98 | 24.480 | 37.236 | 41.890 | 1.00 16.09 |
| ATOM | 752 | CG2ILE | 98 | 25.457 | 39.231 | 40.679 | 1.00 13.30 |
| ATOM | 753 | CD1ILE | 98 | 23.875 | 36.431 | 40.738 | 1.00 13.93 |
| ATOM | 754 | N PHE | 99 | 25.613 | 41.678 | 43.110 | 1.00 14.86 |
| ATOM | 755 | CA PHE | 99 | 25.719 | 43.098 | 42.896 | 1.00 12.44 |
| ATOM | 756 | C PHE | 99 | 26.514 | 43.441 | 41.699 | 1.00 20.37 |
| ATOM | 757 | O PHE | 99 | 27.696 | 43.164 | 41.700 | 1.00 20.07 |
| ATOM | 758 | CB PHE | 99 | 26.401 | 43.770 | 44.084 | 1.00 15.96 |
| ATOM | 759 | CG PHE | 99 | 25.638 | 43.624 | 45.356 | 1.00 21.41 |
| ATOM | 760 | CD1PHE | 99 | 25.863 | 42.524 | 46.189 | 1.00 24.98 |
| ATOM | 761 | CD2PHE | 99 | 24.698 | 44.585 | 45.743 | 1.00 22.94 |
| ATOM | 762 | CE1PHE | 99 | 25.176 | 42.400 | 47.400 | 1.00 32.06 |
| ATOM | 763 | CE2PHE | 99 | 23.992 | 44.469 | 46.946 | 1.00 24.26 |
| ATOM | 764 | CZ PHE | 99 | 24.235 | 43.369 | 47.771 | 1.00 28.19 |
| ATOM | 765 | N PHE | 100 | 25.906 | 44.085 | 40.704 | 1.00 12.53 |
| ATOM | 766 | CA PHE | 100 | 26.679 | 44.522 | 39.554 | 1.00 8.75 |
| ATOM | 767 | C PHE | 100 | 27.294 | 45.855 | 39.872 | 1.00 21.81 |
| ATOM | 768 | O PHE | 100 | 26.599 | 46.775 | 40.308 | 1.00 20.31 |
| ATOM | 769 | CB PHE | 100 | 25.927 | 44.572 | 38.226 | 1.00 5.94 |
| ATOM | 770 | CG PHE | 100 | 25.537 | 43.183 | 37.764 | 1.00 12.75 |
| ATOM | 771 | CD1PHE | 100 | 24.426 | 42.538 | 38.325 | 1.00 16.31 |
| ATOM | 772 | CD2PHE | 100 | 26.317 | 42.484 | 36.843 | 1.00 15.27 |
| ATOM | 773 | CE1PHE | 100 | 24.087 | 41.230 | 37.975 | 1.00 13.50 |

FIG. 5S

| ATOM | 774 | CE2 | PHE | 100 | 25.965 | 41.192 | 36.435 | 1.00 | 21.25 |
|------|-----|-----|-----|-----|--------|--------|--------|------|-------|
| ATOM | 775 | CZ  | PHE | 100 | 24.852 | 40.567 | 37.014 | 1.00 | 21.06 |
| ATOM | 776 | N   | LYS | 101 | 28.603 | 45.946 | 39.737 | 1.00 | 15.49 |
| ATOM | 777 | CA  | LYS | 101 | 29.270 | 47.179 | 40.085 | 1.00 | 17.93 |
| ATOM | 778 | C   | LYS | 101 | 28.732 | 48.349 | 39.287 | 1.00 | 13.71 |
| ATOM | 779 | O   | LYS | 101 | 28.658 | 48.304 | 38.072 | 1.00 | 17.18 |
| ATOM | 780 | CB  | LYS | 101 | 30.784 | 47.069 | 39.950 | 1.00 | 17.13 |
| ATOM | 781 | CG  | LYS | 101 | 31.518 | 48.252 | 40.551 | 1.00 | 18.01 |
| ATOM | 782 | CD  | LYS | 101 | 33.036 | 48.060 | 40.534 | 1.00 | 26.70 |
| ATOM | 783 | CE  | LYS | 101 | 33.797 | 49.116 | 41.332 | 1.00 | 41.58 |
| ATOM | 784 | N   | ASP | 102 | 28.353 | 49.403 | 39.997 | 1.00 | 18.09 |
| ATOM | 785 | CA  | ASP | 102 | 27.805 | 50.618 | 39.368 | 1.00 | 23.08 |
| ATOM | 786 | C   | ASP | 102 | 26.559 | 50.356 | 38.549 | 1.00 | 25.42 |
| ATOM | 787 | O   | ASP | 102 | 26.292 | 51.061 | 37.586 | 1.00 | 23.34 |
| ATOM | 788 | CB  | ASP | 102 | 28.840 | 51.369 | 38.516 | 1.00 | 26.27 |
| ATOM | 789 | CG  | ASP | 102 | 30.109 | 51.629 | 39.296 | 1.00 | 57.01 |
| ATOM | 790 | OD1 | ASP | 102 | 31.206 | 51.233 | 38.931 | 1.00 | 63.33 |
| ATOM | 791 | OD2 | ASP | 102 | 29.886 | 52.200 | 40.464 | 1.00 | 47.66 |
| ATOM | 792 | N   | ASP | 103 | 25.813 | 49.328 | 38.933 | 1.00 | 20.17 |
| ATOM | 793 | CA  | ASP | 103 | 24.602 | 48.949 | 38.233 | 1.00 | 15.70 |
| ATOM | 794 | C   | ASP | 103 | 23.608 | 48.284 | 39.189 | 1.00 | 18.47 |
| ATOM | 795 | O   | ASP | 103 | 23.749 | 48.431 | 40.409 | 1.00 | 17.72 |
| ATOM | 796 | CB  | ASP | 103 | 24.899 | 48.085 | 36.995 | 1.00 | 19.89 |
| ATOM | 797 | CG  | ASP | 103 | 23.946 | 48.387 | 35.860 | 1.00 | 23.93 |
| ATOM | 798 | OD1 | ASP | 103 | 24.238 | 48.274 | 34.688 | 1.00 | 19.05 |
| ATOM | 799 | OD2 | ASP | 103 | 22.774 | 48.809 | 36.283 | 1.00 | 23.89 |
| ATOM | 800 | N   | GLY | 104 | 22.612 | 47.542 | 38.646 | 1.00 | 20.17 |
| ATOM | 801 | CA  | GLY | 104 | 21.598 | 46.900 | 39.498 | 1.00 | 20.22 |
| ATOM | 802 | C   | GLY | 104 | 22.055 | 45.619 | 40.180 | 1.00 | 24.68 |
| ATOM | 803 | O   | GLY | 104 | 23.202 | 45.211 | 40.085 | 1.00 | 18.06 |
| ATOM | 804 | N   | ASN | 105 | 21.125 | 44.967 | 40.872 | 1.00 | 15.71 |
| ATOM | 805 | CA  | ASN | 105 | 21.425 | 43.703 | 41.510 | 1.00 | 8.89  |
| ATOM | 806 | C   | ASN | 105 | 20.399 | 42.620 | 41.181 | 1.00 | 21.85 |
| ATOM | 807 | O   | ASN | 105 | 19.255 | 42.911 | 40.824 | 1.00 | 15.17 |
| ATOM | 808 | CB  | ASN | 105 | 21.605 | 43.840 | 43.001 | 1.00 | 8.58  |
| ATOM | 809 | CG  | ASN | 105 | 20.359 | 44.366 | 43.697 | 1.00 | 43.57 |
| ATOM | 810 | OD1 | ASN | 105 | 19.565 | 43.601 | 44.259 | 1.00 | 36.67 |
| ATOM | 811 | ND2 | ASN | 105 | 20.178 | 45.674 | 43.659 | 1.00 | 36.47 |
| ATOM | 812 | N   | TYR | 106 | 20.826 | 41.365 | 41.328 | 1.00 | 16.80 |
| ATOM | 813 | CA  | TYR | 106 | 19.966 | 40.219 | 41.156 | 1.00 | 13.90 |
| ATOM | 814 | C   | TYR | 106 | 19.763 | 39.543 | 42.475 | 1.00 | 11.05 |

FIG. 5T

| | | | | | | | | |
|---|---|---|---|---|---|---|---|---|
| ATOM | 815 | O | TYR | 106 | 20.678 | 39.404 | 43.281 | 1.00 13.86 |
| ATOM | 816 | CB | TYR | 106 | 20.547 | 39.128 | 40.246 | 1.00 15.88 |
| ATOM | 817 | CG | TYR | 106 | 20.619 | 39.398 | 38.793 | 1.00 15.57 |
| ATOM | 818 | CD1 | TYR | 106 | 19.952 | 40.458 | 38.178 | 1.00 13.14 |
| ATOM | 819 | CD2 | TYR | 106 | 21.373 | 38.524 | 38.006 | 1.00 13.35 |
| ATOM | 820 | CE1 | TYR | 106 | 20.038 | 40.632 | 36.793 | 1.00 13.44 |
| ATOM | 821 | CE2 | TYR | 106 | 21.481 | 38.692 | 36.628 | 1.00 10.87 |
| ATOM | 822 | CZ | TYR | 106 | 20.814 | 39.751 | 36.025 | 1.00 15.93 |
| ATOM | 823 | OH | TYR | 106 | 20.970 | 39.931 | 34.670 | 1.00 17.32 |
| ATOM | 824 | N | LYS | 107 | 18.538 | 39.115 | 42.709 | 1.00 12.39 |
| ATOM | 825 | CA | LYS | 107 | 18.194 | 38.349 | 43.897 | 1.00 11.51 |
| ATOM | 826 | C | LYS | 107 | 17.619 | 37.037 | 43.397 | 1.00 17.25 |
| ATOM | 827 | O | LYS | 107 | 16.704 | 37.010 | 42.562 | 1.00 13.14 |
| ATOM | 828 | CB | LYS | 107 | 17.217 | 39.063 | 44.823 | 1.00 14.82 |
| ATOM | 829 | CG | LYS | 107 | 17.860 | 39.631 | 46.060 | 1.00 40.71 |
| ATOM | 830 | CD | LYS | 107 | 18.528 | 40.974 | 45.793 | 1.00 43.48 |
| ATOM | 831 | N | THR | 108 | 18.205 | 35.951 | 43.835 | 1.00 14.95 |
| ATOM | 832 | CA | THR | 108 | 17.774 | 34.658 | 43.352 | 1.00 11.97 |
| ATOM | 833 | C | THR | 108 | 17.463 | 33.696 | 44.468 | 1.00 15.81 |
| ATOM | 834 | O | THR | 108 | 18.043 | 33.734 | 45.582 | 1.00 18.68 |
| ATOM | 835 | CB | THR | 108 | 18.847 | 34.034 | 42.410 | 1.00 23.81 |
| ATOM | 836 | OG1 | THR | 108 | 20.064 | 33.791 | 43.137 | 1.00 13.88 |
| ATOM | 837 | CG2 | THR | 108 | 19.123 | 34.968 | 41.264 | 1.00 13.04 |
| ATOM | 838 | N | ARG | 109 | 16.560 | 32.804 | 44.154 | 1.00 13.57 |
| ATOM | 839 | CA | ARG | 109 | 16.212 | 31.751 | 45.048 | 1.00 12.56 |
| ATOM | 840 | C | ARG | 109 | 15.939 | 30.498 | 44.254 | 1.00 13.07 |
| ATOM | 841 | O | ARG | 109 | 15.239 | 30.509 | 43.249 | 1.00 12.52 |
| ATOM | 842 | CB | ARG | 109 | 15.069 | 32.100 | 45.959 | 1.00 17.32 |
| ATOM | 843 | CG | ARG | 109 | 14.767 | 30.995 | 46.932 | 1.00 17.92 |
| ATOM | 844 | CD | ARG | 109 | 13.400 | 31.160 | 47.610 | 1.00 19.99 |
| ATOM | 845 | NE | ARG | 109 | 12.821 | 29.854 | 47.883 | 1.00 36.05 |
| ATOM | 846 | CZ | ARG | 109 | 12.968 | 29.244 | 49.035 | 1.00 55.71 |
| ATOM | 847 | NH1 | ARG | 109 | 13.630 | 29.815 | 50.046 | 1.00 44.11 |
| ATOM | 848 | NH2 | ARG | 109 | 12.432 | 28.041 | 49.195 | 1.00 94.34 |
| ATOM | 849 | N | ALA | 110 | 16.577 | 29.414 | 44.635 | 1.00 13.26 |
| ATOM | 850 | CA | ALA | 110 | 16.377 | 28.207 | 43.870 | 1.00 12.68 |
| ATOM | 851 | C | ALA | 110 | 16.346 | 26.979 | 44.734 | 1.00 13.15 |
| ATOM | 852 | O | ALA | 110 | 16.829 | 26.965 | 45.869 | 1.00 16.75 |
| ATOM | 853 | CB | ALA | 110 | 17.465 | 28.059 | 42.822 | 1.00 17.31 |
| ATOM | 854 | N | GLU | 111 | 15.770 | 25.939 | 44.176 | 1.00 15.39 |
| ATOM | 855 | CA | GLU | 111 | 15.741 | 24.655 | 44.823 | 1.00 15.24 |

FIG. 5U

| ATOM | 856 | C | GLU | 111 | 16.438 | 23.678 | 43.926 | 1.00 | 12.08 |
|---|---|---|---|---|---|---|---|---|---|
| ATOM | 857 | O | GLU | 111 | 16.086 | 23.545 | 42.771 | 1.00 | 15.70 |
| ATOM | 858 | CB | GLU | 111 | 14.303 | 24.123 | 44.993 | 1.00 | 19.20 |
| ATOM | 859 | CG | GLU | 111 | 13.744 | 24.242 | 46.399 | 1.00 | 38.62 |
| ATOM | 860 | CD | GLU | 111 | 12.247 | 24.280 | 46.372 | 1.00 | 60.99 |
| ATOM | 861 | OE1 | GLU | 111 | 11.589 | 23.843 | 45.432 | 1.00 | 76.05 |
| ATOM | 862 | OE2 | GLU | 111 | 11.742 | 24.956 | 47.380 | 1.00 | 54.87 |
| ATOM | 863 | N | VAL | 112 | 17.438 | 22.965 | 44.457 | 1.00 | 10.78 |
| ATOM | 864 | CA | VAL | 112 | 18.063 | 21.978 | 43.631 | 1.00 | 10.98 |
| ATOM | 865 | C | VAL | 112 | 17.968 | 20.630 | 44.261 | 1.00 | 8.62 |
| ATOM | 866 | O | VAL | 112 | 18.271 | 20.438 | 45.432 | 1.00 | 15.63 |
| ATOM | 867 | CB | VAL | 112 | 19.428 | 22.358 | 43.012 | 1.00 | 22.75 |
| ATOM | 868 | CG1 | VAL | 112 | 19.966 | 23.704 | 43.487 | 1.00 | 16.69 |
| ATOM | 869 | CG2 | VAL | 112 | 20.452 | 21.232 | 43.078 | 1.00 | 18.47 |
| ATOM | 870 | N | LYS | 113 | 17.415 | 19.732 | 43.516 | 1.00 | 14.67 |
| ATOM | 871 | CA | LYS | 113 | 17.175 | 18.421 | 44.045 | 1.00 | 16.41 |
| ATOM | 872 | C | LYS | 113 | 16.822 | 17.485 | 42.931 | 1.00 | 7.11 |
| ATOM | 873 | O | LYS | 113 | 16.695 | 17.893 | 41.808 | 1.00 | 16.27 |
| ATOM | 874 | CB | LYS | 113 | 16.032 | 18.497 | 45.036 | 1.00 | 22.50 |
| ATOM | 875 | CG | LYS | 113 | 14.792 | 19.084 | 44.376 | 1.00 | 20.40 |
| ATOM | 876 | CD | LYS | 113 | 13.509 | 18.321 | 44.703 | 1.00 | 44.65 |
| ATOM | 877 | CE | LYS | 113 | 12.526 | 19.134 | 45.528 | 1.00 | 54.02 |
| ATOM | 878 | NZ | LYS | 113 | 12.379 | 20.518 | 45.036 | 1.00 | 100.00 |
| ATOM | 879 | N | PHE | 114 | 16.683 | 16.208 | 43.267 | 1.00 | 10.09 |
| ATOM | 880 | CA | PHE | 114 | 16.325 | 15.175 | 42.317 | 1.00 | 11.41 |
| ATOM | 881 | C | PHE | 114 | 14.806 | 14.975 | 42.181 | 1.00 | 14.18 |
| ATOM | 882 | O | PHE | 114 | 14.110 | 14.878 | 43.160 | 1.00 | 15.03 |
| ATOM | 883 | CB | PHE | 114 | 16.866 | 13.838 | 42.838 | 1.00 | 12.89 |
| ATOM | 884 | CG | PHE | 114 | 18.231 | 13.536 | 42.338 | 1.00 | 16.80 |
| ATOM | 885 | CD1 | PHE | 114 | 19.344 | 13.795 | 43.139 | 1.00 | 18.61 |
| ATOM | 886 | CD2 | PHE | 114 | 18.403 | 13.009 | 41.056 | 1.00 | 19.50 |
| ATOM | 887 | CE1 | PHE | 114 | 20.627 | 13.500 | 42.665 | 1.00 | 22.78 |
| ATOM | 888 | CE2 | PHE | 114 | 19.673 | 12.708 | 40.572 | 1.00 | 25.36 |
| ATOM | 889 | CZ | PHE | 114 | 20.780 | 12.953 | 41.387 | 1.00 | 23.99 |
| ATOM | 890 | N | GLU | 115 | 14.354 | 14.819 | 40.966 | 1.00 | 15.29 |
| ATOM | 891 | CA | GLU | 115 | 12.978 | 14.473 | 40.642 | 1.00 | 11.40 |
| ATOM | 892 | C | GLU | 115 | 13.121 | 13.193 | 39.906 | 1.00 | 13.30 |
| ATOM | 893 | O | GLU | 115 | 13.434 | 13.207 | 38.730 | 1.00 | 18.72 |
| ATOM | 894 | CB | GLU | 115 | 12.348 | 15.481 | 39.667 | 1.00 | 9.68 |
| ATOM | 895 | CG | GLU | 115 | 11.856 | 16.747 | 40.376 | 1.00 | 19.54 |
| ATOM | 896 | CD | GLU | 115 | 10.742 | 16.460 | 41.342 | 1.00 | 38.12 |

FIG. 5V

| ATOM | 897 | OE1 GLU | 115 | 10.181 | 15.395 | 41.431 | 1.00 34.84 |
|---|---|---|---|---|---|---|---|
| ATOM | 898 | OE2 GLU | 115 | 10.460 | 17.461 | 42.079 | 1.00 27.88 |
| ATOM | 899 | N GLY | 116 | 13.005 | 12.087 | 40.585 | 1.00 14.51 |
| ATOM | 900 | CA GLY | 116 | 13.225 | 10.861 | 39.869 | 1.00 15.91 |
| ATOM | 901 | C GLY | 116 | 14.727 | 10.767 | 39.641 | 1.00 23.59 |
| ATOM | 902 | O GLY | 116 | 15.516 | 10.922 | 40.570 | 1.00 19.35 |
| ATOM | 903 | N ASP | 117 | 15.137 | 10.564 | 38.439 | 1.00 20.26 |
| ATOM | 904 | CA ASP | 117 | 16.572 | 10.462 | 38.233 | 1.00 28.00 |
| ATOM | 905 | C ASP | 117 | 17.237 | 11.677 | 37.598 | 1.00 22.39 |
| ATOM | 906 | O ASP | 117 | 18.423 | 11.672 | 37.265 | 1.00 21.38 |
| ATOM | 907 | CB ASP | 117 | 17.055 | 9.074 | 37.733 | 1.00 33.06 |
| ATOM | 908 | CG ASP | 117 | 16.624 | 8.677 | 36.348 | 1.00 55.04 |
| ATOM | 909 | OD1 ASP | 117 | 16.230 | 9.468 | 35.495 | 1.00 59.57 |
| ATOM | 910 | OD2 ASP | 117 | 16.805 | 7.391 | 36.130 | 1.00 82.48 |
| ATOM | 911 | N THR | 118 | 16.463 | 12.729 | 37.493 | 1.00 19.62 |
| ATOM | 912 | CA THR | 118 | 16.889 | 13.981 | 36.910 | 1.00 18.21 |
| ATOM | 913 | C THR | 118 | 17.186 | 14.988 | 37.976 | 1.00 18.92 |
| ATOM | 914 | O THR | 118 | 16.498 | 15.064 | 38.996 | 1.00 15.94 |
| ATOM | 915 | CB THR | 118 | 15.806 | 14.497 | 35.952 | 1.00 19.03 |
| ATOM | 916 | OG1 THR | 118 | 15.552 | 13.508 | 34.990 | 1.00 21.42 |
| ATOM | 917 | CG2 THR | 118 | 16.217 | 15.793 | 35.275 | 1.00 15.49 |
| ATOM | 918 | N LEU | 119 | 18.284 | 15.681 | 37.805 | 1.00 13.66 |
| ATOM | 919 | CA LEU | 119 | 18.679 | 16.706 | 38.759 | 1.00 13.50 |
| ATOM | 920 | C LEU | 119 | 18.036 | 17.992 | 38.269 | 1.00 8.81 |
| ATOM | 921 | O LEU | 119 | 18.194 | 18.368 | 37.091 | 1.00 12.49 |
| ATOM | 922 | CB LEU | 119 | 20.243 | 16.815 | 38.839 | 1.00 12.25 |
| ATOM | 923 | CG LEU | 119 | 20.845 | 17.678 | 39.951 | 1.00 3.90 |
| ATOM | 924 | CD1 LEU | 119 | 20.701 | 19.167 | 39.669 | 1.00 10.11 |
| ATOM | 925 | CD2 LEU | 119 | 20.366 | 17.311 | 41.333 | 1.00 7.86 |
| ATOM | 926 | N VAL | 120 | 17.230 | 18.595 | 39.170 | 1.00 13.34 |
| ATOM | 927 | CA VAL | 120 | 16.466 | 19.797 | 38.859 | 1.00 13.77 |
| ATOM | 928 | C VAL | 120 | 16.929 | 21.039 | 39.587 | 1.00 8.56 |
| ATOM | 929 | O VAL | 120 | 17.135 | 21.039 | 40.762 | 1.00 13.32 |
| ATOM | 930 | CB VAL | 120 | 14.939 | 19.566 | 39.082 | 1.00 17.60 |
| ATOM | 931 | CG1 VAL | 120 | 14.133 | 20.790 | 38.642 | 1.00 17.58 |
| ATOM | 932 | CG2 VAL | 120 | 14.501 | 18.351 | 38.246 | 1.00 15.35 |
| ATOM | 933 | N ASN | 121 | 17.067 | 22.111 | 38.839 | 1.00 12.24 |
| ATOM | 934 | CA ASN | 121 | 17.424 | 23.405 | 39.400 | 1.00 11.78 |
| ATOM | 935 | C ASN | 121 | 16.301 | 24.382 | 39.060 | 1.00 11.18 |
| ATOM | 936 | O ASN | 121 | 16.195 | 24.802 | 37.934 | 1.00 11.09 |
| ATOM | 937 | CB ASN | 121 | 18.753 | 23.928 | 38.791 | 1.00 11.41 |

FIG. 5W

| | | | | | | | |
|---|---|---|---|---|---|---|---|
| ATOM | 938 | CG | ASN | 121 | 19.201 | 25.261 | 39.367 | 1.00 11.07 |
| ATOM | 939 | OD | ASN | 121 | 18.773 | 25.654 | 40.461 | 1.00 12.06 |
| ATOM | 940 | ND2 | ASN | 121 | 20.124 | 25.938 | 38.670 | 1.00 11.90 |
| ATOM | 941 | N | ARG | 122 | 15.470 | 24.706 | 40.029 | 1.00 13.69 |
| ATOM | 942 | CA | ARG | 122 | 14.348 | 25.610 | 39.825 | 1.00 12.99 |
| ATOM | 943 | C | ARG | 122 | 14.622 | 26.946 | 40.498 | 1.00 5.89 |
| ATOM | 944 | O | ARG | 122 | 14.749 | 27.011 | 41.723 | 1.00 14.47 |
| ATOM | 945 | CB | ARG | 122 | 13.068 | 25.025 | 40.417 | 1.00 15.99 |
| ATOM | 946 | CG | ARG | 122 | 12.478 | 23.921 | 39.589 | 1.00 30.23 |
| ATOM | 947 | CD | ARG | 122 | 11.282 | 23.244 | 40.281 | 1.00 60.61 |
| ATOM | 948 | N | ILE | 123 | 14.663 | 27.992 | 39.680 | 1.00 11.46 |
| ATOM | 949 | CA | ILE | 123 | 15.030 | 29.340 | 40.095 | 1.00 11.86 |
| ATOM | 950 | C | ILE | 123 | 13.991 | 30.450 | 39.835 | 1.00 10.54 |
| ATOM | 951 | O | ILE | 123 | 13.370 | 30.535 | 38.765 | 1.00 12.83 |
| ATOM | 952 | CB | ILE | 123 | 16.296 | 29.757 | 39.292 | 1.00 15.41 |
| ATOM | 953 | CG1 | ILE | 123 | 17.316 | 28.585 | 39.180 | 1.00 12.27 |
| ATOM | 954 | CG2 | ILE | 123 | 16.944 | 30.993 | 39.918 | 1.00 14.01 |
| ATOM | 955 | CD1 | ILE | 123 | 17.652 | 28.242 | 37.743 | 1.00 7.74 |
| ATOM | 956 | N | GLU | 124 | 13.953 | 31.358 | 40.793 | 1.00 11.36 |
| ATOM | 957 | CA | GLU | 124 | 13.189 | 32.752 | 40.700 | 1.00 15.20 |
| ATOM | 958 | C | GLU | 124 | 14.168 | 33.713 | 40.811 | 1.00 11.93 |
| ATOM | 959 | O | GLU | 124 | 14.919 | 33.797 | 41.780 | 1.00 15.61 |
| ATOM | 960 | CB | GLU | 124 | 12.028 | 32.677 | 41.751 | 1.00 19.74 |
| ATOM | 961 | CG | GLU | 124 | 12.387 | 33.337 | 43.089 | 1.00 72.94 |
| ATOM | 962 | N | LEU | 125 | 14.183 | 34.550 | 39.808 | 1.00 12.19 |
| ATOM | 963 | CA | LEU | 125 | 15.092 | 35.654 | 39.767 | 1.00 15.00 |
| ATOM | 964 | C | LEU | 125 | 14.420 | 37.011 | 39.722 | 1.00 19.35 |
| ATOM | 965 | O | LEU | 125 | 13.563 | 37.267 | 38.893 | 1.00 18.41 |
| ATOM | 966 | CB | LEU | 125 | 15.976 | 35.533 | 38.510 | 1.00 14.29 |
| ATOM | 967 | CG | LEU | 125 | 17.003 | 36.683 | 38.375 | 1.00 17.65 |
| ATOM | 968 | CD1 | LEU | 125 | 18.302 | 36.083 | 37.849 | 1.00 13.46 |
| ATOM | 969 | CD2 | LEU | 125 | 16.511 | 37.732 | 37.367 | 1.00 12.09 |
| ATOM | 970 | N | LYS | 126 | 14.890 | 37.897 | 40.554 | 1.00 12.73 |
| ATOM | 971 | CA | LYS | 126 | 14.391 | 39.260 | 40.579 | 1.00 15.92 |
| ATOM | 972 | C | LYS | 126 | 15.563 | 40.276 | 40.445 | 1.00 18.53 |
| ATOM | 973 | O | LYS | 126 | 16.489 | 40.246 | 41.246 | 1.00 19.86 |
| ATOM | 974 | CB | LYS | 126 | 13.611 | 39.487 | 41.877 | 1.00 17.31 |
| ATOM | 975 | CG | LYS | 126 | 12.853 | 40.786 | 41.923 | 1.00 33.94 |
| ATOM | 976 | CD | LYS | 126 | 11.366 | 40.601 | 41.675 | 1.00 60.87 |
| ATOM | 977 | CE | LYS | 126 | 10.652 | 41.929 | 41.521 | 1.00 52.70 |
| ATOM | 978 | NZ | LYS | 126 | 11.229 | 42.988 | 42.367 | 1.00 47.22 |

FIG. 5X

| | | | | | | | | |
|---|---|---|---|---|---|---|---|---|
| ATOM | 979 | N | GLY | 127 | 15.514 | 41.127 | 39.411 | 1.00 18.71 |
| ATOM | 980 | CA | GLY | 127 | 16.551 | 42.151 | 39.121 | 1.00 17.32 |
| ATOM | 981 | C | GLY | 127 | 16.012 | 43.572 | 39.272 | 1.00 25.32 |
| ATOM | 982 | O | GLY | 127 | 14.981 | 43.908 | 38.693 | 1.00 20.14 |
| ATOM | 983 | N | ILE | 128 | 16.706 | 44.404 | 40.070 | 1.00 18.42 |
| ATOM | 984 | CA | ILE | 128 | 16.282 | 45.787 | 40.243 | 1.00 21.04 |
| ATOM | 985 | C | ILE | 128 | 17.405 | 46.789 | 40.196 | 1.00 25.93 |
| ATOM | 986 | O | ILE | 128 | 18.562 | 46.496 | 40.429 | 1.00 19.37 |
| ATOM | 987 | CB | ILE | 128 | 15.482 | 46.052 | 41.504 | 1.00 23.82 |
| ATOM | 988 | CG1 | ILE | 128 | 16.408 | 45.888 | 42.701 | 1.00 23.86 |
| ATOM | 989 | CG2 | ILE | 128 | 14.272 | 45.120 | 41.577 | 1.00 28.95 |
| ATOM | 990 | CD1 | ILE | 128 | 15.824 | 46.391 | 44.013 | 1.00 29.89 |
| ATOM | 991 | N | ASP | 129 | 16.999 | 48.002 | 39.918 | 1.00 20.26 |
| ATOM | 992 | CA | ASP | 129 | 17.861 | 49.124 | 39.882 | 1.00 18.53 |
| ATOM | 993 | C | ASP | 129 | 18.864 | 49.086 | 38.801 | 1.00 20.36 |
| ATOM | 994 | O | ASP | 129 | 19.949 | 49.632 | 38.953 | 1.00 24.28 |
| ATOM | 995 | CB | ASP | 129 | 18.498 | 49.407 | 41.253 | 1.00 20.57 |
| ATOM | 996 | CG | ASP | 129 | 17.545 | 50.077 | 42.226 | 1.00 43.70 |
| ATOM | 997 | OD1 | ASP | 129 | 16.653 | 50.842 | 41.883 | 1.00 49.42 |
| ATOM | 998 | OD2 | ASP | 129 | 17.770 | 49.740 | 43.475 | 1.00 38.07 |
| ATOM | 999 | N | PHE | 130 | 18.510 | 48.493 | 37.693 | 1.00 16.40 |
| ATOM | 1000 | CA | PHE | 130 | 19.433 | 48.459 | 36.563 | 1.00 16.99 |
| ATOM | 1001 | C | PHE | 130 | 19.330 | 49.732 | 35.576 | 1.00 35.37 |
| ATOM | 1002 | O | PHE | 130 | 18.242 | 50.318 | 35.623 | 1.00 27.34 |
| ATOM | 1003 | CB | PHE | 130 | 19.248 | 47.223 | 35.657 | 1.00 18.07 |
| ATOM | 1004 | CG | PHE | 130 | 19.809 | 45.980 | 36.312 | 1.00 19.10 |
| ATOM | 1005 | CD1 | PHE | 130 | 19.021 | 45.210 | 37.171 | 1.00 16.15 |
| ATOM | 1006 | CD2 | PHE | 130 | 21.126 | 45.572 | 36.073 | 1.00 19.17 |
| ATOM | 1007 | CE1 | PHE | 130 | 19.536 | 44.074 | 37.801 | 1.00 23.37 |
| ATOM | 1008 | CE2 | PHE | 130 | 21.665 | 44.445 | 36.703 | 1.00 21.11 |
| ATOM | 1009 | CZ | PHE | 130 | 20.867 | 43.703 | 37.575 | 1.00 22.13 |
| ATOM | 1010 | N | LYS | 131 | 20.464 | 50.169 | 35.218 | 1.00 31.09 |
| ATOM | 1011 | CA | LYS | 131 | 20.477 | 51.371 | 34.400 | 1.00 27.52 |
| ATOM | 1012 | C | LYS | 131 | 20.105 | 51.045 | 32.992 | 1.00 25.57 |
| ATOM | 1013 | O | LYS | 131 | 20.695 | 50.169 | 32.343 | 1.00 22.97 |
| ATOM | 1014 | CB | LYS | 131 | 21.796 | 52.109 | 34.438 | 1.00 32.64 |
| ATOM | 1015 | CG | LYS | 131 | 22.153 | 52.633 | 35.813 | 1.00 38.34 |
| ATOM | 1016 | CD | LYS | 131 | 23.646 | 52.886 | 35.975 | 1.00 75.76 |
| ATOM | 1017 | N | GLU | 132 | 19.116 | 51.751 | 32.509 | 1.00 26.88 |
| ATOM | 1018 | CA | GLU | 132 | 18.623 | 51.484 | 31.189 | 1.00 28.42 |
| ATOM | 1019 | C | GLU | 132 | 19.710 | 51.514 | 30.140 | 1.00 36.19 |

FIG. 5Y

| | | | | | | | |
|---|---|---|---|---|---|---|---|
| ATOM | 1020 | O | GLU | 132 | 19.617 | 50.862 | 29.101 | 1.00 39.24 |
| ATOM | 1021 | CB | GLU | 132 | 17.374 | 52.331 | 30.830 | 1.00 29.04 |
| ATOM | 1022 | N | ASP | 133 | 20.752 | 52.254 | 30.438 | 1.00 40.08 |
| ATOM | 1023 | CA | ASP | 133 | 21.883 | 52.442 | 29.525 | 1.00 45.36 |
| ATOM | 1024 | C | ASP | 133 | 23.224 | 51.861 | 30.049 | 1.00 50.61 |
| ATOM | 1025 | O | ASP | 133 | 24.299 | 52.243 | 29.572 | 1.00 52.14 |
| ATOM | 1026 | CB | ASP | 133 | 22.063 | 53.946 | 29.332 | 1.00 50.45 |
| ATOM | 1027 | CG | ASP | 133 | 22.109 | 54.642 | 30.670 | 1.00 87.10 |
| ATOM | 1028 | OD1 | ASP | 133 | 21.408 | 54.314 | 31.624 | 1.00 91.27 |
| ATOM | 1029 | OD2 | ASP | 133 | 23.047 | 55.552 | 30.739 | 1.00 100.00 |
| ATOM | 1030 | N | GLY | 134 | 23.159 | 50.970 | 31.053 | 1.00 37.06 |
| ATOM | 1031 | CA | GLY | 134 | 24.349 | 50.376 | 31.639 | 1.00 30.22 |
| ATOM | 1032 | C | GLY | 134 | 24.845 | 49.228 | 30.803 | 1.00 23.10 |
| ATOM | 1033 | O | GLY | 134 | 24.360 | 48.990 | 29.685 | 1.00 19.23 |
| ATOM | 1034 | N | ASN | 135 | 25.807 | 48.486 | 31.341 | 1.00 18.66 |
| ATOM | 1035 | CA | ASN | 135 | 26.339 | 47.370 | 30.563 | 1.00 18.03 |
| ATOM | 1036 | C | ASN | 135 | 25.372 | 46.199 | 30.406 | 1.00 15.75 |
| ATOM | 1037 | O | ASN | 135 | 25.485 | 45.430 | 29.461 | 1.00 16.03 |
| ATOM | 1038 | CB | ASN | 135 | 27.665 | 46.883 | 31.139 | 1.00 19.27 |
| ATOM | 1039 | CG | ASN | 135 | 28.743 | 47.943 | 31.108 | 1.00 20.99 |
| ATOM | 1040 | OD1 | ASN | 135 | 28.969 | 48.595 | 30.078 | 1.00 25.69 |
| ATOM | 1041 | ND2 | ASN | 135 | 29.423 | 48.095 | 32.239 | 1.00 22.57 |
| ATOM | 1042 | N | ILE | 136 | 24.444 | 46.052 | 31.362 | 1.00 18.14 |
| ATOM | 1043 | CA | ILE | 136 | 23.494 | 44.924 | 31.368 | 1.00 19.78 |
| ATOM | 1044 | C | ILE | 136 | 22.331 | 45.086 | 30.384 | 1.00 23.76 |
| ATOM | 1045 | O | ILE | 136 | 22.178 | 44.313 | 29.395 | 1.00 22.53 |
| ATOM | 1046 | CB | ILE | 136 | 23.078 | 44.500 | 32.804 | 1.00 21.24 |
| ATOM | 1047 | CG1 | ILE | 136 | 24.230 | 43.728 | 33.423 | 1.00 28.44 |
| ATOM | 1048 | CG2 | ILE | 136 | 21.899 | 43.543 | 32.770 | 1.00 22.77 |
| ATOM | 1049 | CD1 | ILE | 136 | 25.346 | 44.596 | 33.935 | 1.00 12.39 |
| ATOM | 1050 | N | LEU | 137 | 21.543 | 46.117 | 30.640 | 1.00 18.21 |
| ATOM | 1051 | CA | LEU | 137 | 20.394 | 46.415 | 29.815 | 1.00 23.30 |
| ATOM | 1052 | C | LEU | 137 | 20.828 | 46.875 | 28.470 | 1.00 27.26 |
| ATOM | 1053 | O | LEU | 137 | 20.181 | 46.619 | 27.488 | 1.00 27.00 |
| ATOM | 1054 | CB | LEU | 137 | 19.442 | 47.430 | 30.490 | 1.00 21.74 |
| ATOM | 1055 | CG | LEU | 137 | 18.828 | 46.852 | 31.762 | 1.00 22.56 |
| ATOM | 1056 | CD1 | LEU | 137 | 17.856 | 47.837 | 32.415 | 1.00 22.27 |
| ATOM | 1057 | CD2 | LEU | 137 | 18.118 | 45.554 | 31.424 | 1.00 37.52 |
| ATOM | 1058 | N | GLY | 138 | 21.979 | 47.527 | 28.432 | 1.00 22.14 |
| ATOM | 1059 | CA | GLY | 138 | 22.510 | 48.033 | 27.187 | 1.00 20.03 |
| ATOM | 1060 | C | GLY | 138 | 23.157 | 46.959 | 26.368 | 1.00 20.16 |

FIG. 5Z

| ATOM | 1061 | O | GLY | 138 | 23.600 | 47.202 | 25.264 | 1.00 | 22.44 |
|------|------|------|-----|-----|--------|--------|--------|------|-------|
| ATOM | 1062 | N | HIS | 139 | 23.246 | 45.756 | 26.903 | 1.00 | 18.27 |
| ATOM | 1063 | CA | HIS | 139 | 23.859 | 44.655 | 26.148 | 1.00 | 20.24 |
| ATOM | 1064 | C | HIS | 139 | 25.301 | 44.929 | 25.616 | 1.00 | 20.13 |
| ATOM | 1065 | O | HIS | 139 | 25.605 | 44.745 | 24.439 | 1.00 | 17.97 |
| ATOM | 1066 | CB | HIS | 139 | 22.931 | 44.207 | 25.018 | 1.00 | 22.20 |
| ATOM | 1067 | CG | HIS | 139 | 21.708 | 43.551 | 25.550 | 1.00 | 25.52 |
| ATOM | 1068 | ND1 | HIS | 139 | 21.666 | 42.182 | 25.785 | 1.00 | 25.67 |
| ATOM | 1069 | CD2 | HIS | 139 | 20.525 | 44.092 | 25.927 | 1.00 | 28.09 |
| ATOM | 1070 | CE1 | HIS | 139 | 20.474 | 41.918 | 26.275 | 1.00 | 27.50 |
| ATOM | 1071 | NE2 | HIS | 139 | 19.766 | 43.044 | 26.382 | 1.00 | 29.53 |
| ATOM | 1072 | N | LYS | 140 | 26.187 | 45.311 | 26.525 | 1.00 | 23.51 |
| ATOM | 1073 | CA | LYS | 140 | 27.569 | 45.638 | 26.197 | 1.00 | 25.82 |
| ATOM | 1074 | C | LYS | 140 | 28.600 | 44.537 | 26.560 | 1.00 | 26.28 |
| ATOM | 1075 | O | LYS | 140 | 29.824 | 44.730 | 26.391 | 1.00 | 22.29 |
| ATOM | 1076 | CB | LYS | 140 | 27.977 | 46.937 | 26.911 | 1.00 | 27.56 |
| ATOM | 1077 | CG | LYS | 140 | 27.269 | 48.217 | 26.445 | 1.00 | 31.19 |
| ATOM | 1078 | CD | LYS | 140 | 27.234 | 49.254 | 27.582 | 1.00 | 51.32 |
| ATOM | 1079 | CE | LYS | 140 | 26.924 | 50.696 | 27.169 | 1.00 | 47.92 |
| ATOM | 1080 | NZ | LYS | 140 | 27.112 | 51.663 | 28.284 | 1.00 | 73.76 |
| ATOM | 1081 | N | LEU | 141 | 28.116 | 43.403 | 27.115 | 1.00 | 19.33 |
| ATOM | 1082 | CA | LEU | 141 | 28.987 | 42.296 | 27.559 | 1.00 | 14.32 |
| ATOM | 1083 | C | LEU | 141 | 29.366 | 41.401 | 26.427 | 1.00 | 20.75 |
| ATOM | 1084 | O | LEU | 141 | 28.526 | 41.087 | 25.620 | 1.00 | 19.01 |
| ATOM | 1085 | CB | LEU | 141 | 28.313 | 41.488 | 28.676 | 1.00 | 12.53 |
| ATOM | 1086 | CG | LEU | 141 | 27.979 | 42.352 | 29.875 | 1.00 | 17.54 |
| ATOM | 1087 | CD1 | LEU | 141 | 27.700 | 41.469 | 31.070 | 1.00 | 24.81 |
| ATOM | 1088 | CD2 | LEU | 141 | 29.116 | 43.310 | 30.182 | 1.00 | 27.50 |
| ATOM | 1089 | N | GLU | 142 | 30.644 | 40.987 | 26.346 | 1.00 | 14.76 |
| ATOM | 1090 | CA | GLU | 142 | 31.040 | 40.059 | 25.311 | 1.00 | 13.43 |
| ATOM | 1091 | C | GLU | 142 | 30.462 | 38.691 | 25.641 | 1.00 | 15.69 |
| ATOM | 1092 | O | GLU | 142 | 30.175 | 38.393 | 26.787 | 1.00 | 16.43 |
| ATOM | 1093 | CB | GLU | 142 | 32.558 | 39.866 | 25.204 | 1.00 | 14.73 |
| ATOM | 1094 | CG | GLU | 142 | 33.290 | 41.077 | 24.624 | 1.00 | 29.30 |
| ATOM | 1095 | CD | GLU | 142 | 34.787 | 41.003 | 24.825 | 1.00 | 56.32 |
| ATOM | 1096 | OE1 | GLU | 142 | 35.340 | 40.098 | 25.420 | 1.00 | 31.70 |
| ATOM | 1097 | OE2 | GLU | 142 | 35.430 | 42.015 | 24.321 | 1.00 | 34.10 |
| ATOM | 1098 | N | TYR | 143 | 30.365 | 37.873 | 24.632 | 1.00 | 16.30 |
| ATOM | 1099 | CA | TYR | 143 | 29.837 | 36.542 | 24.764 | 1.00 | 20.04 |
| ATOM | 1100 | C | TYR | 143 | 30.925 | 35.559 | 25.049 | 1.00 | 12.46 |
| ATOM | 1101 | O | TYR | 143 | 31.327 | 34.792 | 24.193 | 1.00 | 16.99 |

FIG. 5AA

| | | | | | | | |
|---|---|---|---|---|---|---|---|
| ATOM | 1102 | CB | TYR | 143 | 29.035 | 36.118 | 23.498 | 1.00 20.96 |
| ATOM | 1103 | CG | TYR | 143 | 28.187 | 34.857 | 23.674 | 1.00 16.12 |
| ATOM | 1104 | CD1 | TYR | 143 | 27.040 | 34.859 | 24.472 | 1.00 18.24 |
| ATOM | 1105 | CD2 | TYR | 143 | 28.512 | 33.684 | 22.986 | 1.00 12.87 |
| ATOM | 1106 | CE1 | TYR | 143 | 26.257 | 33.708 | 24.615 | 1.00 17.91 |
| ATOM | 1107 | CE2 | TYR | 143 | 27.735 | 32.530 | 23.104 | 1.00 16.58 |
| ATOM | 1108 | CZ | TYR | 143 | 26.603 | 32.551 | 23.914 | 1.00 17.35 |
| ATOM | 1109 | OH | TYR | 143 | 25.861 | 31.432 | 24.035 | 1.00 23.40 |
| ATOM | 1110 | N | ASN | 144 | 31.392 | 35.597 | 26.251 | 1.00 12.40 |
| ATOM | 1111 | CA | ASN | 144 | 32.428 | 34.703 | 26.689 | 1.00 12.05 |
| ATOM | 1112 | C | ASN | 144 | 32.433 | 34.675 | 28.193 | 1.00 15.75 |
| ATOM | 1113 | O | ASN | 144 | 31.637 | 35.369 | 28.837 | 1.00 14.58 |
| ATOM | 1114 | CB | ASN | 144 | 33.823 | 35.038 | 26.068 | 1.00 18.45 |
| ATOM | 1115 | CG | ASN | 144 | 34.310 | 36.445 | 26.374 | 1.00 18.98 |
| ATOM | 1116 | OD1 | ASN | 144 | 34.150 | 36.951 | 27.488 | 1.00 20.34 |
| ATOM | 1117 | ND2 | ASN | 144 | 34.891 | 37.085 | 25.382 | 1.00 23.02 |
| ATOM | 1118 | N | TYR | 145 | 33.311 | 33.876 | 28.773 | 1.00 12.16 |
| ATOM | 1119 | CA | TYR | 145 | 33.343 | 33.765 | 30.195 | 1.00 10.63 |
| ATOM | 1120 | C | TYR | 145 | 34.765 | 33.458 | 30.730 | 1.00 14.58 |
| ATOM | 1121 | O | TYR | 145 | 35.510 | 32.751 | 30.090 | 1.00 18.83 |
| ATOM | 1122 | CB | TYR | 145 | 32.404 | 32.627 | 30.571 | 1.00 9.76 |
| ATOM | 1123 | CG | TYR | 145 | 31.698 | 32.916 | 31.826 | 1.00 11.86 |
| ATOM | 1124 | CD1 | TYR | 145 | 30.515 | 33.658 | 31.808 | 1.00 9.04 |
| ATOM | 1125 | CD2 | TYR | 145 | 32.188 | 32.419 | 33.030 | 1.00 10.07 |
| ATOM | 1126 | CE1 | TYR | 145 | 29.860 | 33.948 | 32.999 | 1.00 8.36 |
| ATOM | 1127 | CE2 | TYR | 145 | 31.544 | 32.707 | 34.235 | 1.00 15.32 |
| ATOM | 1128 | CZ | TYR | 145 | 30.375 | 33.469 | 34.206 | 1.00 11.69 |
| ATOM | 1129 | OH | TYR | 145 | 29.730 | 33.735 | 35.376 | 1.00 15.23 |
| ATOM | 1130 | N | ASN | 146 | 35.086 | 33.931 | 31.933 | 1.00 15.36 |
| ATOM | 1131 | CA | ASN | 146 | 36.415 | 33.737 | 32.560 | 1.00 17.00 |
| ATOM | 1132 | C | ASN | 146 | 36.426 | 32.618 | 33.589 | 1.00 19.68 |
| ATOM | 1133 | O | ASN | 146 | 35.395 | 32.043 | 33.848 | 1.00 14.71 |
| ATOM | 1134 | CB | ASN | 146 | 36.844 | 35.062 | 33.235 | 1.00 11.89 |
| ATOM | 1135 | CG | ASN | 146 | 37.013 | 36.147 | 32.215 | 1.00 35.45 |
| ATOM | 1136 | OD1 | ASN | 146 | 37.533 | 35.890 | 31.105 | 1.00 31.63 |
| ATOM | 1137 | ND2 | ASN | 146 | 36.547 | 37.349 | 32.553 | 1.00 19.74 |
| ATOM | 1138 | N | SER | 147 | 37.630 | 32.338 | 34.201 | 1.00 12.09 |
| ATOM | 1139 | CA | SER | 147 | 37.804 | 31.320 | 35.266 | 1.00 8.55 |
| ATOM | 1140 | C | SER | 147 | 37.769 | 31.999 | 36.575 | 1.00 11.70 |
| ATOM | 1141 | O | SER | 147 | 38.219 | 33.125 | 36.671 | 1.00 16.56 |
| ATOM | 1142 | CB | SER | 147 | 39.148 | 30.540 | 35.129 | 1.00 9.87 |
| ATOM | 1143 | OG | SER | 147 | 39.212 | 29.980 | 33.828 | 1.00 33.20 |

FIG. 5AB

| ATOM | 1144 N | HIS | 148 | 37.195 | 31.365 | 37.583 | 1.00 | 5.53 |
|---|---|---|---|---|---|---|---|---|
| ATOM | 1145 CA | HIS | 148 | 37.090 | 31.998 | 38.850 | 1.00 | 8.06 |
| ATOM | 1146 C | HIS | 148 | 37.346 | 31.038 | 39.949 | 1.00 | 11.30 |
| ATOM | 1147 O | HIS | 148 | 37.328 | 29.844 | 39.754 | 1.00 | 16.87 |
| ATOM | 1148 CB | HIS | 148 | 35.648 | 32.608 | 39.067 | 1.00 | 11.29 |
| ATOM | 1149 CG | HIS | 148 | 35.215 | 33.554 | 37.972 | 1.00 | 10.84 |
| ATOM | 1150 ND1 | HIS | 148 | 34.548 | 33.121 | 36.836 | 1.00 | 12.77 |
| ATOM | 1151 CD2 | HIS | 148 | 35.403 | 34.887 | 37.851 | 1.00 | 8.82 |
| ATOM | 1152 CE1 | HIS | 148 | 34.389 | 34.178 | 36.060 | 1.00 | 8.84 |
| ATOM | 1153 NE2 | HIS | 148 | 34.882 | 35.242 | 36.647 | 1.00 | 8.82 |
| ATOM | 1154 N | ASN | 149 | 37.534 | 31.579 | 41.125 | 1.00 | 10.80 |
| ATOM | 1155 CA | ASN | 149 | 37.626 | 30.805 | 42.345 | 1.00 | 13.35 |
| ATOM | 1156 C | ASN | 149 | 36.409 | 31.157 | 43.205 | 1.00 | 14.47 |
| ATOM | 1157 O | ASN | 149 | 36.099 | 32.320 | 43.387 | 1.00 | 18.17 |
| ATOM | 1158 CB | ASN | 149 | 38.890 | 31.093 | 43.184 | 1.00 | 12.67 |
| ATOM | 1159 CG | ASN | 149 | 40.148 | 30.822 | 42.424 | 1.00 | 20.21 |
| ATOM | 1160 OD1 | ASN | 149 | 40.993 | 31.713 | 42.281 | 1.00 | 56.34 |
| ATOM | 1161 ND2 | ASN | 149 | 40.210 | 29.641 | 41.818 | 1.00 | 16.44 |
| ATOM | 1162 N | VAL | 150 | 35.773 | 30.144 | 43.741 | 1.00 | 14.65 |
| ATOM | 1163 CA | VAL | 150 | 34.588 | 30.262 | 44.552 | 1.00 | 12.92 |
| ATOM | 1164 C | VAL | 150 | 34.910 | 29.806 | 45.943 | 1.00 | 16.30 |
| ATOM | 1165 O | VAL | 150 | 35.257 | 28.665 | 46.147 | 1.00 | 17.83 |
| ATOM | 1166 CB | VAL | 150 | 33.482 | 29.382 | 43.914 | 1.00 | 15.22 |
| ATOM | 1167 CG1 | VAL | 150 | 32.252 | 29.297 | 44.765 | 1.00 | 14.09 |
| ATOM | 1168 CG2 | VAL | 150 | 33.172 | 29.791 | 42.464 | 1.00 | 10.94 |
| ATOM | 1169 N | TYR | 151 | 34.796 | 30.716 | 46.900 | 1.00 | 17.64 |
| ATOM | 1170 CA | TYR | 151 | 35.139 | 30.440 | 48.275 | 1.00 | 18.31 |
| ATOM | 1171 C | TYR | 151 | 34.003 | 29.917 | 49.117 | 1.00 | 24.35 |
| ATOM | 1172 O | TYR | 151 | 32.963 | 30.536 | 49.239 | 1.00 | 20.83 |
| ATOM | 1173 CB | TYR | 151 | 35.793 | 31.681 | 48.920 | 1.00 | 20.15 |
| ATOM | 1174 CG | TYR | 151 | 37.025 | 32.033 | 48.141 | 1.00 | 25.86 |
| ATOM | 1175 CD1 | TYR | 151 | 37.003 | 32.989 | 47.127 | 1.00 | 26.00 |
| ATOM | 1176 CD2 | TYR | 151 | 38.200 | 31.315 | 48.355 | 1.00 | 28.66 |
| ATOM | 1177 CE1 | TYR | 151 | 38.151 | 33.234 | 46.369 | 1.00 | 33.73 |
| ATOM | 1178 CE2 | TYR | 151 | 39.360 | 31.550 | 47.619 | 1.00 | 29.01 |
| ATOM | 1179 CZ | TYR | 151 | 39.325 | 32.512 | 46.618 | 1.00 | 29.55 |
| ATOM | 1180 OH | TYR | 151 | 40.449 | 32.737 | 45.877 | 1.00 | 38.69 |
| ATOM | 1181 N | ILE | 152 | 34.250 | 28.791 | 49.753 | 1.00 | 17.71 |
| ATOM | 1182 CA | ILE | 152 | 33.255 | 28.159 | 50.572 | 1.00 | 14.12 |
| ATOM | 1183 C | ILE | 152 | 33.619 | 28.056 | 52.000 | 1.00 | 18.51 |
| ATOM | 1184 O | ILE | 152 | 34.728 | 27.703 | 52.336 | 1.00 | 22.05 |

FIG. 5AC

| | | | | | | | |
|---|---|---|---|---|---|---|---|
| ATOM | 1185 | CB | ILE | 152 | 32.979 | 26.776 | 50.060 | 1.00 16.66 |
| ATOM | 1186 | CG1 | ILE | 152 | 32.431 | 26.875 | 48.638 | 1.00 11.30 |
| ATOM | 1187 | CG2 | ILE | 152 | 32.017 | 26.078 | 51.021 | 1.00 17.96 |
| ATOM | 1188 | CD1 | ILE | 152 | 32.377 | 25.559 | 47.949 | 1.00 13.48 |
| ATOM | 1189 | N | MSE | 153 | 32.623 | 28.278 | 52.841 | 1.00 17.41 |
| ATOM | 1190 | AC | MSE | 153 | 32.789 | 28.162 | 54.269 | 1.00 22.61 |
| ATOM | 1191 | C | MSE | 153 | 31.534 | 27.648 | 54.916 | 1.00 27.31 |
| ATOM | 1192 | O | MSE | 153 | 30.433 | 27.831 | 54.396 | 1.00 20.50 |
| ATOM | 1193 | CB | MSE | 153 | 33.145 | 29.490 | 54.855 | 1.00 19.11 |
| ATOM | 1194 | CG | MSE | 153 | 34.010 | 30.302 | 53.957 | 1.00 100.00 |
| ATOM | 1195 | SE | MSE | 153 | 34.060 | 32.117 | 54.524 | 1.00 100.00 |
| ATOM | 1196 | CE | MSE | 153 | 33.463 | 31.798 | 56.330 | 1.00 30.27 |
| ATOM | 1197 | N | ALA | 154 | 31.733 | 26.983 | 56.053 | 1.00 22.29 |
| ATOM | 1198 | CA | ALA | 154 | 30.669 | 26.389 | 56.796 | 1.00 22.66 |
| ATOM | 1199 | C | ALA | 154 | 29.820 | 27.401 | 57.552 | 1.00 29.00 |
| ATOM | 1200 | O | ALA | 154 | 30.274 | 28.457 | 57.960 | 1.00 27.02 |
| ATOM | 1201 | CB | ALA | 154 | 31.224 | 25.336 | 57.744 | 1.00 19.78 |
| ATOM | 1202 | N | ASP | 155 | 28.566 | 27.063 | 57.726 | 1.00 29.48 |
| ATOM | 1203 | CA | ASP | 155 | 27.669 | 27.887 | 58.484 | 1.00 32.18 |
| ATOM | 1204 | C | ASP | 155 | 26.976 | 27.019 | 59.511 | 1.00 44.51 |
| ATOM | 1205 | O | ASP | 155 | 25.898 | 26.492 | 59.274 | 1.00 39.56 |
| ATOM | 1206 | CB | ASP | 155 | 26.659 | 28.617 | 57.597 | 1.00 31.70 |
| ATOM | 1207 | CG | ASP | 155 | 26.140 | 29.851 | 58.247 | 1.00 49.89 |
| ATOM | 1208 | OD1 | ASP | 155 | 26.595 | 30.297 | 59.277 | 1.00 46.67 |
| ATOM | 1209 | OD2 | ASP | 155 | 25.187 | 30.422 | 57.565 | 1.00 76.07 |
| ATOM | 1210 | N | LYS | 156 | 27.646 | 26.816 | 60.629 | 1.00 46.37 |
| ATOM | 1211 | CA | LYS | 156 | 27.116 | 25.954 | 61.654 | 1.00 53.23 |
| ATOM | 1212 | C | LYS | 156 | 25.750 | 26.369 | 62.224 | 1.00 65.62 |
| ATOM | 1213 | O | LYS | 156 | 25.012 | 25.520 | 62.703 | 1.00 65.54 |
| ATOM | 1214 | CB | LYS | 156 | 28.147 | 25.612 | 62.725 | 1.00 59.51 |
| ATOM | 1215 | N | GLN | 157 | 25.398 | 27.655 | 62.138 | 1.00 68.32 |
| ATOM | 1216 | CA | GLN | 157 | 24.119 | 28.135 | 62.670 | 1.00 73.00 |
| ATOM | 1217 | C | GLN | 157 | 22.891 | 27.767 | 61.817 | 1.00 87.53 |
| ATOM | 1218 | O | GLN | 157 | 21.778 | 27.547 | 62.325 | 1.00 96.16 |
| ATOM | 1219 | N | LYS | 158 | 23.095 | 27.725 | 60.506 | 1.00 72.49 |
| ATOM | 1220 | CA | LYS | 158 | 22.040 | 27.386 | 59.593 | 1.00 66.19 |
| ATOM | 1221 | C | LYS | 158 | 22.235 | 25.985 | 59.040 | 1.00 58.21 |
| ATOM | 1222 | O | LYS | 158 | 21.447 | 25.524 | 58.226 | 1.00 59.85 |
| ATOM | 1223 | N | ASN | 159 | 23.303 | 25.294 | 59.502 | 1.00 40.00 |
| ATOM | 1224 | CA | ASN | 159 | 23.582 | 23.944 | 59.012 | 1.00 36.67 |
| ATOM | 1225 | C | ASN | 159 | 23.755 | 24.002 | 57.500 | 1.00 34.11 |

FIG. 5AD

| | | | | | | | |
|---|---|---|---|---|---|---|---|
| ATOM | 1226 | C O | ASN | 159 | 23.223 | 23.167 | 56.754 | 1.00 31.69 |
| ATOM | 1227 | CB | ASN | 159 | 22.431 | 22.952 | 59.367 | 1.00 46.42 |
| ATOM | 1228 | CG | ASN | 159 | 22.842 | 21.485 | 59.428 | 1.00 80.46 |
| ATOM | 1229 | OD1 | ASN | 159 | 23.850 | 21.121 | 60.054 | 1.00 100.00 |
| ATOM | 1230 | ND2 | ASN | 159 | 22.003 | 20.620 | 58.854 | 1.00 58.09 |
| ATOM | 1231 | N | GLY | 160 | 24.474 | 25.044 | 57.062 | 1.00 22.34 |
| ATOM | 1232 | CA | GLY | 160 | 24.686 | 25.247 | 55.663 | 1.00 17.58 |
| ATOM | 1233 | C | GLY | 160 | 26.055 | 25.791 | 55.433 | 1.00 26.75 |
| ATOM | 1234 | O | GLY | 160 | 26.960 | 25.664 | 56.271 | 1.00 25.57 |
| ATOM | 1235 | N | ILE | 161 | 26.200 | 26.395 | 54.277 | 1.00 23.28 |
| ATOM | 1236 | CA | ILE | 161 | 27.442 | 26.975 | 53.909 | 1.00 16.45 |
| ATOM | 1237 | C | ILE | 161 | 27.200 | 28.354 | 53.395 | 1.00 15.77 |
| ATOM | 1238 | O | ILE | 161 | 26.118 | 28.680 | 52.962 | 1.00 15.95 |
| ATOM | 1239 | CB | ILE | 161 | 28.129 | 26.117 | 52.864 | 1.00 19.27 |
| ATOM | 1240 | CG1 | ILE | 161 | 27.237 | 26.016 | 51.619 | 1.00 18.53 |
| ATOM | 1241 | CG2 | ILE | 161 | 28.351 | 24.735 | 53.445 | 1.00 21.96 |
| ATOM | 1242 | CD1 | ILE | 161 | 28.009 | 25.614 | 50.350 | 1.00 14.44 |
| ATOM | 1243 | N | LYS | 162 | 28.226 | 29.169 | 53.471 | 1.00 17.86 |
| ATOM | 1244 | CA | LYS | 162 | 28.187 | 30.508 | 52.948 | 1.00 14.42 |
| ATOM | 1245 | C | LYS | 162 | 29.216 | 30.524 | 51.857 | 1.00 17.73 |
| ATOM | 1246 | O | LYS | 162 | 30.249 | 29.875 | 51.991 | 1.00 19.16 |
| ATOM | 1247 | CB | LYS | 162 | 28.480 | 31.540 | 54.055 | 1.00 18.15 |
| ATOM | 1248 | CG | LYS | 162 | 27.221 | 31.963 | 54.796 | 1.00 42.08 |
| ATOM | 1249 | CD | LYS | 162 | 27.493 | 32.787 | 56.039 | 1.00 70.42 |
| ATOM | 1250 | N | VAL | 163 | 28.911 | 31.176 | 50.759 | 1.00 13.74 |
| ATOM | 1251 | CA | VAL | 163 | 29.798 | 31.201 | 49.629 | 1.00 11.95 |
| ATOM | 1252 | C | VAL | 163 | 29.928 | 32.610 | 49.103 | 1.00 19.30 |
| ATOM | 1253 | O | VAL | 163 | 28.944 | 33.318 | 48.983 | 1.00 19.84 |
| ATOM | 1254 | CB | VAL | 163 | 29.249 | 30.268 | 48.532 | 1.00 15.89 |
| ATOM | 1255 | CG1 | VAL | 163 | 30.105 | 30.277 | 47.261 | 1.00 12.09 |
| ATOM | 1256 | CG2 | VAL | 163 | 29.029 | 28.852 | 49.077 | 1.00 15.86 |
| ATOM | 1257 | N | ASN | 164 | 31.146 | 32.999 | 48.733 | 1.00 14.03 |
| ATOM | 1258 | CA | ASN | 164 | 31.382 | 34.310 | 48.195 | 1.00 15.58 |
| ATOM | 1259 | C | ASN | 164 | 32.396 | 34.271 | 47.050 | 1.00 20.08 |
| ATOM | 1260 | O | ASN | 164 | 33.268 | 33.386 | 46.988 | 1.00 23.49 |
| ATOM | 1261 | CB | ASN | 164 | 31.732 | 35.325 | 49.308 | 1.00 20.52 |
| ATOM | 1262 | CG | ASN | 164 | 33.196 | 35.697 | 49.330 | 1.00 89.21 |
| ATOM | 1263 | OD1 | ASN | 164 | 34.020 | 34.987 | 49.929 | 1.00 100.00 |
| ATOM | 1264 | ND2 | ASN | 164 | 33.515 | 36.831 | 48.700 | 1.00 91.46 |
| ATOM | 1265 | N | PHE | 165 | 32.244 | 35.207 | 46.109 | 1.00 17.37 |
| ATOM | 1266 | CA | PHE | 165 | 33.133 | 35.301 | 44.953 | 1.00 10.86 |

FIG. 5AE

| | | | | | | | |
|---|---|---|---|---|---|---|---|
| ATOM | 1267 | C   | PHE | 165 | 32.751 | 36.445 | 44.071 | 1.00 15.53 |
| ATOM | 1268 | O   | PHE | 165 | 31.686 | 37.020 | 44.251 | 1.00 17.16 |
| ATOM | 1269 | CB  | PHE | 165 | 33.207 | 33.960 | 44.187 | 1.00 12.86 |
| ATOM | 1270 | CG  | PHE | 165 | 31.862 | 33.486 | 43.622 | 1.00 14.35 |
| ATOM | 1271 | CD1 | PHE | 165 | 31.510 | 33.749 | 42.293 | 1.00 14.61 |
| ATOM | 1272 | CD2 | PHE | 165 | 30.978 | 32.757 | 44.413 | 1.00 13.56 |
| ATOM | 1273 | CE1 | PHE | 165 | 30.300 | 33.297 | 41.759 | 1.00 22.67 |
| ATOM | 1274 | CE2 | PHE | 165 | 29.774 | 32.282 | 43.893 | 1.00 15.78 |
| ATOM | 1275 | CZ  | PHE | 165 | 29.426 | 32.572 | 42.573 | 1.00 16.20 |
| ATOM | 1276 | N   | LYS | 166 | 33.641 | 36.799 | 43.132 | 1.00 10.79 |
| ATOM | 1277 | CA  | LYS | 166 | 33.417 | 37.864 | 42.162 | 1.00 10.74 |
| ATOM | 1278 | C   | LYS | 166 | 33.603 | 37.344 | 40.774 | 1.00 15.95 |
| ATOM | 1279 | O   | LYS | 166 | 34.602 | 36.727 | 40.470 | 1.00 22.80 |
| ATOM | 1280 | CB  | LYS | 166 | 34.387 | 39.055 | 42.249 | 1.00 16.61 |
| ATOM | 1281 | CG  | LYS | 166 | 34.573 | 39.688 | 43.573 | 1.00 18.11 |
| ATOM | 1282 | CD  | LYS | 166 | 35.540 | 40.875 | 43.454 | 1.00 32.56 |
| ATOM | 1283 | CE  | LYS | 166 | 35.272 | 41.966 | 44.476 | 1.00 48.19 |
| ATOM | 1284 | NZ  | LYS | 166 | 34.823 | 41.435 | 45.782 | 1.00 85.81 |
| ATOM | 1285 | N   | ILE | 167 | 32.703 | 37.704 | 39.911 | 1.00  9.75 |
| ATOM | 1286 | CA  | ILE | 167 | 32.768 | 37.340 | 38.558 | 1.00  9.35 |
| ATOM | 1287 | C   | ILE | 167 | 33.203 | 38.542 | 37.823 | 1.00 14.36 |
| ATOM | 1288 | O   | ILE | 167 | 32.811 | 39.640 | 38.170 | 1.00 16.22 |
| ATOM | 1289 | CB  | ILE | 167 | 31.379 | 36.929 | 38.005 | 1.00 13.16 |
| ATOM | 1290 | CG1 | ILE | 167 | 30.909 | 35.624 | 38.669 | 1.00 13.02 |
| ATOM | 1291 | CG2 | ILE | 167 | 31.423 | 36.786 | 36.472 | 1.00  7.91 |
| ATOM | 1292 | CD1 | ILE | 167 | 31.773 | 34.415 | 38.344 | 1.00 19.57 |
| ATOM | 1293 | N   | ARG | 168 | 34.005 | 38.299 | 36.815 | 1.00 12.19 |
| ATOM | 1294 | CA  | ARG | 168 | 34.500 | 39.308 | 35.945 | 1.00 15.07 |
| ATOM | 1295 | C   | ARG | 168 | 33.948 | 39.122 | 34.528 | 1.00 16.64 |
| ATOM | 1296 | O   | ARG | 168 | 34.278 | 38.156 | 33.836 | 1.00 17.70 |
| ATOM | 1297 | CB  | ARG | 168 | 36.024 | 39.287 | 35.944 | 1.00 16.54 |
| ATOM | 1298 | CG  | ARG | 168 | 36.580 | 39.632 | 37.321 | 1.00 25.54 |
| ATOM | 1299 | CD  | ARG | 168 | 37.894 | 38.910 | 37.601 | 1.00 63.52 |
| ATOM | 1300 | NE  | ARG | 168 | 38.380 | 38.191 | 36.416 | 1.00 73.52 |
| ATOM | 1301 | CZ  | ARG | 168 | 38.764 | 36.926 | 36.416 | 1.00 67.92 |
| ATOM | 1302 | NH1 | ARG | 168 | 38.795 | 36.192 | 37.527 | 1.00 57.44 |
| ATOM | 1303 | NH2 | ARG | 168 | 39.192 | 36.375 | 35.271 | 1.00 59.15 |
| ATOM | 1304 | N   | HIS | 169 | 33.090 | 40.064 | 34.098 | 1.00 14.88 |
| ATOM | 1305 | CA  | HIS | 169 | 32.505 | 40.025 | 32.758 | 1.00 13.24 |
| ATOM | 1306 | C   | HIS | 169 | 33.214 | 41.001 | 31.839 | 1.00 12.64 |
| ATOM | 1307 | O   | HIS | 169 | 33.306 | 42.203 | 32.121 | 1.00 14.99 |

FIG. 5AF

| | | | | | | | |
|---|---|---|---|---|---|---|---|
| ATOM | 1308 | CB  HIS | 169 | 30.970 | 40.374 | 32.760 | 1.00 10.46 |
| ATOM | 1309 | CG  HIS | 169 | 30.097 | 39.474 | 33.573 | 1.00  6.54 |
| ATOM | 1310 | ND1 HIS | 169 | 29.724 | 38.246 | 33.111 | 1.00 12.63 |
| ATOM | 1311 | CD2 HIS | 169 | 29.474 | 39.695 | 34.764 | 1.00 10.21 |
| ATOM | 1312 | CE1 HIS | 169 | 28.892 | 37.718 | 34.031 | 1.00 10.53 |
| ATOM | 1313 | NE2 HIS | 169 | 28.734 | 38.566 | 35.063 | 1.00 11.84 |
| ATOM | 1314 | N    ASN | 170 | 33.691 | 40.513 | 30.737 | 1.00 10.66 |
| ATOM | 1315 | CA   ASN | 170 | 34.349 | 41.368 | 29.812 | 1.00 15.87 |
| ATOM | 1316 | C    ASN | 170 | 33.356 | 42.224 | 29.067 | 1.00 25.06 |
| ATOM | 1317 | O    ASN | 170 | 32.386 | 41.701 | 28.537 | 1.00 16.60 |
| ATOM | 1318 | CB   ASN | 170 | 35.110 | 40.550 | 28.755 | 1.00 19.60 |
| ATOM | 1319 | CG   ASN | 170 | 36.245 | 39.717 | 29.312 | 1.00 18.70 |
| ATOM | 1320 | OD1 ASN | 170 | 36.702 | 38.752 | 28.684 | 1.00 48.29 |
| ATOM | 1321 | ND2 ASN | 170 | 36.695 | 40.073 | 30.480 | 1.00 19.13 |
| ATOM | 1322 | N    ILE | 171 | 33.662 | 43.527 | 28.947 | 1.00 18.75 |
| ATOM | 1323 | CA   ILE | 171 | 32.848 | 44.460 | 28.168 | 1.00 16.74 |
| ATOM | 1324 | C    ILE | 171 | 33.459 | 44.638 | 26.791 | 1.00 19.51 |
| ATOM | 1325 | O    ILE | 171 | 34.643 | 44.596 | 26.642 | 1.00 21.06 |
| ATOM | 1326 | CB   ILE | 171 | 32.713 | 45.804 | 28.842 | 1.00 20.46 |
| ATOM | 1327 | CG1 ILE | 171 | 32.089 | 45.617 | 30.193 | 1.00 24.79 |
| ATOM | 1328 | CG2 ILE | 171 | 31.852 | 46.727 | 27.997 | 1.00 19.03 |
| ATOM | 1329 | CD1 ILE | 171 | 32.630 | 46.599 | 31.229 | 1.00 41.65 |
| ATOM | 1330 | N    GLU | 172 | 32.632 | 44.818 | 25.804 | 1.00 16.54 |
| ATOM | 1331 | CA   GLU | 172 | 33.034 | 44.933 | 24.420 | 1.00 17.00 |
| ATOM | 1332 | C    GLU | 172 | 34.110 | 45.967 | 24.147 | 1.00 26.80 |
| ATOM | 1333 | O    GLU | 172 | 34.776 | 45.898 | 23.125 | 1.00 29.20 |
| ATOM | 1334 | CB   GLU | 172 | 31.813 | 45.165 | 23.509 | 1.00 22.46 |
| ATOM | 1335 | CG   GLU | 172 | 31.122 | 46.531 | 23.786 | 1.00 58.53 |
| ATOM | 1336 | CD   GLU | 172 | 29.871 | 46.783 | 22.933 | 1.00 100.00 |
| ATOM | 1337 | OE1 GLU | 172 | 29.415 | 45.970 | 22.156 | 1.00 100.00 |
| ATOM | 1338 | OE2 GLU | 172 | 29.370 | 47.982 | 23.149 | 1.00 100.00 |
| ATOM | 1339 | N    ASP | 173 | 34.277 | 46.934 | 25.034 | 1.00 24.41 |
| ATOM | 1340 | CA   ASP | 173 | 35.292 | 47.978 | 24.852 | 1.00 25.03 |
| ATOM | 1341 | C    ASP | 173 | 36.651 | 47.624 | 25.455 | 1.00 33.40 |
| ATOM | 1342 | O    ASP | 173 | 37.561 | 48.451 | 25.518 | 1.00 30.42 |
| ATOM | 1343 | CB   ASP | 173 | 34.822 | 49.319 | 25.401 | 1.00 23.30 |
| ATOM | 1344 | CG   ASP | 173 | 34.743 | 49.358 | 26.912 | 1.00 32.47 |
| ATOM | 1345 | OD1 ASP | 173 | 34.406 | 50.355 | 27.513 | 1.00 37.58 |
| ATOM | 1346 | OD2 ASP | 173 | 34.949 | 48.196 | 27.504 | 1.00 49.22 |
| ATOM | 1347 | N    GLY | 174 | 36.766 | 46.410 | 25.956 | 1.00 23.87 |
| ATOM | 1348 | CA   GLY | 174 | 38.019 | 45.994 | 26.537 | 1.00 21.30 |

FIG. 5AG

| | | | | | | | |
|---|---|---|---|---|---|---|---|
| ATOM | 1349 C | GLY | 174 | 38.012 | 46.090 | 28.044 | 1.00 19.99 |
| ATOM | 1350 O | GLY | 174 | 38.927 | 45.585 | 28.709 | 1.00 20.45 |
| ATOM | 1351 N | SER | 175 | 36.972 | 46.767 | 28.598 | 1.00 13.88 |
| ATOM | 1352 CA | SER | 175 | 36.898 | 46.931 | 30.034 | 1.00 8.70 |
| ATOM | 1353 C | SER | 175 | 36.296 | 45.728 | 30.765 | 1.00 17.30 |
| ATOM | 1354 O | SER | 175 | 36.136 | 44.655 | 30.175 | 1.00 18.77 |
| ATOM | 1355 CB | SER | 175 | 36.288 | 48.235 | 30.450 | 1.00 14.07 |
| ATOM | 1356 OG | SER | 175 | 36.360 | 48.316 | 31.865 | 1.00 24.79 |
| ATOM | 1357 N | VAL | 176 | 35.963 | 45.912 | 32.051 | 1.00 13.74 |
| ATOM | 1358 CA | VAL | 176 | 35.415 | 44.826 | 32.864 | 1.00 16.46 |
| ATOM | 1359 C | VAL | 176 | 34.191 | 45.204 | 33.703 | 1.00 22.46 |
| ATOM | 1360 O | VAL | 176 | 34.159 | 46.254 | 34.334 | 1.00 21.31 |
| ATOM | 1361 CB | VAL | 176 | 36.477 | 44.285 | 33.818 | 1.00 24.43 |
| ATOM | 1362 CG1 | VAL | 176 | 35.847 | 43.344 | 34.827 | 1.00 27.45 |
| ATOM | 1363 CG2 | VAL | 176 | 37.532 | 43.536 | 33.035 | 1.00 25.65 |
| ATOM | 1364 N | GLN | 177 | 33.234 | 44.269 | 33.787 | 1.00 15.47 |
| ATOM | 1365 CA | GLN | 177 | 32.048 | 44.430 | 34.647 | 1.00 15.40 |
| ATOM | 1366 C | GLN | 177 | 32.102 | 43.457 | 35.813 | 1.00 10.60 |
| ATOM | 1367 O | GLN | 177 | 32.027 | 42.243 | 35.634 | 1.00 13.65 |
| ATOM | 1368 CB | GLN | 177 | 30.709 | 44.283 | 33.872 | 1.00 15.57 |
| ATOM | 1369 CG | GLN | 177 | 29.468 | 44.294 | 34.828 | 1.00 19.13 |
| ATOM | 1370 CD | GLN | 177 | 29.108 | 45.678 | 35.361 | 1.00 14.91 |
| ATOM | 1371 OE1 | GLN | 177 | 28.759 | 46.588 | 34.574 | 1.00 20.17 |
| ATOM | 1372 NE2 | GLN | 177 | 29.128 | 45.821 | 36.690 | 1.00 17.28 |
| ATOM | 1373 N | LEU | 178 | 32.227 | 43.993 | 37.018 | 1.00 8.17 |
| ATOM | 1374 CA | LEU | 178 | 32.313 | 43.180 | 38.181 | 1.00 16.66 |
| ATOM | 1375 C | LEU | 178 | 30.954 | 42.786 | 38.712 | 1.00 20.93 |
| ATOM | 1376 O | LEU | 178 | 30.033 | 43.608 | 38.753 | 1.00 14.66 |
| ATOM | 1377 CB | LEU | 178 | 33.089 | 43.896 | 39.293 | 1.00 20.63 |
| ATOM | 1378 CG | LEU | 178 | 34.286 | 43.110 | 39.815 | 1.00 39.28 |
| ATOM | 1379 CD1 | LEU | 178 | 33.831 | 42.087 | 40.852 | 1.00 45.14 |
| ATOM | 1380 CD2 | LEU | 178 | 35.018 | 42.426 | 38.648 | 1.00 39.52 |
| ATOM | 1381 N | ALA | 179 | 30.869 | 41.550 | 39.171 | 1.00 16.72 |
| ATOM | 1382 CA | ALA | 179 | 29.652 | 41.033 | 39.754 | 1.00 15.55 |
| ATOM | 1383 C | ALA | 179 | 29.932 | 40.277 | 41.040 | 1.00 15.70 |
| ATOM | 1384 O | ALA | 179 | 30.337 | 39.119 | 41.028 | 1.00 15.91 |
| ATOM | 1385 CB | ALA | 179 | 28.853 | 40.197 | 38.731 | 1.00 14.08 |
| ATOM | 1386 N | ASP | 180 | 29.694 | 40.946 | 42.155 | 1.00 8.88 |
| ATOM | 1387 CA | ASP | 180 | 29.897 | 40.407 | 43.480 | 1.00 7.18 |
| ATOM | 1388 C | ASP | 180 | 28.802 | 39.460 | 43.891 | 1.00 17.07 |
| ATOM | 1389 O | ASP | 180 | 27.651 | 39.844 | 43.987 | 1.00 18.22 |

FIG. 5AH

| | | | | | | | |
|---|---|---|---|---|---|---|---|
| ATOM | 1390 | CB | ASP | 180 | 29.934 | 41.509 | 44.509 | 1.00 13.06 |
| ATOM | 1391 | CG | ASP | 180 | 31.285 | 41.902 | 44.935 | 1.00 46.28 |
| ATOM | 1392 | OD1 | ASP | 180 | 31.981 | 41.206 | 45.655 | 1.00 60.46 |
| ATOM | 1393 | OD2 | ASP | 180 | 31.574 | 43.121 | 44.560 | 1.00 46.61 |
| ATOM | 1394 | N | HIS | 181 | 29.173 | 38.242 | 44.197 | 1.00 14.51 |
| ATOM | 1395 | CA | HIS | 181 | 28.213 | 37.223 | 44.575 | 1.00 10.49 |
| ATOM | 1396 | C | HIS | 181 | 28.218 | 36.897 | 46.049 | 1.00 14.28 |
| ATOM | 1397 | O | HIS | 181 | 29.255 | 36.580 | 46.607 | 1.00 17.40 |
| ATOM | 1398 | CB | HIS | 181 | 28.450 | 35.915 | 43.769 | 1.00 9.89 |
| ATOM | 1399 | CG | HIS | 181 | 28.077 | 35.972 | 42.328 | 1.00 10.38 |
| ATOM | 1400 | ND1 | HIS | 181 | 28.606 | 36.926 | 41.455 | 1.00 12.24 |
| ATOM | 1401 | CD2 | HIS | 181 | 27.279 | 35.146 | 41.606 | 1.00 10.42 |
| ATOM | 1402 | CE1 | HIS | 181 | 28.093 | 36.678 | 40.269 | 1.00 9.97 |
| ATOM | 1403 | NE2 | HIS | 181 | 27.314 | 35.594 | 40.316 | 1.00 9.38 |
| ATOM | 1404 | N | TYR | 182 | 27.029 | 36.897 | 46.668 | 1.00 10.40 |
| ATOM | 1405 | CA | TYR | 182 | 26.848 | 36.518 | 48.062 | 1.00 13.86 |
| ATOM | 1406 | C | TYR | 182 | 25.871 | 35.393 | 48.089 | 1.00 20.61 |
| ATOM | 1407 | O | TYR | 182 | 24.819 | 35.520 | 47.532 | 1.00 16.35 |
| ATOM | 1408 | CB | TYR | 182 | 26.359 | 37.664 | 48.934 | 1.00 21.12 |
| ATOM | 1409 | CG | TYR | 182 | 27.421 | 38.693 | 49.062 | 1.00 34.16 |
| ATOM | 1410 | CD1 | TYR | 182 | 27.521 | 39.715 | 48.120 | 1.00 46.06 |
| ATOM | 1411 | CD2 | TYR | 182 | 28.389 | 38.616 | 50.064 | 1.00 38.56 |
| ATOM | 1412 | CE1 | TYR | 182 | 28.532 | 40.674 | 48.197 | 1.00 57.53 |
| ATOM | 1413 | CE2 | TYR | 182 | 29.418 | 39.559 | 50.147 | 1.00 40.76 |
| ATOM | 1414 | CZ | TYR | 182 | 29.480 | 40.594 | 49.216 | 1.00 54.61 |
| ATOM | 1415 | OH | TYR | 182 | 30.461 | 41.534 | 49.308 | 1.00 61.92 |
| ATOM | 1416 | N | GLN | 183 | 26.246 | 34.277 | 48.686 | 1.00 17.63 |
| ATOM | 1417 | CA | GLN | 183 | 25.410 | 33.104 | 48.583 | 1.00 16.37 |
| ATOM | 1418 | C | GLN | 183 | 25.289 | 32.311 | 49.863 | 1.00 21.39 |
| ATOM | 1419 | O | GLN | 183 | 26.260 | 32.174 | 50.623 | 1.00 19.86 |
| ATOM | 1420 | CB | GLN | 183 | 25.984 | 32.219 | 47.422 | 1.00 13.33 |
| ATOM | 1421 | CG | GLN | 183 | 25.651 | 30.688 | 47.457 | 1.00 17.38 |
| ATOM | 1422 | CD | GLN | 183 | 26.411 | 29.884 | 46.389 | 1.00 17.27 |
| ATOM | 1423 | OE1 | GLN | 183 | 26.975 | 30.454 | 45.456 | 1.00 13.80 |
| ATOM | 1424 | NE2 | GLN | 183 | 26.361 | 28.553 | 46.473 | 1.00 13.94 |
| ATOM | 1425 | N | GLN | 184 | 24.080 | 31.739 | 50.055 | 1.00 19.74 |
| ATOM | 1426 | CA | GLN | 184 | 23.760 | 30.829 | 51.168 | 1.00 16.55 |
| ATOM | 1427 | C | GLN | 184 | 23.033 | 29.582 | 50.658 | 1.00 13.60 |
| ATOM | 1428 | O | GLN | 184 | 22.219 | 29.640 | 49.747 | 1.00 18.01 |
| ATOM | 1429 | CB | GLN | 184 | 22.949 | 31.444 | 52.330 | 1.00 20.11 |
| ATOM | 1430 | CG | GLN | 184 | 23.364 | 32.855 | 52.768 | 1.00 74.84 |

FIG. 5AI

| | | | | | | | |
|---|---|---|---|---|---|---|---|
| ATOM | 1431 | CD | GLN | 184 | 22.312 | 33.517 | 53.657 | 1.00 100.00 |
| ATOM | 1432 | OE1 | GLN | 184 | 21.159 | 33.054 | 53.752 | 1.00 97.99 |
| ATOM | 1433 | NE2 | GLN | 184 | 22.639 | 34.625 | 54.286 | 1.00 100.00 |
| ATOM | 1434 | N | ASN | 185 | 23.418 | 28.446 | 51.207 | 1.00 14.76 |
| ATOM | 1435 | CA | ASN | 185 | 22.831 | 27.155 | 50.887 | 1.00 13.86 |
| ATOM | 1436 | C | ASN | 185 | 22.421 | 26.463 | 52.166 | 1.00 16.06 |
| ATOM | 1437 | O | ASN | 185 | 23.176 | 26.402 | 53.172 | 1.00 17.39 |
| ATOM | 1438 | CB | ASN | 185 | 23.761 | 26.212 | 50.119 | 1.00 15.20 |
| ATOM | 1439 | CG | ASN | 185 | 24.110 | 26.696 | 48.748 | 1.00 12.75 |
| ATOM | 1440 | OD1 | ASN | 185 | 24.704 | 27.758 | 48.592 | 1.00 22.56 |
| ATOM | 1441 | ND2 | ASN | 185 | 23.830 | 25.868 | 47.763 | 1.00 17.70 |
| ATOM | 1442 | N | THR | 186 | 21.227 | 25.941 | 52.139 | 1.00 18.01 |
| ATOM | 1443 | CA | THR | 186 | 20.707 | 25.227 | 53.288 | 1.00 17.40 |
| ATOM | 1444 | C | THR | 186 | 19.976 | 24.010 | 52.824 | 1.00 23.63 |
| ATOM | 1445 | O | THR | 186 | 19.389 | 23.991 | 51.730 | 1.00 24.57 |
| ATOM | 1446 | CB | THR | 186 | 19.856 | 26.100 | 54.206 | 1.00 28.82 |
| ATOM | 1447 | OG1 | THR | 186 | 18.874 | 26.752 | 53.446 | 1.00 35.65 |
| ATOM | 1448 | CG2 | THR | 186 | 20.753 | 27.121 | 54.903 | 1.00 28.86 |
| ATOM | 1449 | N | PRO | 187 | 20.101 | 22.951 | 53.620 | 1.00 22.40 |
| ATOM | 1450 | CA | PRO | 187 | 19.504 | 21.683 | 53.269 | 1.00 20.28 |
| ATOM | 1451 | C | PRO | 187 | 17.988 | 21.757 | 53.288 | 1.00 22.41 |
| ATOM | 1452 | O | PRO | 187 | 17.390 | 22.518 | 54.071 | 1.00 25.07 |
| ATOM | 1453 | CB | PRO | 187 | 19.977 | 20.682 | 54.337 | 1.00 19.79 |
| ATOM | 1454 | CG | PRO | 187 | 20.840 | 21.449 | 55.338 | 1.00 26.98 |
| ATOM | 1455 | CD | PRO | 187 | 20.786 | 22.918 | 54.949 | 1.00 22.04 |
| ATOM | 1456 | N | ILE | 188 | 17.382 | 20.957 | 52.453 | 1.00 18.77 |
| ATOM | 1457 | CA | ILE | 188 | 15.907 | 20.855 | 52.407 | 1.00 20.12 |
| ATOM | 1458 | C | ILE | 188 | 15.470 | 19.766 | 53.389 | 1.00 31.58 |
| ATOM | 1459 | O | ILE | 188 | 14.596 | 19.966 | 54.202 | 1.00 38.58 |
| ATOM | 1460 | CB | ILE | 188 | 15.385 | 20.574 | 50.991 | 1.00 21.52 |
| ATOM | 1461 | CG1 | ILE | 188 | 15.555 | 21.775 | 50.102 | 1.00 16.10 |
| ATOM | 1462 | CG2 | ILE | 188 | 13.916 | 20.141 | 50.981 | 1.00 28.85 |
| ATOM | 1463 | CD1 | ILE | 188 | 15.139 | 21.471 | 48.660 | 1.00 15.31 |
| ATOM | 1464 | N | GLY | 189 | 16.142 | 18.618 | 53.352 | 1.00 32.39 |
| ATOM | 1465 | CA | GLY | 189 | 15.833 | 17.531 | 54.283 | 1.00 32.94 |
| ATOM | 1466 | C | GLY | 189 | 16.339 | 17.817 | 55.702 | 1.00 40.20 |
| ATOM | 1467 | O | GLY | 189 | 17.016 | 18.810 | 55.967 | 1.00 35.57 |
| ATOM | 1468 | N | ASP | 190 | 16.003 | 19.928 | 56.617 | 1.00 49.41 |
| ATOM | 1469 | CA | ASP | 190 | 16.392 | 17.047 | 58.021 | 1.00 55.01 |
| ATOM | 1470 | C | ASP | 190 | 17.556 | 16.115 | 58.338 | 1.00 56.16 |
| ATOM | 1471 | O | ASP | 190 | 18.083 | 16.100 | 59.463 | 1.00 58.30 |

FIG. 5AJ

| | | | | | | | |
|---|---|---|---|---|---|---|---|
| ATOM | 1472 | CB | ASP | 190 | 15.195 | 16.734 | 58.955 | 1.00 | 63.89 |
| ATOM | 1473 | CG | ASP | 190 | 14.592 | 15.365 | 58.686 | 1.00 | 99.67 |
| ATOM | 1474 | OD1 | ASP | 190 | 14.599 | 14.466 | 59.514 | 1.00 | 100.00 |
| ATOM | 1475 | OD2 | ASP | 190 | 14.088 | 15.240 | 57.470 | 1.00 | 100.00 |
| ATOM | 1476 | N | GLY | 191 | 17.921 | 15.312 | 57.323 | 1.00 | 47.20 |
| ATOM | 1477 | CA | GLY | 191 | 19.015 | 14.347 | 57.419 | 1.00 | 44.96 |
| ATOM | 1478 | C | GLY | 191 | 20.359 | 15.044 | 57.587 | 1.00 | 34.43 |
| ATOM | 1479 | O | GLY | 191 | 20.452 | 16.266 | 57.438 | 1.00 | 29.96 |
| ATOM | 1480 | N | PRO | 192 | 21.402 | 14.264 | 57.905 | 1.00 | 27.26 |
| ATOM | 1481 | CA | PRO | 192 | 22.737 | 14.834 | 58.100 | 1.00 | 24.01 |
| ATOM | 1482 | C | PRO | 192 | 23.444 | 15.274 | 56.787 | 1.00 | 20.55 |
| ATOM | 1483 | O | PRO | 192 | 23.323 | 14.648 | 55.740 | 1.00 | 23.84 |
| ATOM | 1484 | CB | PRO | 192 | 23.583 | 13.764 | 58.825 | 1.00 | 21.00 |
| ATOM | 1485 | CG | PRO | 192 | 22.739 | 12.501 | 58.915 | 1.00 | 27.49 |
| ATOM | 1486 | CD | PRO | 192 | 21.330 | 12.863 | 58.448 | 1.00 | 27.26 |
| ATOM | 1487 | N | VAL | 193 | 24.193 | 16.363 | 56.892 | 1.00 | 17.87 |
| ATOM | 1488 | CA | VAL | 193 | 24.964 | 16.902 | 55.792 | 1.00 | 19.51 |
| ATOM | 1489 | C | VAL | 193 | 26.380 | 17.108 | 56.249 | 1.00 | 22.37 |
| ATOM | 1490 | O | VAL | 193 | 26.663 | 17.189 | 57.443 | 1.00 | 23.84 |
| ATOM | 1491 | CB | VAL | 193 | 24.449 | 18.245 | 55.256 | 1.00 | 25.24 |
| ATOM | 1492 | CG1 | VAL | 193 | 23.059 | 18.118 | 54.632 | 1.00 | 21.90 |
| ATOM | 1493 | CG2 | VAL | 193 | 24.497 | 19.322 | 56.346 | 1.00 | 24.81 |
| ATOM | 1494 | N | LEU | 194 | 27.253 | 17.241 | 55.277 | 1.00 | 19.04 |
| ATOM | 1495 | CA | LEU | 194 | 28.654 | 17.438 | 55.516 | 1.00 | 20.29 |
| ATOM | 1496 | C | LEU | 194 | 29.006 | 18.930 | 55.571 | 1.00 | 18.71 |
| ATOM | 1497 | O | LEU | 194 | 28.907 | 19.615 | 54.591 | 1.00 | 20.13 |
| ATOM | 1498 | CB | LEU | 194 | 29.412 | 16.806 | 54.327 | 1.00 | 22.92 |
| ATOM | 1499 | CG | LEU | 194 | 29.994 | 15.423 | 54.542 | 1.00 | 30.60 |
| ATOM | 1500 | CD1 | LEU | 194 | 29.227 | 14.642 | 55.595 | 1.00 | 35.19 |
| ATOM | 1501 | CD2 | LEU | 194 | 30.048 | 14.672 | 53.211 | 1.00 | 25.61 |
| ATOM | 1502 | N | LEU | 195 | 29.453 | 19.430 | 56.713 | 1.00 | 17.39 |
| ATOM | 1503 | CA | LEU | 195 | 29.881 | 20.808 | 56.785 | 1.00 | 18.83 |
| ATOM | 1504 | C | LEU | 195 | 31.389 | 20.837 | 56.579 | 1.00 | 28.32 |
| ATOM | 1505 | O | LEU | 195 | 32.161 | 20.152 | 57.281 | 1.00 | 21.98 |
| ATOM | 1506 | CB | LEU | 195 | 29.489 | 21.525 | 58.072 | 1.00 | 22.20 |
| ATOM | 1507 | CG | LEU | 195 | 28.055 | 21.349 | 58.444 | 1.00 | 26.40 |
| ATOM | 1508 | CD1 | LEU | 195 | 27.937 | 21.508 | 59.941 | 1.00 | 31.99 |
| ATOM | 1509 | CD2 | LEU | 195 | 27.225 | 22.395 | 57.726 | 1.00 | 26.90 |
| ATOM | 1510 | N | PRO | 196 | 31.789 | 21.610 | 55.597 | 1.00 | 21.58 |
| ATOM | 1511 | CA | PRO | 196 | 33.177 | 21.666 | 55.154 | 1.00 | 22.17 |
| ATOM | 1512 | C | PRO | 196 | 34.080 | 22.623 | 55.892 | 1.00 | 29.56 |

FIG. 5AK

| | | | | | | | |
|---|---|---|---|---|---|---|---|
| ATOM | 1513 | O   | PRO | 196 | 33.635 | 23.588 | 56.490 | 1.00 29.04 |
| ATOM | 1514 | CB  | PRO | 196 | 33.054 | 22.265 | 53.752 | 1.00 22.77 |
| ATOM | 1515 | CG  | PRO | 196 | 31.761 | 23.104 | 53.735 | 1.00 18.99 |
| ATOM | 1516 | CD  | PRO | 196 | 30.910 | 22.567 | 54.861 | 1.00 16.42 |
| ATOM | 1517 | N   | ASP | 197 | 35.379 | 22.410 | 55.716 | 1.00 22.95 |
| ATOM | 1518 | CA  | ASP | 197 | 36.364 | 23.370 | 56.134 | 1.00 19.71 |
| ATOM | 1519 | C   | ASP | 197 | 36.556 | 24.295 | 54.931 | 1.00 24.74 |
| ATOM | 1520 | O   | ASP | 197 | 36.251 | 23.913 | 53.800 | 1.00 24.88 |
| ATOM | 1521 | CB  | ASP | 197 | 37.711 | 22.730 | 56.446 | 1.00 22.28 |
| ATOM | 1522 | CG  | ASP | 197 | 37.690 | 21.913 | 57.687 | 1.00 43.93 |
| ATOM | 1523 | OD1 | ASP | 197 | 36.912 | 22.117 | 58.608 | 1.00 53.47 |
| ATOM | 1524 | OD2 | ASP | 197 | 38.634 | 21.006 | 57.694 | 1.00 31.58 |
| ATOM | 1525 | N   | ASN | 198 | 37.062 | 25.501 | 55.168 | 1.00 19.74 |
| ATOM | 1526 | CA  | ASN | 198 | 37.254 | 26.470 | 54.118 | 1.00 15.38 |
| ATOM | 1527 | C   | ASN | 198 | 37.974 | 25.889 | 52.971 | 1.00 19.61 |
| ATOM | 1528 | O   | ASN | 198 | 38.958 | 25.236 | 53.134 | 1.00 22.69 |
| ATOM | 1529 | CB  | ASN | 198 | 38.013 | 27.704 | 54.614 | 1.00 24.48 |
| ATOM | 1530 | CG  | ASN | 198 | 37.236 | 28.504 | 55.632 | 1.00 52.21 |
| ATOM | 1531 | OD1 | ASN | 198 | 36.107 | 28.174 | 55.961 | 1.00 34.54 |
| ATOM | 1532 | ND2 | ASN | 198 | 37.854 | 29.556 | 56.150 | 1.00 55.11 |
| ATOM | 1533 | N   | HIS | 199 | 37.462 | 26.125 | 51.801 | 1.00 16.30 |
| ATOM | 1534 | CA  | HIS | 199 | 38.071 | 25.627 | 50.616 | 1.00 15.80 |
| ATOM | 1535 | C   | HIS | 199 | 37.496 | 26.357 | 49.450 | 1.00 14.85 |
| ATOM | 1536 | O   | HIS | 199 | 36.757 | 27.295 | 49.643 | 1.00 16.45 |
| ATOM | 1537 | CB  | HIS | 199 | 37.988 | 24.103 | 50.471 | 1.00 16.53 |
| ATOM | 1538 | CG  | HIS | 199 | 36.597 | 23.628 | 50.218 | 1.00 16.65 |
| ATOM | 1539 | ND1 | HIS | 199 | 35.695 | 23.491 | 51.244 | 1.00 17.85 |
| ATOM | 1540 | CD2 | HIS | 199 | 35.987 | 23.282 | 49.048 | 1.00 18.67 |
| ATOM | 1541 | CE1 | HIS | 199 | 34.561 | 23.052 | 50.688 | 1.00 19.45 |
| ATOM | 1542 | NE2 | HIS | 199 | 34.716 | 22.905 | 49.364 | 1.00 18.74 |
| ATOM | 1543 | N   | TYR | 200 | 37.879 | 25.998 | 48.247 | 1.00 12.56 |
| ATOM | 1544 | CA  | TYR | 200 | 37.334 | 26.689 | 47.100 | 1.00 14.01 |
| ATOM | 1545 | C   | TYR | 200 | 37.207 | 25.824 | 45.870 | 1.00 15.57 |
| ATOM | 1546 | O   | TYR | 200 | 37.793 | 24.751 | 45.768 | 1.00 20.20 |
| ATOM | 1547 | CB  | TYR | 200 | 38.030 | 28.011 | 46.779 | 1.00 19.79 |
| ATOM | 1548 | CG  | TYR | 200 | 39.382 | 27.745 | 46.202 | 1.00 22.25 |
| ATOM | 1549 | CD1 | TYR | 200 | 39.543 | 27.526 | 44.835 | 1.00 22.53 |
| ATOM | 1550 | CD2 | TYR | 200 | 40.473 | 27.605 | 47.057 | 1.00 25.73 |
| ATOM | 1551 | CE1 | TYR | 200 | 40.800 | 27.222 | 44.317 | 1.00 35.51 |
| ATOM | 1552 | CE2 | TYR | 200 | 41.739 | 27.314 | 46.559 | 1.00 29.34 |
| ATOM | 1553 | CZ  | TYR | 200 | 41.896 | 27.132 | 45.186 | 1.00 54.14 |

FIG. 5AL

| | | | | | | | |
|---|---|---|---|---|---|---|---|
| ATOM | 1554 | OH | TYR | 200 | 43.153 | 26.820 | 44.703 | 1.00 62.66 |
| ATOM | 1555 | N | LEU | 201 | 36.393 | 26.309 | 44.946 | 1.00 15.07 |
| ATOM | 1556 | CA | LEU | 201 | 36.147 | 25.680 | 43.678 | 1.00 11.01 |
| ATOM | 1557 | C | LEU | 201 | 36.753 | 26.532 | 42.593 | 1.00 17.30 |
| ATOM | 1558 | O | LEU | 201 | 36.619 | 27.753 | 42.610 | 1.00 20.19 |
| ATOM | 1559 | CB | LEU | 201 | 34.628 | 25.518 | 43.354 | 1.00 10.09 |
| ATOM | 1560 | CG | LEU | 201 | 33.749 | 25.027 | 44.480 | 1.00 13.41 |
| ATOM | 1561 | CD1 | LEU | 201 | 32.293 | 24.938 | 43.954 | 1.00 17.11 |
| ATOM | 1562 | CD2 | LEU | 201 | 34.196 | 23.635 | 44.927 | 1.00 23.03 |
| ATOM | 1563 | N | SER | 202 | 37.407 | 25.868 | 41.651 | 1.00 10.75 |
| ATOM | 1564 | CA | SER | 202 | 38.047 | 26.490 | 40.528 | 1.00 8.51 |
| ATOM | 1565 | C | SER | 202 | 37.222 | 26.189 | 39.294 | 1.00 11.56 |
| ATOM | 1566 | O | SER | 202 | 36.919 | 25.038 | 38.996 | 1.00 14.58 |
| ATOM | 1567 | CB | SER | 202 | 39.485 | 25.987 | 40.442 | 1.00 15.68 |
| ATOM | 1568 | OG | SER | 202 | 40.067 | 26.353 | 39.228 | 1.00 36.44 |
| ATOM | 1569 | N | THR | 203 | 36.798 | 27.241 | 38.601 | 1.00 12.36 |
| ATOM | 1570 | CA | THR | 203 | 35.879 | 27.067 | 37.499 | 1.00 15.60 |
| ATOM | 1571 | C | THR | 203 | 36.417 | 27.521 | 36.195 | 1.00 20.19 |
| ATOM | 1572 | O | THR | 203 | 37.192 | 28.472 | 36.114 | 1.00 18.29 |
| ATOM | 1573 | CB | THR | 203 | 34.565 | 27.892 | 37.757 | 1.00 20.51 |
| ATOM | 1574 | OG1 | THR | 203 | 34.911 | 29.260 | 37.780 | 1.00 20.39 |
| ATOM | 1575 | CG2 | THR | 203 | 33.935 | 27.557 | 39.093 | 1.00 6.80 |
| ATOM | 1576 | N | GLN | 204 | 35.913 | 26.883 | 35.164 | 1.00 10.30 |
| ATOM | 1577 | CA | GLN | 204 | 36.173 | 27.271 | 33.807 | 1.00 14.85 |
| ATOM | 1578 | C | GLN | 204 | 34.956 | 26.980 | 32.921 | 1.00 23.14 |
| ATOM | 1579 | O | GLN | 204 | 34.334 | 25.932 | 33.056 | 1.00 21.66 |
| ATOM | 1580 | CB | GLN | 204 | 37.475 | 26.696 | 33.237 | 1.00 20.33 |
| ATOM | 1581 | CG | GLN | 204 | 37.271 | 25.371 | 32.518 | 1.00 40.16 |
| ATOM | 1582 | CD | GLN | 204 | 38.588 | 24.722 | 32.193 | 1.00 59.76 |
| ATOM | 1583 | OE1 | GLN | 204 | 39.011 | 24.716 | 31.035 | 1.00 41.80 |
| ATOM | 1584 | NE2 | GLN | 204 | 39.276 | 24.241 | 33.235 | 1.00 34.80 |
| ATOM | 1585 | N | SER | 205 | 34.619 | 27.913 | 32.021 | 1.00 15.83 |
| ATOM | 1586 | CA | SER | 205 | 33.447 | 27.762 | 31.172 | 1.00 14.60 |
| ATOM | 1587 | C | SER | 205 | 33.654 | 28.307 | 29.783 | 1.00 20.21 |
| ATOM | 1588 | O | SER | 205 | 34.282 | 29.337 | 29.581 | 1.00 17.82 |
| ATOM | 1589 | CB | SER | 205 | 32.197 | 28.445 | 31.758 | 1.00 11.88 |
| ATOM | 1590 | OG | SER | 205 | 32.121 | 28.406 | 33.177 | 1.00 15.45 |
| ATOM | 1591 | N | ALA | 206 | 33.065 | 27.630 | 28.827 | 1.00 13.00 |
| ATOM | 1592 | CA | ALA | 206 | 33.079 | 28.029 | 27.426 | 1.00 9.99 |
| ATOM | 1593 | C | ALA | 206 | 31.623 | 28.192 | 26.924 | 1.00 21.23 |
| ATOM | 1594 | O | ALA | 206 | 30.809 | 27.306 | 27.139 | 1.00 14.10 |

FIG. 5AM

| | | | | | | | |
|---|---|---|---|---|---|---|---|
| ATOM | 1595 | CB | ALA | 206 | 33.751 | 26.936 | 26.596 | 1.00 13.45 |
| ATOM | 1596 | N | LEU | 207 | 31.335 | 29.320 | 26.263 | 1.00 16.09 |
| ATOM | 1597 | CA | LEU | 207 | 30.036 | 29.167 | 25.706 | 1.00 12.07 |
| ATOM | 1598 | C | LEU | 207 | 30.070 | 29.445 | 24.235 | 1.00 19.76 |
| ATOM | 1599 | O | LEU | 207 | 31.014 | 29.840 | 23.576 | 1.00 20.82 |
| ATOM | 1600 | CB | LEU | 207 | 29.580 | 31.057 | 26.004 | 1.00 8.24 |
| ATOM | 1601 | CG | LEU | 207 | 29.744 | 31.493 | 27.457 | 1.00 16.35 |
| ATOM | 1602 | CD1 | LEU | 207 | 28.955 | 32.790 | 27.707 | 1.00 13.78 |
| ATOM | 1603 | CD2 | LEU | 207 | 29.268 | 30.406 | 28.400 | 1.00 18.79 |
| ATOM | 1604 | N | SER | 208 | 29.011 | 28.863 | 23.698 | 1.00 15.35 |
| ATOM | 1605 | CA | SER | 208 | 28.914 | 28.692 | 22.270 | 1.00 13.74 |
| ATOM | 1606 | C | SER | 208 | 27.449 | 28.852 | 21.794 | 1.00 20.16 |
| ATOM | 1607 | O | SER | 208 | 26.548 | 29.085 | 22.594 | 1.00 15.81 |
| ATOM | 1608 | CB | SER | 208 | 29.495 | 27.367 | 21.822 | 1.00 17.82 |
| ATOM | 1609 | OG | SER | 208 | 28.769 | 26.311 | 22.431 | 1.00 31.45 |
| ATOM | 1610 | N | LYS | 209 | 27.242 | 28.738 | 20.485 | 1.00 16.50 |
| ATOM | 1611 | CA | LYS | 209 | 25.907 | 28.828 | 19.906 | 1.00 18.02 |
| ATOM | 1612 | C | LYS | 209 | 25.637 | 27.610 | 19.031 | 1.00 29.99 |
| ATOM | 1613 | O | LYS | 209 | 26.578 | 27.004 | 18.502 | 1.00 32.55 |
| ATOM | 1614 | CB | LYS | 209 | 25.783 | 30.100 | 19.082 | 1.00 20.96 |
| ATOM | 1615 | CG | LYS | 209 | 24.746 | 31.055 | 19.606 | 1.00 34.50 |
| ATOM | 1616 | CD | LYS | 209 | 25.262 | 31.964 | 20.666 | 1.00 22.72 |
| ATOM | 1617 | CE | LYS | 209 | 24.370 | 33.159 | 290.896 | 1.00 18.96 |
| ATOM | 1618 | NZ | LYS | 209 | 23.565 | 33.067 | 22.116 | 1.00 27.39 |
| ATOM | 1619 | N | ASP | 210 | 24.347 | 27.241 | 18.912 | 1.00 27.01 |
| ATOM | 1620 | CA | ASP | 210 | 23.890 | 26.159 | 18.038 | 1.00 24.62 |
| ATOM | 1621 | C | ASP | 210 | 23.465 | 26.793 | 16.705 | 1.00 26.77 |
| ATOM | 1622 | O | ASP | 210 | 22.468 | 27.514 | 16.605 | 1.00 23.00 |
| ATOM | 1623 | CB | ASP | 210 | 22.744 | 25.361 | 18.691 | 1.00 24.43 |
| ATOM | 1624 | CG | ASP | 210 | 22.197 | 24.249 | 17.839 | 1.00 35.55 |
| ATOM | 1625 | OD1 | ASP | 210 | 22.333 | 24.185 | 16.631 | 1.00 36.53 |
| ATOM | 1626 | OD2 | ASP | 210 | 21.499 | 23.400 | 18.535 | 1.00 45.51 |
| ATOM | 1627 | N | PRO | 211 | 24.306 | 26.618 | 15.708 | 1.00 30.25 |
| ATOM | 1628 | CA | PRO | 211 | 24.120 | 27.224 | 14.397 | 1.00 30.30 |
| ATOM | 1629 | C | PRO | 211 | 22.733 | 26.982 | 13.770 | 1.00 39.72 |
| ATOM | 1630 | O | PRO | 211 | 22.253 | 27.782 | 12.959 | 1.00 37.65 |
| ATOM | 1631 | CB | PRO | 211 | 25.197 | 26.620 | 13.500 | 1.00 29.99 |
| ATOM | 1632 | CG | PRO | 211 | 25.782 | 25.418 | 14.255 | 1.00 38.59 |
| ATOM | 1633 | CD | PRO | 211 | 25.158 | 25.405 | 15.647 | 1.00 35.05 |
| ATOM | 1634 | N | ASN | 212 | 22.102 | 25.868 | 14.140 | 1.00 39.64 |
| ATOM | 1635 | CA | ASN | 212 | 20.808 | 25.515 | 13.592 | 1.00 39.60 |

FIG. 5AN

| | | | | | | | |
|---|---|---|---|---|---|---|---|
| ATOM | 1636 | C | ASN | 212 | 19.642 | 25.894 | 14.497 | 1.00 41.92 |
| ATOM | 1637 | O | ASN | 212 | 18.485 | 25.518 | 14.263 | 1.00 42.30 |
| ATOM | 1638 | CB | ASN | 212 | 20.788 | 24.028 | 13.236 | 1.00 48.64 |
| ATOM | 1639 | CG | ASN | 212 | 21.883 | 23.678 | 12.230 | 1.00 53.61 |
| ATOM | 1640 | N | GLU | 213 | 19.947 | 26.675 | 15.520 | 1.00 27.84 |
| ATOM | 1641 | CA | GLU | 213 | 18.953 | 27.080 | 16.478 | 1.00 20.43 |
| ATOM | 1642 | C | GLU | 213 | 18.485 | 28.527 | 16.241 | 1.00 29.95 |
| ATOM | 1643 | O | GLU | 213 | 19.247 | 29.475 | 16.324 | 1.00 32.77 |
| ATOM | 1644 | CB | GLU | 213 | 19.535 | 26.878 | 17.894 | 1.00 16.45 |
| ATOM | 1645 | CG | GLU | 213 | 18.594 | 27.326 | 18.995 | 1.00 18.29 |
| ATOM | 1646 | CD | GLU | 213 | 17.229 | 26.703 | 18.853 | 1.00 38.01 |
| ATOM | 1647 | OE1 | GLU | 213 | 16.238 | 27.334 | 18.508 | 1.00 25.07 |
| ATOM | 1648 | OE2 | GLU | 213 | 17.223 | 25.423 | 19.122 | 1.00 19.17 |
| ATOM | 1649 | N | LYS | 214 | 17.223 | 28.713 | 15.963 | 1.00 22.99 |
| ATOM | 1650 | CA | LYS | 214 | 16.721 | 30.081 | 15.726 | 1.00 22.84 |
| ATOM | 1651 | C | LYS | 214 | 16.252 | 30.778 | 16.982 | 1.00 21.50 |
| ATOM | 1652 | O | LYS | 214 | 16.130 | 32.016 | 17.032 | 1.00 28.15 |
| ATOM | 1653 | CB | LYS | 214 | 15.653 | 30.197 | 14.606 | 1.00 27.58 |
| ATOM | 1654 | CG | LYS | 214 | 16.153 | 29.816 | 13.209 | 1.00 32.71 |
| ATOM | 1655 | CD | LYS | 214 | 16.752 | 30.979 | 12.431 | 1.00 55.31 |
| ATOM | 1656 | N | ARG | 215 | 15.947 | 30.028 | 18.014 | 1.00 14.52 |
| ATOM | 1657 | CA | ARG | 215 | 15.518 | 30.726 | 19.209 | 1.00 15.58 |
| ATOM | 1658 | C | ARG | 215 | 16.719 | 31.382 | 19.892 | 1.00 21.87 |
| ATOM | 1659 | O | ARG | 215 | 17.848 | 31.075 | 19.572 | 1.00 26.69 |
| ATOM | 1660 | CB | ARG | 215 | 14.808 | 29.804 | 20.159 | 1.00 18.82 |
| ATOM | 1661 | CG | ARG | 215 | 13.660 | 29.067 | 19.475 | 1.00 23.30 |
| ATOM | 1662 | CD | ARG | 215 | 13.220 | 27.806 | 20.205 | 1.00 15.45 |
| ATOM | 1663 | NE | ARG | 215 | 14.107 | 26.668 | 19.929 | 1.00 28.08 |
| ATOM | 1664 | CZ | ARG | 215 | 14.022 | 25.473 | 20.543 | 1.00 21.38 |
| ATOM | 1665 | NH1 | ARG | 215 | 13.074 | 25.215 | 21.455 | 1.00 23.92 |
| ATOM | 1666 | NH2 | ARG | 215 | 14.893 | 24.514 | 20.225 | 1.00 20.46 |
| ATOM | 1667 | N | ASP | 216 | 16.466 | 32.275 | 20.830 | 1.00 16.72 |
| ATOM | 1668 | CA | ASP | 216 | 17.556 | 32.895 | 21.617 | 1.00 19.06 |
| ATOM | 1669 | C | ASP | 216 | 18.047 | 31.817 | 22.607 | 1.00 20.02 |
| ATOM | 1670 | O | ASP | 216 | 17.261 | 31.214 | 23.350 | 1.00 18.45 |
| ATOM | 1671 | CB | ASP | 216 | 17.066 | 34.169 | 22.383 | 1.00 21.33 |
| ATOM | 1672 | CG | ASP | 216 | 18.138 | 35.140 | 22.893 | 1.00 20.97 |
| ATOM | 1673 | OD1 | ASP | 216 | 17.869 | 36.079 | 23.620 | 1.00 28.46 |
| ATOM | 1674 | OD2 | ASP | 216 | 19.342 | 34.900 | 22.441 | 1.00 20.37 |
| ATOM | 1675 | N | HIS | 217 | 19.332 | 31.537 | 22.589 | 1.00 13.18 |
| ATOM | 1676 | CA | HIS | 217 | 19.813 | 30.482 | 23.433 | 1.00 11.21 |

FIG. 5AO

| | | | | | | | |
|---|---|---|---|---|---|---|---|
| ATOM | 1677 | C | HIS | 217 | 21.313 | 30.614 | 23.723 | 1.00 21.35 |
| ATOM | 1678 | O | HIS | 217 | 22.014 | 31.471 | 23.163 | 1.00 15.03 |
| ATOM | 1679 | CB | HIS | 217 | 19.587 | 29.168 | 22.690 | 1.00 13.03 |
| ATOM | 1680 | CG | HIS | 217 | 20.525 | 29.025 | 21.542 | 1.00 15.49 |
| ATOM | 1681 | ND1 | HIS | 217 | 20.463 | 29.871 | 20.449 | 1.00 17.88 |
| ATOM | 1682 | CD2 | HIS | 217 | 21.589 | 28.172 | 21.361 | 1.00 17.51 |
| ATOM | 1683 | CE1 | HIS | 217 | 21.457 | 29.524 | 19.635 | 1.00 17.94 |
| ATOM | 1684 | NE2 | HIS | 217 | 22.152 | 28.501 | 20.151 | 1.00 17.59 |
| ATOM | 1685 | N | MSE | 218 | 21.794 | 29.725 | 24.576 | 1.00 11.26 |
| ATOM | 1686 | CA | MSE | 218 | 23.186 | 29.642 | 24.887 | 1.00 11.49 |
| ATOM | 1687 | C | MSE | 218 | 23.560 | 28.198 | 25.094 | 1.00 24.15 |
| ATOM | 1688 | O | MSE | 218 | 22.822 | 27.446 | 25.751 | 1.00 20.70 |
| ATOM | 1689 | CB | MSE | 218 | 23.539 | 30.421 | 26.172 | 1.00 12.84 |
| ATOM | 1690 | CG | MSE | 218 | 24.809 | 30.004 | 26.907 | 1.00 12.59 |
| ATOM | 1691 | SE | MSE | 218 | 25.267 | 31.128 | 28.434 | 1.00 29.94 |
| ATOM | 1692 | CE | MSE | 218 | 24.039 | 30.502 | 29.781 | 1.00 13.54 |
| ATOM | 1693 | N | VAL | 219 | 24.727 | 27.824 | 24.558 | 1.00 15.62 |
| ATOM | 1694 | CA | VAL | 219 | 25.309 | 26.518 | 24.782 | 1.00 10.58 |
| ATOM | 1695 | C | VAL | 219 | 26.473 | 26.689 | 25.753 | 1.00 16.54 |
| ATOM | 1696 | O | VAL | 219 | 27.280 | 27.604 | 25.585 | 1.00 15.54 |
| ATOM | 1697 | CB | VAL | 219 | 25.774 | 25.883 | 23.498 | 1.00 15.08 |
| ATOM | 1698 | CG1 | VAL | 219 | 26.330 | 24.495 | 23.824 | 1.00 14.34 |
| ATOM | 1699 | CG2 | VAL | 219 | 24.599 | 25.766 | 22.512 | 1.00 15.78 |
| ATOM | 1700 | N | LEU | 220 | 26.523 | 25.836 | 26.783 | 1.00 10.95 |
| ATOM | 1701 | CA | LEU | 220 | 27.490 | 25.939 | 27.850 | 1.00 11.01 |
| ATOM | 1702 | C | LEU | 220 | 28.206 | 24.643 | 28.184 | 1.00 21.26 |
| ATOM | 1703 | O | LEU | 220 | 27.592 | 23.577 | 28.324 | 1.00 15.94 |
| ATOM | 1704 | CB | LEU | 220 | 26.807 | 26.545 | 29.100 | 1.00 13.75 |
| ATOM | 1705 | CG | LEU | 220 | 27.624 | 26.578 | 30.402 | 1.00 21.10 |
| ATOM | 1706 | CD1 | LEU | 220 | 28.433 | 27.875 | 30.483 | 1.00 23.53 |
| ATOM | 1707 | CD2 | LEU | 220 | 26.663 | 26.556 | 31.586 | 1.00 22.04 |
| ATOM | 1708 | N | LEU | 221 | 29.570 | 24.758 | 28.273 | 1.00 19.04 |
| ATOM | 1709 | CA | LEU | 221 | 30.498 | 23.666 | 28.697 | 1.00 13.22 |
| ATOM | 1710 | C | LEU | 221 | 31.309 | 24.178 | 29.887 | 1.00 10.73 |
| ATOM | 1711 | O | LEU | 221 | 31.846 | 25.267 | 29.857 | 1.00 12.98 |
| ATOM | 1712 | CB | LEU | 221 | 31.382 | 23.102 | 27.549 | 1.00 13.74 |
| ATOM | 1713 | CG | LEU | 221 | 32.580 | 22.257 | 28.045 | 1.00 18.64 |
| ATOM | 1714 | CD1 | LEU | 221 | 32.149 | 20.868 | 28.496 | 1.00 17.38 |
| ATOM | 1715 | CD2 | LEU | 221 | 33.571 | 22.109 | 26.911 | 1.00 26.97 |
| ATOM | 1716 | N | GLU | 222 | 31.316 | 23.446 | 30.963 | 1.00 9.31 |
| ATOM | 1717 | CA | GLU | 222 | 31.936 | 23.929 | 32.144 | 1.00 9.97 |

FIG. 5AP

| ATOM | 1718 C | GLU | 222 | 32.548 | 22.803 | 32.951 | 1.00 12.94 |
|------|--------|-----|-----|--------|--------|--------|------------|
| ATOM | 1719 O | GLU | 222 | 32.072 | 21.662 | 32.966 | 1.00 13.38 |
| ATOM | 1720 CB | GLU | 222 | 30.836 | 24.762 | 32.896 | 1.00 12.14 |
| ATOM | 1721 CG | GLU | 222 | 31.092 | 25.119 | 34.364 | 1.00 13.88 |
| ATOM | 1722 CD | GLU | 222 | 29.895 | 25.891 | 34.934 | 1.00 13.57 |
| ATOM | 1723 OE1 | GLU | 222 | 29.128 | 26.477 | 34.240 | 1.00 19.47 |
| ATOM | 1724 OE2 | GLU | 222 | 29.752 | 25.789 | 36.207 | 1.00 18.51 |
| ATOM | 1725 N | PHE | 223 | 33.687 | 23.123 | 33.542 | 1.00 15.86 |
| ATOM | 1726 CA | PHE | 223 | 34.476 | 22.227 | 34.373 | 1.00 9.34 |
| ATOM | 1727 C | PHE | 223 | 34.711 | 22.864 | 35.722 | 1.00 11.08 |
| ATOM | 1728 O | PHE | 223 | 35.028 | 24.055 | 35.828 | 1.00 19.86 |
| ATOM | 1729 CB | PHE | 223 | 35.847 | 21.919 | 33.684 | 1.00 8.30 |
| ATOM | 1730 CG | PHE | 223 | 35.703 | 21.134 | 32.431 | 1.00 10.50 |
| ATOM | 1731 CD1 | PHE | 223 | 35.570 | 19.747 | 32.469 | 1.00 13.56 |
| ATOM | 1732 CD2 | PHE | 223 | 35.750 | 21.750 | 31.184 | 1.00 11.32 |
| ATOM | 1733 CE1 | PHE | 223 | 35.481 | 19.010 | 31.287 | 1.00 12.58 |
| ATOM | 1734 CE2 | PHE | 223 | 35.667 | 21.032 | 29.995 | 1.00 12.17 |
| ATOM | 1735 CZ | PHE | 223 | 35.521 | 19.648 | 30.050 | 1.00 10.87 |
| ATOM | 1736 N | VAL | 224 | 34.542 | 22.081 | 36.765 | 1.00 9.28 |
| ATOM | 1737 CA | VAL | 224 | 34.708 | 22.587 | 38.080 | 1.00 11.18 |
| ATOM | 1738 C | VAL | 224 | 35.324 | 21.553 | 39.010 | 1.00 17.52 |
| ATOM | 1739 O | VAL | 224 | 34.848 | 20.418 | 39.137 | 1.00 13.17 |
| ATOM | 1740 CB | VAL | 224 | 33.370 | 23.078 | 38.662 | 1.00 16.61 |
| ATOM | 1741 CG1 | VAL | 224 | 33.622 | 23.736 | 40.022 | 1.00 13.90 |
| ATOM | 1742 CG2 | VAL | 224 | 32.674 | 24.048 | 37.697 | 1.00 13.85 |
| ATOM | 1743 N | THR | 225 | 36.380 | 21.965 | 39.676 | 1.00 11.71 |
| ATOM | 1744 CA | THR | 225 | 37.026 | 21.099 | 40.617 | 1.00 11.61 |
| ATOM | 1745 C | THR | 225 | 37.366 | 21.798 | 41.927 | 1.00 14.76 |
| ATOM | 1746 O | THR | 225 | 37.702 | 23.002 | 41.962 | 1.00 16.64 |
| ATOM | 1747 CB | THR | 225 | 38.162 | 20.279 | 40.014 | 1.00 20.38 |
| ATOM | 1748 OG1 | THR | 225 | 39.288 | 20.337 | 40.822 | 1.00 30.44 |
| ATOM | 1749 CG2 | THR | 225 | 38.468 | 20.722 | 38.631 | 1.00 10.89 |
| ATOM | 1750 N | ALA | 226 | 37.222 | 21.065 | 43.011 | 1.00 7.89 |
| ATOM | 1751 CA | ALA | 226 | 37.478 | 21.595 | 44.352 | 1.00 11.63 |
| ATOM | 1752 C | ALA | 226 | 38.969 | 21.558 | 44.677 | 1.00 16.61 |
| ATOM | 1753 O | ALA | 226 | 39.687 | 20.699 | 44.199 | 1.00 15.60 |
| ATOM | 1754 CB | ALA | 226 | 36.695 | 20.847 | 45.444 | 1.00 12.17 |
| ATOM | 1755 N | ALA | 227 | 39.395 | 22.490 | 45.479 | 1.00 13.95 |
| ATOM | 1756 CA | ALA | 227 | 40.789 | 22.550 | 45.871 | 1.00 19.64 |
| ATOM | 1757 C | ALA | 227 | 40.987 | 23.299 | 47.170 | 1.00 26.33 |
| ATOM | 1758 O | ALA | 227 | 40.042 | 23.715 | 47.840 | 1.00 25.39 |

FIG. 5AQ

| | | | | | | | |
|---|---|---|---|---|---|---|---|
| ATOM | 1759 | CB | ALA | 227 | 41.557 | 23.246 | 44.760 | 1.00 18.42 |
| ATOM | 1760 | N | GLY | 228 | 42.245 | 23.476 | 47.523 | 1.00 23.28 |
| ATOM | 1761 | CA | GLY | 228 | 42.616 | 24.292 | 48.658 | 1.00 21.61 |
| ATOM | 1762 | C | GLY | 228 | 42.805 | 23.562 | 49.939 | 1.00 32.93 |
| ATOM | 1763 | O | GLY | 228 | 42.948 | 24.201 | 51.009 | 1.00 32.53 |
| ATOM | 1764 | N | ILE | 229 | 42.803 | 22.231 | 49.842 | 1.00 33.59 |
| ATOM | 1765 | CA | ILE | 229 | 43.006 | 21.375 | 50.998 | 1.00 31.81 |
| ATOM | 1766 | C | ILE | 229 | 44.016 | 20.291 | 50.633 | 1.00 28.78 |
| ATOM | 1767 | O | ILE | 229 | 45.090 | 20.176 | 51.246 | 1.00 96.02 |
| ATOM | 1768 | CB | ILE | 229 | 41.691 | 20.772 | 51.519 | 1.00 35.70 |
| ATOM | 1769 | CG1 | ILE | 229 | 40.890 | 21.807 | 52.325 | 1.00 30.66 |
| ATOM | 1770 | CG2 | ILE | 229 | 41.990 | 19.549 | 52.392 | 1.00 33.37 |
| ATOM | 1771 | CD1 | ILE | 229 | 39.386 | 21.715 | 52.092 | 1.00 38.74 |
| ATOM | 1772 | O | HOH | 301 | 27.530 | 12.735 | 38.010 | 1.00 15.09 |
| ATOM | 1773 | O | HOH | 302 | 23.919 | 34.589 | 37.331 | 1.00 10.29 |
| ATOM | 1774 | O | HOH | 303 | 27.229 | 34.816 | 35.487 | 1.00 11.12 |
| ATOM | 1775 | O | HOH | 304 | 29.914 | 18.943 | 44.692 | 1.00 16.10 |
| ATOM | 1776 | O | HOH | 305 | 30.956 | 21.886 | 49.900 | 1.00 21.47 |
| ATOM | 1777 | O | HOH | 306 | 20.072 | 31.196 | 43.592 | 1.00 16.85 |
| ATOM | 1778 | O | HOH | 307 | 26.660 | 48.630 | 33.797 | 1.00 24.67 |
| ATOM | 1779 | O | HOH | 308 | 22.329 | 33.239 | 41.399 | 1.00 14.11 |
| ATOM | 1780 | O | HOH | 309 | 22.465 | 48.025 | 32.810 | 1.00 18.51 |
| ATOM | 1781 | O | HOH | 310 | 31.012 | 39.126 | 29.118 | 1.00 16.01 |
| ATOM | 1782 | O | HOH | 311 | 33.067 | 35.809 | 33.010 | 1.00 19.92 |
| ATOM | 1783 | O | HOH | 312 | 31.130 | 37.076 | 30.841 | 1.00 12.68 |
| ATOM | 1784 | O | HOH | 313 | 40.304 | 30.058 | 38.616 | 1.00 56.07 |
| ATOM | 1785 | O | HOH | 314 | 34.166 | 26.379 | 57.222 | 1.00 22.58 |
| ATOM | 1786 | O | HOH | 315 | 36.215 | 35.320 | 43.598 | 1.00 22.30 |
| ATOM | 1787 | O | HOH | 316 | 33.866 | 29.786 | 34.671 | 1.00 12.21 |
| ATOM | 1865 | O | HOH | 317 | 42.341 | 20.166 | 43.534 | 1.00 26.67 |
| ATOM | 1788 | O | HOH | 318 | 10.270 | 28.684 | 30.403 | 1.00 43.66 |
| ATOM | 1789 | O | HOH | 319 | 28.448 | 16.822 | 30.655 | 1.00 25.44 |
| ATOM | 1790 | O | HOH | 320 | 30.612 | 20.922 | 37.231 | 1.00 21.57 |
| ATOM | 1791 | O | HOH | 321 | 11.639 | 37.421 | 26.801 | 1.00 34.12 |
| ATOM | 1792 | O | HOH | 322 | 27.030 | 37.308 | 36.869 | 1.00 13.10 |
| ATOM | 1793 | O | HOH | 323 | 33.119 | 14.524 | 43.070 | 1.00 30.93 |
| ATOM | 1794 | O | HOH | 324 | 37.973 | 14.036 | 53.352 | 1.00 35.39 |
| ATOM | 1795 | O | HOH | 235 | 32.015 | 49.100 | 37.028 | 1.00 59.37 |
| ATOM | 1796 | O | HOH | 326 | 11.959 | 12.020 | 43.429 | 1.00 29.06 |
| ATOM | 1797 | O | HOH | 327 | 36.760 | 29.941 | 31.666 | 1.00 22.03 |
| ATOM | 1864 | O | HOH | 328 | 15.305 | 26.513 | 15.694 | 1.00 39.62 |

FIG. 5AR

| | | | | | | | |
|---|---|---|---|---|---|---|---|
| ATOM | 1798 | O | HOH | 329 | 33.005 | 46.924 | 36.994 | 1.00 22.07 |
| ATOM | 1863 | O | HOH | 330 | 23.801 | 36.134 | 22.715 | 1.00 45.30 |
| ATOM | 1799 | O | HOH | 331 | 33.609 | 31.296 | 26.261 | 1.00 23.65 |
| ATOM | 1862 | O | HOH | 332 | 34.942 | 24.780 | 29.532 | 1.00 38.93 |
| ATOM | 1800 | O | HOH | 333 | 25.235 | 12.919 | 54.611 | 1.00 36.20 |
| ATOM | 1861 | O | HOH | 334 | 38.048 | 23.467 | 36.645 | 1.00 37.73 |
| ATOM | 1801 | O | HOH | 335 | 12.284 | 43.511 | 38.338 | 1.00 33.79 |
| ATOM | 1802 | O | HOH | 336 | 9.826 | 47.020 | 32.568 | 1.00 46.67 |
| ATOM | 1803 | O | HOH | 337 | 7.671 | 41.532 | 29.806 | 1.00 40.88 |
| ATOM | 1804 | O | HOH | 338 | 15.430 | 23.713 | 26.808 | 1.00 34.73 |
| ATOM | 1805 | O | HOH | 339 | 24.344 | 20.385 | 25.121 | 1.00 53.42 |
| ATOM | 1806 | O | HOH | 340 | 31.550 | 10.656 | 40.819 | 1.00 47.85 |
| ATOM | 1807 | O | HOH | 341 | 17.569 | 23.030 | 25.796 | 1.00 28.17 |
| ATOM | 1808 | O | HOH | 342 | 19.174 | 38.552 | 23.965 | 1.00 45.54 |
| ATOM | 1809 | O | HOH | 343 | 24.268 | 37.527 | 25.415 | 1.00 30.97 |
| ATOM | 1810 | O | HOH | 344 | 21.266 | 29.482 | 41.551 | 1.00 19.69 |
| ATOM | 1811 | O | HOH | 345 | 20.668 | 26.999 | 41.933 | 1.00 11.81 |
| ATOM | 1812 | O | HOH | 346 | 24.780 | 24.795 | 43.460 | 1.00 20.95 |
| ATOM | 1813 | O | HOH | 347 | 42.962 | 13.170 | 46.312 | 1.00 31.00 |
| ATOM | 1814 | O | HOH | 348 | 32.322 | 14.088 | 47.013 | 1.00 28.20 |
| ATOM | 1815 | O | HOH | 349 | 31.708 | 13.186 | 49.679 | 1.00 35.57 |
| ATOM | 1816 | O | HOH | 350 | 22.408 | 35.801 | 50.514 | 1.00 40.71 |
| ATOM | 1817 | O | HOH | 351 | 25.366 | 47.090 | 42.583 | 1.00 38.15 |
| ATOM | 1818 | O | HOH | 352 | 27.243 | 47.647 | 43.977 | 1.00 41.55 |
| ATOM | 1819 | O | HOH | 353 | 29.868 | 45.076 | 42.906 | 1.00 29.32 |
| ATOM | 1820 | O | HOH | 354 | 14.175 | 22.269 | 42.680 | 1.00 74.11 |
| ATOM | 1821 | O | HOH | 355 | 13.414 | 10.739 | 35.791 | 1.00 29.92 |
| ATOM | 1822 | O | HOH | 356 | 20.338 | 9.974 | 37.765 | 1.00 30.46 |
| ATOM | 1823 | O | HOH | 357 | 23.520 | 40.420 | 24.953 | 1.00 29.75 |
| ATOM | 1824 | O | HOH | 358 | 25.718 | 41.692 | 26.023 | 1.00 30.43 |
| ATOM | 1825 | O | HOH | 359 | 26.826 | 38.466 | 25.345 | 1.00 31.72 |
| ATOM | 1826 | O | HOH | 360 | 37.768 | 42.373 | 25.123 | 1.00 41.53 |
| ATOM | 1827 | O | HOH | 361 | 40.078 | 42.268 | 25.852 | 1.00 37.12 |
| ATOM | 1828 | O | HOH | 362 | 31.483 | 38.677 | 22.083 | 1.00 54.21 |
| ATOM | 1829 | O | HOH | 363 | 33.891 | 37.723 | 30.126 | 1.00 23.35 |
| ATOM | 1860 | O | HOH | 364 | 39.936 | 26.543 | 36.329 | 1.00 47.93 |
| ATOM | 1830 | O | HOH | 365 | 36.631 | 34.210 | 41.636 | 1.00 62.74 |
| ATOM | 1831 | O | HOH | 366 | 37.038 | 29.783 | 52.197 | 1.00 40.07 |
| ATOM | 1832 | O | HOH | 367 | 37.289 | 37.407 | 40.231 | 1.00 37.59 |
| ATOM | 1833 | O | HOH | 368 | 18.930 | 17.517 | 52.472 | 1.00 35.80 |
| ATOM | 1834 | O | HOH | 369 | 19.506 | 18.914 | 57.913 | 1.00 45.72 |

FIG. 5AS

| | | | | | | | |
|---|---|---|---|---|---|---|---|
| ATOM | 1835 | O | HOH | 370 | 30.903 | 26.708 | 41.139 | 1.00 21.54 |
| ATOM | 1836 | O | HOH | 371 | 30.369 | 25.678 | 24.583 | 1.00 22.46 |
| ATOM | 1837 | O | HOH | 372 | 21.000 | 33.705 | 20.826 | 1.00 26.00 |
| ATOM | 1838 | O | HOH | 373 | 13.648 | 32.794 | 21.329 | 1.00 27.98 |
| ATOM | 1839 | O | HOH | 374 | 29.735 | 25.683 | 38.707 | 1.00 21.00 |
| ATOM | 1859 | O | HOH | 375 | 33.670 | 24.419 | 60.503 | 1.00 50.04 |
| ATOM | 1840 | O | HOH | 376 | 30.034 | 11.047 | 37.420 | 1.00 43.28 |
| ATOM | 1841 | O | HOH | 377 | 8.662 | 35.846 | 35.068 | 1.00 51.94 |
| ATOM | 1842 | O | HOH | 378 | 10.847 | 36.466 | 39.503 | 1.00 42.32 |
| ATOM | 1843 | O | HOH | 379 | 14.395 | 48.943 | 39.085 | 1.00 29.72 |
| ATOM | 1844 | O | HOH | 380 | 36.676 | 11.660 | 40.172 | 1.00 39.81 |
| ATOM | 1845 | O | HOH | 381 | 35.968 | 7.212 | 34.763 | 1.00 58.66 |
| ATOM | 1846 | O | HOH | 382 | 17.426 | 21.988 | 21.077 | 1.00 41.69 |
| ATOM | 1847 | O | HOH | 383 | 29.837 | 22.623 | 39.378 | 1.00 32.82 |
| ATOM | 1848 | O | HOH | 384 | 23.855 | 29.386 | 55.164 | 1.00 55.00 |
| ATOM | 1849 | O | HOH | 385 | 17.408 | 35.360 | 47.495 | 1.00 61.61 |
| ATOM | 1850 | O | HOH | 386 | 27.900 | 49.720 | 42.445 | 1.00 47.70 |
| ATOM | 1851 | O | HOH | 387 | 13.932 | 36.230 | 44.385 | 1.00 45.08 |
| ATOM | 1852 | O | HOH | 388 | 12.650 | 28.021 | 43.288 | 1.00 49.86 |
| ATOM | 1853 | O | HOH | 389 | 16.974 | 42.367 | 43.435 | 1.00 34.38 |
| ATOM | 1854 | O | HOH | 390 | 37.335 | 42.653 | 28.295 | 1.00 64.46 |
| ATOM | 1855 | O | HOH | 391 | 29.701 | 49.856 | 35.323 | 1.00 62.61 |
| ATOM | 1856 | O | HOH | 392 | 27.267 | 50.835 | 33.976 | 1.00 66.60 |
| ATOM | 1857 | O | HOH | 393 | 19.661 | 29.181 | 51.537 | 1.00 34.01 |
| ATOM | 1858 | O | HOH | 394 | 29.412 | 17.505 | 59.089 | 1.00 51.78 |
| TER | | | | | | | | |
| END | | | | | | | | |

FIG. 5AT

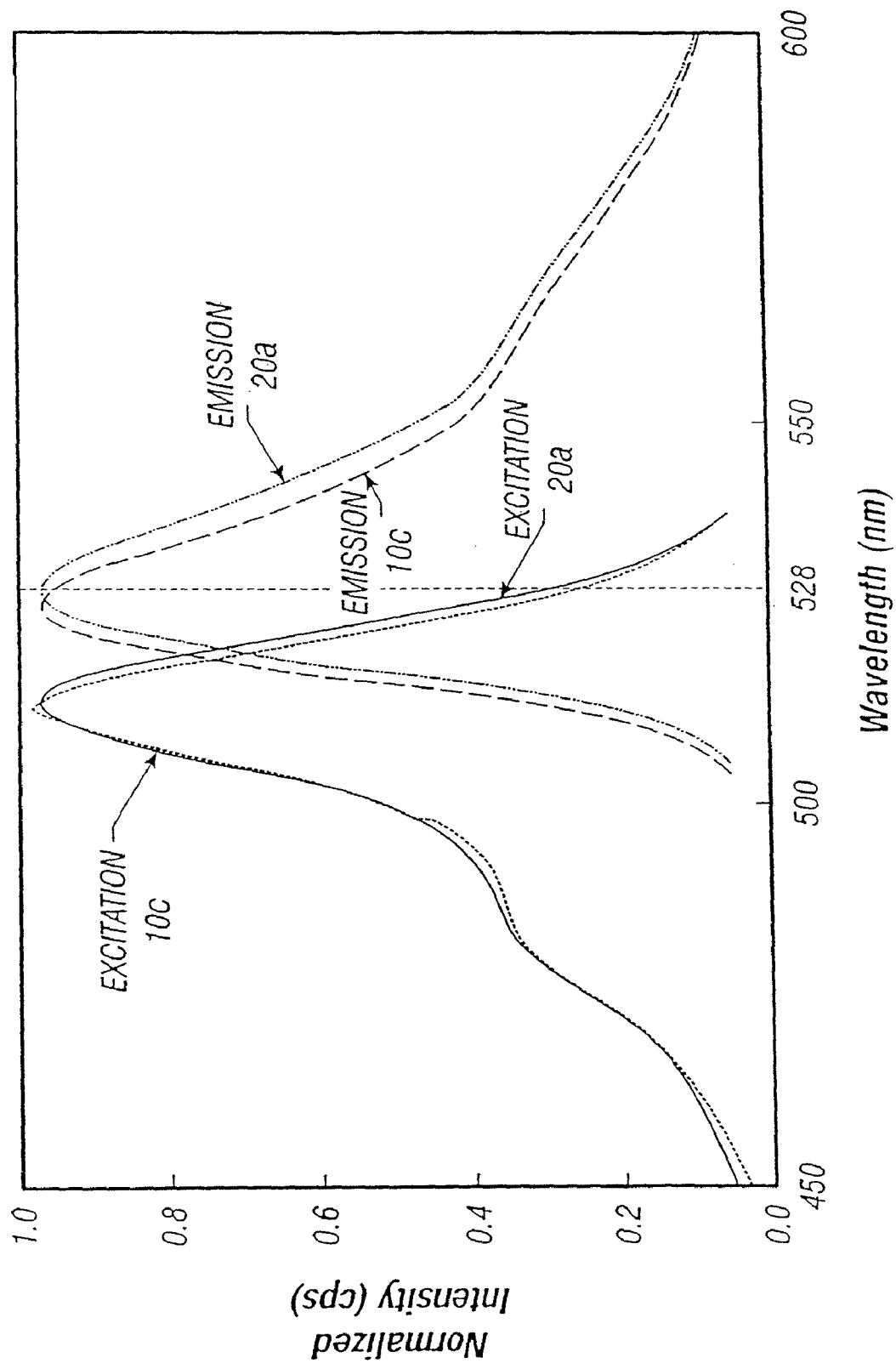

LONG WAVELENGTH ENGINEERED FLUORESCENT PROTEINS

This invention was made in part with Government support under grant no. MCB 9418479 awarded by the National Science Foundation. The Government may have rights in this invention.

BACKGROUND OF THE INVENTION

This a continuation in part of application Ser. No. 08/974,737, filed Nov. 19, 1997, now allowed, which is a continuation of application Ser. No. 08/911,825, filed Aug. 15, 1997, now issued as U.S. Pat. No. 6,054,321, which is a continuation in part of application Ser. No. 08/706,408, filed Aug. 30, 1996, now allowed, which claims the benefit of the earlier filing date of a U.S. provisional patent application Ser. No. 60/024,050 filed on Aug. 16, 1996 each of which are herein incorporated by reference.

Fluorescent molecules are attractive as reporter molecules in many assay systems because of their high sensitivity and ease of quantification. Recently, fluorescent proteins have been the focus of much attention because they can be produced in vivo by biological systems, and can be used to trace intracellular events without the need to be introduced into the cell through microinjection or permeablization. The green fluorescent protein of *Aequorea victoria* is particularly interesting as a fluorescent protein. A cDNA for the protein has been cloned. (D. C. Prasher et al., "Primary structure of the *Aequorea victoria* green-fluorescent protein," *Gene* (1992) 111:229-33.) Not only can the primary amino acid sequence of the protein be expressed from the cDNA, but the expressed protein can fluoresce. This indicates that the protein can undergo the cyclization and oxidation believed to be necessary for fluorescence. *Aequorea* green fluorescent protein ("GFP") is a stable, proteolysis-resistant single chain of 238 residues and has two absorption maxima at around 395 and 475 nm. The relative amplitudes of these two peaks is sensitive to environmental factors (W. W. Ward. *Bioluminescence and Chemiluminescence* (M. A. DeLuca and W. D. McElroy, eds) Academic Press pp. 235-242 (1981); W. W. Ward & S. H. Bokman *Biochemistry* 21:4535-4540 (1982); W. W. Ward et al. *Photochem. Photobiol.* 35:803-808 (1982)) and illumination history (A. B. Cubitt et al. *Trends Biochem. Sci.* 20:448-455 (1995)), presumably reflecting two or more ground states. Excitation at the primary absorption peak of 395 nm yields an emission maximum at 508 nm with a quantum yield of 0.72-0.85 (O. Shimomura and F. H. Johnson *J. Cell. Comp. Physiol.* 59:223 (1962); J. G. Morin and J. W. Hastings, *J. Cell. Physiol.* 77:313 (1971); H. Morise et al. *Biochemistry* 13:2656 (1974); W. W. Ward *Photochem. Photobiol. Reviews* (Smith, K. C. ed.) 4:1 (1979); A. B. Cubitt et al. *Trends Biochem. Sci.* 20:448-455 (1995); D. C. Prasher *Trends Genet.* 11:320-323 (1995); M. Chalfie *Photochem. Photobiol.* 62:651-656 (1995); W. W. Ward. *Bioluminescence and Chemiluminescence* (M. A. DeLuca and W. D. McElroy, eds) Academic Press pp. 235-242 (1981); W. W. Ward & S. H. Bokman *Biochemistry* 21:4535-4540 (1982); W. W. Ward et al. *Photochem. Photobiol.* 35:803-808 (1982)). The fluorophore results from the autocatalytic cyclization of the polypeptide backbone between residues Ser[65] and Gly[67] and oxidation of the –β bond of Tyr[66] (A. B. Cubitt et al. *Trends Biochem. Sci.* 20:448-455 (1995); C. W. Cody et al. *Biochemistry* 32:1212-1218 (1993); R. Heim et al. *Proc. Natl. Acad. Sci.* USA 91:12501-12504 (1994)). Mutation of Ser[65] to Thr (S65T) simplifies the excitation spectrum to a single peak at 488 nm of enhanced amplitude (R. Heim et al. *Nature* 373: 664-665 (1995)), which no longer gives signs of conformational isomers (A. B. Cubitt et al. *Trends Biochem. Sci.* 20:448-455 (1995)).

Fluorescent proteins have been used as markers of gene expression, tracers of cell lineage and as fusion tags to monitor protein localization within living cells. (M. Chalfie et al., "Green fluorescent protein as a marker for gene expression," *Science* 263:802-805; A. B. Cubitt et al., "Understanding, improving and using green fluorescent proteins," *TIBS* 20, November 1995, pp. 448-455. U.S. Pat. No. 5,491,084, M. Chalfie and D. Prasher. Furthermore, engineered versions of *Aequorea* green fluorescent protein have been identified that exhibit altered fluorescence characteristics, including altered excitation and emission maxima, as well as excitation and emission spectra of different shapes. (R. Heim et al., "Wavelength mutations and posttranslational autoxidation of green fluorescent protein," *Proc. Natl. Acad. Sci. USA*, (1994) 91:12501-04; R. Heim et al., "Improved green fluorescence," *Nature* (1995) 373:663-665.)

A second class of applications rely on GFP as a specific indicator of some cellular property, and hence depend on the particular spectral characteristics of the variant employed. For recent reviews on GFP variants and their applications, see (Palm & Wlodawer, 1999; Tsien, 1998), and for a review volume on specialized applications, see (Sullivan & Kay, 1999). Biosensor applications include the use of differently colored GFPs for fluorescence resonance energy transfer (FRET) to monitor protein-protein interactions (Heim, 1999) or Ca2+ concentrations (Miyawaki et al., 1999), and receptor insertions within GFP surface loops to monitor ligand binding (Baird et al., 1999; Doi & Yanagawa, 1999).

The fluorescence emission of a number of variants is highly sensitive to the acidity of the environment (Elsliger et al., 1999; Wachter et al., 1998). Hence, one particularly successful application of green fluorescent protein (GFP) as a visual reporter in live cells has been the determination of organelle or cytosol pH (Kneen et al., 1998; Llopis et al., 1998; Miesenbock et al., 1998; Robey et al., 1998). The two chromophore charge states have been found to be relevant to the pH sensitivity of the intact protein, and have been characterized crystallographically in terms of conformational changes in the vicinity of the phenolic end (Elsliger et al., 1999), and spectroscopically using Raman studies (Bell et al., 2000). The neutral form of the chromophore, band A, absorbs around 400 nm in most variants, whereas the chromophore anion with the phenolic end deprotonated (band B) absorbs in the blue to green, depending on the particular mutations in the vicinity of the chromophore. WT GFP exhibits spectral characteristics that are consistent with two ground states characterized by a combination of bands A and B, the ratio of which is relatively invariant between pH 6 and 10 (Palm & Wlodawer, 1999; Ward et al., 1982). It has been suggested that an internal equilibrium exists where a proton is shared between the chromophore phenolate and the carboxylate of Glu222 over a broad range of pH (Brejc et al., 1997; Palm et al., 1997). Recent electrostatic calculations support this model (Scharnagl et al., 1999), and estimate the theoretical $pK_a$ for complete chromophore deprotonation to be about 13, consistent with the observation of a doubling of emission intensity at pH 11-12 (Bokman & Ward, 1981; Palm & Wlodawer, 1999).

In contrast to WT GFP, the chromophore of most variants titrates with a single $pK_a$. The color emission and the chromophore $pK_a$ are strongly modulated by the protein surroundings (Llopis et al., 1998). G1u222 is completely conserved among GFP homologs (Matz et al., 1999), and its substitution by a glutamine has been shown to dramatically reduce efficiency of chromophore generation (Elsliger et al., 1999).

Protonation of Glu222 in S65T and in GFPs containing the T203Y mutation (YFPs) is generally thought to be responsible for lowering the chromophore pKa from that of WT to about 5.9 in GFP S65T (Elsliger et al., 1999; Kneen et al., 1998), and 5.2-5.4 in YFP (GFP S65GN68L/S72A/T203Y) (Ormo et al., 1996; Wachter & Remington, 1999). In the YFPs, it is thought that the crystallographically identified stacking interaction of the chromophore with Tyr203 is largely responsible for the spectral red-shift (Wachter et al., 1998).

Unlike other variants, we have discovered that the YFP chromophore $pK_a$ shows a strong dependence on the concentration of certain small anions such as chloride (Wachter & Remington, 1999), and increases in $pK_a$ from about 5.2 to 7.0 in the presence of 140 mM NaCl (Elsliger et al., 1999). This sensitivity can be exploited to enable the creation of novel GFPs as biosensors to measure ions present both in the cytoplasm or in cellular compartments (Wachter & Remington, 1999) within living cells. The present invention includes the creation and use of novel GFP variants that permit the fluorescent measurement of a variety of ions, including halides such as chloride and iodide. These properties add variety and utility to the arsenal of biologically based fluorescent indicators. There is a need for engineered fluorescent proteins with varied fluorescent properties and with the ability to respond to ion concentrations via a change in fluorescence characteristics.

BRIEF DESCRIPTION OF THE DRAWINGS

FIG. 3 depicts the nucleotide sequence (SEQ ID NO:1) and deduced amino acid sequence (SEQ ID NO:2) of an *Aequorea* green fluorescent protein.

FIGS. 4A-B depict the nucleotide sequence (SEQ ID NO:3) and deduced amino acid sequence (SEQ ID NO:4) of the engineered *Aequorea*-related fluorescent protein S65G/S72A/T203Y utilizing preferred mammalian codons and optimal Kozak sequence.

FIGS. 5A to 5AT present the coordinates for the crystal structure of *Aequorea*-related green fluorescent protein S65T.

FIG. 6 shows the fluorescence excitation and emission spectra for engineered fluorescent proteins 20A and 10C (Table F). The vertical line at 528 nm compares the emission maxima of 10C, to the left of the line, and 20A, to the right of the line.

SUMMARY OF THE INVENTION

Figure 1A:
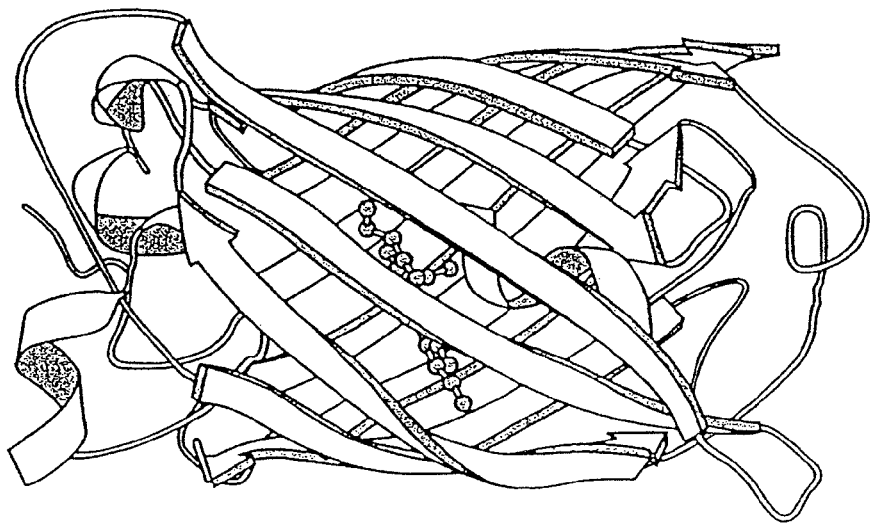
FIGS. 1A-1B. (A) Schematic drawing of the backbone of GFP produced by Molscript (J. P. Kraulis, *J. Appl. Cryst.*, 24:946 (1991)). The chromophore is shown as a ball and stick model. (B) Schematic drawing of the overall fold of GFP. Approximate residue numbers mark the beginning and ending of the secondary structure elements.

This invention provides functional engineered fluorescent proteins with varied fluorescence characteristics that can be easily distinguished from currently existing green and blue fluorescent proteins. Such engineered fluorescent proteins enable the simultaneous measurement of two or more processes within cells and can be used as fluorescence energy donors or acceptors, as well as biosensors for detecting anions. Longer wavelength engineered fluorescent proteins are particularly useful because photodynamic toxicity and auto-fluorescence of cells are significantly reduced at longer wavelengths. In particular, the introduction of the substitution T203X, wherein X is an aromatic amino acid, results in an increase in the excitation and emission wavelength maxima of *Aequorea*-related fluorescent proteins.

In one aspect, this invention provides a nucleic acid molecule comprising a nucleotide sequence encoding a functional engineered fluorescent protein whose amino acid sequence is substantially identical to the amino acid sequence of *Aequorea* green fluorescent protein (SEQ ID NO:2) and which differs from SEQ ID NO:2 by at least an amino acid substitution located no more than about 0.5 nm from the chromophore of the engineered fluorescent protein, wherein the substitution alters the electronic environment of the chromophore, whereby the functional engineered fluorescent protein has a different fluorescent property than *Aequorea* green fluorescent protein.

In one aspect this invention provides a nucleic acid molecule comprising a nucleotide sequence encoding a functional engineered fluorescent protein whose amino acid sequence is substantially identical to the amino acid sequence of *Aequorea* green fluorescent protein (SEQ ID NO:2) and which differs from SEQ ID NO:2 by at least a substitution at T203 and, in particular, T203X, wherein X is an aromatic amino acid selected from H, Y, W or F, said functional engineered fluorescent protein having a different fluorescent property than *Aequorea* green fluorescent protein. In one embodiment, the amino acid sequence further comprises a substitution at S65, wherein the substitution is selected from S65G, S65T, S65A, S65L, S65C, S65V and S65I. In another embodiment, the amino acid sequence differs by no more than the substitutions S65T/T203H; S65T/T203Y; S72A/F64L/S65G/T203Y; S65G/V68L/Q69K/S72A/T203Y; S72A/S65G/V68L/T203Y; S65G/S72A1T203Y; or S65G/S72A/T203W. In another embodiment, the amino acid sequence further comprises a substitution at Y66, wherein the substitution is selected from Y66H, Y66F, and Y66W. In another embodiment, the amino acid sequence further comprises a mutation from Table A. In another embodiment, the amino acid sequence further comprises a folding mutation. In another embodiment, the nucleotide sequence encoding the protein differs from the nucleotide sequence of SEQ ID NO:1 by the substitution of at least one codon by a preferred mammalian codon. In another embodiment, the nucleic acid molecule encodes a fusion protein wherein the fusion protein comprises a polypeptide of interest and the functional engineered fluorescent protein.

In another aspect, this invention provides a nucleic acid molecule comprising a nucleotide sequence encoding a functional engineered fluorescent protein whose amino acid sequence is substantially identical to the amino acid sequence of *Aequorea* green fluorescent protein (SEQ ID NO:2) and which differs from SEQ ID NO:2 by at least an amino acid substitution at L42, V61, T62, V68, Q69, Q94, N121, Y145, H148, V150, F165, I167, Q183, N185, L220, E222 (not E222G), or V224, said functional engineered fluorescent protein having a different fluorescent property than *Aequorea* green fluorescent protein. In one embodiment, amino acid substitution is:

L42X, wherein X is selected from C, F, H, W and Y,
V61X, wherein X is selected from F, Y, H and C,
T62X, wherein X is selected from A, V, F, S, D, N, Q, Y, H and C,
V68X, wherein X is selected from F, Y and H,
Q69X, wherein X is selected from K, R, E and G,
Q94X, wherein X is selected from D, E, H, K and N,
N121X, wherein X is selected from F, H, W and Y,
Y145X, wherein X is selected from W, C, F, L, E, H, K and Q,
H148X, wherein X is selected from F, Y, N, K, Q and R,
V150X, wherein X is selected from F, Y and H,
F165X, wherein X is selected from H, Q, W and Y,
I167X, wherein X is selected from F, Y and H,
Q183X, wherein X is selected from H, Y, E and K,
N185X, wherein X is selected from D, E, H, K and Q,
L220X, wherein X is selected from H, N, Q and T,
E222X, wherein X is selected from N and Q, or
V224X, wherein X is selected from H, N, Q, T, F, W and Y.

In a further aspect, this invention provides an expression vector comprising expression control sequences operatively linked to any of the aforementioned nucleic acid molecules. In a further aspect, this invention provides a recombinant host cell comprising the aforementioned expression vector.

In another aspect, this invention provides a functional engineered fluorescent protein whose amino acid sequence is substantially identical to the amino acid sequence of *Aequorea* green fluorescent protein (SEQ ID NO:2) and which differs from SEQ ID NO:2 by at least an amino acid substitution located no more than about 0.5 nm from the chromophore of the engineered fluorescent protein, wherein the substitution alters the electronic environment of the chromophore, whereby the functional engineered fluorescent protein has a different fluorescent property than *Aequorea* green fluorescent protein.

In another aspect, this invention provides a functional engineered fluorescent protein whose amino acid sequence is substantially identical to the amino acid sequence of *Aequorea* green fluorescent protein (SEQ ID NO:2) and which differs from SEQ ID NO:2 by at least the amino acid substitution at T203, and in particular, T203X, wherein X is an aromatic amino acid selected from H, Y, W or F, said functional engineered fluorescent protein having a different fluorescent property than *Aequorea* green fluorescent protein. In one embodiment, the amino acid sequence further comprises a substitution at S65, wherein the substitution is selected from S65G, S65T, S65A, S65L, S65C, S65V and S65I. In another embodiment, the amino acid sequence differs by no more than the substitutions S65T/T203H; S65T/T203Y; S72A/F64L/S65G/T203Y; S72A/S65GN68L/T203Y; S65G/V68L/Q69K/S72A/T203Y; S65G/S72A/T203Y; or S65G/S72A/T203W. In another embodiment, the amino acid sequence further comprises a substitution at Y66, wherein the substitution is selected from Y66H, Y66F, and Y66W. In another embodiment, the amino acid sequence further comprises a folding mutation. In another embodiment, the engineered fluorescent protein is part of a fusion protein wherein the fusion protein comprises a polypeptide of interest and the functional engineered fluorescent protein.

In another aspect this invention provides a functional engineered fluorescent protein whose amino acid sequence is substantially identical to the amino acid sequence of *Aequorea* green fluorescent protein (SEQ ID NO:2) and which differs from SEQ ID NO:2 by at least an amino acid substitution at L42, V61, T62, V68, Q69, Q94, N121, Y145, H148, V150, F165, I167, Q183, N185, L220, E222, or V224, said functional engineered fluorescent protein having a different fluorescent property than *Aequorea* green fluorescent protein.

In another aspect, this invention provides a fluorescently labelled antibody comprising an antibody coupled to any of the aforementioned functional engineered fluorescent proteins. In one embodiment, the fluorescently labelled antibody is a fusion protein wherein the fusion protein comprises the antibody fused to the functional engineered fluorescent protein.

In another aspect, this invention provides a nucleic acid molecule comprising a nucleotide sequence encoding an antibody fused to a nucleotide sequence encoding a functional engineered fluorescent protein of this invention.

In another aspect, this invention provides a fluorescently labelled nucleic acid probe comprising a nucleic acid probe coupled to a functional engineered fluorescent protein whose amino acid sequence of this invention. The fusion can be through a linker peptide.

In another aspect, this invention provides a method for determining whether a mixture contains a target comprising contacting the mixture with a fluorescently labelled probe comprising a probe and a functional engineered fluorescent protein of this invention; and determining whether the target has bound to the probe. In one embodiment, the target molecule is captured on a solid matrix.

In another aspect, this invention provides a method for engineering a functional engineered fluorescent protein having a fluorescent property different than Aequorea green fluorescent protein, comprising substituting an amino acid that is located no more than 0.5 nm from any atom in the chromophore of an Aequorea-related green fluorescent protein with another amino acid; whereby the substitution alters a fluorescent property of the protein. In one embodiment, the amino acid substitution alters the electronic environment of the chromophore.

In another aspect, this invention provides a method for engineering, a functional engineered fluorescent protein having a different fluorescent property than Aequorea green fluorescent protein comprising substituting amino acids in a loop domain of an Aequorea-related green fluorescent protein with amino acids so as to create a consensus sequence for phosphorylation or for proteolysis.

In another aspect, this invention provides a method for producing fluorescence resonance energy transfer comprising providing a donor molecule comprising a functional engineered fluorescent protein this invention; providing an appropriate acceptor molecule for the fluorescent protein; and bringing the donor molecule and the acceptor molecule into sufficiently close contact to allow fluorescence resonance energy transfer.

In another aspect, this invention provides a method for producing fluorescence resonance energy transfer comprising providing an acceptor molecule comprising a functional engineered fluorescent protein of this invention; providing an appropriate donor molecule for the fluorescent protein; and bringing the donor molecule and the acceptor molecule into sufficiently close contact to allow fluorescence resonance energy transfer. In one embodiment, the donor molecule is a engineered fluorescent protein whose amino acid sequence comprises the substitution T203I and the acceptor molecule is an engineered fluorescent protein whose amino acid sequence comprises the substitution T203X, wherein X is an aromatic amino acid selected from H, Y, W or F, said functional engineered fluorescent protein having a different fluorescent property than Aequorea green fluorescent protein.

In another aspect, this invention provides a crystal of a protein comprising a fluorescent protein with an amino acid sequence substantially identical to SEQ ID NO: 2, wherein said crystal diffracts with at least a 2.0 to 3.0 angstrom resolution.

In another embodiment, this invention provides computational method of designing a fluorescent protein comprising determining from a three dimensional model of a crystallized fluorescent protein comprising a fluorescent protein with a bound ligand, at least one interacting amino acid of the fluorescent protein that interacts with at least one first chemical moiety of the ligand, and selecting at least one chemical modification of the first chemical moiety to produce a second chemical moiety with a structure to either decrease or increase an interaction between the interacting amino acid and the second chemical moiety compared to the interaction between the interacting amino acid and the first chemical moiety.

In another embodiment, this invention provides a computational method of modeling the three dimensional structure of a fluorescent protein comprising determining a three dimensional relationship between at least two atoms listed in the atomic coordinates of FIGS. 5A-5AT.

In another embodiment, this invention provides a device comprising a storage device and, stored in the device, at least 10 atomic coordinates selected from the atomic coordinates listed in FIGS. 5A-5AT. In one embodiment, the storage device is a computer readable device that stores code that receives as input the atomic coordinates. In another embodiment, the computer readable device is a floppy disk or a hard drive.

In another embodiment this invention provides a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by at least one first substitution at position T203, wherein the substitution selected from the group consisting H, Y, W or F, and at least one second substitution at position H148.

In another aspect the present invention includes a method of determining the presence of an anion of interest in a sample, comprising the steps of introducing an engineered green fluorescent protein into a sample, said engineered green fluorescent protein comprising an amino acid sequence substantially identical to the amino acid sequence of Aequorea green fluorescent protein (SEQ ID NO:2) and which differs from SEQ ID NO:2 by at least one first substitution at position T203, wherein the substitution selected from the group consisting H, Y, W or F, and determining the fluorescence of said engineered green fluorescent protein in said sample.

In another embodiment, the invention includes a functional engineered fluorescent protein whose amino acid sequence is substantially identical to the amino acid sequence of Aequorea green fluorescent protein (SEQ ID NO:2) and which differs from SEQ ID NO:2 by at least one first substitution at position T203, wherein the substitution selected from the group consisting H, Y, W or F, and at least one second substitution at position H148, wherein said functional engineered fluorescent protein has a different fluorescent property than Aequorea green fluorescent protein.

In another embodiment the invention includes a host cell comprising a functional engineered fluorescent protein whose amino acid sequence is substantially identical to the amino acid sequence of Aequorea green fluorescent protein (SEQ ID NO:2) and which differs from SEQ ID NO:2 by at least one first substitution at position T203, wherein the substitution selected from the group consisting H, Y, W or F, and at least one second substitution at position H148, wherein said functional engineered fluorescent protein has a different fluorescent property than Aequorea green fluorescent protein.

DETAILED DESCRIPTION OF THE INVENTION

I. Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. For purposes of the present invention, the following terms are defined below.

"Binding pair" refers to two moieties (e.g. chemical or biochemical) that have an affinity for one another. Examples of binding pairs include antigen/antibodies, lectin/avidin, target polynucleotide/probe oligonucleotide, antibody/anti-antibody, receptor/ligand, enzyme/ligand and the like. "One member of a binding pair" refers to one moiety of the pair, such as an antigen or ligand.

"Nucleic acid" refers to a deoxyribonucleotide or ribonucleotide polymer in either single- or double-stranded form, and, unless otherwise limited, encompasses known analogs of natural nucleotides that can function in a similar manner as naturally occurring nucleotides. It will be understood that when a nucleic acid molecule is represented by a DNA sequence, this also includes RNA molecules having the corresponding RNA sequence in which "U" replaces "T."

"Recombinant nucleic acid molecule" refers to a nucleic acid molecule which is not naturally occurring, and which comprises two nucleotide sequences which are not naturally joined together. Recombinant nucleic acid molecules are produced by artificial recombination, e.g., genetic engineering techniques or chemical synthesis.

Reference to a nucleotide sequence "encoding" a polypeptide means that the sequence, upon transcription and translation of mRNA, produces the polypeptide. This includes both the coding strand, whose nucleotide sequence is identical to mRNA and whose sequence is usually provided in the sequence listing, as well as its complementary strand, which is used as the template for transcription. As any person skilled in the art recognizes, this also includes all degenerate nucleotide sequences encoding the same amino acid sequence. Nucleotide sequences encoding a polypeptide include sequences containing introns.

"Expression control sequences" refers to nucleotide sequences that regulate the expression of a nucleotide sequence to which they are operatively linked. Expression control sequences are "operatively linked" to a nucleotide sequence when the expression control sequences control and regulate the transcription and, as appropriate, translation of the nucleotide sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

"Control sequence" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

"Isolated polynucleotide" refers a polynucleotide of genomic, cDNA, or synthetic origin or some combination there of, which by virtue of its origin the "isolated polynucleotide" (1) is not associated with the cell in which the "isolated polynucleotide" is found in nature, or (2) is operably linked to a polynucleotide which it is not linked to in nature.

"Polynucleotide" refers to a polymeric form of nucleotides of at least 10 bases in length, either ribonucleotides or deoxynucleotides or a modified form of either type of nucleotide. The term includes single and double stranded forms of DNA.

The term "probe" refers to a substance that specifically binds to another substance (a "target"). Probes include, for example, antibodies, nucleic acids, receptors and their ligands.

"Modulation" refers to the capacity to either enhance or inhibit a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "modulator" refers to a chemical (naturally occurring or non-naturally occurring), such as a synthetic molecule (e.g., nucleic acid, protein, non-peptide, or organic molecule), or an extract made from biological materials such as bacteria, plants, fungi, or animal (particularly mammalian) cells or tissues. Modulators can be evaluated for potential activity as inhibitors or activators (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

The term "test chemical" refers to a chemical to be tested by one or more screening method(s) of the invention as a putative modulator. A test chemical is usually not known to bind to the target of interest. The term "control test chemical" refers to a chemical known to bind to the target (e.g., a known agonist, antagonist, partial agonist or inverse agonist). Usually, various predetermined concentrations of test chemicals are used for screening, such as 0.01 µM, 0.1 µM, 1.0 µM, and 10.0 µM.

The term "target" refers to a biochemical entity involved a biological process. Targets are typically proteins that play a useful role in the physiology or biology of an organism. A therapeutic chemical binds to target to alter or modulate its function. As used herein targets can include cell surface receptors, G-proteins, kinases, ion channels, phopholipases and other proteins mentioned herein.

The term "label" refers to a composition detectable by spectroscopic, photochemical, biochemical, immunochemical, or chemical means. For example, useful labels include $^{32}P$, fluorescent dyes, fluorescent proteins, electron-dense reagents, enzymes (e.g., as commonly used in an ELISA), biotin, dioxigenin, or haptens and proteins for which antisera or monoclonal antibodies are available. For example, polypeptides of this invention can be made as detectable labels, by e.g., incorporating a them as into a polypeptide, and used to label antibodies specifically reactive with the polypeptide. A label often generates a measurable signal, such as radioactivity, fluorescent light or enzyme activity, which can be used to quantitate the amount of bound label.

The term "nucleic acid probe" refers to a nucleic acid molecule that binds to a specific sequence or sub-sequence of another nucleic acid molecule. A probe is preferably a nucleic acid molecule that binds through complementary base pairing to the full sequence or to a sub-sequence of a target nucleic acid. It will be understood that probes may bind target sequences lacking complete complementarity with the probe sequence depending upon the stringency of the hybridization conditions. Probes are preferably directly labelled as with isotopes, chromophores, lumiphores, chromogens, fluorescent proteins, or indirectly labelled such as with biotin to which a streptavidin complex may later bind. By assaying for the presence or absence of the probe, one can detect the presence or absence of the select sequence or sub-sequence.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The terms "polypeptide" and "protein" refers to a polymer of amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "recombinant host cell" refers to a cell that comprises a recombinant nucleic acid molecule. Thus, for example, recombinant host cells can express genes that are not found within the native (non-recombinant) form of the cell.

The terms "isolated" "purified" or "biologically pure" refer to material which is substantially or essentially free from components which normally accompany it as found in its native state. Purity and homogeneity are typically determined using analytical chemistry techniques such as polyacrylamide gel electrophoresis or high performance liquid chromatography. A protein or nucleic acid molecule which is the predominant protein or nucleic acid species present in a preparation is substantially purified. Generally, an isolated protein or nucleic acid molecule will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies.

The term "immunoassay" refers to an assay that utilizes an antibody to specifically bind an analyte. The immunoassay is characterized by the use of specific binding properties of a particular antibody to isolate, target, and/or quantify the analyte.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11-17 (1988); Smith and Waterman (1981) Adv. Appl. Math. 2: 482; Needleman and Wunsch (1970) J. Mol. Biol. 48: 443; Pearson and Lipman (1988) Proc. Natl. Acad. Sci. USA 85: 2444; Higgins and Sharp (1988) Gene, 73: 237-244 and Higgins and Sharp (1989) CABIOS 5: 151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a to codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "complementary" means that one nucleic acid molecule has the sequence of the binding partner of another nucleic acid molecule. Thus, the sequence 5'-ATGC-3' is complementary to the sequence 5'-GCAT-3'.

An amino acid sequence or a nucleotide sequence is "substantially identical" or "substantially similar" to a reference sequence if the amino acid sequence or nucleotide sequence has at least 80% sequence identity with the reference sequence over a given comparison window. Thus, substantially similar sequences include those having, for example, at least 85% sequence identity, at least 90% sequence identity, at least 95% sequence identity or at least 99% sequence identity. Two sequences that are identical to each other are, of course, also substantially identical.

A subject nucleotide sequence is "substantially complementary" to a reference nucleotide sequence if the complement of the subject nucleotide sequence is substantially identical to the reference nucleotide sequence.

The term "stringent conditions" refers to a temperature and ionic conditions used in nucleic acid hybridization. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

The term "allelic variants" refers to polymorphic forms of a gene at a particular genetic locus, as well as cDNAs derived from mRNA transcripts of the genes and the polypeptides encoded by them.

The term "preferred mammalian codon" refers to the subset of codons from among the set of codons encoding an amino acid that are most frequently used in proteins expressed in mammalian cells as chosen from the following list:

Amino Acid Preferred codons for high level mammalian expression

| | | |
|---|---|---|
| Gly | GGC, GGG | |
| Glu | GAG | |
| Asp | GAC | |
| Val | GUG, GUC | |
| Ala | GCC, GCU | |
| Ser | AGC, UCC | |
| Lys | AAG | |
| Asn | AAC | |
| Met | AUG | |
| Ile | AUC | |
| Thr | ACC | |
| Trp | UGG | |
| Cys | UGC | |
| Tyr | UAU, UAC | |
| Leu | CUG | |
| Phe | UUC | |
| Arg | CGC, AGG, AGA | |
| Gln | CAG | |
| His | CAC | |
| Pro | CCC | |

Fluorescent molecules are useful in fluorescence resonance energy transfer ("FRET"). FRET involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should likewise be as high as possible to maximize $R_0$, the distance at which energy transfer efficiency is 50%. However, the excitation spectra of the donor and acceptor should overlap as little as possible so that a wavelength region can be found at which the donor can be excited efficiently without directly exciting the acceptor. Fluorescence arising from direct excitation of the acceptor is difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type *Aequorea* GFP and the mutant form is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

II. Long Wavelength Engineered Fluorescent Proteins

A. Fluorescent Proteins

As used herein, the term "fluorescent protein" refers to any protein capable of fluorescence when excited with appropriate electromagnetic radiation. This includes fluorescent proteins whose amino acid sequences are either naturally occurring or engineered (i.e., analogs or mutants). Many cnidarians use green fluorescent proteins ("GFPs") as energy-transfer acceptors in bioluminescence. A "green fluorescent protein," as used herein, is a protein that fluoresces green light. Similarly, "blue fluorescent proteins" fluoresce blue light and "red fluorescent proteins" fluoresce red light. GFPs have been isolated from the Pacific Northwest jellyfish, *Aequorea victoria*, the sea pansy, *Renilla reniformis*, and *Phialidium gregarium*. W. W. Ward et al., *Photochem. Photobiol.*, 35:803-808 (1982); L. D. Levine et al., *Comp. Biochem. Physiol.*, 72B:77-85 (1982).

A variety of *Aequorea*-related fluorescent proteins having useful excitation and emission spectra have been engineered by modifying the amino acid sequence of a naturally occurring GFP from *Aequorea victoria*. (D. C. Prasher et al., *Gene*, 111:229-233 (1992); R. Heim et al., *Proc. Natl. Acad. Sci., USA*, 91:12501-04 (1994); U.S. patent application Ser. No. 08/337,915, filed Nov. 10, 1994; International application PCT/US95/14692, filed Nov. 10, 1995.)

As used herein, a fluorescent protein is an "*Aequorea*-related fluorescent protein" if any contiguous sequence of 150 amino acids of the fluorescent protein has at least 85% sequence identity with an amino acid sequence, either contiguous or non-contiguous, from the 238 amino-acid wild-type *Aequorea* green fluorescent protein of FIG. 3 (SEQ ID NO:2). More preferably, a fluorescent protein is an *Aequorea*-related fluorescent protein if any contiguous sequence of 200 amino acids of the fluorescent protein has at least 95% sequence identity with an amino acid sequence, either contiguous or non-contiguous, from the wild type *Aequorea* green fluorescent protein of FIG. 3 (SEQ ID NO:2). Similarly, the fluorescent protein may be related to *Renilla* or *Phialidium* wild-type fluorescent proteins using the same standards.

*Aequorea*-related fluorescent proteins include, for example and without limitation, wild-type (native) *Aequorea victoria* GFP (D. C. Prasher et al., "Primary structure of the *Aequorea victoria* green fluorescent protein," *Gene*, (1992) 111:229-33), whose nucleotide sequence (SEQ ID NO:1) and deduced amino acid sequence (SEQ ID NO:2) are presented in FIG. 3; allelic variants of this sequence, e.g., Q80R, which has the glutamine residue at position 80 substituted with arginine (M. Chalfie et al., *Science*, (1994) 263:802-805); those engineered *Aequorea*-related fluorescent proteins described herein, e.g., in Table A or Table F, variants that include one or more folding mutations and fragments of these proteins that are fluorescent, such as *Aequorea* green fluorescent protein from which the two amino-terminal amino acids have been removed. Several of these contain different aromatic amino acids within the central chromophore and fluoresce at a distinctly shorter wavelength than wild type species. For example, engineered proteins P4 and P4-3 contain (in addition to other mutations) the substitution Y66H, whereas W2 and W7 contain (in addition to other mutations) Y66W. Other mutations both close to the chromophore region of the protein and remote from it in primary sequence may affect the spectral properties of GFP and are listed in the first part of the table below.

TABLE A

| Clone | Mutation(s) | Excitation max (nm) | Emission max (nm) | Extinct. Coeff. $(M^{-1}cm^{-1})$ | Quantum yield |
|---|---|---|---|---|---|
| Wild type | None | 395 (475) | 508 | 21,000 (7,150) | 0.77 |
| P4 | Y66H | 383 | 447 | 13,500 | 0.21 |
| P4-3 | Y66H<br>Y145F | 381 | 445 | 14,000 | 0.38 |
| P4-3E | Y66H<br>Y145F<br>V163A | 384 | 448 | 22,000 | 0.27 |
| W7 | Y66W<br>N146I<br>M153T<br>V163A<br>N212K | 433 (453) | 475 (501) | 18,000 (17,100) | 0.67 |
| W2 | Y66W<br>I123V<br>Y145H<br>H148R<br>M153T<br>V163A<br>N212K | 432 (453) | 480 | 10,000 (9,600) | 0.72 |
| W1C | S65A<br>Y66W<br>S72A<br>N146I<br>M153T<br>V163A | 435 | 495 | 21,200 | 0.39 |

TABLE A-continued

| Clone | Mutation(s) | Excitation max (nm) | Emission max (nm) | Extinct. Coeff. ($M^{-1}cm^{-1}$) | Quantum yield |
|---|---|---|---|---|---|
| W1B | F64L S65T Y66W N146I M153T V163A | 434 (452) | 476 (505) | 32,500 | 0.4 |
| S65T | S65T | 489 | 511 | 39,200 | 0.68 |
| P4-1 | S65T M153A K238E | 504 (396) | 514 | 14,500 (8,600) | 0.53 |
| Emerald | S65T, S72A, N149K, M153T, I167T | 487 | 509 | 57,500 | 0.68 |
| EGFP | F64L, S65T | 488 | 507 | 55,900 | 0.64 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |
| Topaz | S65G S72A K79R T203Y | 514 | 527 | 94,500 | 0.6 |
| 10C YFP | S65G V68L S72A T203Y | 514 | 527 | 83,400 | 0.61 |
| Sapphire | S72A, Y145F T203I | 399 | 511 | 29,000 | 0.64 |

Additional mutations in *Aequorea*-related fluorescent proteins, referred to as "folding mutations," improve the ability of fluorescent proteins to fold at higher temperatures, and to be more fluorescent when expressed in mammalian cells, but have little or no effect on the peak wavelengths of excitation and emission. It should be noted that these may be combined with mutations that influence the spectral properties of GFP to produce proteins with altered spectral and folding properties. Folding mutations include: F64L, V68L, S72A, and also T44A, F99S, Y145F, N146I, M153T or A, V163A, I167T, S175G, S205T and N212K.

Figure 1B:
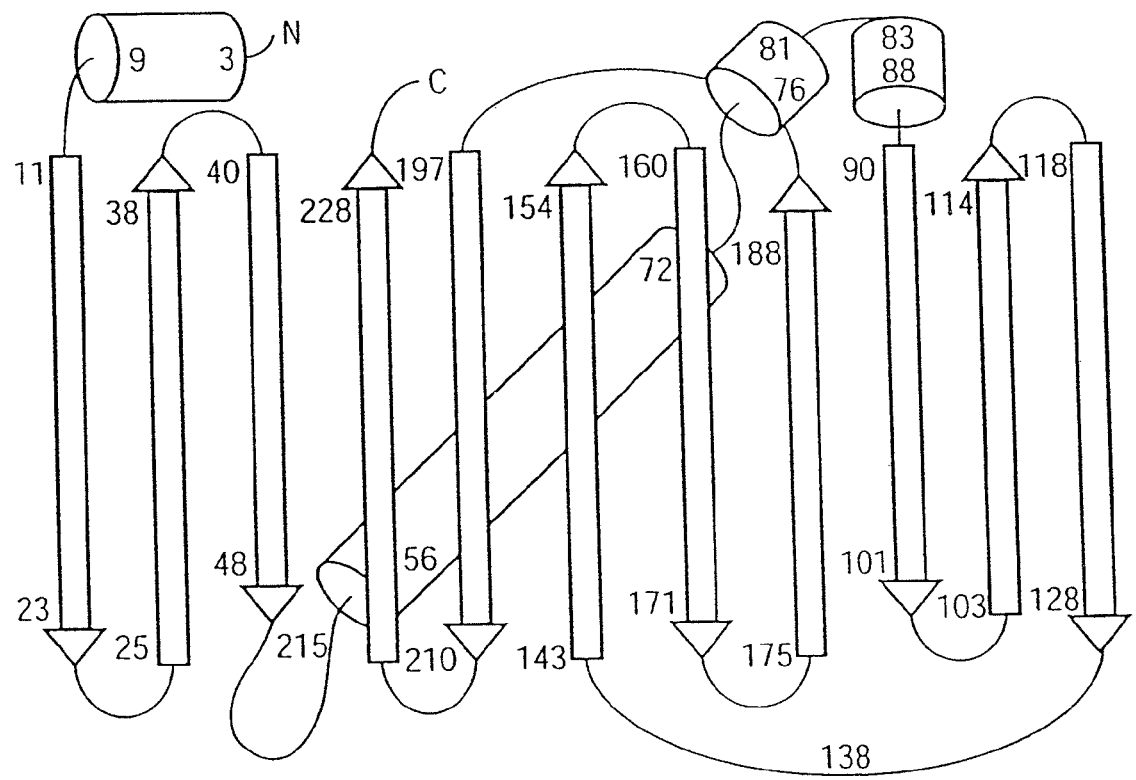

As used herein, the term "loop domain" refers to an amino acid sequence of an *Aequorea*-related fluorescent protein that connects the amino acids involved in the secondary structure of the eleven strands of the β-barrel or the central α-helix (residues 56-72) (see FIGS. 1A and 1B).

As used herein, the "fluorescent protein moiety" of a fluorescent protein is that portion of the amino acid sequence of a fluorescent protein which, when the amino acid sequence of the fluorescent protein substrate is optimally aligned with the amino acid sequence of a naturally occurring fluorescent protein, lies between the amino terminal and carboxy terminal amino acids, inclusive, of the amino acid sequence of the naturally occurring fluorescent protein.

It has been found that fluorescent proteins can be genetically fused to other target proteins and used as markers to identify the location and amount of the target protein produced. Accordingly, this invention provides fusion proteins comprising a fluorescent protein moiety and additional amino acid sequences. Such sequences can be, for example, up to about 15, up to about 50, up to about 150 or up to about 1000 amino acids long. The fusion proteins possess the ability to fluoresce when excited by electromagnetic radiation. In one embodiment, the fusion protein comprises a polyhistidine tag to aid in purification of the protein.

B. Use of the Crystal Structure of Green Fluorescent Protein to Design Mutants Having Altered Fluorescent Characteristics Using X-ray crystallography and computer processing, we have created a model of the crystal structure of *Aequorea* green fluorescent protein showing the relative location of the atoms in the molecule. This information is useful in identifying amino acids whose substitution alters fluorescent properties of the protein.

Fluorescent characteristics of *Aequorea*-related fluorescent proteins depend, in part, on the electronic environment of the chromophore. In general, amino acids that are within about 0.5 nm of the chromophore influence the electronic environment of the chromophore. Therefore, substitution of such amino acids can produce fluorescent proteins with altered fluorescent characteristics. In the excited state, electron density tends to shift from the phenolate towards the carbonyl end of the chromophore. Therefore, placement of increasing positive charge near the carbonyl end of the chromophore tends to decrease the energy of the excited state and cause a red-shift in the absorbance and emission wavelength maximum of the protein. Decreasing positive charge near the carbonyl end of the chromophore tends to have the opposite effect, causing a blue-shift in the protein's wavelengths.

Amino acids with charged (ionized D, E, K, and R), dipolar (H, N, Q, S, T, and uncharged D, E and K), and polarizable side groups (e.g., C, F, H, M, W and Y) are useful for altering the electronic environment of the chromophore, especially when they substitute an amino acid with an uncharged, nonpolar or non-polarizable side chain. In general, amino acids with polarizable side groups alter the electronic environment least, and, consequently, are expected to cause a comparatively smaller change in a fluorescent property. Amino acids with charged side groups alter the environment most, and, consequently, are expected to cause a comparatively larger change in a fluorescent property. However, amino acids with charged side groups are more likely to disrupt the structure of the protein and to prevent proper folding if buried next to the chromophore without any additional solvation or salt bridging. Therefore charged amino acids are most likely to be tolerated and to give useful effects when they replace other charged or highly polar amino acids that are already solvated or involved in salt bridges. In certain cases, where substitution with a polarizable amino acid is chosen, the structure of the protein may make selection of a larger amino acid, e.g., W, less appropriate. Alternatively, positions occupied by amino acids with charged or polar side groups that are unfavorably oriented may be substituted with amino acids that have less charged or polar side groups. In another alternative, an amino acid whose side group has a dipole Oriented in one direction in the protein can be substituted with an amino acid having a dipole oriented in a different direction.

More particularly, Table B lists several amino acids located within about 0.5 nm from the chromophore whose substitution can result in altered fluorescent characteristics. The table indicates, underlined, preferred amino acid substitutions at the indicated location to alter a fluorescent characteristic of the protein. In order to introduce such substitutions, the table also provides codons for primers used in site-directed mutagenesis involving amplification. These primers have been selected to encode economically the preferred amino acids, but they encode other amino acids as well, as indicated, or even a stop codon, denoted by Z. In introducing substitutions using such degenerate primers the most efficient strategy is to screen the collection to identify mutants with the desired properties and then sequence their DNA to find out which of the possible substitutions is responsible. Codons are shown in double-stranded form with sense strand above, antisense strand below. In nucleic acid sequences, R=(A or g); Y=(C or T); M=(A or C); K=(g or T); S=(g or C); W=(A or T); H=(A, T, or C); B=(g, T, or C); V=(g, A, or C); D=(g, A, or T); N=(A, C, g, or T).

TABLE B

| | Original position and presumed role | Change to | Codon |
|---|---|---|---|
| L42 | Aliphatic residue near C=N of chromophore | CFHLQRWYZ | 5'YDS 3'<br>3'RHS 5' |
| V61 | Aliphatic residue near central —CH= of chromophore | FYHCLR | YDC<br>RHg |
| T62 | Almost directly above center of chromophore bridge | AVFS | KYC<br>MRg |
| | | DEHKNQ | VAS<br>BTS |
| | | FYHCLR | YDC<br>RHg |
| V68 | Aliphatic residue near carbonyl and G67 | FYHL | YWC<br>RWg |
| N121 | Near C—N site of ring closure between T65 and G67 | CFHLQRWYZ | YDS<br>RHS |
| Y145 | Packs near tyrosine ring of chromophore | WCFL | TKS<br>AMS |
| | | DEHNKQ | VAS<br>BTS |
| H148 | H-bonds to phenolate oxygen | FYNI | WWC<br>WWg |
| | | KQR | MRg<br>KYC |
| V150 | Aliphatic residue near tyrosine ring of chromophore | FYHL | YWC<br>RWg |
| F165 | Packs near tyrosine ring | CHQRWYZ | YRS<br>RYS |
| I167 | Aliphatic residue near phenolate; I167T has effects | FYHL | YWC<br>RWg |
| T203 | H-bonds to phenolic oxygen of chromophore | FHLQRWYZ | YDS<br>RHS |
| E222 | Protonation regulates ionization of chromophore | HKNQ | MAS<br>KTS |

Examples of amino acids with polar side groups that can be substituted with polarizable side groups include, for example, those in Table C.

TABLE C

| | Original position and presumed role | Change to | Codon |
|---|---|---|---|
| Q69 | Terminates chain of H-bonding waters | KREG | RRg<br>YYC |
| Q94 | H-bonds to carbonyl terminus of chromophore | DEHKNQ | VAS<br>BTS |

TABLE C-continued

| Original position and presumed role | | Change to | Codon |
|---|---|---|---|
| Q183 | Bridges Arg96 and center of chromophore bridge | HY<br><br>EK | YAC<br>RTG<br>RAg<br>YTC |
| N185 | Part of H-bond network near carbonyl of chromophore | DEHNKQ | VAS<br>BTS |

In another embodiment, an amino acid that is close to a second amino acid within about 0.5 nm of the chromophore can, upon substitution, alter the electronic properties of the second amino acid, in turn altering the electronic environment of the chromophore. Table D presents two such amino acids. The amino acids, L220 and V224, are close to E222 and oriented in the same direction in the β pleated sheet.

TABLE D

| Original position and presumed role | | Change to | Codon |
|---|---|---|---|
| L220 | Packs next to Glu222; to make GFP pH sensitive | HKNPQT | MMS<br>KKS |
| V224 | Packs next to Glu222; to make GFP pH sensitive | HKNPQT<br><br>CFHLQRWYZ | MMS<br>KKS<br>YDS<br>RHS |

One embodiment of the invention includes a nucleic acid molecule comprising a nucleotide sequence encoding a functional engineered fluorescent protein whose amino acid sequence is substantially identical to the amino acid sequence of *Aequorea* green fluorescent protein (SEQ ID NO:2) and which differs from SEQ ID NO:2 by at least a substitution at Q69, wherein the functional engineered fluorescent protein has a different fluorescent property than *Aequorea* green fluorescent protein. Preferably, the substitution at Q69 is selected from the group of K, R, E and G. The Q69 substitution can be combined with other mutations to improve the properties of the protein, such as a functional mutation at S65.

One embodiment of the invention includes a nucleic acid molecule comprising a nucleotide sequence encoding a functional engineered fluorescent protein whose amino acid sequence is substantially identical to the amino acid sequence of *Aequorea* green fluorescent protein (SEQ ID NO:2) and which differs from SEQ ID NO:2 by at least a substitution at E222, but not including E222G, wherein the functional engineered fluorescent protein has a different fluorescent property than *Aequorea* green fluorescent protein. Preferably, the substitution at E222 is selected from the group of N and Q. The E222 substitution can be combined with other mutations to improve the properties of the protein, such as a functional mutation at F64.

One embodiment of the invention includes a nucleic acid molecule comprising a nucleotide sequence encoding a functional engineered fluorescent protein whose amino acid sequence is substantially identical to the amino acid sequence of *Aequorea* green fluorescent protein (SEQ ID NO:2) and which differs from SEQ ID NO:2 by at least a substitution at Y145, wherein the functional engineered fluorescent protein has a different fluorescent property than *Aequorea* green fluorescent protein. Preferably, the substitution at Y145 is selected from the group of W, C, F, L, E, H, K and Q. The Y145 substitution can be combined with other mutations to improve the properties of the protein, such as a Y66.

The invention also includes computer related embodiments, including computational methods of using the crystal coordinates for designing new fluorescent protein mutations and devices for storing the crystal data, including coordinates. For instance the invention includes a device comprising a storage device and, stored in the device, at least 10 atomic coordinates selected from the atomic coordinates listed in FIGS. 5A-5AT. More coordinates can be storage depending of the complexity of the calculations or the objective of using the coordinates (e.g. about 100, 1,000, or more coordinates). For example, larger numbers of coordinates will be desirable for more detailed representations of fluorescent protein structure. Typically, the storage device is a computer readable device that stores code that it receives as input the atomic coordinates. Although, other storage means as known in the art are contemplated. The computer readable device can be a floppy disk or a hard drive.

C. Use of the Crystal Structure of YFP to Design Mutants Having Altered Anion Binding Characteristics In another aspect the invention includes the use of X-ray crystallography and computer processing, to create a model of the crystal structure of YFP showing the relative location, and amino acids that interact with bound ions. This information is useful in identifying amino acids whose substitution alters the specificity and affinity of the binding site to various anions. Because the binding of the anion is close to the chromophore of YFP, binding results in a modulation of the fluorescent properties of YFP that can be used to monitor anion binding and therefore the concentration of the anion.

The anion binding site found in YFP-H148Q exhibits many of the characteristics generally found in halide binding sites in other proteins. In the case of the anion-containing cavity in YFP-H148Q, the binding site is amphiphilic in nature, with one side lined with polar and charged groups (Tyr203, the chromophore, Arg96, Gln69, and Gln183), and the other with hydrophobic residues (Ile152, Leu201, Val163, Val150, and Phe165).

The design of engineered fluorescent proteins with altered anion binding specificities requires consideration of a number of factors. For example, one of the most significant factors contributing to the anion affinity and selectivity is the electrostatic configuration and make up of the binding pocket. In YFP these include the groups listed in Table E below.

TABLE E

| Original position and presumed role | |
|---|---|
| S65, Y66, G67 | Forms chromophore, aromatic edge interaction with ion |
| Q69 | Hydrogen bonds to ion |
| R96 | Charge interaction with ion |
| Q183 | Charge interaction with ion |
| Y203 | Hydrogen bonds to ion (Y) |

In general, anion binding can be improved by creating more and or tighter binding interactions between the anion of interest and polar groups within the binding pocket. For example either directly substituting the polar residues above with more polar residues, or by substituting residues of different sizes, that may interact more effectively with the anion, can improve ion binding. For example the size and position of the chromophore may be altered by the substitution of S65 to G, A, C, V, L, I or T; Y66 may be altered by substitution to H, F or W; Q69 may be substituted to N or K; R96 to K; Q183 to N or K.

Hydration Energy

Additionally the binding of an anion in a buried cavity near the chromophore requires replacement of ion-solvent interactions with ion-protein interactions. Relative binding energies of monovalent anions to YFP (Table J) and YFP-H148Q (Jayaraman et al., 2000) in relation to their hydration energy indicate that hydration forces make important contributions towards binding. In the following series of monoanions, the hydration energies are ordered from weak to strong: $CO_4^-<I^-<NO_3^-<SCN^-<Br^-<Cl^-<F^-$ (Wright & Diamond, 1977) Polyatomic monoanions and iodide have relatively weak hydration energies, whereas the other halides interact more strongly with water. In case of the spherically symmetric halides, hydration energy increases with decreasing atomic volume (Born, 1920), which is why larger halides are easier to bury in the more hydrophobic environment of a protein's interior. The trend observed for anion binding to the YFPs roughly follows the above series (Table J). Protein interaction generally increases with decreasing hydration energy, with the exception of fluoride, which may not completely dehydrate upon protein binding due to its small size.

The development of higher affinity anion binding sites therefore requires the creation of sufficient ion-protein interactions for example by the substitution of hydrophobic residues that line the ion binding pocket with more polar residues with more hydrogen bonding potential. Examples for these type of substitutions for improving the ion binding for larger and smaller anions are presented in Table F

TABLE F

| Original position and presumed role | | Change to |
|---|---|---|
| i) Mutation of amino acids around the ion binding pocket to increase binding affinity for smaller anions than iodide. | | |
| V150 | Lines binding pocket | S, T, Q, N |
| I152 | Lines binding pocket | L, V, F, S, T, Q, N |
| V163 | Lines binding pocket | S, T, Q, N |
| F165 | Lines binding pocket | Y, W |
| H181 | Lines binding pocket | F, W |
| Q183 | Lines binding pocket | K, R, N |
| L201 | Lines binding pocket | S, T, Q, N, V, I |
| ii) Mutation of amino acids around the ion binding pocket to increase binding affinity for larger anions than iodide. | | |
| V150 | Lines binding pocket | A, C, M, G, S, L |
| I152 | Lines binding pocket | A, C, M, G, S |
| V163 | Lines binding pocket | A, C, M, G, S, L |
| F165 | Lines binding pocket | Y, L |
| H181 | Lines binding pocket | K, R |
| Q183 | Lines binding pocket | N, S, C |
| L201 | Lines binding pocket | A, C, M, G, S |

Size of the Binding Pocket

The size and shape of the binding pocket may also be of particular importance due to the buried nature of the binding site for larger anions. TCA, with a mean geometric diameter of 6.2 Å (Halm & Frizzell, 1992), is apparently too large to interact with YFP to a measurable extent, whereas the somewhat smaller TFA does show weak binding (Table J). Improvements in the binding affinity of larger anions could thus be achieved via the substitution of amino acids lining the binding pocket with smaller residues, as outlined in Table F above, as well as increasing solvent accessibility as discussed below.

Conformational Changes Upon Anion Binding

A series of conformational changes of various side chains lining the binding pocket in YFP are necessary for halide binding. The largest movements are observed for Gln69, and Gln183 although the apolar side chains of Leu201, Ile152, Val150, and Val163 (FIG. 11) all undergo movements to increase the cavity size in the presence of a bound halide. Another approach towards tighter anion binding therefore is the substitution of the residues that undergoe the most dramatic conformational change upon binding, for smaller residues. These changes may reduce the need for structural rearrangements upon binding thereby making anion binding, more energetically favorable. These changes include those listed in Table F above as well as the substitution of Q69 for N.

Solvent Accessibility

The results from the structural determinations of various mutations at His 148 suggests that specific mutations at this position can result in overall structural adjustments in the beta barrel that can directly affect both solvent accessibility and the volume of the binding pocket. Substitution of His148 for example to smaller amino acids such Q, N, G, A, L, V and I would therefore be predicted to increase solvent access to the chromophore and therefore improve binding of larger anions. Likewise substitution of His 148 with larger amino acids such as F or W would be likely to reduce anion access to the chromophore. Similarly more subtle changes could be achieved by substituting positions 147 and 149 with smaller or larger amino acids.

These mutations will typically be introduced in the YFP template protein via oligo-mediated site directed mutagenesis to create libraries of mutant proteins that typically have a 10% probability of containing the wild-type amino acid residue and a 90% probability of containing one of the various mutant residues. Using this approach it is possible to rapidly screen libraries containing various combinations of mutants to identify the best combinations for a specific anion of interest. Typically this process can be repeated iteratively to ensure that sequence space around the binding pocket has been completely explored for any specific anion of interest.

D. Production of Engineered Fluorescent Proteins

Recombinant production of a fluorescent protein involves expressing a nucleic acid molecule having sequences that encode the protein.

In one embodiment, the nucleic acid encodes a fusion protein in which a single polypeptide includes the fluorescent protein moiety within a longer polypeptide. The longer polypeptide can include a second functional protein, such as FRET partner or a protein having a second function (e.g., an enzyme, antibody or other binding protein). Nucleic acids that encode fluorescent proteins are useful as starting materials.

The fluorescent proteins can be produced as fusion proteins by recombinant DNA technology. Recombinant production of fluorescent proteins involves expressing nucleic acids having sequences that encode the proteins. Nucleic acids encoding fluorescent proteins can be obtained by methods known in the art. Fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations. See, e.g., U.S. patent application Ser. No. 08/337,915, filed Nov. 10, 1994 or International application PCT/US95/14692, filed Nov. 10, 1995. The nucleic acid encoding a green fluorescent protein can be isolated by polymerase chain reaction of cDNA from *A. victoria* using primers based on the DNA sequence of *A. victoria* green fluorescent protein, as presented in FIG. 3. PCR methods are described in, for example, U.S. Pat. No. 4,683,195; Mullis et al. (1987) *Cold Spring Harbor Symp. Quant. Biol.* 51:263; and Erlich, ed., *PCR Technology*, (Stockton Press, N.Y., 1989).

The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc.). The expression vector can be adapted for function in prokaryotes or eukaryotes by inclusion of appropriate promoters, replication sequences, markers, etc.

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent protein coding sequence and appropriate transcriptional/translational control signals. These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or $RbCl$ can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen. In one embodiment recombinant fluorescent proteins can be produced by expression of nucleic acid encoding for the protein in *E. coli*. *Aequorea*-related fluorescent proteins are best expressed by cells cultured between about 15° C. and 30° C. but higher temperatures (e.g. 37° C.) are possible. After synthesis, these enzymes are stable at higher temperatures (e.g., 37° C.) and can be used in assays at those temperatures.

A variety of host-expression vector systems may be utilized to express fluorescent protein coding sequence. These include but are not limited to microorganisms such as bacteria transformed with recombinant bacteriophage DNA, plasmid DNA or cosmid DNA expression vectors containing a fluorescent protein coding sequence; yeast transformed with recombinant yeast expression vectors containing the fluorescent protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fluorescent protein coding sequence; insect cell systems infected with recombinant virus expression vectors (e.g., baculovirus) containing a fluorescent protein coding sequence; or animal cell systems infected with recombinant virus expression vectors (e.g., retroviruses, adenovirus, vaccinia virus) containing a fluorescent protein coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516-544, 1987). For example, when cloning in bacterial systems, inducible promoters such as pL of bacteriophage $\Sigma$, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus to 7.5K promoter) may be used. Promoters produced by recombinant DNA or synthetic techniques may also be used to provide for transcription of the inserted fluorescent protein coding sequence.

In bacterial systems a number of expression vectors may be advantageously selected depending upon the use intended for the fluorescent protein expressed. For example, when large quantities of the fluorescent protein are to be produced, vectors which direct the expression of high levels of fusion protein products that are readily purified may be desirable. Those which are engineered to contain a cleavage site to aid in recovering fluorescent protein are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516-544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673-684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

In cases where plant expression vectors are used, the expression of a fluorescent protein coding sequence may be driven by any of a number of promoters. For example, viral promoters such as the 35S RNA and 19S RNA promoters of CaMV (Brisson, et al., *Nature* 310:511-514, 1984), or the coat protein promoter to TMV (Takamatsu, et al., *EMBO J.* 6:307-311, 1987) may be used; alternatively, plant promoters such as the small subunit of RUBISCO (Coruzzi, et al., 1984, *EMBO J.* 3:1671-1680; Broglie, et al., *Science* 224:838-843, 1984); or heat shock promoters, e.g., soybean hsp17.5-E or hsp17.3-B (Gurley, et al., *Mol. Cell. Biol.* 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology*, Academic Press, NY, Section VIII, pp. 421-463, 1988; and Grierson & Corey, *Plant Molecular Biology*, 2d Ed., Blackie, London, Ch. 7-9, 1988.

An alternative expression system which could be used to express fluorescent protein is an insect system. In one such system, *Autographa californica* nuclear poly-hedrosis virus (AcNPV) is used as a vector to express foreign genes. The virus grows in *Spodoptera frugiperda* cells. The fluorescent protein coding sequence may be cloned into non-essential regions (for example, the polyhedrin gene) of the virus and placed under control of an AcNPV promoter (for example the polyhedrin promoter). Successful insertion of the fluorescent protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent protein. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the fluorescent protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent protein in infected hosts (e.g., see Logan & Shenk, *Proc. Natl. Acad. Sci. USA*, 81: 3655-3659, 1984). Alternatively, the vaccinia virus 7.5K promoter may be used. (e.g., see, Mackett, et al., *Proc. Natl. Acad. Sci. USA*, 79: 7415-7419, 1982; Mackett, et al., *J. Virol.* 49: 857-864, 1984; Panicali, et al., *Proc. Natl. Acad. Sci. USA* 79: 4927-4931, 1982). Of particular interest are vectors based on bovine papilloma virus which have the ability to replicate as extra-chromosomal elements (Sarver, et al., *Mol. Cell. Biol.* 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent protein gene in host cells (Cone & Mulligan, *Proc. Natl. Acad. Sci. USA*, 81:6349-6353, 1984). High level expression may also be achieved using inducible promoters, including, but not limited to, the metallothionine IIA promoter and heat shock promoters.

The invention can also include a localization sequence, such as a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", chapter 35 of Stryer, L., *Biochemistry* (4th ed.). W. H. Freeman, 1995. The localization sequence can also be a localized protein. Some important localization sequences include those targeting the nucleus (KKKRK), mitochondrion (amino terminal MLRTSSLFTRRVQPSLFRNILRLQST-), endoplasmic reticulum (KDEL at C-terminus, assuming a signal sequence present at N-terminus), peroxisome (SKF at C-terminus), prenylation or insertion into plasma membrane (CaaX, CC, CXC, or CCXX at C-terminus), cytoplasmic side of plasma membrane (fusion to SNAP-25), or the Golgi apparatus (fusion to furin).

For long-term, high-yield production of recombinant proteins, stable expression is preferred. Rather than using expression vectors which contain viral origins of replication, host cells can be transformed with the fluorescent protein cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., *Cell*, 11: 223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22: 817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA*, 77: 3567, 1980; O'Hare, et al., *Proc. Natl. Acad. Sci. USA*, 8: 1527, 1981); gpt, which confers resistance to mycophenolic acid (Mulligan & Berg, *Proc. Natl. Acad. Sci. USA*, 78: 2072, 1981; neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30: 147, 1984) genes. Recently, additional selectable genes have been described, namely trpB, which allows Cells to utilize indole in place of tryptophan; hisD, which allows cells to utilize histinol in place of histidine (Hartman & Mulligan, *Proc. Natl. Acad. Sci. USA*, 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory, ed., 1987).

DNA sequences encoding the fluorescence protein polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

The expression vector can be transfected into a host cell for expression of the recombinant nucleic acid. Host cells can be selected for high levels of expression in order to purify the fluorescent protein fusion protein. *E. coli* is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell in vivo.

A primary advantage of fluorescent protein fusion proteins is that they are prepared by normal protein biosynthesis, thus completely avoiding organic synthesis and the requirement for customized unnatural amino acid analogs. The constructs can be expressed in *E. coli* in large scale for in vitro assays. Purification from bacteria is simplified when the sequences include polyhistidine tags for one-step purification by nickel-chelate chromatography. Alternatively, the substrates can be expressed directly in a desired host cell for assays in situ.

In another embodiment, the invention provides a transgenic non-human animal that expresses a nucleic acid sequence which encodes the fluorescent protein.

The "non-human animals" of the invention comprise any non-human animal having nucleic acid sequence which encodes a fluorescent protein. Such non-human animals include vertebrates such as rodents, non-human primates, sheep, dog, cow, pig, amphibians, and reptiles. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Retroviral infection can also be used to introduce transgene into a non-human animal. The developing non-human embryo can be cultured in vitro to the blastocyst stage. During this time, the blastomeres can be targets for retro viral infection (Jaenich, R., *Proc. Natl. Acad. Sci USA* 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927-6931, 1985; Van der Putten, et al., *Proc. Natl. Acad. Sci USA* 82:6148-6152, 1985). Transfection is easily and efficiently obtained by culturing the blastomeres on a monolayer of virus-producing cells (Van der Putten, supra; Stewart, et al., *EMBO J.* 6:383-388, 1987). Alternatively, infection can be performed at a later stage. Virus or virus-producing cells can be injected into the blastocoele (D. Jahner et al., *Nature* 298:623-628, 1982). Most of the founders will be mosaic for the transgene since Incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154-156, 1981; M. O. Bradley et al., *Nature* 309: 255-258, 1984; Gossler, et al., *Proc. Natl. Acad. Sci USA* 83: 9065-9069, 1986; and Robertson et al., *Nature* 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468-1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode which encodes the fluorescent protein which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

III. Uses of Engineered Fluorescent Proteins

The proteins of this invention are useful in any methods that employ fluorescent proteins.

The engineered fluorescent proteins of this invention are useful as fluorescent markers in the many ways fluorescent markers already are used. This includes, for example, coupling engineered fluorescent proteins to antibodies, nucleic acids or other receptors for use in detection assays, such as immunoassays or hybridization assays.

The engineered fluorescent proteins of this invention are useful to track the movement of proteins in cells. In this embodiment, a nucleic acid molecule encoding the fluorescent protein is fused to a nucleic acid molecule encoding the protein of interest in an expression vector. Upon expression inside the cell, the protein of interest can be localized based on fluorescence. In another version, two proteins of interest are fused with two engineered fluorescent proteins having different fluorescent characteristics.

The engineered fluorescent proteins of this invention are useful in systems to detect induction of transcription. In certain embodiments, a nucleotide sequence encoding the engineered fluorescent protein is fused to expression control sequences of interest and the expression vector is transfected into a cell. Induction of the promoter can be measured by detecting the expression and/or quantity of fluorescence. Such constructs can be used to follow signaling pathways from receptor to promoter.

The engineered fluorescent proteins of this invention are useful in applications involving FRET. Such applications can detect events as a function of the movement of fluorescent donors and acceptor towards or away from each other. One or both of the donor/acceptor pair can be a fluorescent protein. A preferred donor and receptor pair for FRET based assays is a donor with a T203I mutation and an acceptor with the mutation T203X, wherein X is an aromatic amino acid-39, especially T203Y, T203W, or T203H. In a particularly useful pair the donor contains the following mutations: S72A, K79R, Y145F, M153A and T203I (with a excitation peak of 395 nm and an emission peak of 511 nm) and the acceptor contains the following mutations S65G, S72A, K79R, and T203Y. This particular pair provides a wide separation between the excitation and emission peaks of the donor and provides good overlap between the donor emission spectrum and the acceptor excitation spectrum. Other red-shifted mutants, such as those described herein, can also be used as the acceptor in such a pair.

In one aspect, FRET is used to detect the cleavage of a substrate having the donor and acceptor coupled to the substrate on opposite sides of the cleavage site. Upon cleavage of the substrate, the donor/acceptor pair physically separate, eliminating FRET. Assays involve contacting the substrate with a sample, and determining a qualitative or quantitative change in FRET. In one embodiment, the engineered fluorescent protein is used in a substrate for β-lactamase. Examples of such substrates are described in U.S. patent application Ser. No. 08/407,544, filed Mar. 20, 1995 and International Application PCT/US96/04059, filed Mar. 20, 1996. In another embodiment, an engineered fluorescent protein donor/acceptor pair are part of a fusion protein coupled by a peptide having a proteolytic cleavage site. Such tandem fluorescent proteins are described in U.S. patent application Ser. No. 08/594,575, filed Jan. 31, 1996.

In another aspect, FRET is used to detect changes in potential across a membrane. A donor and acceptor are placed on opposite sides of a membrane such that one translates across the membrane in response to a voltage change. This creates a measurable FRET. Such a method is described in U.S. patent application Ser. No. 08/481,977, filed Jun. 7, 1995 and International Application PCT/US96/09652, filed Jun. 6, 1996.

The engineered proteins of this invention are useful in the creation of biosensors for determining the concentrations of ions within samples and living cells and transgenic organisms. Upon binding of an ion to the fluorescent protein, a change in at least one measurable fluorescent property of the engineered fluorescent protein occurs that provides the basis for determining the presence of the ion of interest.

The engineered protein of this invention are useful in the creation of fluorescent substrates for protein kinases. Such substrates incorporate an amino acid sequence recognizable by protein kinases. Upon phosphorylation, the engineered fluorescent protein undergoes a change in a fluorescent property. Such substrates are useful in detecting and measuring protein kinase activity in a sample of a cell, upon transfection and expression of the substrate. Preferably, the kinase recognition site is placed within about 20 amino acids of a terminus of the engineered fluorescent protein. The kinase recognition site also can be placed in a loop domain of the protein. (See, e.g. FIG. 1B.) Methods for making fluorescent substrates for protein kinases are described in U.S. patent application Ser. No. 08/680,877, filed Jul. 16, 1996.

A protease recognition site also can be introduced into a loop domain. Upon cleavage, fluorescent property changes in a measurable fashion.

The invention also includes a method of identifying a test chemical. Typically, the method includes contacting a test chemical a sample containing a biological entity labeled with a functional, engineered fluorescent protein or a polynucleotide encoding said functional, engineered fluorescent protein. By monitoring fluorescence (i.e. a fluorescent property) from the sample containing the functional engineered fluorescent protein it can be determined whether a test chemical is active. Controls can be included to insure the specificity of the signal. Such controls include measurements of a fluorescent property in the absence of the test chemical, in the presence of a chemical with an expected activity (e.g., a known modulator) or engineered controls (e.g., absence of engineered fluorescent protein, absence of engineered fluorescent protein polynucleotide or the absence of operably linkage of the engineered fluorescent protein).

The fluorescence in the presence of a test chemical can be greater or less than in the absence of said test chemical. For instance if the engineered fluorescent protein is used a reporter of gene expression, the test chemical may up or down regulate gene expression. For such types of screening, the polynucleotide encoding the functional, engineered fluorescent protein is operatively linked to a genomic polynucleotide or a re. Alternatively, the functional, engineered fluorescent protein is fused to second functional protein. This embodiment can be used to track localization of the second protein or to track protein-protein interactions using energy transfer.

IV. Procedures

Fluorescence in a sample is measured using a fluorimeter. In general, excitation radiation from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform to the data collected during the assay into another format for presentation. This process can be miniaturized and automated to enable screening many thousands of compounds.

Methods of performing assays on fluorescent materials are well known in the art and are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219-243; Turro, N. J., *Modern Molecular Photochemistry*, Menlo Park: Benjamin/Cummings Publishing Col, Inc. (1978), pp. 296-361.

Mutagenesis and Protein Preparation

YFP variants and revertants were prepared using the PCR-based QuikChange™ Site-Directed Mutagenesis Kit (Stratagene, La Jolla, Calif.), according to the manufacturer's directions and using the YFP clone 10c as a template (Ormo et al., 1996). Mutations were verified by sequencing the entire gene, and all GFP variants were expressed and purified as described (Ormo et al., 1996).

Fluorescence Measurements

Small aliquots of concentrated protein were diluted 25-fold into a series of buffers (20 mM MES pH 6.0, MES pH 6.5, PIPES 7.0, HEPES 7.5, and TAPS 8.0) with constant ionic strength. The buffers contained varying concentrations of either potassium chloride or potassium iodide, and the ionic strength was adjusted to 150 mM with potassium D-gluconate. Fluorescence measurements as a function of pH and halide concentration were carried out on a Hitachi F4500 fluorescence spectrophotometer at room temperature ($\lambda_{ex}$=514 nm), scanning the emission between 520 and 550 nm three times at a rate of 60 nm/min. Maximum emission at 528 nm was averaged, and normalized with respect to fluorescence in the absence of halides.

Crystal Growth and Data Collection

YFP-H148Q was concentrated to 15 mg/ml in 20 mM TRIS pH 7.9, and crystals were grown in hanging drops containing 5 µl protein and 5 µl mother liquor. The mother liquor contained 22% PEG 1550 at pH 5.5 in 100 mM sodium acetate and 90 mM $MgCl_2$. The rod-shaped crystals were approximately 0.04 mm across and up to 1.0 mm long, and grew within 1.5 to 2 years at 4 C. One crystal was soaked in synthetic mother liquor containing the above ingredients without $MgCl_2$ but 100 mM potassium iodide, and 20% ethylene glycol for cryo-protection (referred to as iodide soak). Another crystal was soaked in the above mother liquor containing 100 mM $MgCl_2$ and 20% ethylene glycol (referred to as chloride soak). Both soaks were carried out at pH 4.6 for 4 hours at room temperature, and data collection proceeded immediately thereafter. The crystals were flash-frozen, and X-ray diffraction data were collected at 100 K using a RAXIS-IIc image plate mounted on a Rigaku RUH3 rotating anode generator equipped with mirrors.

Structure Determination of YFP-H148Q, and Identification of Iodide Binding Sites The two data sets were processed with Denzo v1.9 and scaled using ScalePack (Otwinowski & Minor, 1997). The spacegroup is $P2_12_12_1$, with unit cell parameters a=51.2, b=62.8, and c=68.7 Å for the iodide soak, and a=51.7, b=62.6, and c=66.2 Å for the chloride soak. The crystals are nearly isomorphous to YFP-H148G (Wachter et al., 1998) and GFP S65T crystals (Ormo et al., 1996) previously described, and the YFP-H148G coordinate file 2yfp (Wachter et al., 1998) was used as a model for phasing. A model for the anionic chromophore was obtained by semi-empirical molecular orbital calculations using AM1 in the program SPARTAN version 4.1 (Wavefunction Inc., Irvine, Calif.).

An anomalous difference map was calculated from the data set derived from the iodide soak (anomalous data 65% complete), since iodine exhibits a significant anomalous signal at the in-house $CuK_\alpha$ wavelength of 1.54 Å. Heavy atom phases were approximated by subtraction of 90° from calculated protein phases using the program scaleit in the CCP4 program suite (Collaborative Computational Project N. 4, 1994). The anomalous difference map identified two iodide positions, one buried in the protein interior and one on the protein surface.

Refinement of YFP-H148Q with and without Bound Iodide

The two datasets, derived from the iodide and from the chloride soak, were refined in a similar manner. After initial rigid body refinement to 4.0 Å, positional refinement was carried out using the data to 3.0 Å, then to the limit of resolution (Table 1), using the program TNT (Tronrud et al., 1987). During early cycles of refinement, bound halides were not modeled, and the glutamine in position 148 was modeled as a glycine. Electron density maps ($2F_o$-$F_c$ and $F_o$-$F_c$) were inspected intermittently using O (Jones et al., 1991). The $F_o$-$F_c$ maps clearly indicated the positions of the buried and surface iodides, at 11 and 5.5 rms deviations respectively, located in the centers of the two anomalous difference density peaks, though no positive difference density consistent with buried chloride binding was observed. Density for the Gln148 side chain was clearly visible early on, allowing for the modeling of the glutamine as a rotamer different from the original histidine.

B-factors were refined using the default TNT B-factor correlation library. B-factor correlation values derived from His and Phe were used to model the chromophore atoms. Bound solvent molecules were added to the model where appropriate as judged from difference density and proximity of hydrogen bond partners. Before refining the occupancy of the bound halides, the B-factors for these halides were fixed. The thermal factor of the buried iodide was set to the average B-factor of the twelve atoms closest to it, 30 Å$^2$, FIGS. 5A-5AT, and the thermal factor for the surface iodide was set to the average B-factor of the six closest solvent molecules bound to the protein surface, 39 Å$^2$. The last step in refinement was the refinement of the occupancy of the two bound halides.

Determination of Chromophore $pK_a$ and Iodide Binding Constants by Absorbance

The chromophore $pK_a$ was determined from absorbance scans at varying anion concentrations. Absorbance scans were collected at room temperature between 250 and 600 nm (Shimadzu 2101 spectrophotometer) on 0.05 mg/ml YFP under two different pH conditions appropriate for the particular anion, chosen from a series of buffers (20 mM malic acid pH 5.8, malic acid pH 6.1, MES pH 6.4, HEPES pH 7.1). The optical density of the chromophore anion (514 to 515 nm for YFP and YFP-H148Q) at the buffer pH, as well as the optical density at pH 9 in the absence of interacting anions, were used in the Henderson-Hasselbalch equation to estimate the chromophore $pK_a$ for each condition examined. Microscopic binding constants for anion binding to the protein were extracted by curve fitting of the chromophore $pK_a$ to the anion concentration, using an expression for a linked equilibrium involving two different ligands.

The following examples are provided by way of illustration, not by way of limitation.

EXAMPLES

As a step in understanding the properties of GFP, and to aid in the tailoring of GFPs with altered characteristics, we have determined the three dimensional structure at 1.9 Å resolution of the S65T mutant (R. Heim et al. Nature 373:664-665 (1995)) of A. victoria GFP. This mutant also contains the ubiquitous Q80R substitution, which accidentally occurred in the early distribution of the GFP cDNA and is not known to have any effect on the protein properties (M. Chalfie et al. Science 263:802-805 (1994)).

Histidine-tagged S65T GFP (R. Heim et al. Nature 373:664-665 (1995)) was overexpressed in JM109/pRSET$_B$ in 4l YT broth plus ampicillin at 37° C., 450 rpm and 5 l/min air flow. The temperature was reduced to 25° C. at $A_{595}$=0.3, followed by induction with 1 mM isopropylthiogalactoside for 5 h. Cell paste was stored at −80° C. overnight, then was resuspended in 50 mM HEPES pH 7.9, 0.3 M NaCl, 5 mM 2-mercaptoethanol, 0.1 mM phenylmethyl-sulfonylfluoride (PMSF), passed once through a French press at 10,000 psi, then centrifuged at 20 K rpm for 45 min. The supernatant was applied to a Ni-NTA-agarose column (Qiagen), followed by a wash with 20 mM imidazole, then eluted with 100 mM imidazole. Green fractions were pooled and subjected to chymotryptic (Sigma) proteolysis (1:50 w/w) for 22 h at RT. After addition of 0.5 mM PMSF, the digest was reapplied to the Ni column. N-terminal sequencing verified the presence of the correct N-terminal methionine. After dialysis against 20 mM HEPES, pH 7.5 and concentration to $A_{490}$=20, rod-shaped crystals were obtained at RT in hanging drops containing 5 μl protein and 5 μl well solution, 22-26% PEG 4000 (Serva), 50 mM HEPES pH 8.0-8.5, 50 mM $MgCl_2$ and 10 mM 2-mercapto-ethanol within 5 days. Crystals were 0.05 mm across and up to 1.0 mm long. The space group is $P2_12_12_1$ with a=51.8, b=62.8, c=70.7 A, Z=4. Two crystal forms of wild-type GFP, unrelated to the present form, have been described by M. A. Perrozo, K. B. Ward, R. B. Thompson, & W. W. Ward. J. Biol. Chem. 203, 7713-7716 (1988).

The structure of GFP was determined by multiple isomorphous replacement and anomalous scattering (Table E), solvent flattening, phase combination and crystallographic refinement. The most remarkable feature of the fold of GFP is an eleven stranded β-barrel wrapped around a single central helix (FIGS. 1A and 1B), where each strand consists of approximately 9-13 residues. The barrel forms a nearly perfect cylinder 42 Å long and 24 Å in diameter. The N-terminal half of the polypeptide comprises three anti-parallel strands, the central helix, and then 3 more anti-parallel strands, the latter of which (residues 118-123) is parallel to the N-terminal strand (residues 11-23). The polypeptide backbone then crosses the "bottom" of the molecule to form the second half of the barrel in a five-strand Greek Key motif. The top end of the cylinder is capped by three short, distorted helical segments, while one short, very distorted helical segment caps the bottom of the cylinder. The main-chain hydrogen bonding lacing the surface of the cylinder very likely accounts for the unusual stability of the protein towards denaturation and proteolysis. There are no large segments of the polypeptide that could be excised while preserving the intactness of the shell around the chromophore. Thus it would seem difficult to re-engineer GFP to reduce its molecular weight (J. Dopf & T. M. Horiagon Gene 173:39-43 (1996)) by a large percentage.

Figure 2A:
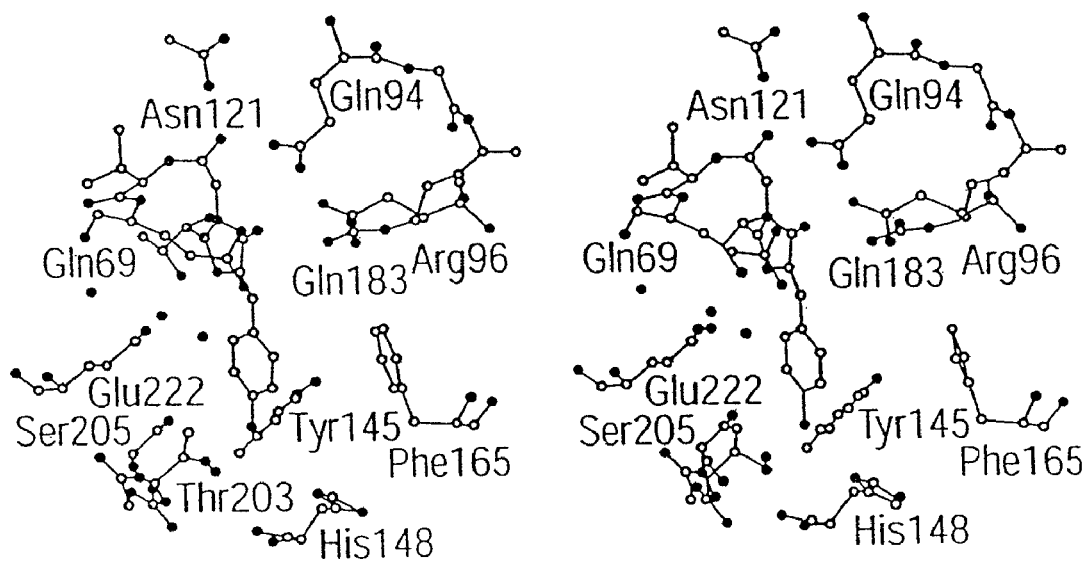
FIGS. 2A-2C. (A). Stereo drawing of the chromophore and residues in the immediate vicinity. Carbon atoms are drawn as open circles, oxygen is filled and to nitrogen is shaded. Solvent molecules are shown as isolated filled circles. (B) Portion of the final $2F_o-F_c$ electron density map contoured at $1.0\sigma$, showing the electron density surrounding the chromophore. (C) Schematic diagram showing the first and second spheres of coordination of the chromophore. Hydrogen bonds are shown as dashed lines and have the indicated lengths in Å. Inset: proposed structure of the carbinolamine intermediate that is presumably formed during generation of the chromophore.
Figure 2B:
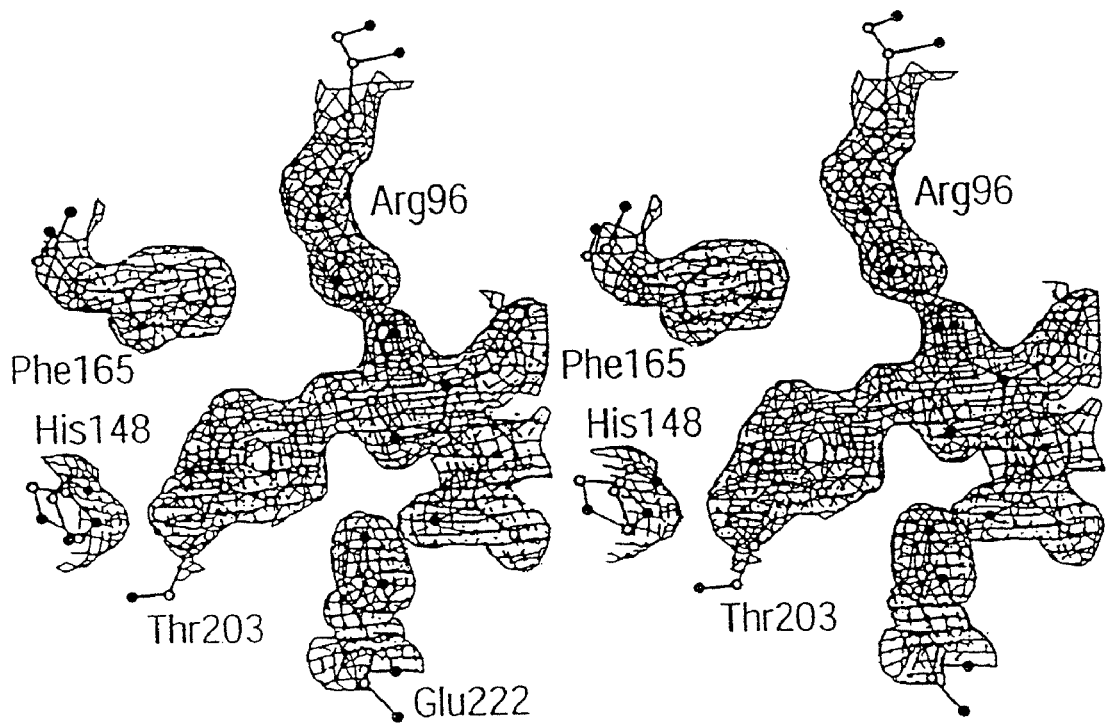

The p-hydroxybenzylideneimidazolidinone chromophore (C. W. Cody et al. Biochemistry 32:1212-1218 (1993)) is completely protected from bulk solvent and centrally located in the molecule. The total and presumably rigid encapsulation is probably responsible for the small Stokes' shift (i.e. wavelength difference between excitation and emission maxima), high quantum yield of fluorescence, inability of $O_2$ to quench the excited state (B. D. Nageswara Rao et al. Biophys. J. 32:630-632 (1980)), and resistance of the chromophore to titration of the external pH (W. W. Ward. Bioluminescence and Chemiluminescence (M. A. DeLuca and W. D. McElroy, eds) Academic Press pp. 235-242 (1981); W. W. Ward & S. H. Bokman. Biochemistry 21:4535-4540 (1982); W. W. Ward et al. Photochem. Photobiol. 35:803-808 (1982)). It also allows one to rationalize why fluorophore formation should be a spontaneous intramolecular process (R. Heim et al. Proc. Natl. Acad. Sci. USA 91:12501-12504 (1994)), as it is difficult to imagine how an enzyme could gain access to the substrate. The plane of the chromophore is roughly perpendicular (60) to the symmetry axis of the surrounding barrel. One side of the chromophore faces a surprisingly large cavity, that occupies a volume of approximately 135 $Å^3$ (B. Lee & F. M. Richards. J. Mol. Biol. 55:379-400 (1971)). The atomic radii were those of Lee & Richards, calculated using the program MS with a probe radius of 1.4 Å. (M. L. Connolly, Science 221:709-713 (1983)). The cavity does not open out to bulk solvent. Four water molecules are located in the cavity, forming a chain of hydrogen bonds linking the buried side chains of $Glu^{222}$ and $Gln^{69}$. Unless occupied, such a large cavity would be expected to de-stabilize the protein by several kcal/mol (S. J. Hubbard et al., Protein Engineering 7:613-626 (1994); A. E. Eriksson et al. Science 255:178-183 (1992)). Part of the volume of the cavity might be the consequence of the compaction resulting from cyclization and dehydration reactions. The cavity might also temporarily accommodate the oxidant, most likely $O_2$ (A. B. Cubitt et al. Trends Biochem. Sci. 20:448-455 (1995); R. Heim et al. Proc. Natl. Acad. Sci. USA 91:12501-12504 (1994); S. Inouye & F. I. Tsuji. FEBS Lett. 351:211-214 (1994)), that dehydrogenates the α-β bond of $Tyr^{66}$. The chromophore, cavity, and side chains that contact the chromophore are shown in FIG. 2A and a portion of the final electron density map in this vicinity in 2B.

Figure 2C:
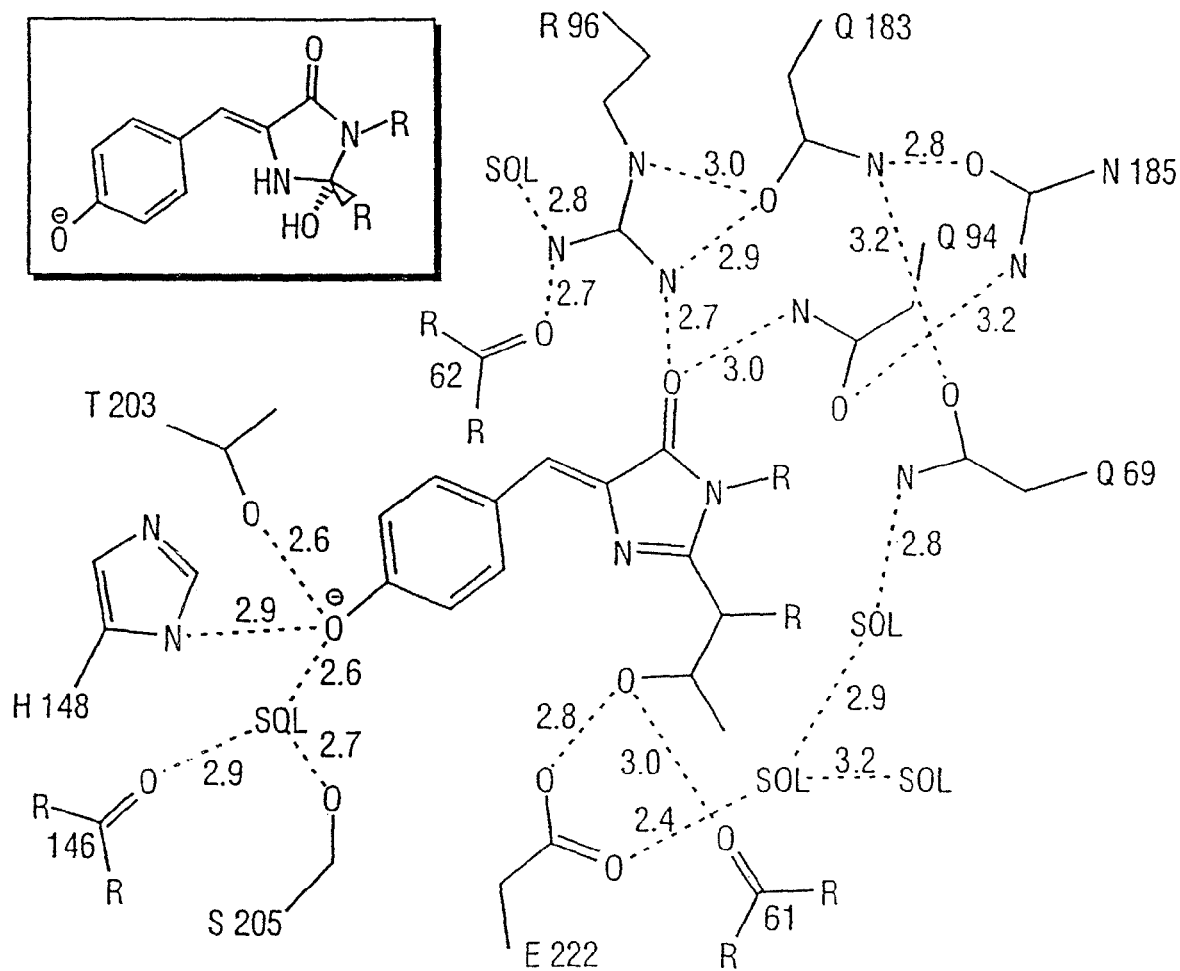

The opposite side of the chromophore is packed against several aromatic and polar side chains. Of particular interest is the intricate network of polar interactions with the chromophore (FIG. 2C). $His^{148}$, $Thr^{203}$ and $Ser^{205}$ form hydrogen bonds with the phenolic hydroxyl; $Arg^{96}$ and $Gln^{94}$ interact with the carbonyl of the imidazolidinone ring and $Glu^{222}$ forms a hydrogen bond with the side chain of $Thr^{65}$. Additional polar interactions, such as hydrogen bonds to $Arg^{96}$ from the carbonyl of Thr$^{62}$, and the side-chain carbonyl of Gln$^{183}$, presumably stabilize the buried Arg$^{96}$ in its protonated form. In turn, this buried charge suggests that a partial negative charge resides on the carbonyl oxygen of the imidazolidinone ring of the deprotonated fluorophore, as has previously been suggested (W. W. Ward. *Bioluminescence and Chemiluminescence* (M. A. DeLuca and W. D. McElroy, eds) Academic Press pp. 235-242 (1981); W. W. Ward & S. H. Bokman. *Biochemistry* 21:4535-4540 (1982); W. W. Ward et al. *Photochem. Photobiol.* 35:803-808 (1982)). Arg$^{96}$ is likely to be essential for the formation of the fluorophore, and may help catalyze the initial ring closure. Finally, Tyr$^{145}$ shows a typical stabilizing edge-face interaction with the benzyl ring. Trp$^{57}$, the only tryptophan in GFP, is located 13 Å to 15 Å from the chromophore and the long axes of the two ring systems are nearly parallel. This indicates that efficient energy transfer to the latter should occur, and explains why no separate tryptophan emission is observable (D. C. Prasher et al. *Gene* 111:229-233 (1992). The two cysteines in GFP, Cys$^{48}$ and Cys$^{70}$, are 24 Å apart, too distant to form a disulfide bridge. Cys$^{70}$ is buried, but Cys$^{48}$ should be relatively accessible to sulfhydryl-specific reagents. Such a reagent, 5,5'-dithiobis(2-nitrobenzoic acid), is reported to label GFP and quench its fluorescence (S. Inouye & F. I. Tsuji *FEBS Lett.* 351:211-214 (1994)). This effect was attributed to the necessity for a free sulfhydryl, but could also reflect specific quenching by the 5-thio-2-nitrobenzoate moiety that would be attached to Cys$^{48}$.

Although the electron density map is for the most part consistent with the proposed structure of the chromophore (D. C. Prasher et al. *Gene* 111:229-233 (1992); C. W. Cody et al. *Biochemistry* 32:1212-1218 (1993)) in the cis [Z-] configuration, with no evidence for any substantial fraction of the opposite isomer around the chromophore double bond, difference features are found at >4σ in the final ($F_o$-$F_c$) electron density map that can be interpreted to represent either the intact, uncyclized polypeptide or a carbinolamine (inset to FIG. 2C). This suggests that a significant fraction, perhaps as much as 30% of the molecules in the crystal, have failed to undergo the final dehydration reaction. Confirmation of incomplete dehydration comes from electrospray mass spectrometry, which consistently shows that the average masses of both wild-type and S65T GFP (31,086±4 and 31,099.5±4 Da, respectively) are 6-7 Da higher than predicted (31,079 and 31,093 Da, respectively) for the fully matured proteins. Such a discrepancy could be explained by a 30-35% mole fraction of apoprotein or carbinolamine with 18 or 20 Da higher molecular weight The natural abundance of $^{13}$C and $^2$H and the finite resolution of the Hewlett-Packard 5989B electrospray mass spectrometer used to make these measurements do not permit the individual peaks to be resolved, but instead yields an average mass peak with a full width at half maximum of approximately 15 Da. The molecular weights shown include the His-tag, which has the sequence MRGSHHH-HHH GMASMTGGQQM GRDLYDDDDK DPPAEF (SEQ ID NO:5). Mutants of GFP that increase the efficiency of fluorophore maturation might yield somewhat brighter preparations. In a model for the apoprotein, the Thr$^{65}$-Tyr$^{66}$ peptide bond is approximately in the α-helical conformation, while the peptide of Tyr$^{66}$-Gly$^{67}$ appears to be tipped almost perpendicular to the helix axis by its interaction with Arg$^{96}$. This further supports the speculation that Arg$^{96}$ is important in generating the conformation required for cyclization, and possibly also for promoting the attack of Gly$^{67}$ on the carbonyl carbon of Thr$^{65}$ (A. B. Cubitt et al. *Trends Biochem. Sci.* 20:448-455 (1995)).

The results of previous random mutagenesis have implicated several amino acid side chains to have substantial effects on the spectra and the atomic model confirms that these residues are close to the chromophore. The mutations T203I and E222G have profound but opposite consequences on the absorption spectrum (T. Ehrig et al. *FEBS Letters* 367:163-166 (1995)). T203I (with wild-type Ser$^{65}$) lacks the 475 nm absorbance peak usually attributed to the anionic chromophore and shows only the 395 nm peak thought to reflect the neutral chromophore (R. Heim et al. *Proc. Natl. Acad. Sci. USA* 91:12501-12504 (1994); T. Ehrig et al. *FEES Letters* 367:163-166 (1995)). Indeed, Thr$^{203}$ is hydrogen-bonded to the phenolic oxygen of the chromophore, so replacement by He should hinder ionization of the phenolic oxygen. Mutation of Glu$^{222}$ to Gly (T. Ehrig et al. *FEBS Letters* 367:163-166 (1995)) has much the same spectroscopic effect as replacing Ser$^{65}$ by Gly, Ala, Cys, Val, or Thr, namely to suppress the 395 nm peak in favor of a peak at 470-490 nm (R. Heim et al. *Nature* 373:664-665 (1995); S. Delagrave et al. *Bio/Technology* 13:151-154 (1995)). Indeed Glu$^{222}$ and the remnant of Thr$^{65}$ are hydrogen-bonded to each other in the present structure, probably with the uncharged carboxyl of Glu$^{222}$ acting as donor to the side chain oxygen of Thr$^{65}$. Mutations E222G, S65G, S65A, and S65V would all suppress such H-bonding. To explain why only wild-type protein has both excitation peaks, Ser$^{65}$, unlike Thr$^{65}$, may adopt a conformation in which its hydroxyl donates a hydrogen bond to and stabilizes Glu$^{222}$ as an anion, whose charge then inhibits ionization of the chromophore. The structure also explains why some mutations seem neutral. For example, Gln$^{80}$ is a surface residue far removed from the chromophore, which explains why its accidental and ubiquitous mutation to Arg seems to have no obvious intramolecular spectroscopic effect (M. Chalfie et al. *Science* 263:802-805 (1994)).

The development of GFP mutants with red-shifted excitation and emission maxima is an interesting challenge in protein engineering (A. B. Cubitt et al. *Trends Biochem. Sci.* 20:448-455 (1995); R. Heim et al. *Nature* 373:664-665 (1995); S. Delagrave et al. *Bio/Technology* 13:151-154 (1995)). Such mutants would also be valuable for avoidance of cellular autofluorescence at short wavelengths, for simultaneous multicolor reporting of the activity of two or more cellular processes, and for exploitation of fluorescence resonance energy transfer as a signal of protein-protein interaction (R. Heim & R. Y. Tsien. *Current Biol.* 6:178-182 (1996)). Extensive attempts using random mutagenesis have shifted the emission maximum by at most 6 nm to longer wavelengths, to 514 nm (R. Heim & R. Y. Tsien. *Current Biol.* 6:178-182 (1996)); previously described "red-shifted" mutants merely suppressed the 395 nm excitation peak in favor of the 475 nm peak without any significant reddening of the 505 nm emission (S. Delagrave et al. *Bio/Technology* 13:151-154 (1995)). Because Thr$^{203}$ is revealed to be adjacent to the phenolic end of the chromophore, we mutated it to polar aromatic residues such as His, Tyr, and Trp in the hope that the additional polarizability of their systems would lower the energy of the excited state of the adjacent chromophore. All three substitutions did indeed shift the emission peak to greater than 520 nm (Table F). A particularly attractive mutation was T203Y/S65G/V68L/S72A, with excitation and emission peaks at 513 and 527 nm respectively. These wavelengths are sufficiently different from previous GFP mutants to be readily distinguishable by appropriate filter sets on a fluorescence microscope. The extinction coefficient, 36,500 $M^{-1}cm^{-1}$, and quantum yield, 0.63, are almost as high as those of S65T (R. Heim et al. *Nature* 373:664-665 (1995)).

Comparison of *Aequorea* GFP with other protein pigments is instructive. Unfortunately, its closest characterized homolog, the GFP from the sea pansy *Renilla reniformis* (O. Shimomura and F. H. Johnson *J. Cell. Comp. Physiol.* 59:223 (1962); J. G. Morin and J. W. Hastings, *J. Cell. Physiol.* 77:313 (1971); H. Morise et al. *Biochemistry* 13:2656 (1974); W. W. Ward *Photochem. Photobiol. Reviews* (Smith, K. C. ed.) 4:1 (1979); W. W. Ward. *Bioluminescence and Chemiluminescence* (M. A. DeLuca and W. D. McElroy, eds) Academic Press pp. 235-242 (1981); W. W. Ward & S. H. Bokman *Biochemistry* 21:4535-4540 (1982); W. W. Ward et al. *Photochem. Photobiol.* 35:803-808 (1982)), has not been sequenced or cloned, though its chromophore is derived from the same FSYG sequence as in wild-type *Aequorea* GFP (R. M. San Pietro et al. *Photochem. Photobiol.* 57:63S (1993)). The closest analog for which a three dimensional structure is available is the photoactive yellow protein (PYP, G. E. O. Borgstahl et al. *Biochemistry* 34:6278-6287 (1995)), a 14-kDa photoreceptor from halophilic bacteria. PYP in its native dark state absorbs maximally at 446 nm and transduces light with a quantum yield of 0.64, rather closely matching wild-type GFP's long wavelength absorbance maximum near 475 nm and fluorescence quantum yield of 0.72-0.85. The fundamental chromophore in both proteins is an anionic p-hydroxycinnamyl group, which is covalently attached to the protein via a thioester linkage in PYP and a heterocyclic iminolactam in GFP. Both proteins stabilize the negative charge on the chromophore with the help of buried cationic arginine and neutral glutamic acid groups, $Arg^{52}$ and $Glu^{46}$ in PYP and $Arg^{96}$ and $Glu^{222}$ in GFP, though in PYP the residues are close to the oxyphenyl ring whereas in GFP they are nearer the carbonyl end of the chromophore. However, PYP has an overall $\alpha/\beta$ fold with appropriate flexibility and signal transduction domains to enable it to mediate the cellular phototactic response, whereas GFP is a much more regular and rigid $\beta$-barrel to minimize parasitic dissipation of the excited state energy as thermal or conformational motions. GFP is an elegant example of how a visually appealing and extremely useful function, efficient fluorescence, can be spontaneously generated from a cohesive and economical protein structure.

A. Summary of GFP Structure Determination

Data were collected at room temperature in house using either Molecular Structure Corp. R-axis II or San Diego Multiwire Systems (SDMS) detectors (Cu Kα) and later at beamline X4A at the Brookhaven National Laboratory at the selenium absorption edge ($\lambda$=0.979 Å) using image plates. Data were evaluated using the HKL package (Z. Otwinowski, in *Proceedings of the CCP4 Study Weekend: Data Collection and Processing*, L. Sawyer, N. Issacs, S. Bailey, Eds. (Science and Engineering Research Council (SERC), Daresbury Laboratory, Warrington, UK, (1991)), pp 56-62; W. Minor, XDISPLAYF (Purdue University, West Lafayette, Ind., 1993)) or the SDMS software (A. J. Howard et al. *Meth. Enzymol.* 114:452-471 (1985)). Each data set was collected from a single crystal. Heavy atom soaks were 2 mM in mother liquor for 2 days. Initial electron density maps were based on three heavy atom derivatives using in-house data, then later were replaced with the synchrotron data. The EMTS difference Patterson map was solved by inspection, then used to calculate difference Fourier maps of the other derivatives. Lack of closure refinement of the heavy atom parameters was performed using the Protein package (W. Steigemann, in Ph.D. Thesis (Technical University, Munich, 1974)). The MIR maps were much poorer than the overall figure of merit would suggest, and it was clear that the EMTS isomorphous differences dominated the phasing. The enhanced anomalous occupancy for the synchrotron data provided a partial solution to the problem. Note that the phasing power was reduced for the synchrotron data, but the figure of merit was unchanged. All experimental electron density maps were improved by solvent flattening using the program DM of the CCP4 (CCP4: *A Suite of Programs for Protein Crystallography* (SERC Daresbury Laboratory, Warrington WA4 4AD UK, 1979)) package assuming a solvent content of 38%. Phase combination was performed with PHASCO2 of the Protein package using a weight of 1.0 on the atomic model Heavy atom parameters were subsequently improved by refinement against combined phases. Model building proceeded with FRODO and O (T. A. Jones et al. *Acta. Crystallogr. Sect. A* 47:110 (1991); T. A. Jones, in *Computational Crystallography* D. Sayre, Ed. (Oxford University Press, Oxford, 1982) pp. 303-317) and crystallographic refinement was performed with the TNT package (D. E. Tronrud et al. *Acta Cryst. A* 43:489-503 (1987)). Bond lengths and angles for the chromophore were estimated using CHEM3D (Cambridge Scientific Computing). Final refinement and model building was performed against the X4A selenomethione data set, using $(2F_o-F_c)$ electron density maps. The data beyond 1.9 Å resolution have not been used at this stage. The final model contains residues 2-229 as the terminal residues are not visible in the electron density map, and the side chains of several disordered surface residues have been omitted. Density is weak for residues 156-158 and coordinates for these residues are unreliable. This disordering is consistent with previous analyses showing that residues 1 and 233-238 are dispensable but that further truncations may prevent fluorescence (J. Dopf & T. M. Horiagon. *Gene* 173:39-43 (1996)). The atomic model has been deposited in the Protein Data Bank (access code 1EMA).

TABLE G

Diffraction Data Statistics

| Crystal | Resolution (Å) | Total obs | Unique obs | Compl. (%)[a] | Compl. (shell)[b] | Rmerge (%)[c] | Riso (%)[d] |
|---|---|---|---|---|---|---|---|
| R-axix II | | | | | | | |
| Native | 2.0 | 51907 | 13582 | 80 | 69 | 4.1 | 5.8 |
| EMTS[e] | 2.6 | 17727 | 6787 | 87 | 87 | 5.7 | 20.6 |
| SeMet | 2.3 | 44975 | 10292 | 92 | 88 | 10.2 | 9.3 |
| Multiwire | | | | | | | |
| HGI4—Se X4a | 3.0 | 15380 | 4332 | 84 | 79 | 7.2 | 28.8 |
| SeMet | 1.8 | 126078 | 19503 | 80 | 55 | 9.3 | 9.4 |
| EMTS | 2.3 | 57812 | 9204 | 82 | 66 | 7.2 | 26.3 |

TABLE G-continued

| Derivative | Resolution (Å) | Number of sites | Phasing power[f] | Phasing Power(shell) | FOM[g] | FOM (shell) |
|---|---|---|---|---|---|---|
| In House | | | | | | |
| EMTS | 3.0 | 2 | 2.08 | 2.08 | 0.77 | .072 |
| SeMet | 3.0 | 4 | 1.66 | 1.28 | — | — |
| HGI4—Se X4a | 3.0 | 9 | 1.77 | 1.90 | — | — |
| EMTS | 3.0 | 2 | 1.36 | 1.26 | 0.77 | .072 |
| SeMet | 3.0 | 4 | 1.31 | 1.08 | — | — |

Atomic Model Statistics

| | |
|---|---|
| Protein atoms | 1790 |
| Solvent atoms | 94 |
| Resol. range (Å) | 20-1.9 |
| Number of reflections (F > 0) | 17676 |
| Completeness | 84. |
| R. factor[h] | 0.175 |
| Mean B-value (Å$^2$) | 24.1 |
| Deviations from ideality | |
| Bond lengths (Å) | 0.014 |
| Bond angles (°) | 1.9 |
| Restrained B-values (Å$^2$) | 4.3 |
| Ramachandran outliers | 0 |

Notes:
[a]Completeness is the ratio of observed reflections to theoretically possible expressed as a percentage.
[b]Shell indicates the highest resolution shell, typically 0.1-0.4 Å wide.
[c]Rmerge = $\Sigma |I - \langle I \rangle| / \Sigma I$, where $\langle I \rangle$ is the mean of individual observations of intensities I.
[d]Riso = $\Sigma |I_{DER} - I_{NAT}| / \Sigma I_{NAT}$
[e]Derivatives were EMTS = ethymercurithiosalicylate (residues modified Cys$^{48}$ and Cys$^{70}$), SeMet = selenomethionine substituted protein (Met$^1$ and Met$^{233}$ could not be located); HgI$_4$—SeMet = double derivative HgI$_4$ on SeMet background.
[f]Phasing power = $\langle F_H \rangle / \langle E \rangle$ where $\langle F_H \rangle$ = r.m.s. heavy atom scattering and $\langle E \rangle$ = lack of closure.
[g]FOM, mean figure of merit
[h]Standard crystallographic R-factor, R = $\Sigma ||F_{obs}| - |F_{calc}||/\Sigma |F_{obs}|$ B. Spectral Properties of Thr$^{203}$ ("T203") Mutants Compared to S65T The mutations F64L, V68L and S72A improve the folding of GFP at 37° (B. P. Cormack et al. *Gene* 173:33 (1996)) but do not significantly shift the emission spectra.

TABLE H

| Clone | Mutations | Excitation max. (nm) | Extinction coefficient ($10^3$ M$^{-1}$cm$^{-1}$) | Emission max. (nm) |
|---|---|---|---|---|
| S65T | S65T | 489 | 39.2 | 511 |
| 5B | T203H/S65T | 512 | 19.4 | 524 |
| 6C | T203Y/S65T | 513 | 14.5 | 525 |
| 10B | T203Y/F64L/S65G/S72A | 513 | 30.8 | 525 |
| 10C | T203Y/F65G/V68L/S72A | 513 | 36.5 | 527 |
| 11 | T203W/S65G/S72A | 502 | 33.0 | 512 |
| 12H | T203Y/S65G/S72A | 513 | 36.5 | 527 |
| 20A | T203Y/S65G/V68L/Q69K/S72A | 515 | 46.0 | 527 |

C. YFP and YFP-H148Q as Halide Sensors at Acidic and Neutral pH

Figure 7:
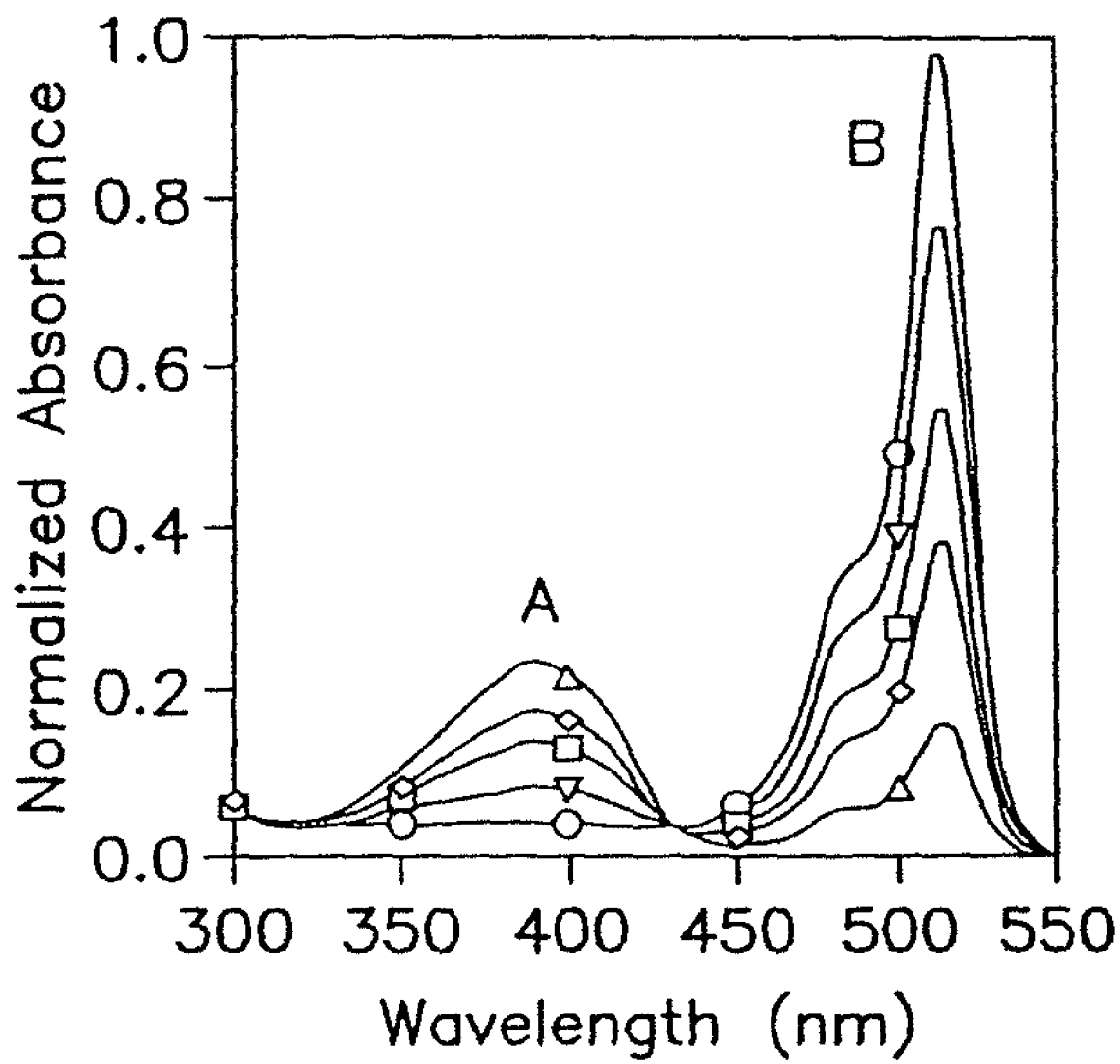
FIG. 7. Shows absorbance scans of YFP at varying NaCl concentration and constant pH 6.4, buffered with 20 mM MES (-○-0 mM NaCl, -∇-15 mM NaCl, -□-50 mM NaCl, -◇-100 mM NaCl, and -Δ-400 mM NaCl). Band A corresponds to the neutral form of the chromophore ($\lambda_{max}=392$ nm), and band B corresponds to the chromophore anion ($\lambda_{max}=514$ nm).

The absorbance spectrum of YFP is a function of NaCl concentration (FIG. 7), with conversion of band B, the chromophore anion ($\lambda$max 514 nm), to band A, the neutral form ($\lambda$max 392 nm) upon addition of chloride. Since only the anion is fluorescent in the YFPs, suppression of fluorescence occurs concomitant with increasing [NaCl]. For YFP, a clean isosbestic point is observed (FIG. 7), whereas for YFP-H148Q, the isosbestic point is less well defined (Jayaraman et al., 2000). The effect is fully reversible. In YFP-H148Q and YFP-H148G, the absorbance maximum of band A is blue-shifted by 20 nm (from 415 nm to 395 nm) upon addition of salt, though the absorbance maximum of band B is unaffected. The detailed binding equilibria and anion specificities are discussed below.

Figure 8A:
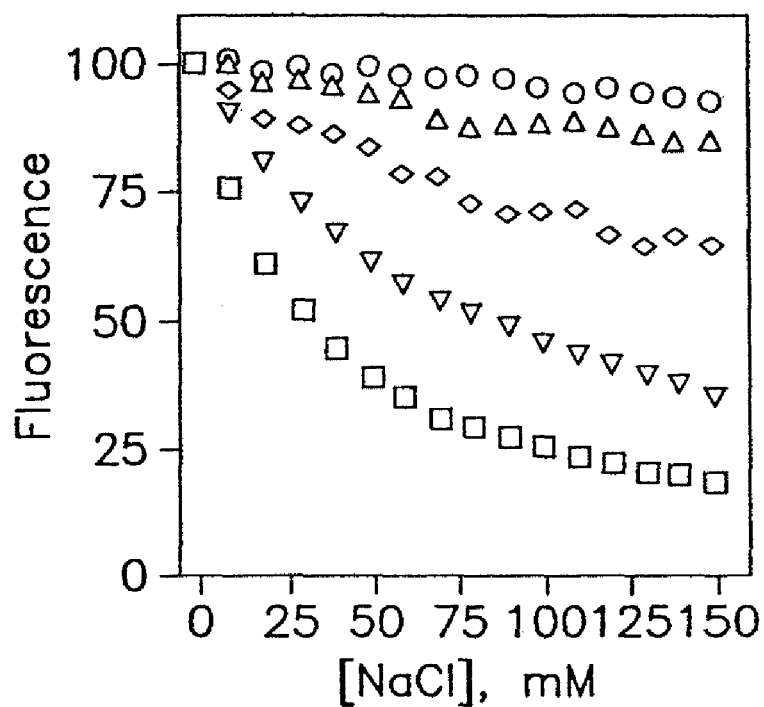
FIG. 8. Shows normalized fluorescence emission of (a) YFP and (b) YFP-H148Q, as a function of pH and [Cl⁻] at constant ionic strength of 150 mM. The pH was controlled with 20 mM TAPS pH 8.0 (○), 20 mM HEPES pH 7.5 (Δ), 20 mM PIPES pH 7.0 (◇), and 20 mM MES pH 6.5 (∇) and pH 6.0 ( ).
FIG. 8(b) also includes the fluorescence emission of YFP-H148Q as a function of [I⁻] at pH 7.5 (*). Potassium chloride (or iodide) was added to the indicated concentration, and the ionic strength was adjusted to 150 mM with potassium gluconate. The samples, containing approximately 0.01 mg/ml protein, were excited at 514 nm, and emission intensity was determined at 528 nm.
Figure 8B:
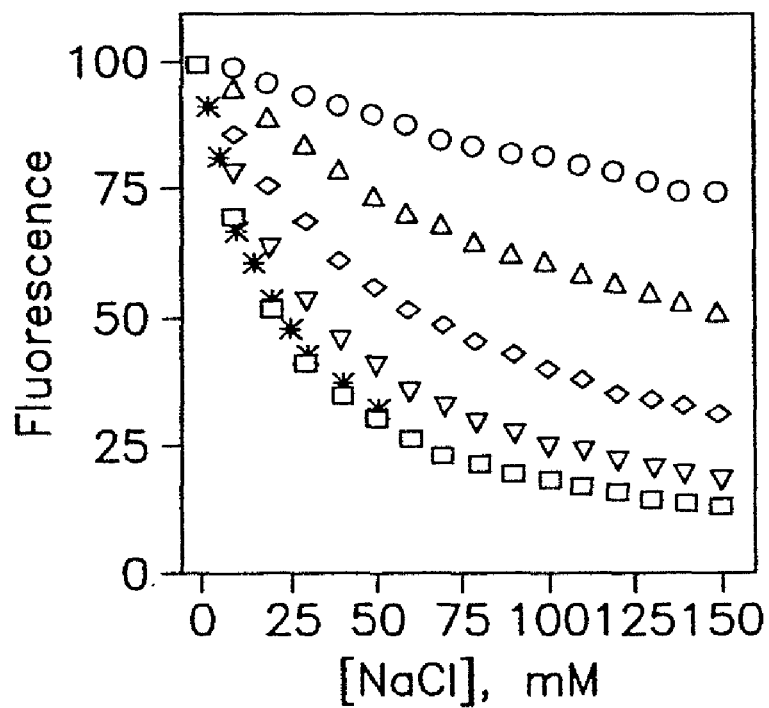

To further establish the usefulness of the YFPs as halide sensors, in particular for organelles that are more acidic than the cytosol (pH 7.4) where CFTR pumping was assayed (Jayaraman et al., 2000), emission intensity of YFP and YFP-H148Q was measured between 0 and 150 mM NaCl at pH 6.0 to 8.0 (FIG. 8A,B), under conditions of constant ionic strength. We found that YFP constitutes an excellent probe under acidic conditions. At pH 6.0, fluorescence decreased by 39% from 0 to 20 mM NaCl, whereas at the cytosolic pH of 7.5, the decrease is only 3.2% under identical conditions. For YFP-H148Q titrated with NaCl, fluorescence loss is also large at pH 6.0 (48%), and remains fairly significant (11%) at pH 7.5. For measurements of chloride concentrations in the low millimolar range near neutral pH, YFP-H148Q appears to be the preferred probe. If iodide is substituted for chloride, YFP-H148Q fluorescence loss is much larger, even at pH 7.5 where a loss of 50% is observed (0 to 20 mM NaI) (FIG. 8B). This observation has recently been exploited in vivo, in studies of Cl$^-$/I$^-$ exchange by the CFTR channel in plasma membranes (Jayaraman et al., 2000). In contrast to the above variant, in the original YFP the magnitude of the iodide effect is more comparable to the chloride effect (see binding data below).

D. Crystallographic Identification and Description of Halide Binding Sites

We determined two crystal structures of YFP-H148Q, one containing two bound iodides (100 mM iodide soak), and the other containing no bound halides at all (200 mM chloride soak). The respective R-factors are 18.8% and 20.4% to a resolution of 2.1 Å, and the geometry is reasonably good. A summary of the relevant crystallographic statistics is presented in Table I. Since iodine has an anomalous signal at the in-house CuKα wavelength, an anomalous difference map was calculated for the iodide soak in order to identify heavy atom positions. We found two distinct electron density peaks at 7.7 and 5.5 rms deviations respectively, one located close to the chromophore and buried in the protein interior, the other in a small indentation on the protein surface near Trp57 at the cap of the barrel (Data not shown).

Figure 9:
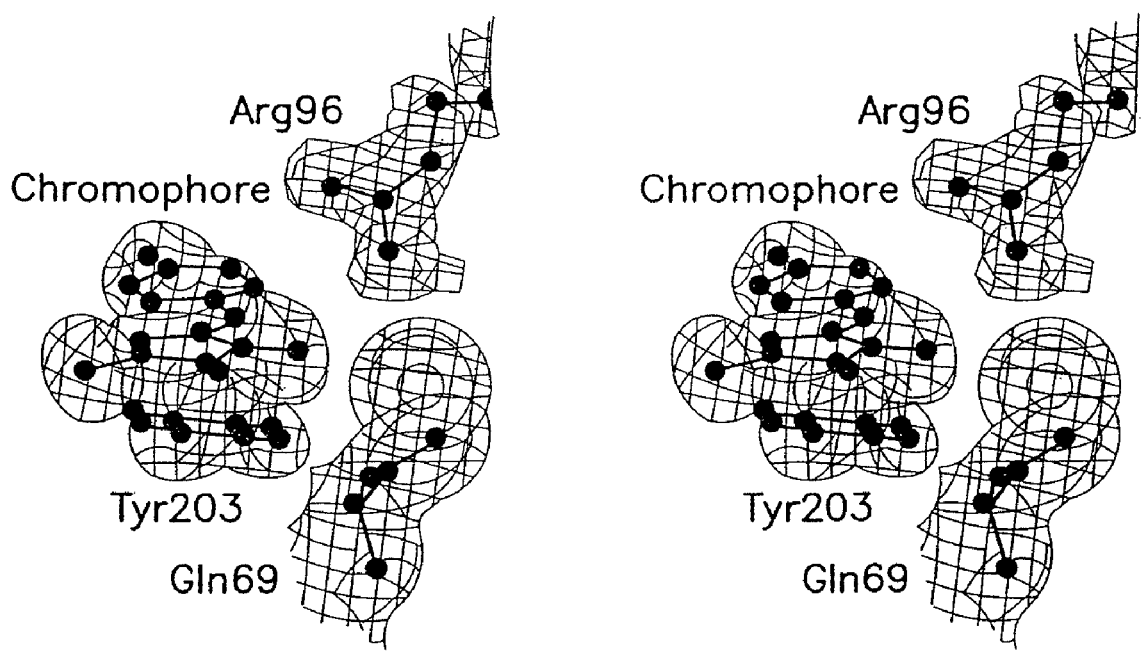
FIG. 9 Shows a stereoview of the $2F_o-F_c$ electron-density map of the YFP-H148Q chromophore, Tyr203, Arg96, Gln69, and the buried iodide after refinement. The 2.1 Å resolution map was contoured at +1 standard deviation. This figure was drawn by the program BOBSCRIPT.
Figure 10:
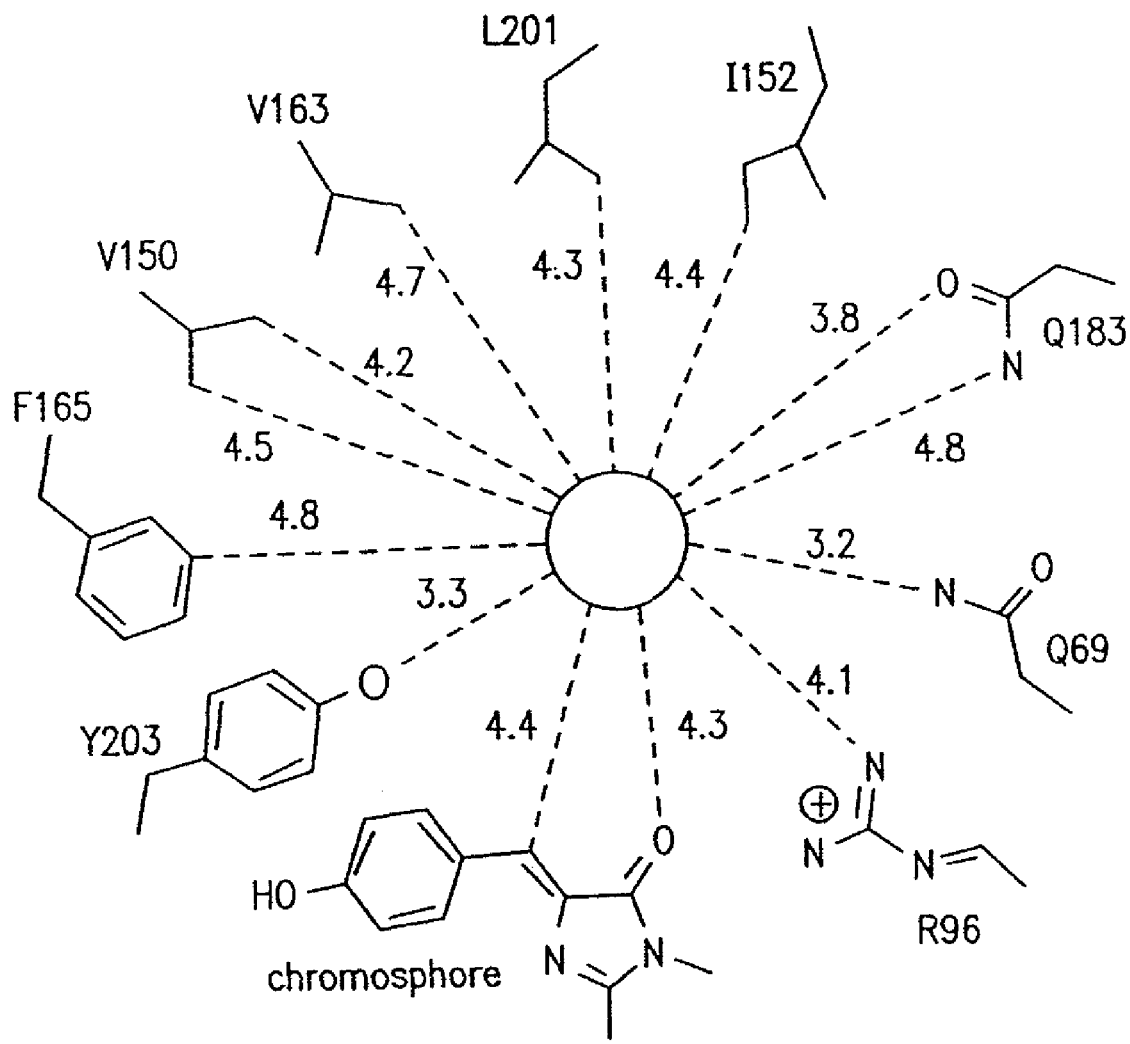
FIG. 10 Shows a schematic diagram showing all residues that contain atoms within 5 Å of the buried iodide in the crystal structure of YFP-H148Q (iodide soak).

The buried iodide refined to an occupancy of 0.60 with the thermal factor fixed at 30 Å$^2$, indicating that binding in the crystal at 100 mM iodide is not nearly as tight as in solution, where the binding constant is 2.7 mM (see below). This iodide is located 4.3 Å away from the chromophore heterocyclic carbonyl oxygen, and is involved in a charge interaction with Arg96, with a distance of 4.1 Å to NE2 of the guanidinium group (FIGS. 9 and 10), a buried positive charge that is likely providing a large fraction of the anion binding energy. Furthermore, the iodide is hydrogen bonded to both the phenolic hydroxyl of Tyr203 and the side chain amide nitrogen of Gln69, with hydrogen bonding distances of 3.3 and 3.2 Å respectively (FIGS. 9 and 10). These distances are within the range of hydrogen bonding distances expected for iodide interacting with oxygen or nitrogen. A statistical database analysis of small molecule crystal structures found that the mean distance between iodide and a phenolic hydroxyl is 3.47 Å, and between iodide and a sp$^2$-hybridized nitrogen is 3.66 Å (Steiner, 1998). In a crystal structure of haloalkane dehalogenase with bound iodide, it was found that the iodide is 3.4 and 3.6 Å away from the indole nitrogens of two tryptophans, 3.3 Å from a solvent molecule, and 4.2 Å from the phenolic oxygen of a tyrosine (Verschueren et al., 1993).

The buried halide also interacts with the aromatic rings of the chromophore and Tyr203 (FIG. 9). Anions are often preferentially located in or near the plane of aromatic rings, since aromatic ring hydrogens carry a partial positive charge (Burley & Petsko, 1988). In YFP-H148Q, the iodide is not quite in the plane of either of the two π systems, but is located roughly equidistant from the 2 planes, offset from the center of the stacking interaction, 4.1 Å from the aromatic CE1 of Tyr203 and 4.5 Å from the aromatic CD2 of the chromophore (FIG. 9). On the opposite side of the binding site, a series of hydrophobic residues line the halide binding site, consisting of Ile152, Leu201, Val163, Val150, and Phe165, all near van der Waals contact with the iodide. Both aromatic edge interactions with tyrosines and tryptophans, as well as apolar interactions with hydrophobic side chains are commonly found in other halide binding sites in proteins, such as in haloalkane dehalogenases (Pikkemaat et al., 1999).

The second, surface-bound iodide is hydrogen-bonded to the amide nitrogen of Trp 57 and several ordered solvent molecules. This exposed anion is 16 Å from the chromophore phenolic oxygen, indicating that its influence on the chromophore charge state is negligible. The occupancy of this halide refines to 0.41 with the B-factor fixed at 39 Å$^2$, consistent weak binding as compared to the primary iodide adjacent to the chromophore.

E. Conformational Changes Adjacent to the Buried Iodide

The anion-binding pocket near the chromophore appears to be empty in the apo-structure of YFP-H148Q, in spite of the fact that the crystals were grown in the presence of 180 mM chloride, followed by soaking in 200 mM chloride. The solution binding constant of 28 mM for chloride predicts that most of the pocket is occupied by chloride at the pH of the crystal mother liquor, 4.6 (see below). As has been found with the iodide soak, the molecules in the crystals do not appear to bind anions as tightly as in solution, possibly due to crystal packing forces. The volume of the internal cavity in YFP-H148Q is 55 Å$^3$, calculated using a probe with a radius of 1.2 Å (Connolly, 1985).

Figure 11:
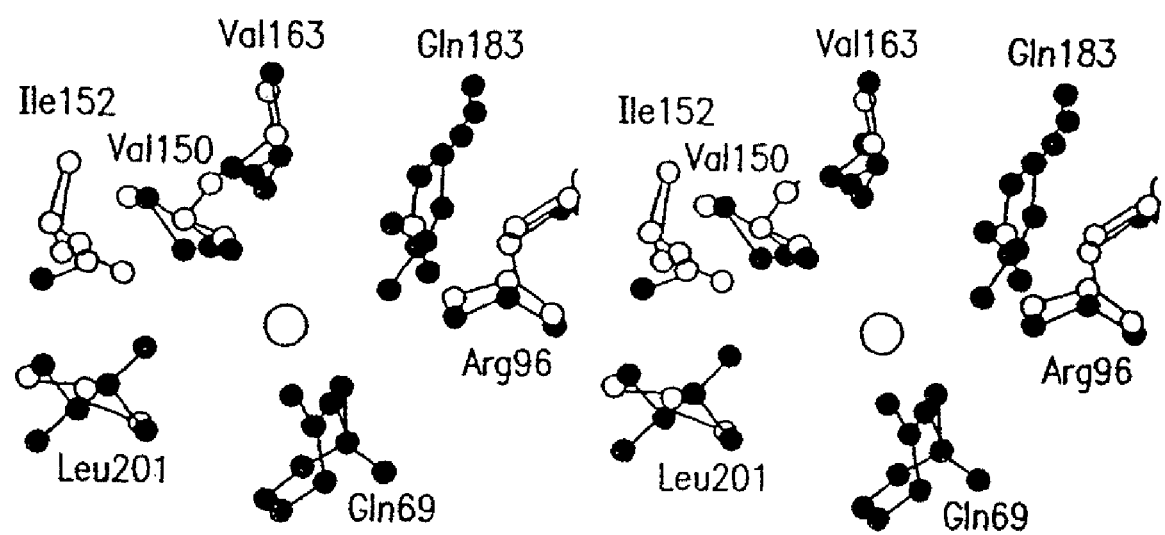
FIG. 11 Shows a stereoview of an overlay of a subset of residues lining the anion binding cavity of YFP-H148Q, with and without iodide (iodide-bound structure, grey; apo-structure, black). The iodide is represented by the center sphere. This figure was drawn by the program MOLSCRIPT (Kraulis, 1991).
Figure 12A:
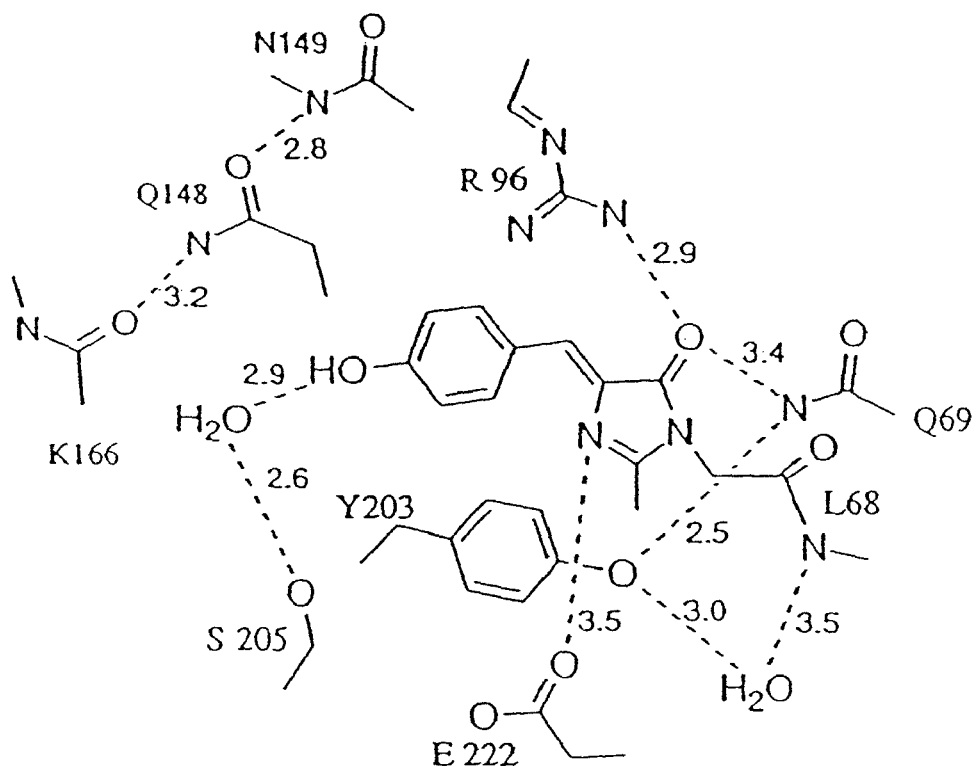
FIG. 12. Shows a schematic diagram of the immediate chromophore environment of YFP-H148Q in the (a) apo-structure, and (b) iodide-bound structure.
Figure 12B:
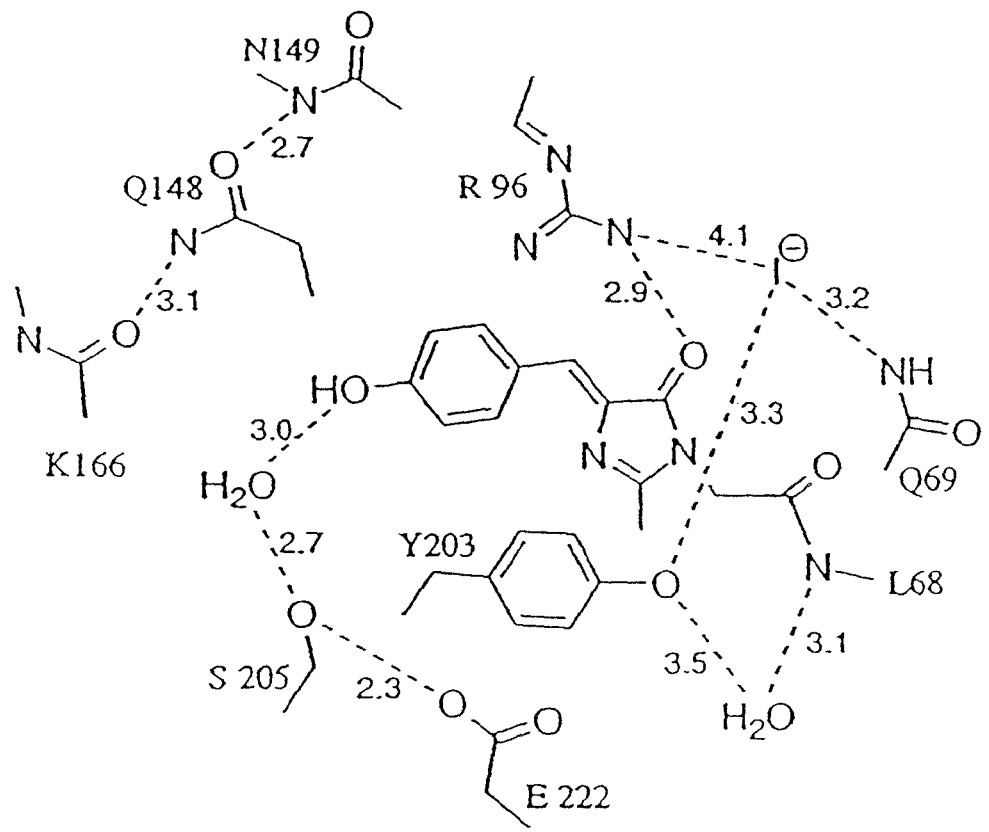

The iodide-containing cavity in the bound structure of YFP-H148Q is larger, 91 Å$^3$, to accommodate the rather large iodide which has a van der Waals volume of 42 Å$^3$. A series of conformational changes of various side chains lining the pocket are observed (FIG. 11). The largest movement is observed by Gln69, where the side chain amide has swung out from the center of the cavity, resulting in a 2.6 Å movement of the NE2 which is hydrogen-bonded to the halide (FIGS. 11 and 12). Gln183 NE2 has moved out by 1.0 Å, though it is not clear whether it is a hydrogen bond donor to the iodide or Gln94 (NE2 and OE may be assigned oppositely). The apolar side chains of Leu201, Ile152, Val150, and Val163 (FIG. 11) all undergo movements to increase the cavity size in the presence of iodide, with their terminal carbons (CD1 for leucine and isoleucine, CG1 for valines) shifting by 2.4 Å, 1.9 Å, 1.6 Å, and 1.2 Å respectively. The aromatic ring plane of Phe165 has rotated by about 25°.

The phenolic hydroxyl of Tyr203 has shifted towards the iodide-containing cavity by 0.6 Å, likely to improve the hydrogen bonding interaction with the halide (FIG. 12). There appears to be some flexibility in positioning the Tyr203 side chain next to the chromophore, presumably since it protrudes into a large water-filled cavity originally identified in the structure of GFP S65T (Ormo et al., 1996). An C$_\alpha$-carbon overlay of 5 structures of YFP and its variants (Wachter et al., 1998) shows that the C$_\beta$s of Tyr203 overlay quite well, whereas the phenolic oxygen varies by up to 1.4 Å. The hydrogen bond between Tyr203 and the halide appears to be of major importance in the generation of a halide binding site with reasonably tight affinity (see mutational analysis below). The chromophore shift toward the halide may also serve to improve aromatic edge interactions with the anion. As a consequence, the carboxylate of Glu222 has rotated away from the chromophore ring nitrogen (distance increases from 3.3 to 3.6 Å), and is now involved in a tight hydrogen bond to Ser205 (FIG. 12).

F. Relationship Between Anion Binding and Cavity Size

Figure 13:
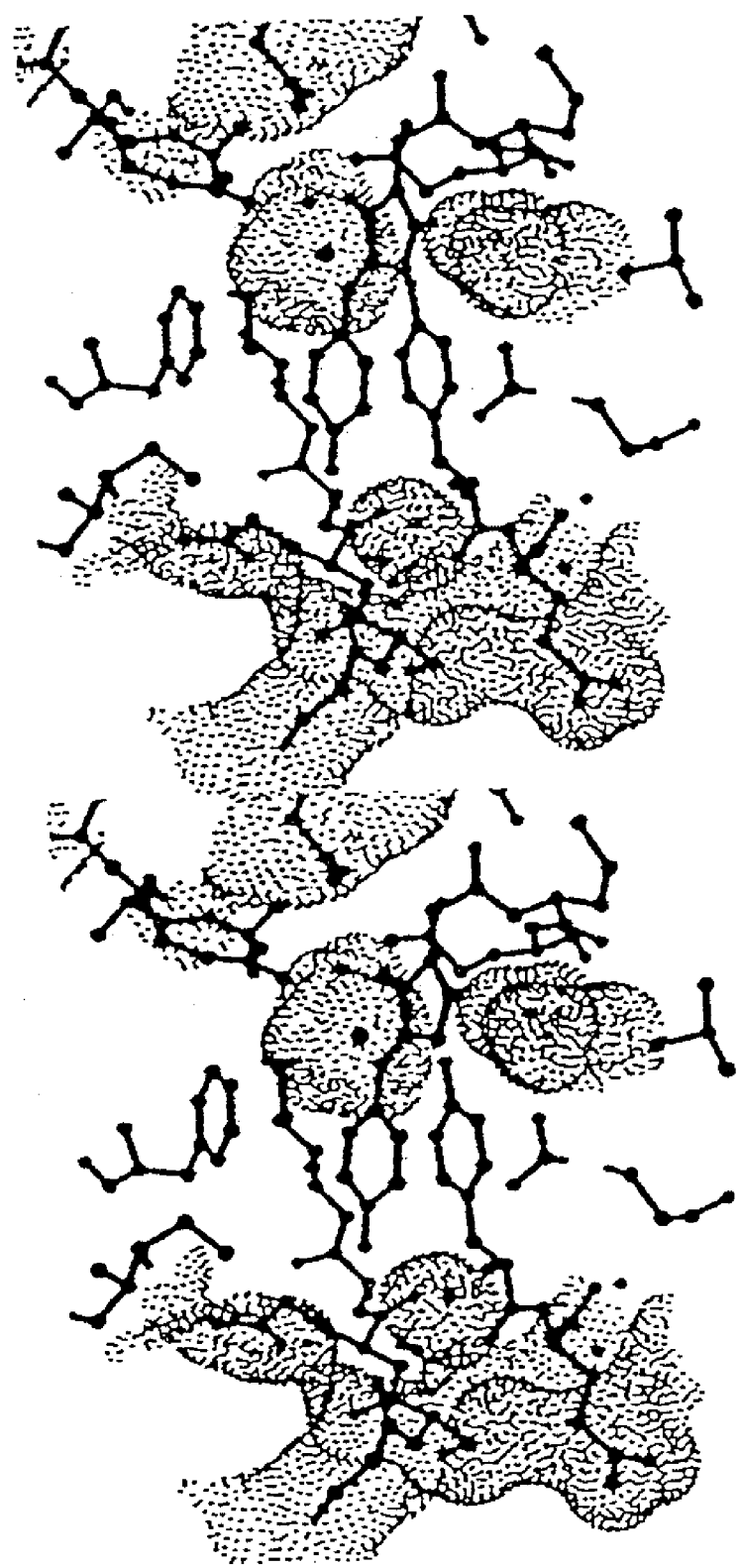
FIG. 13 Shows a stereoview of the solvent-accessible surface of the iodide-bound YFP-H148Q structure, calculated using a 1.4 Å probe radius. The surface was calculated after deleting all water molecules and the iodide. The chromophore and all surface segments in contact with the chromophore are also shown. The outer surface of the protein is along the left edge of the figure. This figure was generated using the program MidasPlus™ (UCSF, 1994).

The buried iodide site in YFP-H148Q identifies a small cavity that is present in a number of structures examined and does not vary much in size (FIG. 13). Calculating van der Waals volumes using a sphere with a probe radius of 1.2 Å (Connolly, 1985), the volume of this cavity is 21 Å$^3$ in WT GFP (Brejc et al., 1997), 19 Å$^3$ in GFP S65T (Ormo et al., 1996), 16 Å$^3$ in YFP and YFP-H148G (Wachter et al., 1998), and 21 Å$^3$ in YFP-H148G soaked in 500 mM KBr, where the crystallographic analysis shows that the binding site is also empty (unpublished data). The position of these cavities is essentially the same in the GFPs listed above, with its center close to Val150, Val163, Leu201, Ile152, Gln183, and Gln69, but about 6.6 Å distant from the chromophore methylene bridge and 6.1 Å from Arg96. WT (see below) and S65T GFP (Wachter & Remington, 1999) do not appear to interact with NaCl. On the other hand, all YFPs examined show anion interactions, with tightest Cl$^-$ binding observed for YFP (see below). Clearly, cavity size and position are not directly correlated with Cl$^-$ binding.

The cavities described above are too small to bind chloride, bromide, or iodide, whose van der Waals volumes range from 24.8 to 54 Å$^3$. Conformational changes are clearly necessary to allow for the interaction with any anions. In the apo-structure of YFP-H148Q, the cavity is somewhat larger, even in the absence of bound anions, with a volume of 55 Å$^3$. In this variant, the cavity is extended towards the chromophore, and the volume is increased by small movements of side chain atoms (0.4 Å and 1.2 Å) lining the binding site (Gln69, Tyr203, Val150, Val163, Phe165, Arg96, His181), and the chromophore itself. Many of these residues undergo further shifts upon iodide binding, as described above and FIG. 6. Compensating movements of the terminal side-chain carbons of Ile152 (2.1 Å) and Leu201 (2.3 Å) lead to some repacking of the hydrophobic core, without changing the adjacent cavity surface much. The larger cavity size of YFP-H148Q may in part be responsible for the unexpectedly tight binding of iodide compared to chloride.

Figure 14:
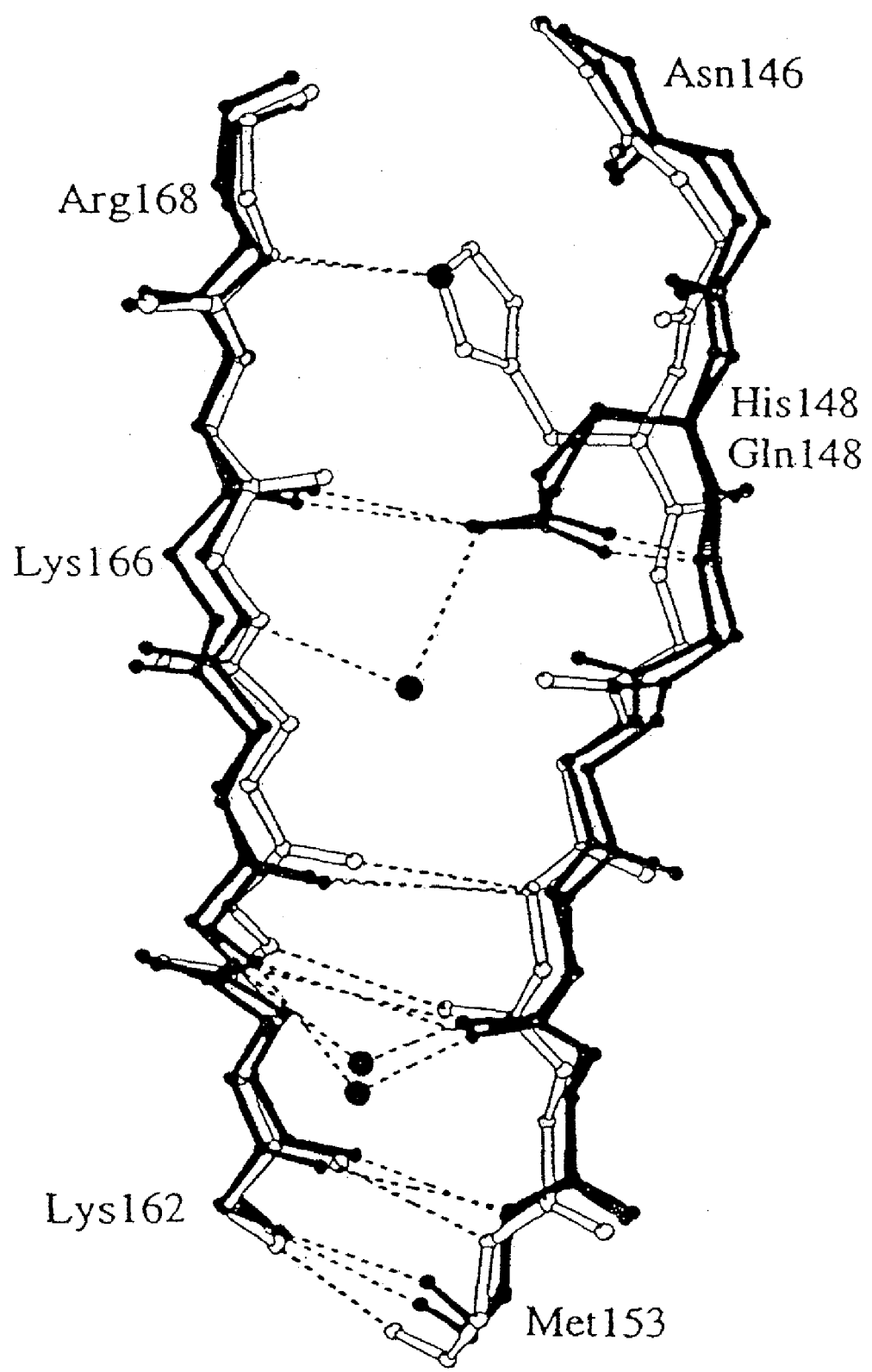
FIG. 14 Shows the backbone atom trace of β-strands 7 and 8 of YFP, the apo-structure of YFP-H148Q, and the iodide-bound structure of YFP-H148Q. The side chain of His148 (YFP) and Gln148 (YFP-H148Q), and a few water molecules are also shown. The dashed lines represent possible hydrogen bonds.

G. Relaxation of the β-Barrel in Response to the H148Q Substitution and Iodide Binding Both the introduction of H148Q in YFP background in the absence of halides, and the binding of iodide to YFP-H148Q lead to structural adjustments of β-strands 7 (residues 143 to 154) and 8 (residues 160 to 171). These adjustments are evident from C$_α$ overlays of YFP and YFP-H148Q, with an rms deviation of 0.42 Å, and of YFP-H148Q with and without I$^-$, with an rms deviation of 0.47 Å (FIG. 14). At one cap of the barrel, strands 7 and 8 are connected via a turn centered on residue 158, whereas near the other cap of the barrel, strand 7 forms a β-bulge around residue 148, and main chain β-sheet interactions are disrupted (Ormo et al., 1996; Wachter et al., 1998). Instead, several ordered solvent molecules and side-chain contacts (His148 in YFP, Gln148 in YFP-H148Q) form a hydrogen bond network between the strands (FIG. 14). Upon substitution of His148 with Gln, the α-carbon of residue 166 is pulled in towards the center of the barrel by 0.94 Å, and the α-carbon of residue 148 is pushed out by 0.94 Å. These movements are compensated for by structural adjustments within the adjacent loop regions (1.4 Å shift by the α-carbon of residue 172, and 0.94 Å by the α-carbon of residue 157). None of these residues are involved in crystal contacts in either of the two structures.

Upon binding of iodide to YFP-H148Q, Lys166 is pushed back out from the center of the barrel by 1.0 Å, and is located near its original position in YFP (FIG. 14). Likely, this shift in position occurs in response to the expansion of the buried cavity. Lys166 is not involved in a crystal contact in either of the two structures, whereas nearby Arg168 forms an intermolecular salt bridge with Asp149 upon iodide binding, but not without. The hydrogen bond of the Lys166 backbone oxygen to the side chain of Gln148 is not disrupted by this movement. Compensating shifts are again observed at the end of this strand, where the backbone loop residues 172 and 173 are pulled in by up to 1.7 Å, though density in this area is less well defined. Whether halide binding to YFP has a similar effect on the β-bulge region as in YFP-H148Q is not known. Backbone movements in position 148 have been observed previously in YFP-H148G (Wachter et al., 1998), consistent with increased flexibility in that part of the barrel.

H. Solvent Accessibility of the Chromophore in YFP-H148Q

The structure of YFP-H148Q shows that the Gln148 side chain is swung out towards the protein exterior (FIG. 9), unlike the original histidine imidazole that is hydrogen bonded to the chromophore hydroxyl (Wachter et al., 1998), and constitutes a barrier to bulk solvent. Even before a structure was available, we predicted that Gln148 may be flipped out into the solvent (Elsliger et al., 1999), since partial chromophore exposure to exterior solvent may explain the higher pK$_a$ of YFP-H148Q as compared to YFP (see Table K). Both in the apo and iodide-bound structure of YFP-H148Q, the Gln148 side chain amide nitrogen NE2 is hydrogen-bonded to the backbone carbonyl oxygen of Lys166, and the amide oxygen OE1 to the backbone nitrogen of Asn149 (FIGS. 12 and 14), well away from the chromophore. Calculations of solvent-accessible surface (Connolly, 1983) using a probe sphere radius of 1.4 Å, as implemented by MidasPlus™, show that a shallow invagination on the protein surface is formed where the wild-type imidazole of His148 was located (FIG. 13). This solvent pocket is nearly in contact with the chromophore van der Waals surface. If one considers protein breathing motions, some solvent access that is not observable in the crystal structure is likely to occur. As compared to YFP-H148G (Wachter et al., 1998), where the solvent channel is directly in contact with the chromophore cavity, the channel of YFP-H148Q is truncated, consistent with triplet state photobleaching experiments which suggested that the chromophore is not exposed to aqueous-phase quenchers (Jayaraman et al., 2000).

I. Energetic Analysis of Linkage Between Anion and Proton Binding

The strong dependence of chromophore pKa on specific anion binding can be described by a linked binding equilibrium that considers the interaction between two different ligands, the anion that binds adjacent to Arg96, and the proton that binds to the phenolic end of the chromophore. Positive cooperativity is indicated by the fact that binding of the anion facilitates binding of the proton, raising the pK$_a$ of the chromophore. The binding constant for anion binding is therefore influenced by the amount of proton binding, and vice versa. Hence, in a simple system with one binding site each for two different ligands; one can define two microscopic binding constants, k$_1$ for anion binding when the proton is on and k$_2$ for anion binding when the proton is off. Our crystallographic analysis for YFP-H148Q is consistent with one relevant binding site for the anion, and a previous crystallographic analysis on S65T is consistent with one proton binding site on the chromophore (Elsliger et al., 1999). The observed extent of anion binding is a function of pH, hence the macroscopic binding constants lie somewhere between the limiting values of k$_1$ and k$_2$.

A mathematical description has been developed by J. Wyman (1964) and is presented by Cantor and Schimmel in Biophysical Chemistry, Part III, (Cantor & Schimmel, 1980). Here, we apply the general equation 15-79 to the special case of having one binding site for each ligand, with pK$_a$° representing the chromophore pK$_a$ in the absence of any bound anions:

$$pK_a = \log\{(k_1+[\text{chloride}])/k_1\} - \log\{(k_2+[\text{chloride}])/k_2\} + pK_a° \quad \text{equation (1)}$$

Figure 15:
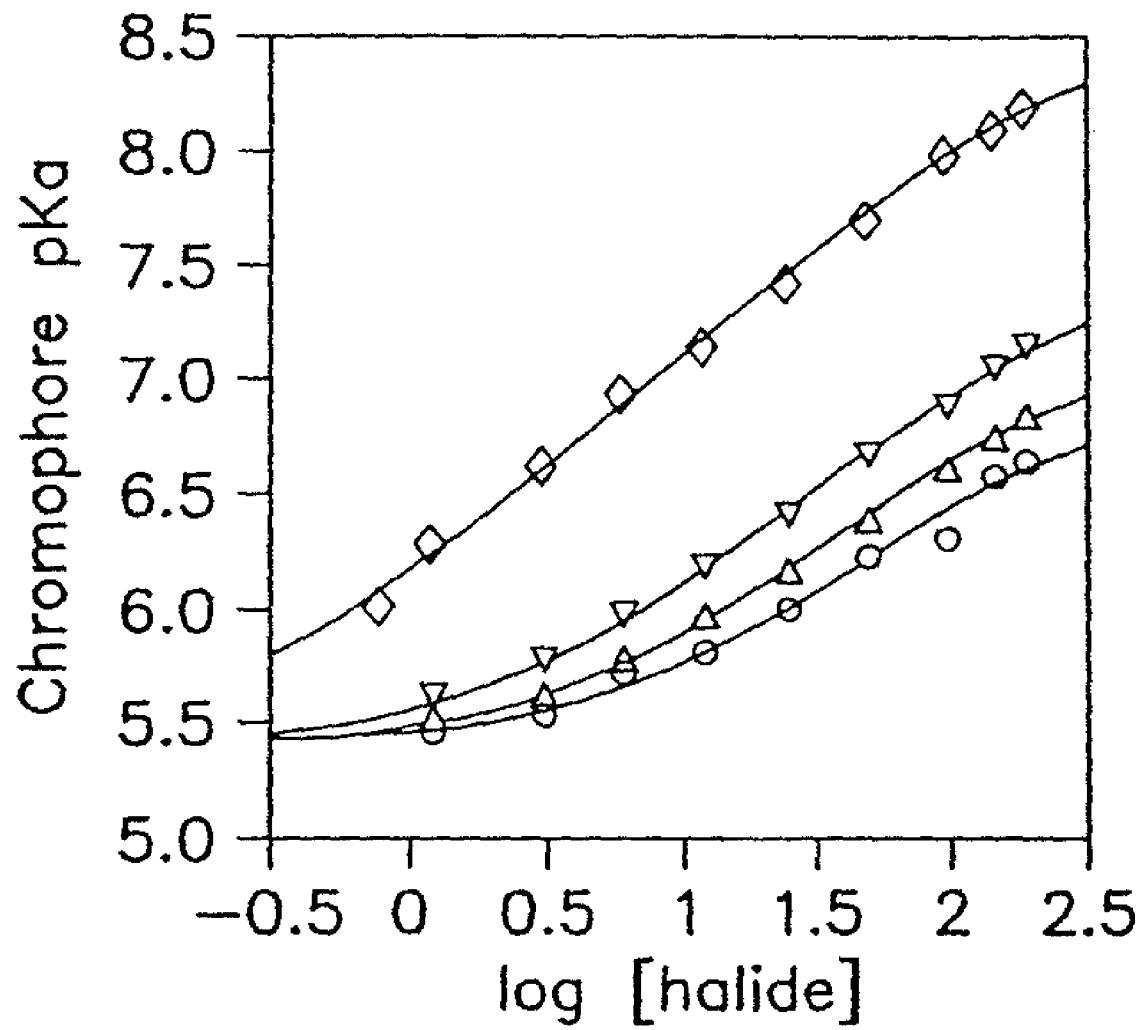
FIG. 15 Shows YFP chromophore $pK_a$ as a function of halide concentration (-◇-fluoride, -∇-iodide, -Δ-chloride, -○-bromide). The chromophore $pK_a$ was estimated from absorbance scans at varying halide concentrations (see Materials and Methods). The data were curve-fit to equation 1 (see text).

Using absorbance measurements at both pH 6.5 and pH 7.0, the pK$_a$ of YFP was determined as a function of anion concentration for a large number of different ions. The concentration of the particular anion of interest was varied between 0 and at least 150 mM (for the halides as high as 400 mM, FIG. 15), and ionic strength was controlled by the addition of potassium gluconate which does not interact with the YFPs (Wachter & Remington, 1999). Results for interacting anions were fit to equation (1), and the microscopic binding constants k$_1$ and k$_2$ where possible, were extracted from the curve fit (FIG. 15 and Table J). In general, small monovalent anions appear to show some interaction with YFP. Binding is tightest for fluoride, with k$_1$=0.214 mM. Other anions that were found to interact, including the other halides, have microscopic binding constants in the low millimolar range, with trifluoroacetic acid (TFA) giving the weakest interaction in this series ($k_1$=21.2 mM).

There does not appear to be any particular molecular shape dependence for this interaction, since triatomic linear (e.g. thiocyanate), square planar molecules (e.g. perchlorate), trigonal (e.g. nitrite), and spherical (e.g. halides) molecules are also found to bind. Formate modulated the chromophore $pK_a$ as well ($k_1$=7.47 mM), though a previous, somewhat preliminary experiment by fluorescence indicated no interaction (Wachter & Remington, 1999). As expected, anion binding to the anionic chromophore is unfavorable, with $k_2$ in the high millimolar or in the molar range, often outside the range of measurement (Table J).

TABLE J

Anion binding to the YFP chromophore in order of decreasing interaction strength.[a]

| Interacting anions | $k_1$ (mM)[b] | $k_2$ (mM)[b] |
|---|---|---|
| Fluoride F− | 0.214 (0.009) | 301 (64) |
| Thiocyanate SCN− | 1.37 (0.02) | large[c] |
| Perchlorate ClO$_4$− | 1.46 (0.36) | 175 (11) |
| Nitrite NO$_2$− | 2.12 (0.40) | 273 (200) |
| Iodide I− | 2.46 (0.11) | 325 (64) |
| Nitrate NO$_3$− | 4.44 (0.25) | large[c] |
| Chloride Cl− | 4.69 (0.17) | 288 (40) |
| Formate HCOO− | 7.47 (0.004) | large[c] |
| Bromide Br− | 7.76 (1.00) | 280 (126) |
| TFA CF$_3$COO− | 21.2 (3.7) | large[c] |

[a]Conjugate bases (prevalent ion at pH 6 to 7) are listed in order of decreasing interaction strength.
[b]The numbers in parenthesis are a lower estimate of the standard deviation as determined by Kaleidagraph™.
[c]These binding constants could not be determined since they fall outside the range of measurement, and are likely in the molar range.

Divalent anions such as phosphate and sulfate, and larger monovalent anions such as gluconate, Good buffers (e.g. HEPES, PIPES), isethionate (2-hydroxyethanesulfonic acid), and TCA (trichloroacetic acid), do not interact (Table J), as indicated by a constant $pK_a$ of about 5.4 for YFP, essentially the same as when measurements are carried out in low ionic strength buffers without addition of salts (Wachter & Remington, 1999). Somewhat smaller monovalent anions that do not interact include phosphoric acid, bicarbonate, and acetate. The hydration energy may be of importance in discrimination of anions, since acetate is strongly solvated, whereas TCA is only weakly hydrated in aqueous solvents (March, 1992). The series presented for YFP in Table J is very similar to the one determined for YFP-H148Q by fluorescence at pH 7.5 (Jayaraman et al., 2000), with only minor differences in ordering. For example, YFP-H148Q binds Br− more strongly than Cl, whereas for YFP, the order is reversed, likely due to the larger binding site in YFP-H148Q.

J. Identification of Key Residues for Anion Binding by Mutational Analysis

To identify which substitutions in YFP (S65G/V68L/S72A/T203Y) are contributors to specific anion binding near the chromophore, we carried out a mutational analysis, converting the four substitutions back to wild-type one-by-one. We then determined the $pK_a$ of these revertants in the absence of interacting anions, and measured their affinity to chloride and iodide by $pK_a$ determination as a function of halide concentration, followed by curve fitting to equation (1). Revertant 1 (S65G/S72A/T203Y) and revertant 2 (S65G/V68L/S72A) exhibited well-behaved pH and halide titration behavior as is observed for the YFPs, and their $pK_a$ and $k_1$ for chloride and iodide binding are compared with those obtained for the YFPs in Table K. Reversion of residue 68 or residue 203 raises the chromophore pKa to 5.8 and 6.4 respectively. Reversion of residue 68 leads to a slight loss of chloride affinity ($k_1$=13.2 mM, as compared to 4.69 mM in YFP), whereas reversion of residue 203 dramatically weakens the interaction ($k_1$=153 mM). As is evident from Table K, chloride affinity is strongly coupled to chromophore pKa, with a weakening of the anion interaction with increasing pKa.

TABLE K

Microscopic dissociation constants for chloride and iodide binding to the YFPs and its revertants.

| variant | substitutions | $k_1$ (mM)[a] for Cl− | $k_1$ (mM)[a] for I− | $pK_a$[b] |
|---|---|---|---|---|
| YFP | S65G/V68L/S72A/T203Y | 4.69 (0.17) | 2.46 (0.11) | 5.4 |
| revertant 1 | S65G/S72A/T203Y | 13.2 (0.34) | 3.04 (0.11) | 5.8 |
| YFP-H148Q | S65G/V68L/S72A/H148Q/T203Y | 28.4 (5.1) | 2.68 (0.11) | 6.7 |
| YFP-H148G | S65G/V68L/S72A/H148G/T203Y | 82.8 (18.3) | 15.73 (2.6) | 7.5 |
| revertant 2 | S65G/V68L/S72A | 153 (26) | 117 (16) | 6.4 |

[a]A lower estimate of the standard deviation (as reported by Kaleidagraph™) is given in parenthesis.
[b]The chromophore $pK_a$ determined by absorbance in the absence of any interfering anions, such as chloride (buffered with either HEPES or PIPES, 150 mM gluconate).

Since the only exception to this rule is revertant 2, it appears that the correlation is intact only in the presence of T203Y. This substitution appears to be indispensable for strong anion interactions.

Iodide binding appears to be considerably tighter than chloride binding for all variants tested (Table K). Any correlation with chromophore pKa is weak at best. The relative selectivity of iodide over chloride is strongest for YFP-H148Q, followed by YFP-H148G. This may reflect the fact that iodide is a larger, softer ion than chloride, more difficult to fit into a small cavity unless the particular variant allows for structural relaxation of the β-barrel (see above).

Revertants 3 (S72A/T203Y) and 4 (T203Y) were more difficult to analyze, since their titration behavior is similar to WT GFP. Their absorbance spectra exhibit a mixed ground state of bands A and B, and are nearly pH-independent above pH 6.5. Excitation of either band A or B leads to green fluorescence in these revertants, reminiscent of the excited-state deprotonation described for WT GFP (Chattoraj et al., 1996). Addition of NaCl to 250 mM to revertants 3 and 4 at pH 6.5 changes the ratio of the two absorbance bands only to a small degree, resulting in roughly a 20% decrease of band B in favor of band A. In WT GFP at pH 6.5, no spectral change is observed upon addition of 250 mM NaCl under conditions of constant ionic strength, consistent with a sensitivity towards ionic strength (Ward et al., 1982) but not specific anion binding.

The present invention provides novel long wavelength engineered fluorescent proteins. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

PUBLICATIONS

Baird, G. S., Zacharias, D. A. & Tsien, R. Y. (1999). Circular permutation and receptor insertion within green fluorescent proteins. *Proc. Natl. Acad. Sci. USA* 96, 11241-11246.

Bell, A. F., He, X., Wachter, R. M. & Tonge, P. J. (2000). Probing the ground state structure of the green fluorescent protein chromophore using Raman spectroscopy. *Biochemistry* (in press).

Bokman, S. H. & Ward, W. W. (1981). Renaturation of *Aequorea* green fluorescent protein. *Biochem. Biophys. Res. Commun.* 101, 1372-1380.

Born, M. (1920). Volumen and hydratationswaerme der ionen. *Z. Physik* 1, 45-48.

Brejc, K., Sixma, T. K., Kitts, P. A., Kain, S. R., Tsien, R. Y., Ormö, M. & Remington, S. J. (1997). Structural basis for dual excitation and photoisomerization of the *Aequorea victoria* Green Fluorescent Protein. *Proc. Natl. Acad. Sci. USA.* 94, 2306-2311.

Burley, S. K. & Petsko, G. A. (1988). Weakly polar interactions in proteins. *Adv. Protein Chem.* 39, 125-189.

Cantor, C. R. & Schimmel, P. R. (1980). *Biophysical Chemistry Part III: The behavior of biological macromolecules*, W. H. Freeman and Company, New York, pp 866-878.

Chattoraj, M., King, B. A., Bublitz, G. U. & Boxer, S. G. (1996). Ultra-fast excited state dynamics in Green Fluorescent Protein: Multiple states and proton transfer. *Proc. Natl. Acad. Sci. USA* 93, 8362-8367.

Collaborative Computational Project N. 4 (1994). The CCP4 Suite: Programs for protein crystallography. *Acta Cryst.* D50, 760-763.

Connolly, M. L. (1983). Solvent-accessible surfaces of proteins and nucleic acids. *Science* 221(4612), 709-713.

Connolly, M. L. (1985). Computation of molecular volume. *J. Am. Chem. Soc.* 107, 1118-1124.

De Giorgi, F., Ahmed, Z., Bastianutto, C., Brini, M., Jouvaille, L. S., Marsault, L. S., Murgia, M., Pinton, P., Pozzan, T. & Rizzutto, R. (1999). *Meth. Cell Biol.* 58, 75-85.

Doi, N. & Yanagawa, H. (1999). Design of generic biosensors based on green fluorescent proteins with allosteric sites by directed evolution. *FEBS Lett.* 453, 305-307.

Elsliger, M.-A., Wachter, R. M., Hanson, G. T., Kallio, K. & Remington, S. J. (1999). Structural and spectral response of green fluorescent protein variants to changes in pH. *Biochemistry* 38, 5296-5301.

Feller, G., le Bussy, O., Houssier, C. & Gerday, C. (1996). Structural and functional aspects of chloride binging to Alteromonas haloplanctis alpha-amylase. *J. Biol. Chem.* 271, 23836-23841.

Fersht, A. (1985). *Enzyme structure and mechanism*, W. H. Freeman and Company, New York, N.Y., pg 298.

Halm, D. R. & Frizzell, R. A. (1992). Anion permeation in an apical membrane chloride channel of a secretory epithelial cell. *J. Gen. Physiol.* 99, 339-366.

Heim, R. (1999). Green fluorescent protein forms for energy transfer. *Methods Enzymol.* 302, 408-423.

Heim, R., Prasher, D. C. & Tsien, R. Y. (1994). Wavelength mutations and posttranslational autoxidation of green fluorescent protein. *Proc. Natl. Acad. Sci. USA* 91, 12501-12504.

Jayaraman, S., Haggie, P., Wachter, R. M., Remington, S. J. & Verkman, A. S. (2000). Mechanism and cellular applications of a green fluorescent protein-based halide sensor. *J. Biol. Chem.* (in press).

Jones, T. A., Zou, J.-Y., Cowan, S. W. & Kjelgaard, M. (1991). Improved methods for building protein models in electron density maps and the location of errors in these models. *Acta Crystallogr. Sect. A* 47, 110-119.

Kneen, M., Farinas, J., Li, Y. & Verkman, A. S. (1998). Green fluorescent protein as a noninvasive intracellular pH indicator. *Biophys. J* 74, 1591-1599.

Kraulis, P. (1991). MOLSCRIPT: A program to produce both detailed and schematic plots of protein structures. *J. Appl. Crystallog.* 24, 946-950.

Llopis, J., McCaffery, J. M., Miyawaki, A., Farquhar, M. & Tsien, R. Y. (1998). Measurement of cytosolic, mitochondrial, and Golgi pH in single living cells with green fluorescent proteins. *Proc. Natl. Acad. Sci. USA* 95, 6803-6808.

March, J. (1992). *Advanced Organic Chemistry*, John Wiley & Sons, New York, pg 272.

Matz, M. V., Fradkov, A. F., Labas, Y. A., Savitsky, A. P., Zaraisky, A. G., Markelov, M. L. & Lukyanov, S. A. (1999). Fluorescent proteins from nonbioluminescent *Anthozoa* species. *Nature Biotechnol.* 17, 969-973.

Miesenbock, G., De Angelis, D. A. & Rothman, J. E. (1998). Visualizing secretion and synaptic transmission with pH-sensitive green fluorescent proteins. *Nature* 394, 192-195.

Miyawaki, A., Griesbeck, O., Heim, R. & Tsien, R. Y. (1999). Dynamic and quantitative Ca2+ measurements using improved cameleons. *Proc. Natl. Acad. Sci. USA* 96, 2135-2140.

Ormö, M., Cubitt, A. B., Kallio, K., Gross, L. A., Tsien, R. Y. & Remington, S. J. (1996). Crystal structure of the *Aequorea victoria* Green Fluorescent Protein. *Science* 273, 1392-1395.

Otwinowski, Z. & Minor, W. (1997). Processing of X-ray diffraction data collected in oscillation mode. *Methods Enzymol.* 276, 307-326.

Palm, G. J. & Wlodawer, A. (1999). Spectral variants of green fluorescent protein. *Methods Enzymol.* 302, 378-394.

Palm, G. J., Zdanov, A., Gaitanaris, G. A., Stauber, R., Pavlakis, G. N. & Wlodawer, A. (1997). The structural basis for spectral variations in green fluorescent protein. *Nat. Struct. Biol.* 4(5), 361-365.

Pikkemaat, M. G., Ridder, I. S., Rozeboom, H. J., Kalk, K. H., Dijkstra, B. W. & Janssen, D. B. (1999). Crystallographic and kinetic evidence of a collision complex formed during halide import in haloalkane dehalogenase. *Biochemistry* 38, 12052-12061.

Robey, R. B. Ruiz, O., Santos, A. V. P., Ma, J., Kear, F., Wang, L.-J., Li, C.-J., Bernardo, A. A. & Arruda, J. A. L. (1998). pH-Dependent fluorescence of a heterologously expressed *Aequorea* Green Fluorescent Protein mutant: In situ spectral characteristics and applicability to intracellular pH estimation. *Biochemistry* 37, 9894-9901.

Scharnagl, C., Raupp-Kossmann, R. & Fischer, S. F. (1999). Molecular basis for pH sensitivity and proton transfer in Green Fluorescent Protein: Protonation and Conformational substates from electrostatic calculations. *Biophys. J.* 77, 1839-1857.

Steiner, T. (1998). Hydrogen-bond distances to halide ions in organic and organometallic crystal structures: Up-to-date database study. *Acta Cryst.* B54, 456-463.

Sullivan, K. F. & Kay, S. A. E., eds (1999). Green fluorescent proteins. *Methods Cell Biol.* 58, Academic Press, San Diego.

Topell, S., Hennecke, J. & Glockshuber, R. (1999). Circularly permuted variants of the green fluorescent protein. *FEBS Lett.* 457, 283-289.

Tronrud, D. E., Ten Eyck, L. F. & Matthews, B. W. (1987). An efficient general-purpose least-squares refinement program for macromolecular structures. *Acta Crystallogr. Sect. A* 43, 489-501.

Tsien, R. Y. (1998). The green fluorescent protein. *Ann. Rev. Biochem.* 67, 509-544.

Verschueren, K. H. G., Kingma, J., Rozeboom, H. J., Kalk, K. H., Janssen, D. B. & Dijkstra, B. W. (1993). Crystallographic and fluorescence studies of the interaction of haloalkane dehalogenase with halide ions. Studies with halide compounds reveal a halide binding site in the active site. *Biochemistry* 32, 9031-9037.

Wachter, R. M., Elsliger, M.-A., Kallio, K., Hanson, G. T. & Remington, S. J. (1998). Structural basis of spectral shifts in the yellow-emission variants of green fluorescent protein. *Structure* 6(10), 1267-1277.

Wachter, R. M. & Remington, S. J. (1999). Sensitivity of the yellow variant of green fluorescent protein to halides and nitrate. *Curr. Biol.* 9(17), R628-R629.

Wang, Z., Asenjo, A. B. & Oprian, D. D. (1993). Identification of the Cl⁻ binding site in the human red and green color vision pigments. *Biochemistry* 32, 2125-2130.

Ward, W. W., Prentice, H. J., Roth, A. F., Cody, C. W. & Reeves, S. C. (1982). Spectral perturbations of the *Aequorea* green-fluorescent protein. *Photochem. Photobiol.* 35, 803-808.

Wright, E. M. & Diamond, J. M. (1977). Anion selectivity in biological systems. *Physiological Reviews* 57, 109-156.

Yang, F., Moss, L. G. & Phillips, G. N. (1996). The molecular structure of green fluorescent protein. *Nature Biotech.* 14, 1246-1251.

Yuan, C., Kuwata, O., Liang, J., Misra, S., Balashov, S. P. & Ebrey, T. G. (1999). Chloride binding regulates the Schiff base pK in Gecko P521 cone-type visual pigment. *Biochemistry* 38, 4649-4654.

All publications and patent documents cited in this application are incorporated by reference in their entirety for all purposes to the same extent as if each individual publication or patent document were so individually denoted.

SEQUENCE LISTING

```
<160> NUMBER OF SEQ ID NOS: 10

<210> SEQ ID NO 1
<211> LENGTH: 716
<212> TYPE: DNA
<213> ORGANISM: Aequorea victoria
<220> FEATURE:
<223> OTHER INFORMATION: green fluorescent protein (GFP)
<220> FEATURE:
<221> NAME/KEY: CDS
<222> LOCATION: (1)...(714)
<223> OTHER INFORMATION: GFP

<400> SEQUENCE: 1 atg agt aaa gga gaa gaa ctt ttc act gca gtt gtc cca att ctt gtt       48
Met Ser Lys Gly Glu Glu Leu Phe Thr Ala Val Val Pro Ile Leu Val
1               5                   10                  15 gaa tta gat ggt gat gtt aat ggg cac aaa ttt tct gtc agt gga gag       96
Glu Leu Asp Gly Asp Val Asn Gly His Lys Phe Ser Val Ser Gly Glu
                20                  25                  30 ggt gaa ggt gat gta aca tac gga aaa ctt acc ctt aaa ttt att tgc      144
Gly Glu Gly Asp Val Thr Tyr Gly Lys Leu Thr Leu Lys Phe Ile Cys
            35                  40                  45 act act gga aaa cta cct gtt cca tgg cca aca ctt gtc act act ttc      192
Thr Thr Gly Lys Leu Pro Val Pro Trp Pro Thr Leu Val Thr Thr Phe
        50                  55                  60 tct tat ggt gtt caa tgc ttt tca aga tac cca gat cat atg aaa cgg      240
Ser Tyr Gly Val Gln Cys Phe Ser Arg Tyr Pro Asp His Met Lys Arg
65                  70                  75                  80 cat gac ttt ttc aag agt gcc atg ccc gaa ggt tat gta cag caa aga      288
His Asp Phe Phe Lys Ser Ala Met Pro Glu Gly Tyr Val Gln Gln Arg
                85                  90                  95 act ata ttt ttc aaa gat gac ggg aac tac aag aca cgt gct gaa gtc      336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att      384
Lys Phe Glu Gly Asp Thr Leu Val Asn Arg Ile Glu Leu Lys Gly Ile
        115                 120                 125 gat ttt aaa gaa gat gga aac att ctt gga cat aaa ttg gaa tac aac      432
Asp Phe Lys Glu Asp Gly Asn Ile Leu Gly His Lys Leu Glu Tyr Asn
    130                 135                 140 tat aac tca cac aat gta tac atc atg gca gac aaa caa aag aat gga      480
Tyr Asn Ser His Asn Val Tyr Ile Met Ala Asp Lys Gln Lys Asn Gly
145                 150                 155                 160
```

| | | | | | | | | | | | | |
|---|---|---|---|---|---|---|---|---|---|---|---|---|
| atc | aaa | gtt | aac | ttc | aaa | att | aga | cac | aac | att | gaa | gat | gga | agc | gtt | | 528 |
| Ile | Lys | Val | Asn | Phe | Lys | Ile | Arg | His | Asn | Ile | Glu | Asp | Gly | Ser | Val | |
| | | | 165 | | | | | 170 | | | | | 175 | | | |

```
atc aaa gtt aac ttc aaa att aga cac aac att gaa gat gga agc gtt      528
Ile Lys Val Asn Phe Lys Ile Arg His Asn Ile Glu Asp Gly Ser Val
            165                 170                 175 caa cta gca gac tat tat caa caa aat act cca att ctc gat ggc cct      576
Gln Leu Ala Asp Tyr Tyr Gln Gln Asn Thr Pro Ile Leu Asp Gly Pro
            180                 185                 190 gtc ctt tta cca gac aac cat tac ctg tcc aca caa tct gcc ctt tcg      624
Val Leu Leu Pro Asp Asn His Tyr Leu Ser Thr Gln Ser Ala Leu Ser
            195                 200                 205 aaa gat ccc aac gaa aag aga gac cac atg gtc ctt ctt gag ttt gta      672
Lys Asp Pro Asn Glu Lys Arg Asp His Met Val Leu Leu Glu Phe Val
            210                 215                 220 aca gct gct ggg att aca cat ggc atg gat gaa cta tac aaa ta           716
Thr Ala Ala Gly Ile Thr His Gly Met Asp Glu Leu Tyr Lys
225                 230                 235
```

<210> SEQ ID NO 2
<211> LENGTH: 238
<212> TYPE: PRT
<213> ORGANISM: Aequorea victoria
<220> FEATURE:
<223> OTHER INFORMATION: green fluorescent protein (GFP)

<400> SEQUENCE: 2

```
Met Ser Lys Gly Glu Glu Leu Phe Thr Ala Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Val Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Gln Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp Tyr Tyr Gln Gln Asn Thr Pro Ile Leu Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 3
<211> LENGTH: 720
<212> TYPE: DNA

<213> ORGANISM: Artificial Sequence
<220> FEATURE:
<223> OTHER INFORMATION: synthetic engineered Aequorea-related
    fluorescent protein S65G/S72A/T203Y utilizing preferred
    mammalian codons and optimal Kozak sequence
<220> FEATURE:
<221> NAME/KEY: CDS
<222> LOCATION: (1)...(720)
<223> OTHER INFORMATION: engineered Aequorea-related fluorescent protein
    S65G/S72A/T203Y

<400> SEQUENCE: 3

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ttc ggc tac ggc gtg cag tgc ttc gcc cgc tac ccc gac cac atg aag     240
Phe Gly Tyr Gly Val Gln Cys Phe Ala Arg Tyr Pro Asp His Met Lys
 65                  70                  75                  80 cag cag gac ttc ttc aag tcc gcc atg ccc gaa ggc tac gtc cag gag     288
Gln Gln Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gac gac ggc aac atc ctg ggg cac aag ctg gag tac     432
Ile Asp Phe Lys Asp Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ccc gcc gac cac tac cag cag aac acc ccc atc ggc gac ggc     576
Val Gln Pro Ala Asp His Tyr Gln Gln Asn Thr Pro Ile Gly Asp Gly
            180                 185                 190 ccc gtg ctg ctg ccc gac aac cac tac ctg agc tac cag tcc gcc ctg     624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220 gtg acc gcc gcc ggg atc act cac ggc atg gac gag ctg tac aag taa    720
Val Thr Ala Ala Gly Ile Thr His Gly Met Asp Glu Leu Tyr Lys
225                 230                 235
```

<210> SEQ ID NO 4
<211> LENGTH: 239
<212> TYPE: PRT
<213> ORGANISM: Artificial Sequence
<220> FEATURE:
<223> OTHER INFORMATION: synthetic engineered Aequorea-related fluorescent protein S65G/S72A/T203Y

<400> SEQUENCE: 4

| | | | | | | | | | | | | | | |
|---|---|---|---|---|---|---|---|---|---|---|---|---|---|---|
|Met|Val|Ser|Lys|Gly|Glu|Glu|Leu|Phe|Thr|Gly|Val|Val|Pro|Ile|Leu|
|1| | | |5| | | | |10| | | | |15|

Val Glu Leu Asp Gly Asp Val Asn Gly His Lys Phe Ser Val Ser Gly
              20            25            30

Glu Gly Glu Gly Asp Ala Thr Tyr Gly Lys Leu Thr Leu Lys Phe Ile
        35              40              45

Cys Thr Thr Gly Lys Leu Pro Val Pro Trp Pro Thr Leu Val Thr Thr
 50               55              60

Phe Gly Tyr Gly Val Gln Cys Phe Ala Arg Tyr Pro Asp His Met Lys
65              70              75            80

Gln Gln Asp Phe Phe Lys Ser Ala Met Pro Glu Gly Tyr Val Gln Glu
        85              90              95

Arg Thr Ile Phe Phe Lys Asp Asp Gly Asn Tyr Lys Thr Arg Ala Glu
        100            105            110

Val Lys Phe Glu Gly Asp Thr Leu Val Asn Arg Ile Glu Leu Lys Gly
       115           120            125

Ile Asp Phe Lys Asp Asp Gly Asn Ile Leu Gly His Lys Leu Glu Tyr
130              135              140

Asn Tyr Asn Ser His Asn Val Tyr Ile Met Ala Asp Lys Gln Lys Asn
145              150            155            160

Gly Ile Lys Val Asn Phe Lys Ile Arg His Asn Ile Glu Asp Gly Ser
             165             170            175

Val Gln Pro Ala Asp His Tyr Gln Gln Asn Thr Pro Ile Gly Asp Gly
       180           185            190

Pro Val Leu Leu Pro Asp Asn His Tyr Leu Ser Tyr Gln Ser Ala Leu
       195           200            205

Ser Lys Asp Pro Asn Glu Lys Arg Asp His Met Val Leu Leu Glu Phe
210              215            220

Val Thr Ala Ala Gly Ile Thr His Gly Met Asp Glu Leu Tyr Lys
225              230            235

```
<210> SEQ ID NO 5
<211> LENGTH: 37
<212> TYPE: PRT
<213> ORGANISM: Artificial Sequence
<220> FEATURE:
<223> OTHER INFORMATION: synthetic His-tag sequence from
      histidine-tagged S65T GFP
```

<400> SEQUENCE: 5

Met Arg Gly Ser His His His His His His Gly Met Ala Ser Met Thr
1              5              10              15

Gly Gly Gln Gln Met Gly Arg Asp Leu Tyr Asp Asp Asp Asp Lys Asp
             20             25            30

Pro Pro Ala Glu Phe
             35

```
<210> SEQ ID NO 6
<211> LENGTH: 228
<212> TYPE: PRT
<213> ORGANISM: Artificial Sequence
<220> FEATURE:
<223> OTHER INFORMATION: synthetic engineered Aequorea-related green
      fluorescent protein S65T
<220> FEATURE:
<221> NAME/KEY: MOD_RES
<222> LOCATION: (64)...(66)
```

```
<223> OTHER INFORMATION: amide nitrogen of Gly 66 is cyclized onto the
      amide of Tyr 65, the amide oxygen of Thr 64 has been removed and
      the bond between the alpha and beta carbons of Tyr 65 is
      oxidized to form a conjugated GFP chromophore

<400> SEQUENCE: 6

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Ser Gly Glu Gly
            20                  25                  30

Glu Gly Asp Ala Thr Tyr Gly Lys Leu Thr Leu Lys Phe Ile Cys Thr
        35                  40                  45

Thr Gly Lys Leu Pro Val Pro Trp Pro Thr Leu Val Thr Thr Phe Thr
    50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Phe Phe Lys Asp Asp Gly Asn Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Tyr
    130                 135                 140

Asn Ser His Asn Val Tyr Ile Met Ala Asp Lys Gln Lys Asn Gly Ile
145                 150                 155                 160

Lys Val Asn Phe Lys Ile Arg His Asn Ile Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Ala Leu Ser Lys
        195                 200                 205

Asp Pro Asn Glu Lys Arg Asp His Met Val Leu Leu Glu Phe Val Thr
    210                 215                 220

Ala Ala Gly Ile
225

<210> SEQ ID NO 7
<211> LENGTH: 5
<212> TYPE: PRT
<213> ORGANISM: Artificial Sequence
<220> FEATURE:
<223> OTHER INFORMATION: synthetic localization sequence targeting the
      nucleus

<400> SEQUENCE: 7

Lys Lys Lys Arg Lys
1               5

<210> SEQ ID NO 8
<211> LENGTH: 26
<212> TYPE: PRT
<213> ORGANISM: Artificial Sequence
<220> FEATURE:
<223> OTHER INFORMATION: synthetic amino terminal localization sequence
      targeting the mitochondrion

<400> SEQUENCE: 8

Met Leu Arg Thr Ser Ser Leu Phe Thr Arg Arg Val Gln Pro Ser Leu
1               5                   10                  15
```

```
Phe Arg Asn Ile Leu Arg Leu Gln Ser Thr
            20                  25

<210> SEQ ID NO 9
<211> LENGTH: 4
<212> TYPE: PRT
<213> ORGANISM: Artificial Sequence
<220> FEATURE:
<223> OTHER INFORMATION: synthetic C-terminus localization sequence
      targeting the endoplasmic reticulum

<400> SEQUENCE: 9

Lys Asp Glu Leu
 1

<210> SEQ ID NO 10
<211> LENGTH: 4
<212> TYPE: PRT
<213> ORGANISM: Artificial Sequence
<220> FEATURE:
<223> OTHER INFORMATION: synthetic FSYG sequence which derives the
      choromophore in wild-type Aequorea and sea pansy
      Renilla reniformis GFP

<400> SEQUENCE: 10

Phe Ser Tyr Gly
 1
```

What is claimed is:

1. A method for screening the effects of a test compound on ion channel activity in a cell comprising the steps of,
   i) providing a cell comprising an ion channel of interest and an engineered green fluorescent protein comprising an amino acid sequence at least 85% identical to the amino acid sequence of the *Aequorea* green fluorescent protein set forth in SEQ ID NO:2 and which differs from SEQ ID NO:2 by
      (1) at least one first substitution at position T203, wherein the substituting amino acid is selected from the group consisting of H, Y, W and F,
      (2) at least one second substitution at position H148, wherein the substituting amino acid is selected from the group consisting of R, G, Q, A, N, and K, and
      (3) at least one third amino acid substitution at position V150, wherein the substituting amino acid is selected from the group consisting of A, C, M, G, L, Q, S, T and N; and
   ii) contacting said cell with the test compound,
   iii) measuring fluorescence from said engineered green fluorescent protein, and
   iv) comparing the fluorescence of said engineered green fluorescent protein in said cell to the fluorescence of a control engineered green fluorescent protein introduced into a control cell wherein the control cell is not contacted with the test compound.

2. The method of claim 1, further comprising the step of contacting said cell with a known activator of said ion channel of interest.

3. The method of claim 1, wherein said ion channel of interest transports halides.

4. The method of claim 1, wherein said at least one second substitution at position H148 is H148Q.

5. The method of claim 1, wherein said at least one second substitution at position H148 is H148G.

6. The method of claim 1, wherein said at least one second substitution at position H148 is H148R.

* * * * *

UNITED STATES PATENT AND TRADEMARK OFFICE
CERTIFICATE OF CORRECTION

PATENT NO. : 8,263,412 B2
APPLICATION NO. : 13/011432
DATED : September 11, 2012
INVENTOR(S) : Wachter et al.

Page 1 of 1

It is certified that error appears in the above-identified patent and that said Letters Patent is hereby corrected as shown below:

On the Title Page:

In the Inventors section, item (75), first col., line 4:
please delete "James S. Remington" and insert --S. James Remington--.

Signed and Sealed this
Sixth Day of August, 2013

Teresa Stanek Rea
*Acting Director of the United States Patent and Trademark Office*